(12) United States Patent
Aicher et al.

(10) Patent No.: US 8,933,077 B2
(45) Date of Patent: *Jan. 13, 2015

(54) GLUCOKINASE ACTIVATORS

(75) Inventors: Thomas D. Aicher, Superior, CO (US); Wai-man Lee, Sacramento, CA (US); Ronald Jay Hinklin, Longmont, CO (US); Mark Joseph Chicarelli, Longmont, CO (US); Steven Armen Boyd, Longmont, CO (US); Kevin Ronald Condroski, Broomfield, CO (US); Yi-Wen Yeh, legal representative, Rowland Heights, CA (US)

(73) Assignee: Array BioPharma Inc., Boulder, CO (US)

( * ) Notice: Subject to any disclaimer, the term of this patent is extended or adjusted under 35 U.S.C. 154(b) by 228 days.

This patent is subject to a terminal disclaimer.

(21) Appl. No.: 12/092,233

(22) PCT Filed: Oct. 24, 2006

(86) PCT No.: PCT/US2006/041251
§ 371 (c)(1),
(2), (4) Date: Jan. 7, 2009

(87) PCT Pub. No.: WO2007/053345
PCT Pub. Date: May 10, 2007

(65) Prior Publication Data
US 2010/0056530 A1    Mar. 4, 2010

Related U.S. Application Data

(60) Provisional application No. 60/732,037, filed on Nov. 1, 2005.

(51) Int. Cl.
A01N 43/58    (2006.01)
A01N 43/60    (2006.01)
C07D 417/12    (2006.01)
C07D 417/14    (2006.01)
C07D 495/04    (2006.01)
C07D 513/04    (2006.01)

(52) U.S. Cl.
CPC ............ *C07D 417/12* (2013.01); *C07D 417/14* (2013.01); *C07D 495/04* (2013.01); *C07D 513/04* (2013.01)
USPC .......................................... 514/248; 552/553

(58) Field of Classification Search
USPC ............ 564/390; 546/193; 548/174; 544/353
See application file for complete search history.

(56) References Cited

U.S. PATENT DOCUMENTS

| | | | |
|---|---|---|---|
| 6,586,423 B2 | 7/2003 | Bilodeau et al. | |
| 6,596,746 B1 | 7/2003 | Das et al. | |
| 2006/0258701 A1 | 11/2006 | Mitsuya et al. | |
| 2008/0032996 A1 | 2/2008 | Mitsuya et al. | |

OTHER PUBLICATIONS

Caplus 2001:185751, Bilodeau et al.as evidenced by WO200101799.*
STN Accession No. 2000:756524.*
International Search Reports corresponding to related PCT Application PCT/US2006/041251.

* cited by examiner

*Primary Examiner* — Sreeni Padmanabhan
*Assistant Examiner* — Jean Cornet
(74) *Attorney, Agent, or Firm* — Sarah S. Mastous; Viksnins Harris & Padys PLLP

(57) ABSTRACT

Provided are compounds of Formula I wherein $R^1$, $R^2$, Y, Z and G are as defined herein, that are useful in the treatment and/or prevention of diseases mediated by deficient levels of glucokinase activity, such as diabetes mellitus. Also provided are methods of treating or preventing diseases and disorders characterized by underactivity of glucokinase or which can be treated by activating glucokinase.

(I)

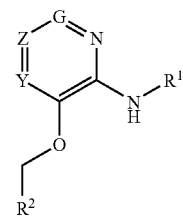

16 Claims, No Drawings

GLUCOKINASE ACTIVATORS

PRIORITY OF INVENTION

This application claims priority to U.S. Provisional Application No. 60/732,037 that was filed on 1 Nov. 2005. The entire content of this provisional application is hereby incorporated herein by reference.

FIELD OF THE INVENTION

Provided are compounds that are useful in the treatment and/or prevention of diseases mediated by deficient levels of glucokinase activity, such as diabetes mellitus, and methods of preparing such compounds. Also provided are methods of treating diseases and disorders characterized by underactivation of glucokinase activity or which can be treated by activating glucokinase, comprising administering an effective amount of a compound of this invention.

BACKGROUND OF THE INVENTION

Diabetes mellitus comprises a group of syndromes characterized by an inability of the body to produce adequate insulin or to properly use insulin. Most diabetes patients can be classified clinically as having either insulin-dependent diabetes mellitus (IDDM) or non-insulin-dependent diabetes mellitus (NIDDM). Nearly all forms of diabetes mellitus result from either a decrease in the secretion and blood concentration of insulin or a decrease in the response of tissues to insulin (insulin resistance), often associated with an elevated level of hormones (e.g., glucagon) that act contrary to insulin. Such abnormalities give rise to changes in carbohydrate, lipid and protein metabolism. The syndrome's hallmark is hyperglycemia; other complications can include cardiovascular disease, retinopathy, neuropathy, nephropathy, skin disorders and gastroparesis.

Diabetes mellitus affects millions of persons worldwide, including over 18 million in the United States. It is estimated that IDDM (Type I diabetes), which results from the body's failure to produce insulin, accounts for 5-10% of the cases of diabetes diagnosed in the United States. The majority of diabetes patients in the United States are diagnosed with NIDDM (Type II diabetes), which results from insulin resistance combined with the inability of the pancreas to secrete sufficient insulin to overcome such resistance. Type II diabetes occurs in at least 5% of the United States population, and in 1996 alone NIDDM affected 16 million people (Roman, S. H.; Harris, M. I., *Endocrinology and Metabolism Clinics of North America*, 1997, 26.3, 443-474). Impaired glucose tolerance (IGT), a syndrome characterized by impaired glucose processing that presents symptoms similar to a mild form of Type II diabetes, is even more prevalent, affecting 35 to 40 million adults in the United States.

Diabetes is most frequently diagnosed either by the presentation of a fasting plasma glucose of greater than or equal to 126 mg/dL on two occasions, or by an oral glucose tolerance test (OGTT) with a 2 hour post load value of greater than 200 mg/dL plus classic symptoms such as polydipsia, polyphagia and/or polyuria (The Expert Committee on the Diagnosis and Classification of Diabetes Mellitus, *Diabetes Care*, 1998, 21, S5-19). In the case of IGT, a fasting plasma glucose of less than 126 mg/dL but 2 hour post-oral glucose challenge lever greater than 140 mg/dL is observed.

A primary goal in the treatment of each of these conditions is the reduction and control of blood glucose levels. The reduction of hyperglycemia in insulin-dependent diabetes (IDDM) can attenuate the development of many of the attendant complications of IDDM (Diabetes Control and Complications Trial Research Group, *New England J. Med.*, 1993, 329, 977-986). For example, tight control of blood glucose levels through intensive insulin therapy can reduce the development of retinopathy, nephropathy and neuropathy by >50% each in IDDM patients. These findings, together with the similarity of the pathologies seen in IDDM and NIDDM, suggest that control of blood glucose levels would produce similar benefits in NIDDM patients (American Diabetes Association, *Diabetes Care*, 1998, 21, S88-90), as has been reported (Ohkubo, Y., et al., *Diabetes Res. Clin. Pract.* 1995, 28, 103-117).

Several methods to treat hyperglycemia have been attempted. Patients with Type I diabetes receive insulin. In patients with Type II diabetes, the pancreas secretes insulin, but in insufficient amounts to overcome the intrinsic insulin resistance of the disease. The administration of agents such as metformin (De Fronzo, R. A.; Goodman, A. M. *N. Engl. J. Med.*, 1995, 333, 541-549; Bailey, C. J. Biguanides and NIDDM, *Diabetes Care* 1992, 15, 773-784) and the glitazones (PPAR agonist class of drugs; Willson, T. M., et al., *J. Med. Chem.* 1996, 39, 665-668) can at least partially ameliorate insulin resistance, but these agents do not promote insulin secretion. Treatment with certain sulfonylureas has been shown to promote insulin secretion by affecting an ion channel; however, the increase in insulin caused by this class of drugs is not glucose dependent or even glucose sensitive, and such treatment can actually raise the risk of overt hypoglycemia. DPPV inhibitors, such as GLP or a GLP mimetic (such as Exedin), promote cAMP secretion at the β-cell through an incretin mechanism, and administration of these agents promotes insulin release in a glucose dependent manner (Vahl, T. P., D'Alessio, D. A., *Expert Opinion on Invest. Drugs* 2004, 13, 177-188). However, even with these potential treatments, it is difficult to achieve tight control of blood glucose levels in NIDMM patients in accordance with the guidelines recommended by the American Diabetes Association. Accordingly, there is significant demand for novel therapeutic approaches that allow sufficient glycemic control.

Possible approaches to glycemic control include enhancing clearance of glucose from the blood and increasing the rate of glucose storage or utilization. Glucose enters most cells by a specific transport protein, where it is phosphorylated to form glucose-6-phosphate in a reaction catalyzed by a hexokinase. Inside the cell, glucose-6-phosphate has one of several fates: it can be broken down via the glycolytic pathway, converted into glycogen or it can be oxidized via the pentose phosphate pathway.

Glucokinase (GK) (ATP: D-hexose 6-phosphotransferase), one of the four types of mammalian hexokinases (hexokinase IV), plays an essential role in blood glucose homeostasis. Expression of glucokinase is largely localized in the liver and pancreatic β-cells, where several types of glucokinase are expressed: these types differ in the sequence of the 15 N-terminal amino acids due to differences in splicing, but their enzymatic properties are virtually identical. Glucokinase is also expressed in a population of neurones in the hypothalamus.

Unlike the enzymatic activities of the other three hexokinases (I, II, III), each of which becomes saturated at a glucose concentration of below 1 mM, glucokinase has a $K_m$ for glucose of 8 mM, which is close to the physiological glucose level (5 mM). Thus, at lower glucose levels, glucose is more rapidly utilized in brain, muscle and other peripheral tissues—through conversion by a hexokinase other than glucokinase—than in the liver. At elevated glucose levels, such as after a meal or overnutrition (the postprandial glucose level can exceed 10-15 mM), glucokinase-mediated glucose metabolism in the liver and pancreas is accelerated. Moreover, hexokinases I, II and III are inhibited by high concentrations of glucose-6-phosphate, lowering glucose utilization, whereas glucokinase continues to catalyze utilization of glucose even at high levels of glucose-6-phosphate.

In tissues where glucokinase is expressed, it plays an important role in glucose uptake and utilization: in the β-cell, the glucose-6-phosphate produced is a necessary signal for insulin release; in the hypothalamus glucose-6-phosphate acts as a satiety signal and might contribute to the secretion of enteroincretins; and in the liver, where glucose-6-phosphate production by the action of glucokinase acts as a mechanism for disposal of excessive glucose through storage as glycogen (Printz, R. L., et al., *Annu. Rev. Nutr.*, 1993, 13, 463-496). Glucokinase-catalyzed glucose phosphorylation is the rate-limiting reaction for glycolysis in hepatocytes and pancreatic β-cells. In the liver, glucokinase determines the rates of both glucose uptake and glycogen synthesis, and it is also thought to be essential for the regulation of various glucose-responsive genes (Girard, J., et al., *Annu. Rev. Nutr.*, 1997, 17, 325-352). In both liver and pancreatic β-cells, glucokinase is rate limiting for glucose utilization, and consequently is a major component of the regulation of insulin secretion from the β-cell and glycogen storage in the liver. The control of insulin secretion and the control of glycogen storage are deficient in diabetes (DeFronzo, R. A., *Diabetes*, 1988, 37, 667-687).

The theoretical importance of glucokinase in diabetes is supported by studies of genetic populations and genetic manipulation of animal models of NIDDM. Mutation of glucokinase to a less active form of the kinase is the cause of the Maturity Onset of Diabetes in the Young (MODY-2) (Froguel, P., et al., *New England J. Med.*, 1993, 328, 697-702; Bell, G. I., et al., *Annual Rev. of Physiol.*, 1996, 58, 171-186). Conversely, humans with a glucokinase activation mutation are less prone to hyperglycemia and have increased insulin secretion in response to a glucose challenge (Christesen, H. B., et al., *Diabetes*, 2002, 51, 1240-1246; Gloyn, A. L, et al., *Diabetes*, 2003, 52, 2433-2440; Glaser, B., et al., *New England J. Med.*, 1998, 338, 226-230). Also, NIDDM patients have been reported to have inappropriately low glucokinase activity. Furthermore, over expression of glucokinase in dietary or genetic animal models of diabetes either prevents, ameliorates, or reverses the progress of pathological symptoms in the disease (Caro, J. F., et al., *Hormone & Metabolic Res.*, 1995, 27, 19-22). For these reasons, compounds that activate glucokinase have been sought by the pharmaceutical industry.

Substituted benzyl carbamoyl, substituted heterobenzyl carbamoyl, substituted phenyl carbamoyl, and substituted heteroaryl carbamoyl compounds have been disclosed as glucokinase activators. See, for example, WO 03/000267, WO 03/015774, WO 04/045614, WO 04/046139, WO 05/04480, WO 05/054200, WO 05/054233, WO 05/044801, WO 05/056530, WO 03/080585, WO 04/076420, WO 04/081001, WO 04/063194, WO 04/050645, WO 03/055482, WO 04/002481, WO 05/066145, WO 04/072031, WO 04/072066, U.S. Pat. No. 6,610,846, WO 00/058293, WO 03/095438, WO 01/44216, WO 01/083465, WO 01/083478, WO 01/085706, WO 01/085707, WO 02/008209, WO 02/014312, WO 02/046173, WO 02/048106, WO 03/095438, WO 04/031179, and WO 04/052869. These compounds either lower the $K_m$ for glucose and/or increase the $V_{max}$ of glucokinase. A class of glucokinase activators that can lower the $K_m$ of glucose moderately to 2-5 mM at low activator concentrations is desirable.

SUMMARY OF THE INVENTION

In one aspect, the present invention relates to compounds that are activators of glucokinase which are useful in the treatment of diseases and disorders that would benefit from activation of glucokinase.

More specifically, one aspect of this invention provides compounds of Formula I

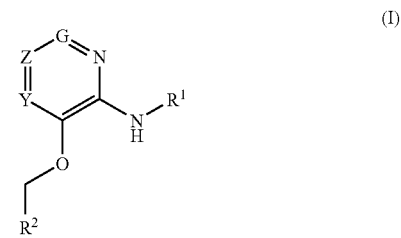

(I)

and solvates, metabolites and pharmaceutically acceptable salts and prodrugs thereof, wherein G, Z, Y, $R^1$ and $R^2$ are as defined herein.

The invention also provides pharmaceutical compositions comprising a therapeutically effective amount of a compound of Formula I, or a solvate, metabolite, or pharmaceutically acceptable salt or prodrug thereof, and a pharmaceutically acceptable carrier.

The inventive compounds may be used advantageously in combination with other known therapeutic agents. Accordingly, this invention also provides pharmaceutical compositions comprising a therapeutically effective amount of a compound of Formula I or a solvate, metabolite, or pharmaceutically acceptable salt or prodrug thereof, in combination with a second therapeutic agent.

This invention also provides methods of preventing or treating a disease or disorder characterized by underactivation of glucokinase or which can be treated by activating glucokinase in a mammal, comprising administrating to said mammal one or more compounds of Formula I, or a metabolite, solvate, or pharmaceutically acceptable salt or prodrug thereof, in an amount effective to treat said disease or disorder. The compounds of the present invention can be used, for example, as prophylactics or therapeutic agents for treating diseases or disorders mediated by deficient levels of glucokinase activity, including, but not limited to, diabetes mellitus (type I and type II), impaired glucose tolerance, IFG (impaired fasting glucose) and IFG (impaired fasting glycemia), as well as other diseases and disorders characterized by underactivation of glucokinase or which can be treated by activation of glucokinase, such as those discussed below.

This invention also provides compound of Formula I for use as medicaments in the treatment of diseases or disorders characterized by underactivation of glucokinase or which can be treated by activating glucokinase.

An additional aspect of the invention is the use of a compound of Formula I in the preparation of a medicament for the treatment or prevention of a disease or disorder characterized by underactivation of glucokinase or which can be treated by activating glucokinase in a mammal suffering from such disorder.

This invention further provides kits for the treatment or prevention of a disease or disorder characterized by underactivation of glucokinase, said kit comprising a compound of Formula I, or a solvate, metabolite, or pharmaceutically acceptable salt or prodrug thereof, a container, and optionally a package insert or label indicating a treatment. The kits may further comprise a second compound or formulation comprising a second pharmaceutical agent useful for treating said disease or disorder.

This invention further includes methods of preparing, methods of separating, and methods of purifying of the compounds of this invention, as well as synthetic intermediates disclosed herein that are useful for preparing compounds of Formula I, such as, for example, synthetic intermediates such as those disclosed in Schemes A-Q and in the Examples below.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature and similar materials differs from or contradicts this application, including but not limited to defined terms, term usage, described techniques, or the like, this application controls.

DEFINITIONS

The term "alkyl" as used herein refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl (Me, —CH$_3$), ethyl (Et, —CH$_2$CH$_3$), 1-propyl (n-Pr, n-propyl, —CH$_2$CH$_2$CH$_3$), 2-propyl (i-Pr, i-propyl, —CH(CH$_3$)$_2$), 1-butyl (n-Bu, n-butyl, —CH$_2$CH$_2$CH$_2$CH$_3$), 2-methyl-1-propyl (i-Bu, i-butyl, —CH$_2$CH(CH$_3$)$_2$), 2-butyl (s-Bu, s-butyl, —CH(CH$_3$)CH$_2$CH$_3$), 2-methyl-2-propyl (t-Bu, t-butyl, —C(CH$_3$)$_3$), 1-pentyl (n-pentyl, —CH$_2$CH$_2$CH$_2$CH$_2$CH$_3$), 2-pentyl (—CH(CH$_3$)CH$_2$CH$_2$CH$_3$), 3-pentyl (—CH(CH$_2$CH$_3$)$_2$), 2-methyl-2-butyl (—C(CH$_3$)$_2$CH$_2$CH$_3$), 3-methyl-2-butyl (—CH(CH$_3$)CH(CH$_3$)$_2$), 3-methyl-1-butyl (—CH$_2$CH$_2$CH(CH$_3$)$_2$), 2-methyl-1-butyl (—CH$_2$CH(CH$_3$)CH$_2$CH$_3$), 1-hexyl (—CH$_2$CH$_2$CH$_2$CH$_2$CH$_2$CH$_3$), 2-hexyl (—CH(CH$_3$)CH$_2$CH$_2$CH$_2$CH$_3$), 3-hexyl (—CH(CH$_2$CH$_3$)(CH$_2$CH$_2$CH$_3$)), 2-methyl-2-pentyl (—C(CH$_3$)$_2$CH$_2$CH$_2$CH$_3$), 3-methyl-2-pentyl (—CH(CH$_3$)CH(CH$_3$)CH$_2$CH$_3$), 4-methyl-2-pentyl (—CH(CH$_3$)CH$_2$CH(CH$_3$)$_2$), 3-methyl-3-pentyl (—C(CH$_3$)(CH$_2$CH$_3$)$_2$), 2-methyl-3-pentyl (—CH(CH$_2$CH$_3$)CH(CH$_3$)$_2$), 2,3-dimethyl-2-butyl (—C(CH$_3$)$_2$CH(CH$_3$)$_2$), 3,3-dimethyl-2-butyl (—CH(CH$_3$)C(CH$_3$)$_3$), 1-heptyl, 1-octyl, cyclopropyl, cyclobutyl, cyclopentyl, cyclohexyl, cycloheptyl, and cyclooctyl.

In certain embodiments, the term "alkyl" refers to a saturated linear or branched-chain monovalent hydrocarbon radical of one to six carbon atoms, wherein the alkyl radical may be optionally substituted independently with one or more substituents described below.

The term "alkylene" as used herein refers to a linear or branched saturated divalent hydrocarbon radical of one to twelve carbon atoms, wherein the alkylene radical may be optionally substituted independently with one or more substituents described herein. Examples include, but are not limited to, methylene, ethylene, propylene, 2-methylpropylene, pentylene, and the like.

In certain embodiments, the term "alkylene" refers to a linear or branched saturated divalent hydrocarbon radical of one to four carbon atoms, wherein the alkylene radical may be optionally substituted independently with one or more substituents described herein.

The term "alkenyl" as used herein refers to a linear or branched-chain monovalent hydrocarbon radical of two to twelve carbon atoms with at least one site of unsaturation, i.e., a carbon-carbon, sp$^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH═CH$_2$), allyl (—CH$_2$CH═CH$_2$), 1-cyclopent-1-enyl, 1-cyclopent-2-enyl, 1-cyclopent-3-enyl, 5-hexenyl, 1-cyclohex-1-enyl, 1-cyclohex-2-enyl, and 1-cyclohex-3-enyl.

In certain embodiments, the term "alkenyl" as used herein refers to a linear or branched-chain monovalent hydrocarbon radical of two to six carbon atoms with at least one site of unsaturation, wherein the alkenyl radical may be optionally substituted independently with one or more substituents described herein, and includes radicals having "cis" and "trans" orientations.

The term "alkenylene" as used herein refers to a linear or branched divalent hydrocarbon radical of two to twelve carbons containing at least one double bond, wherein the alkenylene radical may be optionally substituted independently with one or more substituents described herein. Examples include, but are not limited to, ethenylene, propenylene, and the like.

The term "alkenylene" includes linear or branched divalent hydrocarbon radical of two to four carbons containing at least one double bond, wherein the alkenylene radical may be optionally substituted independently with one or more substituents described herein.

The term "alkynyl" as used herein refers to a linear or branched monovalent hydrocarbon radical of two to twelve carbon atoms with at least one site of unsaturation, i.e., a carbon-carbon, sp triple bond, wherein the alkynyl radical may be optionally substituted independently with one or more substituents described herein. Examples include, but are not limited to, ethynyl (—C≡CH) and propynyl (propargyl, —CH$_2$C≡CH).

In certain embodiments, the term "alkynyl" refers to a linear or branched monovalent hydrocarbon radical of two to six carbon atoms with at least one carbon-carbon sp triple bond.

The term "alkynylene" as used herein refers to a linear or branched divalent hydrocarbon radical of two to twelve carbons containing at least one triple bond, wherein the alkynylene radical may be optionally substituted independently with one or more substituents described herein. Examples include, but are not limited to, ethynylene, propynylene, and the like.

In certain embodiments, the term "alkynylene" refers to a linear or branched divalent hydrocarbon radical of two to four carbons containing at least one triple bond.

The term "heteroalkyl" as used herein refers to saturated linear or branched-chain monovalent hydrocarbon radical of one to twelve carbon atoms, wherein at least one of the carbon atoms is replaced with a heteroatom independently selected from N, O, or S, and wherein the radical may be a carbon radical or heteroatom radical. The heteroalkyl radical may be optionally substituted independently with one or more substituents described herein. The term "heteroalkyl" encompasses alkoxy and heteroalkoxy radicals.

The terms "cycloalkyl," "carbocycle," and "carbocyclyl" as used herein are used interchangeably and refer to saturated or partially unsaturated cyclic hydrocarbon radical having from three to twelve carbon atoms. The term "cycloalkyl" includes monocyclic and polycyclic (e.g., bicyclic and tricyclic) cycloalkyl structures, wherein the polycyclic structures optionally include a saturated or partially unsaturated cycloalkyl fused to a saturated or partially unsaturated cycloalkyl or heterocycloalkyl ring or an aryl or heteroaryl ring. Examples of cycloalkyl groups include, but are not limited to, cyclopropyl, cyclobutyl, cyclopentyl, cyclohexyl, cycloheptyl, and the like. Bicyclic carbocycles include those having 7 to 12 ring atoms arranged, for example, as a bicyclo[4,5], [5,5], [5,6] or [6,6] system, or as bridged systems such as bicyclo[2.2.1]heptane, bicyclo[2.2.2]octane, and bicyclo[3.2.2]nonane. The cycloalkyl may be optionally substituted independently at one or more substitutable positions with one or more substituents described herein.

The terms "heterocycloalkyl," "heterocycle" and "heterocyclyl" as used herein are used interchangeably and refer to a saturated or partially unsaturated carbocyclic radical of 3 to 8 ring atoms in which at least one ring atom is a heteroatom independently selected from nitrogen, oxygen and sulfur, the remaining ring atoms being C, where one or more ring atoms may be optionally substituted independently with one or more substituents described below. The radical may be a carbon radical or heteroatom radical. The term "heterocycle" includes heterocycloalkoxy. "Heterocycloalkyl" also includes radicals where heterocycle radicals are fused with a saturated, partially unsaturated, or fully unsaturated (i.e., aromatic) carbocyclic or heterocyclic ring. Examples of heterocycloalkyl rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyclo[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. The heterocycle may be C-attached or N-attached where such is possible. For instance, a group derived from pyrrole may be pyrrol-1-yl (N-attached) or pyrrol-3-yl (C-attached). Further, a group derived from imidazole may be imidazol-1-yl (N-attached) or imidazol-3-yl (C-attached). Examples of heterocyclic groups wherein 2 ring carbon atoms are substituted with oxo (=O) moieties are isoindoline-1,3-dionyl and 1,1-dioxo-thiomorpholinyl. The heterocycle groups herein are unsubstituted or, as specified, substituted in one or more substitutable positions with various groups.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Further examples of carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of an isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Aryl" as used herein means a monovalent aromatic hydrocarbon radical of 6-20 carbon atoms derived by the removal of one hydrogen atom from a single carbon atom of a parent aromatic ring system. Aryl includes bicyclic radicals comprising an aromatic ring fused to a non-aromatic ring, a partially unsaturated ring, or an aromatic ring. Exemplary aryl groups include, but are not limited to, radicals derived from benzene, naphthalene, anthracene, biphenyl, indene, indane, 1,2-dihydronapthalene, 1,2,3,4-tetrahydronapthalene, and the like.

The term "heteroaryl" as used herein refers to a monovalent aromatic radical of a 5-, 6-, or 7-membered ring and includes fused ring systems (at least one of which is aromatic) of 5-10 atoms containing at least one and up to four heteroatoms independently selected from nitrogen, oxygen, and sulfur. Examples of heteroaryl groups include, but are not limited to, pyridinyl, imidazolyl, imidazopyridinyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Spiro moieties are also included within the scope of this definition. Heteroaryl groups are optionally substituted with one or more substituents independently selected from, for example, halogen, lower alkyl, lower alkoxy, haloalkyl, aryl, heteroaryl, and hydroxy.

The term "halogen" as used herein means fluoro, chloro, bromo or iodo.

The term "a" as used herein means one or more.

In general, the various moieties or functional groups of the compounds of this invention may be optionally substituted by one or more substituents. Examples of substituents suitable for purposes of this invention include, but are not limited to, oxo, halogen, cyano, nitro, trifluoromethyl, fluoromethoxy, difluoromethoxy, trifluoromethoxy, azido, —NR"SO$_2$R', —SO$_2$NR'R", —C(=O)R', —C(=O)OR', —OC(=O)R', —NR"C(=O)OR', —NR"C(=O)R', —C(=O)NR'R", —NR'R", —NR'"C(=O)N'R", —OR', —SR', —S(O)R', —S(O)$_2$R', alkyl, alkenyl, alkynyl, heteroalkyl, cycloalkyl, heterocycloalkyl, aryl, heteroaryl, arylalkyl, heteroarylalkyl, and heterocyclylalkyl, where R', R" and R'" are independently H, alkyl, alkenyl, alkynyl, heteroalkyl, cycloalkyl, heterocycloalkyl, aryl, or heteroaryl.

It is to be understood that in instances where two or more radicals are used in succession to define a substituent attached to a structure, the first named radical is considered to be terminal and the last named radical is considered to be attached to the structure in question. Thus, for example, an arylalkyl radical is attached to the structure in question by the alkyl group.

Glucokinase Activators

The present invention provides compounds, and pharmaceutical formulations thereof, that are useful in the treatment of diseases, conditions and/or disorders characterized by underactivation of glucokinase or which can be treated by activation of glucokinase.

One aspect of the invention provides compounds of Formula I

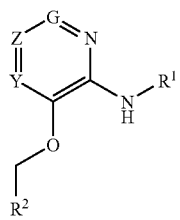

(I)

and solvates, metabolites and pharmaceutically acceptable salts and prodrugs thereof, wherein:

G is N or CR$^{11}$;
Z is N or CR$^3$;
Y is N or CR$^4$, wherein at least one of G or Z is not N;
R$^1$ is a heteroaryl ring represented by the formula

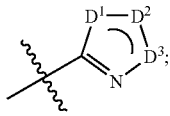

D$^1$ is S, O, or N;
D$^2$ is N or CR$^{12}$;
D$^3$ is S, O or CR$^{13}$;
R$^2$ is a monocyclic or bicyclic aryl or heteroaryl, wherein said monocyclic and bicyclic aryl and heteroaryl are optionally substituted with one or more groups independently selected from alkyl, alkenyl, alkynyl, heteroalkyl, saturated and partially unsaturated V$_n$-cycloalkyl, saturated and partially unsaturated V$_n$-heterocycloalkyl, V$_n$-aryl, V$_n$-heteroaryl, F, Cl, Br, I, CF$_3$, cyano, V$_n$—OR$^6$, V$_n$—C(=O)R$^6$, V$_n$—C(=O)OR$^6$, V$_n$—OC(=O)R$^6$, V$_n$—O(CH$_2$)$_n$C(=O)OR$^6$, V$_n$—O(CH$_2$)$_n$C(=O)NR$^6$R$^7$, V$_n$—C(=O)NR$^6$R$^7$, V$_n$—NR$^6$R$^7$, V$_n$—NR$^6$C(=O)R$^7$, V$_n$—SR$^6$, V$_n$S(O)R$^6$, and V$_n$—S(O)$_2$R$^6$, wherein said alkyl, alkenyl, alkynyl, heteroalkyl, V$_n$-cycloalkyl, V$_n$-heterocycloalkyl, V$_n$-aryl, and V$_n$-heteroaryl are optionally substituted with one or more groups independently selected from oxo, alkyl, alkenyl, alkynyl, heteroalkyl, saturated and partially unsaturated V$_n$-cycloalkyl, saturated and partially unsaturated V$_n$-heterocycloalkyl, V$_n$-aryl, V$_n$-heteroaryl, F, Cl, Br, I, CF$_3$, cyano, V$_n$—OR$^8$, V$_n$—C(=O)R$^8$, V$_n$—C(=O)OR$^8$, V$_n$—OC(=O)R$^8$, V$_n$—C(=O)NR$^8$R$^9$, V$_n$—NR$^8$R$^9$, V$_n$—NR$^8$C(=O)R$^9$, V$_n$—SR$^8$, V$_n$—S(O)R$^8$, and V$_n$—S(O)$_2$R$^8$;

R$^3$ is H, alkyl, alkenyl, alkynyl, heteroalkyl, saturated or partially unsaturated V$_n$-cycloalkyl, saturated or partially unsaturated V$_n$-heterocycloalkyl, V$_n$-aryl, V$_n$-heteroaryl, F, Cl, Br, I, CN, V$_n$—OR$^6$, V$_n$—C(=O)R$^6$, V$_n$—C(=O)OR$^6$, V$_n$—OC(=O)R$^6$, V$_n$—C(O)NR$^6$R$^7$, V$_n$—NR$^6$R$^7$, V$_n$—NR$^6$C(=O)R$^7$, V$_n$—SR$^6$, V$_n$—S(O)R$^6$, V$_n$—S(O)$_2$R$^6$, or V$_n$—S(O)$_2$NR$^6$R$^7$, wherein said alkyl, alkenyl, alkynyl, heteroalkyl, V$_n$-cycloalkyl, V$_n$-heterocycloalkyl, V$_n$-aryl, and V$_n$-heteroaryl are optionally substituted with one or more groups independently selected from oxo, alkyl, alkenyl, alkynyl, heteroalkyl, saturated and partially unsaturated V$_n$-cycloalkyl, saturated and partially unsaturated V$_n$-heterocycloalkyl, V$_n$-aryl, V$_n$-heteroaryl, F, Cl, Br, I, CF$_3$, cyano, V$_n$—OR$^8$, V$_n$—C(=O)R$^8$, V$_n$—C(=O)OR$^8$, V$_n$—OC(=O)R$^8$, V$_n$—C(=O)NR$^8$R$^9$, V$_n$—NR$^8$R$^9$, V$_n$—NR$^8$C(=O)R$^9$, V$_n$—SR$^8$, V$_n$—S(O)R$^8$, V$_n$—S(O)$_2$R$^8$, and V$_n$—S(O)$_2$NR$^8$R$^9$;

R$^4$ is H, methyl, ethyl, F, Cl, Br, I, CF$_3$, CHF$_2$, or CH$_2$F;

R$^6$ and R$^7$ are independently H, alkyl, alkenyl, alkynyl, saturated or partially unsaturated V$_n$-cycloalkyl, saturated or partially unsaturated V$_n$-heterocycloalkyl, V$_n$-aryl, V$_n$-heteroaryl, V$_n$—OR$^8$, V$_n$—NR$^8$R$^9$, V$_n$—C(=O)NR$^8$R$^9$, or V$_n$—C(=O)R$^8$, wherein said alkyl, alkenyl, alkynyl, V$_n$-cycloalkyl, V$_n$-heterocycloalkyl, V$_n$-aryl, and V$_n$-heteroaryl are optionally substituted with one or more groups independently selected from oxo, alkyl, alkenyl, alkynyl, heteroalkyl, saturated and partially unsaturated V$_n$-cycloalkyl, saturated and partially unsaturated V$_n$-heterocycloalkyl, V$_n$-aryl, V$_n$-heteroaryl, F, Cl, Br, I, CF$_3$, cyano, V$_n$—OR$^8$, V$_n$—C(=O)R$^8$, V$_n$—C(=O)OR$^8$, V$_n$—OC(=O)R$^8$, V$_n$—C(=O)NR$^8$R$^9$, V$_n$—NR$^8$R$^9$, V$_n$—NR$^8$C(=O)R$^9$, V$_n$—SR$^8$, V$_n$—S(O)R$^8$, V$_n$—S(O)$_2$R$^8$, and V$_n$—S(O)$_2$NR$^8$R$^9$;

or R$^6$ and R$^7$ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, F, Cl, Br, I, V$_n$—OR$^8$, V$_n$—C(=O)OR$^8$, V$_n$—C(=O)NR$^8$R$^9$, V$_n$—NR$^8$R$^9$, V$_n$—NR$^8$C(=O)R$^9$, V$_n$—NR$^8$C(=O)NR$^9$R$^{10}$, alkyl, alkenyl, and alkynyl;

R$^8$, R$^9$ and R$^{10}$ are independently H, alkyl, alkenyl, alkynyl, saturated or partially unsaturated V$_n$-cycloalkyl, saturated or partially unsaturated V$_n$-heterocycloalkyl, V$_n$-aryl or V$_n$-heteroaryl, wherein said alkyl, alkenyl, alkynyl, V$_n$-cycloalkyl, V$_n$-heterocycloalkyl, V$_n$-aryl and V$_n$-heteroaryl are optionally substituted with one or more groups independently selected from oxo, alkyl, alkenyl, alkynyl, saturated and partially unsaturated V$_n$-cycloalkyl, saturated and partially unsaturated V$_n$-heterocycloalkyl, V$_n$-aryl, V$_n$-heteroaryl, F, Cl, Br, I, V$_n$—OR$^a$, V$_n$—NR$^a$R$^b$, V$_n$—C(=O)OR$^a$, V$_n$—C(=O)NR$^a$R$^b$, and V$_n$—NR$^a$C(=O)R$^b$, or R$^8$ and R$^9$ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, alkyl, alkenyl, alkynyl, F, Cl, Br, I, $V_n$—$OR^a$, and CN;

or $R^9$ and $R^{10}$ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, alkyl, alkenyl, alkynyl, F, Cl, Br, I, $V_n$—$OR^a$, and CN;

$R^{11}$ is H, methyl, ethyl, F, Cl, Br, I, $CF_3$, $CHF_2$, $CH_2F$, OH, O—($C_1$-$C_4$ alkyl), or $NH_2$;

$R^{12}$ and $R^{13}$ are independently H, alkyl, alkenyl, alkynyl, heteroalkyl, saturated or partially unsaturated $V_n$-cycloalkyl, saturated or partially unsaturated $V_n$-heterocycloalkyl, $V_n$-aryl, $V_n$-heteroaryl, F, Cl, Br, I, $CF_3$, cyano, $V_n$—$OR^6$, $V_n$—C(=O)$R^6$, $V_n$—C(=O)$OR^6$, $(CH_2)_nOC(=O)R^6$, $V_n$—C(=O)$NR^6R^7$, $V_n$—$NR^6R^7$, $V_n$—$NR^6C(=O)R^7$, $V_n$—$SR^6$, $V_n$—S(O)$R^6$, $V_n$—S(O)$_2R^6$, $V_n$—$NR^aC(O)NHR^b$ or $V_n$—$NHSO_2NR^aR^b$, wherein said alkyl, alkenyl, alkynyl, $V_n$-cycloalkyl, $V_n$-heterocycloalkyl, $V_n$-aryl, and $V_n$-heteroaryl are optionally substituted with one or more groups independently selected from oxo, F, Cl, Br, I, $CF_3$, cyano, $V_n$—$OR^8$, $V_n$—C(=O)$OR^8$, $V_n$—OC(O)$R^8$, $V_n$—C(=O)$NR^8R^9$, $V_n$—$NR^8R^9$, $V_n$—$NR^8C(=O)R^9$, $C_1$-$C_6$ alkyl, $C_2$-$C_6$ alkenyl, $C_2$-$C_6$ alkynyl, saturated and partially unsaturated $V_n$-cycloalkyl, saturated and partially unsaturated $V_n$-heterocycloalkyl, $V_n$-aryl, and $V_n$-heteroaryl, wherein said heterocycloalkyl is optionally substituted with one or more oxo;

or $R^{12}$ and $R^{13}$ together with the atoms to which they are attached form a saturated, partially unsaturated or fully unsaturated carbocyclic or heterocyclic ring, wherein said carbocyclic and heterocyclic rings are optionally substituted with one or more groups independently selected from oxo, F, Cl, Br, I, $CF_3$, cyano, $V_n$—$OR^6$, $V_n$—C(=O)$R^6$, $V_n$—C(=O)$OR^6$, $V_n$—OC(=O)$R^6$, $V_n$—C(=O)$NR^6R^7$, $V_n$—$NR^6R^7$, $V_n$—$NR^6C(=O)R^7$, $V_n$—$SR^6$, $V_n$—S(O)$R^6$, $V_n$—S(O)$_2R^6$, $V_n$—S(O)$_2NR^6R^7$, alkyl, alkenyl, alkynyl, heteroalkyl, saturated and partially unsaturated $V_n$-cycloalkyl, saturated and partially unsaturated $V_n$-heterocycloalkyl, $V_n$-aryl, and $V_n$-heteroaryl;

$R^a$ and $R^b$ are independently H, alkyl, alkenyl, alkynyl, saturated or partially unsaturated $V_n$-cycloalkyl, saturated or partially unsaturated $V_n$-heterocycloalkyl, $V_n$-aryl, or $V_n$-heteroaryl, wherein said alkyl, alkenyl, alkynyl, saturated or partially unsaturated $V_n$-cycloalkyl, saturated or partially unsaturated $V_n$-heterocycloalkyl, $V_n$-aryl, or $V_n$-heteroaryl are optionally substituted by OH;

V is alkylene having from 1 to 4 carbons, or alkenylene or alkynylene each having from 2 to 4 carbons, wherein said alkylene, alkenylene, or alkynylene are optionally substituted with one or more groups independently selected from alkyl, alkenyl, alkynyl, heteroalkyl, saturated and partially unsaturated $V_n$-cycloalkyl, saturated and partially unsaturated $V_n$-heterocycloalkyl, $V_n$-aryl, $V_n$-heteroaryl, F, Cl, Br, I, $CF_3$, cyano, $V_n$—$OR^8$, $V_n$—C(=O)$OR^8$, $V_n$—OC(=O)$R^8$, $V_n$—C(=O)$NR^8R^9$, $V_n$—$NR^8R^9$, and $V_n$—$NR^8C(=O)R^9$; and n is 0, 1, 2, 3 or 4.

In certain embodiments of Formula I wherein $R^1$ and $R^2$ are each 5 membered single-ring heteroaryl groups, $R^1$ does not have a substituent represented by C(=O)$OR^d$ or C(=O)$NR^eR^f$, wherein $R^d$ is H, alkyl, alkenyl, alkynyl, cycloalkyl, cycloalkyl-alkyl, cycloalkenyl-alkyl, arylalkyl or aryl, and $R^e$ and $R^f$ are independently H, alkyl, alkenyl, alkynyl, cycloalkyl, cycloalkyl-alkyl, cycloalkenyl-alkyl, arylalkyl, aryl heterocyclyl, or acyl, or $R^e$ and $R^f$ together with the N atom form a heterocyclic ring. The compounds according to this definition were disclosed in the provisional application from which the present invention claims priority, and are provided as an embodiment of the invention.

In certain embodiments of Formula I, $R^{12}$ and $R^{13}$ are independently H, alkyl, alkenyl, alkynyl, heteroalkyl, saturated or partially unsaturated $V_n$-cycloalkyl, saturated or partially unsaturated $V_n$-heterocycloalkyl, $V_n$-aryl, $V_n$-heteroaryl, F, Cl, Br, I, $CF_3$, cyano, $V_n$—$OR^6$, $V_n$—C(=O)$R^6$, $V_n$—C(=O)$OR^6$, $(CH_2)_nOC(=O)R^6$, $V_n$—C(=O)$NR^6R^7$, $V_n$—$NR^6R^7$, $V_n$—$NR^6C(=O)R^7$, $V_n$—$SR^6$, $V_n$—S(O)$R^6$, or $V_n$—S(O)$_2R^6$, wherein said alkyl, alkenyl, alkynyl, $V_n$-cycloalkyl, $V_n$-heterocycloalkyl, $V_n$-aryl, and $V_n$-heteroaryl are optionally substituted with one or more groups independently selected from oxo, F, Cl, Br, I, $CF_3$, cyano, $V_n$—$OR^8$, $V_n$—C(=O)$OR^8$, $V_n$—OC(=O)$R^8$, $V_n$—C(=O)$NR^8R^9$, $V_n$—$NR^8R^9$, $V_n$—$NR^8C(=O)R^9$, alkyl, alkenyl, alkynyl, saturated and partially unsaturated $V_n$-cycloalkyl, saturated and partially unsaturated $V_n$-heterocycloalkyl, $V_n$-aryl, and $V_n$-heteroaryl, wherein said heterocycloalkyl is optionally substituted with one or more oxo;

or $R^{12}$ and $R^{13}$ together with the atoms to which they are attached form a saturated, partially unsaturated or fully unsaturated carbocyclic or heterocyclic ring, wherein said carbocyclic and heterocyclic rings are optionally substituted with one or more groups independently selected from F, Cl, Br, I, $CF_3$, cyano, $V_n$—$OR^6$, $V_n$—C(=O)$R^6$, $V_n$—C(=O)$OR^6$, OC(=O)$R^6$, $V_n$—C(=O)$NR^6R^7$, $V_n$—$NR^6R^7$, $V_n$—$NR^6C(=O)R^7$, $V_n$—$SR^6$, $V_n$—S(O)$R^6$, $V_n$—S(O)$_2R^6$, $V_n$—S(O)$_2NR^6R^7$, alkyl, alkenyl, alkynyl, heteroalkyl, saturated and partially unsaturated $V_n$-cycloalkyl, saturated and partially unsaturated $V_n$-heterocycloalkyl, $V_n$-aryl, and $V_n$-heteroaryl.

In certain embodiments, G is $CR^{11}$.

In certain embodiments, $R^{11}$ is H or Cl. In particular embodiments, $R^{11}$ is H.

In certain embodiments, Z is $CR^3$.

In certain embodiments, Y is $CR^4$. In particular embodiments, $R^4$ is H.

In certain embodiments, provided are compounds of Formula I wherein: G is $CR^{11}$; Z is $CR^3$; Y is N or $CR^4$; $R^4$ is H; and $R^{11}$ is H or Cl.

In certain embodiments, provided are compounds of Formula I wherein: G is CH or Cl; Z is $CR^3$; Y is $CR^4$ or N;

$R^1$ is a heteroaryl ring represented by the formula

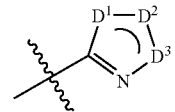

$D^1$ is S; $D^2$ is $CR^{12}$ or N; $D^3$ is $CR^{13}$;

$R^2$ is phenyl or a 5-10 membered monocyclic or bicyclic heteroaryl ring having one or two ring heteroatoms selected from N or S, wherein said phenyl is optionally substituted with one or more groups independently selected from Cl, $V_n$—$OR^6$, $V_n$—C(=O)$NR^6R^7$, $V_n$—$NR^6C(=O)R^7$, $V_n$—O($CH_2$)C(=O)$NR^6R^7$, and $V_n$—O($CH_2)_nC(=O)OR^6$;

$R^3$ is H, $C_1$-$C_6$ alkyl, $C_2$-$C_6$ alkenyl, $V_n$—($C_6$-$C_{10}$ aryl) [optionally substituted with $C_1$-$C_6$ alkyl], Cl, Br, I, CN, $V_n$—$OR^6$, $V_nC(=O)R^6$, $V_n$—C(=O)$OR^6$, $V_n$—C(=O)$NR^6R^7$, $V_n$—$NR^6R^7$, $V_n$—$SR^6$, $V_n$—S(O)$R^6$, $V_n$—S(O)$_2R^6$, or $V_n$-heteroaryl, wherein heteroaryl for $R^3$ is selected from a 5-10 membered monocyclic or bicyclic ring having one or two ring heteroatoms independently selected from N, O and S;

$R^4$ is H, methyl, ethyl, F, Cl, Br, I, $CF_3$, $CHF_2$, or $CH_2F$;

$R^6$ and $R^7$ are independently H, alkyl, $V_n NR^8 R^9$, $V_n C(O)NR^8 R^9$, $V_n C(O)OR^8$, saturated or partially unsaturated $V_n$-cycloalkyl, saturated or partially unsaturated $V_n$-heterocycloalkyl, $V_n$-phenyl (optionally substituted with one or more groups independently selected from $OR^a$ or Cl), or $V_n$-heteroaryl, wherein heteroaryl for $R^6$ and $R^7$ is a 5-10 membered ring having one to three ring heteroatoms independently selected from N, S and O and optionally substituted by $C_1$-$C_6$ alkyl, or $R^6$ and $R^7$ together with the atom to which they are attached form a saturated or partially unsaturated heterocyclic ring having 1 to 3 ring heteroatoms independently selected from N, O or S, wherein said ring is optionally substituted by $C_1$-$C_6$ alkyl;

$R^8$, $R^9$ and $R^{10}$ are independently H or alkyl, or $R^8$ and $R^9$ form a 6 membered heterocyclic ring one or two ring nitrogen atoms, wherein said heterocyclic ring is optionally substituted with $C_1$-$C_6$ alkyl;

$R^{12}$ and $R^{13}$ are independently H, $C_1$-$C_6$ alkyl, $C_2$-$C_6$ alkenyl, $C_2$-$C_6$ alkynyl, heteroalkyl, saturated or partially unsaturated $V_n$-cycloalkyl, saturated or partially unsaturated $V_n$-heterocycloalkyl, $V_n$-aryl, $V_n$-heteroaryl, F, Cl, Br, I, $CF_3$, cyano, $V_n$—$OR^6$, $V_n$—$C(=O)R^6$, $V_n$—$C(=O)OR^6$, $(CH_2)_n OC(=O)R^6$, $V_n$—$C(=O)NR^6R^7$, $V_n$—$NR^6R^7$, $V_n$—$NR^6C(=O)R^7$, $V_n$—$SR^6$, $V_n$—$S(O)R^6$, $V_n$—$S(O)_2R^6$, $V_n$—$NR^aC(O)NHR^b$ or $V_n$—$NHSO_2NR^aR^b$, or $R^{12}$ and $R^{13}$ together with the atoms to which they are attached form a saturated or fully unsaturated 5-6 membered carbocyclic or 6-membered heterocyclic ring having one or two ring nitrogen atoms, wherein said carbocyclic and heterocyclic rings are optionally substituted with one or more groups independently selected from oxo, F, Cl, Br, I, $CF_3$, cyano, $V_n$—$OR^6$, $V_n$—$C(=O)R^6$, $V_n$—$C(=O)OR^6$, $V_n$—$OC(=O)R^6$, $V_n$—$C(=O)NR^6R^7$, $V_n$—$NR^6R^7$, $V_n$—$NR^6C(=O)R^7$, $V_n$—$SR^6$, $V_n$—$S(O)R^6$, $V_n$—$S(O)_2R^6$, $V_n$—$S(O)_2NR^6R^7$, alkyl, alkenyl, alkynyl, heteroalkyl, saturated and partially unsaturated $V_n$-cycloalkyl, saturated and partially unsaturated $V_n$-heterocycloalkyl, $V_n$-aryl, and $V_n$-heteroaryl;

each V is independently alkylene or alkenylene having from 1 to 4 carbons, wherein said alkylene is optionally substituted with one or more groups independently selected from $C_1$-$C_6$ alkyl and OH; and each n is independently 0 or 1.

Exemplary embodiments of $R^1$ include, but are not limited to, heteroaryl rings selected from

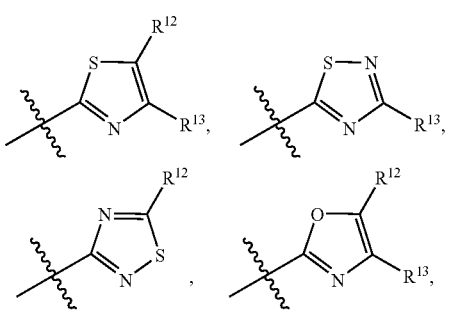

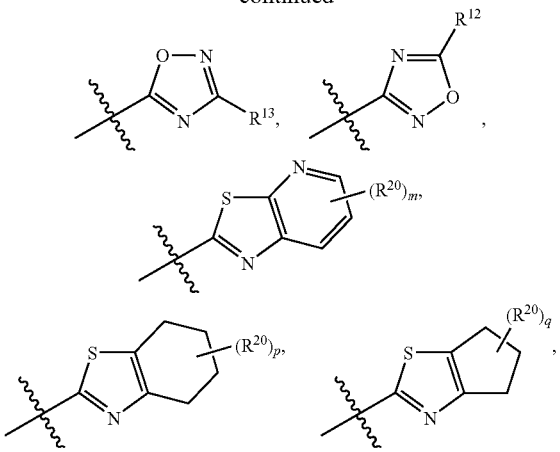

wherein $R^{12}$ and $R^{13}$ are as defined herein;

each $R^{20}$ is independently oxo, F, Cl, Br, I, $CF_3$, cyano, $V_n$—$OR^6$, $V_n$—$C(=O)R^6$, $V_n$—$C(=O)OR^6$, $OC(=O)R^6$, $V_n$—$C(=O)NR^6R^7$, $V_n$—$NR^6$, $R^7$, $V_n$—$NR^6C(=O)R^7$, $V_n$—$SR^6$, $V_n$—$S(O)R^6$, $V_n$—$S(O)_2R^6$, $V_n$—$S(O)_2NR^6R^7$, alkyl, alkenyl, alkynyl, heteroalkyl, saturated and partially unsaturated $V_n$-cycloalkyl, saturated and partially unsaturated $V_n$-heterocycloalkyl, $V_n$-aryl, and $V_n$-heteroaryl;

m is 0, 1, 2 or 3;

p is 0, 1, 2, 3, 4, 5, 6, 7 or 8; and q is 1, 2, 3, 4, 5, 6.

In certain embodiments of Formula I, $R^1$ is selected from the structures

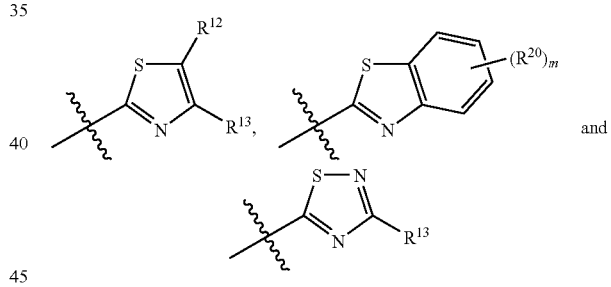

wherein $R^{12}$, $R^{13}$ and $R^{20}$ are as defined herein. In certain embodiments, m is 0 or 1.

In certain embodiments of Formula I, $R^{12}$ and $R^{13}$ are independently selected from H, alkyl, alkenyl, alkynyl, $V_n$—$OR^6$, $V_n$—$C(=O)OR^6$, $V_n$—$C(=O)NR^6R^7$, $V_n$—$NR^6R^7$, and $V_n$—$NR^6C(=O)R^7$.

In certain embodiments of Formula I, $R^{12}$ and $R^{13}$ are independently selected from H, Cl, $C_1$-$C_6$ alkyl, $C_2$-$C_6$ alkenyl, $V_n$-heterocyclyl (optionally substituted with $C_1$-$C_6$ alkyl), $V_n$—$OR^6$, $V_n$—$C(=O)OR^6$, $V_n$—$C(=O)NR^6R^7$, $V_n$—$NR^6R^7$, $V_n$—$NR^6C(=O)R^7$, $V_n$—$NR^aC(O)NHR^b$, $V_n$—$NHSO_2$—$NR^aR^b$, and $V_n$-heteroaryl (optionally substituted with $C_1$-$C_6$ alkyl), in which each V is independently $C_1$-$C_4$ alkylene or $C_2$-$C_4$ alkenylene and each n is independently 0 or 1. Particular embodiments for $R^6$ and $R^7$ include H or $C_1$-$C_6$ alkyl [optionally substituted by ($C_1$-$C_6$ alkyl)N($C_1$-$C_6$ alkyl)$_2$, phenyl, or a 5-6 membered heterocycle having one or two heteroatoms independently selected from N and O], or $NR^6R^7$ form a 5-6 membered heterocyclic ring optionally having an additional ring heteroatom selected from N and O and optionally substituted by ($C_1$-$C_6$ alkyl).

Examples where $R^{12}$ and $R^{13}$ represent $C_1$-$C_6$ alkyl include methyl, ethyl, isopropyl, butyl, and isobutyl.

Examples where $R^{12}$ and $R^{13}$ represent cycloalkyl include cyclopropyl and cyclohexyl.

An example where $R^{12}$ and $R^{13}$ represent $V_n$—$OR^6$ includes groups wherein V is $C_1$-$C_6$ alkyl, n is 1, and $R^6$ is H. A particular embodiment includes —$CH_2CH_2OH$.

Examples where $R^{12}$ and $R^{13}$ represent $V_n$—$C(=O)OR^6$ include groups wherein V is $C_1$-$C_6$ alkyl, n is 1, and $R^6$ is H or $C_1$-$C_6$ alkyl (for example methyl or ethyl). Particular examples include —$CO_2H$, —$(CH_2)_2CO_2H$, —$CH_2CO_2CH_3$ and —$(CH_2)_2CO_2CH_3$.

Examples where $R^{12}$ and $R^{13}$ represent $V_n$—$C(=O)NR^6R^7$ include groups wherein V is $C_1$-$C_6$ alkyl, n is 1, $R^6$ is H, and $R^7$ is $(CH_2)_mNR^aR^b$ wherein m is 1 or 2 and $R^a$ and $R^b$ are independently H or $C_1$-$C_3$ alkyl, or $NR^6R^7$ form a 5-6 membered heterocycle optionally having an additional ring heteroatom selected from N and O and optionally substituted by $C_1$-$C_3$ alkyl. Examples of such heterocycles include pyrrolidinyl, piperidinyl, 1-methylpiperidin-4-yl, piperazinyl, 1-methyl-piperazin-4-yl, and morpholinyl.

Particular examples where $R^{12}$ and $R^{13}$ represent $V_n$—$C(=O)NR^6R^7$ include —$CH_2C(O)NH_2$,

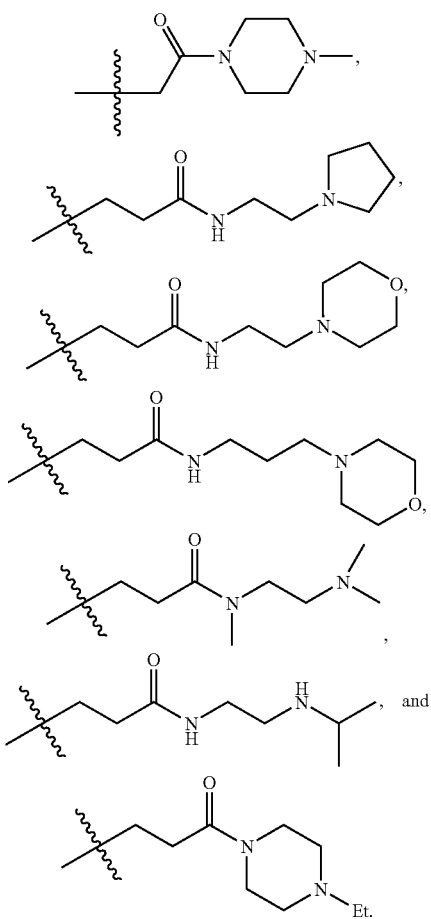

Examples where $R^{12}$ and $R^{13}$ represent $V_n$—$NR^6C(=O)R^7$ include groups wherein V is $C_1$-$C_6$ alkyl, n is 1, $R^6$ is H, and $R^7$ is $C_1$-$C_6$ alkyl or phenyl. Particular examples include —$(CH_2)_2NHC(O)CH_3$ and —$(CH_2)_2NHC(O)$phenyl.

Examples where $R^{12}$ and $R^{13}$ represent $V_n$—$NHSO_2$—$NR^aR^b$ include groups wherein V is $C_1$-$C_6$ alkyl, n is 1, and $R^a$ and $R^b$ are independently H or $C_1$-$C_6$ alkyl (for example methyl). A particular example includes —$CH_2CH_2NHSO_2$—$N(CH_3)_2$.

Examples where $R^{12}$ and $R^{13}$ represent $V_n$—$NR^aC(O)NHR^b$ include groups wherein V is $C_1$-$C_6$ alkyl, n is 1, and $R^a$ and $R^b$ are independently H, $C_1$-$C_6$ alkyl (for example methyl) or phenyl. Particular examples include —$(CH_2)_2NHC(O)NH$phenyl and —$(CH_2)_2NHC(O)NHCH_3$.

Examples where $R^{12}$ and $R^{13}$ represent $V_n$-heterocycle include groups wherein V is $C_1$-$C_6$ alkyl, n is 1, and the heterocycle is a 5-6 membered azacyclic group such as pyrrolidinyl and piperidinyl. A particular example includes 4-piperidyl. In a certain embodiment, the azacyclic group is substituted with one or two oxo groups, such as, for example an isoindoline-1,3-dionyl group. A particular example of $R^{12}$ or $R^{13}$ is —$(CH_2)_2$— isoindoline-1,3-dion-2-yl.

Examples where $R^{12}$ and $R^{13}$ represent $V_n$-heteroaryl optionally substituted by $C_1$-$C_6$ alkyl include 5 membered heteroaryl rings having one to three heteroatoms independently selected from N and O provided the ring does not contain two adjacent oxygen atoms, or a 6 membered heteroaryl ring having one to three nitrogen atoms, wherein said 5-6 membered heteroaryl rings are optionally substituted by methyl.

Particular examples where $R^{12}$ and $R^{13}$ represent $V_n$-heteroaryl optionally substituted by $C_1$-$C_6$ alkyl include

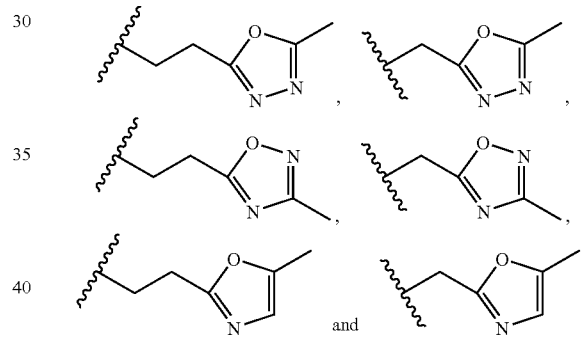

In certain embodiments of Formula I, $R^{12}$ is H.

In certain embodiments of Formula I, $R^2$ is an aryl ring selected from phenyl, 1-naphthyl, 2-naphthyl, 5-tetrahydronaphthalenyl, 6-tetrahydronaphthalenyl, and substituted forms thereof.

Exemplary embodiments of $R^2$ include, but are not limited to,

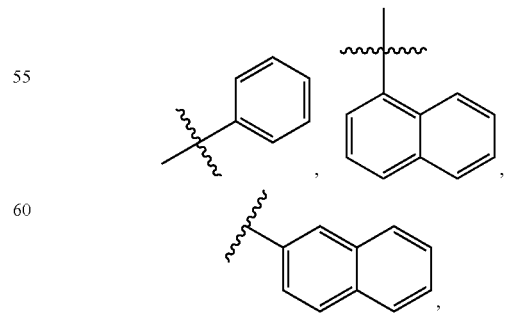

and substituted forms thereof. For example, $R^2$ can be phenyl optionally substituted with one or more groups independently selected from F, Cl, Br, I, $CF_3$, alkyl, $V_n$—$OR^6$, $V_n$-aryl, $V_n$—C(=O)$OR^6$, $V_n$—C(=O)$R^6$, $V_n$—C(=O)$NR^6R^7$, $V_n$—$NR^6$C(=O)$R^7$, $V_n$—O(CH$_2$)$_n$C(=O)$OR^6$ and $V_n$—O(CH$_2$)$_n$C(=O)$NR^6R^7$.

In certain embodiments of Formula I, $R^2$ is phenyl optionally substituted with one or two groups independently selected from Cl, $C_1$-$C_6$ alkyl, $V_n$—$OR^6$, $V_n$—C(=O)$NR^6R^7$, $V_n$—$NR^6$C(=O)$R^7$, $V_n$—OCH$_2$C(=O)$OR^6$ and $V_n$—O(CH$_2$)$_n$C(=O)$NR^6R^7$, wherein V is $C_1$-$C_4$ alkylene and n is 0 or 1. In certain embodiments, $R^6$ and $R^7$ are independently H, $C_1$-$C_6$ alkyl, $V_n$—$COOR^8$, $V_n NR^8R^9$, or $V_n$-heteroaryl, or $R^6$ and $R^7$ together with the atom to which they are attached form a 5-6 membered heterocyclic ring optionally substituted with $C_1$-$C_6$ alkyl. In certain embodiments, $R^8$ and $R^9$ are independently H or $C_1$-$C_6$ alkyl.

In certain embodiments of Formula I, $R^2$ is phenyl optionally substituted with one or two groups independently selected from Cl, —OCH$_3$, OH, —OC(=O)H, —NHC(=O)Me, —OCH$_2$C(=O)OH, —OCH$_2$C(=O)NH(CH$_2$)$_2$NMe$_2$, —OCH$_2$C(=O)NHCH$_2$COOH,

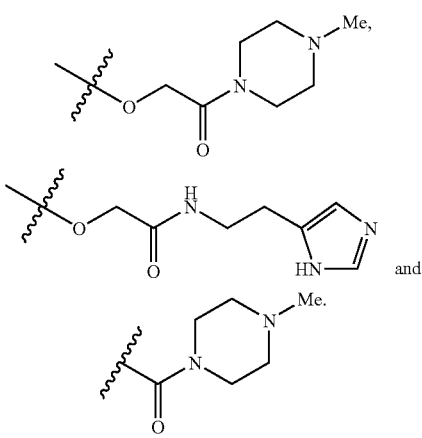

In certain embodiments of Formula I, $R^2$ is phenyl, 2-methoxyphenyl, 3-methoxyphenyl, 3-hydroxyphenyl, 3-(OCH$_2$CO$_2$t-Bu)phenyl, 3-(OCH$_2$CO$_2$H)phenyl, 3-(OCH$_2$C(O)NHCH$_2$CO$_2$H)phenyl, 2-chlorophenyl, 2,6-dichlorophenyl, 2-acetamidephenyl,

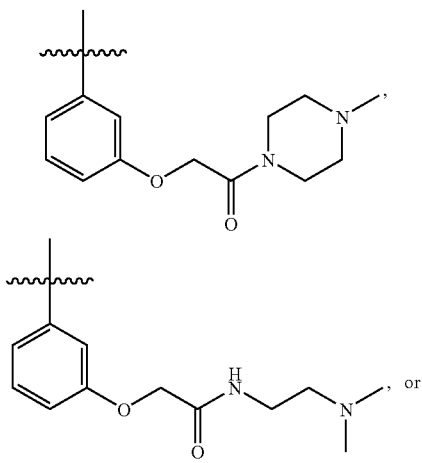

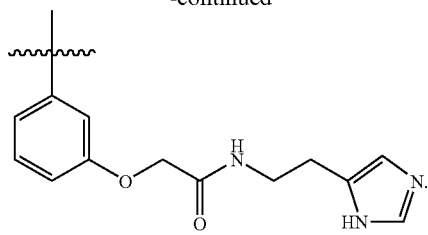

In certain embodiments of Formula I, $R^2$ is heteroaryl selected from pyridyl, quinolinyl, quinoxalinyl, benzo[d]thiazoyl, 1H-benzo[d]inidazolyl, thiophenyl, tetrahydroquinolinyl, tetrahydroisoquinolinyl, thiazolyl and substituted forms thereof. In certain embodiments, $R^2$ is a heteroaryl ring selected from 2-pyridyl, 3-pyridyl, 4-pyridyl, 2-quinolinyl, 3-quinolinyl, 4-quinolinyl, 5-quinolinyl, 6-quinolinyl, 7-quinolinyl, 8-quinolinyl, 2-quinoxalinyl, 3-quinoxalinyl, 5-quinoxalinyl, 6-quinoxalinyl, 7-quinoxalinyl, 8-quinoxalinyl, benzo[d]thiazol-2-yl, 4-benzo[d]thiazolyl, 5-benzo[d]thiazolyl, 6-benzo[d]thiazolyl, 7-benzo[d]thiazolyl, 2-1H-benzo[d]imidazolyl, 1H-benzo[d]imidazole-4-yl, 1H-benzo[d]imidazole-5-yl, 1H-benzo[d]imidazole-6-yl, 1H-benzo[d]imidazole-7-yl, 2-thiophenyl, 3-thiophenyl, 5-tetrahydroquinolinyl, 6-tetrahydroquinolinyl, 7-tetrahydroquinolinyl, 8-tetrahydroquinolinyl, 5-tetrahydroisoquinolinyl, 6-tetrahydroisoquinolinyl, 7-tetrahydroisoquinolinyl, 8-tetrahydroisoquinolinyl, and substituted forms thereof.

Exemplary embodiments of $R^2$ further include, but are not limited to,

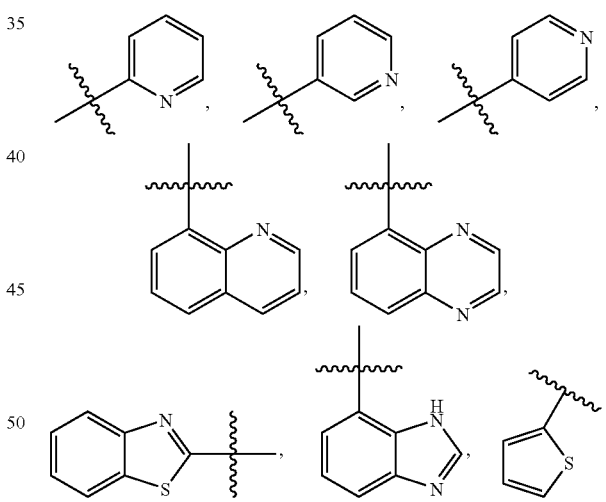

and substituted forms thereof.

In certain embodiments of Formula I, $R^2$ is selected from

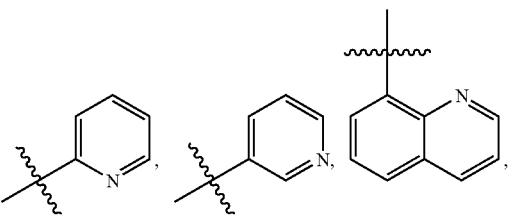

19
-continued

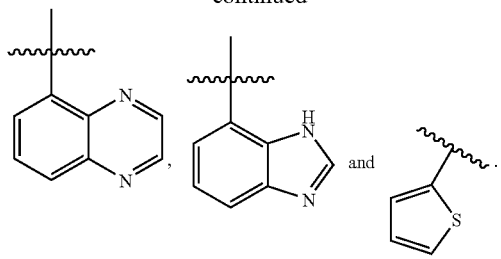

and

In certain embodiments of Formula I, $R^3$ is F, Cl, Br, I, $V_n$—$OR^6$, $V_n$—$SR^6$, $V_n$—$S(O)R^6$, $V_n$—$S(O)_2R^6$, $V_n$—C(=O)$NR^6R^7$, $V_n$—C(=O)$OR^6$, $V_n$—C(=O)$R^6$, $V_n$-aryl, $V_n$-heteroaryl, alkyl, alkenyl or alkynyl, wherein said aryl, heteroaryl, alkyl, alkenyl and alkynyl are substituted or unsubstituted.

In certain embodiments of Formula I, $R^3$ is H, Cl, Br, I, $V_n$—$OR^6$, $V_n$—$SR^6$, $V_n$—$S(O)R^6$, $V_n$—$S(O)_2R^6$, $V_n$—C(=O)$NR^6R^7$, $V_n$—C(=O)$OR^6$, $V_n$—C(=O)$R^6$, $V_n NR^6R^7$, $V_n$-aryl, $V_n$-heteroaryl, $C_1$-$C_6$ alkyl or $C_2$-$C_6$ alkenyl, wherein V is $C_1$-$C_4$ alkylene or $C_2$-$C_4$ alkenylene and n is 0 or 1.

In certain embodiments of Formula I, $R^3$ is $SR^6$ and $R^6$ is alkyl, alkenyl, alkynyl, $V_n$-cycloalkyl, $V_n$-heterocycle, $V_n$-aryl or $V_n$-heteroaryl, wherein said alkyl, alkenyl, alkynyl, $V_n$-cycloalkyl, $V_n$-heterocycle, $V_n$-aryl and $V_n$-heteroaryl are optionally substituted.

In certain embodiments of Formula I, $R^3$ is a group having the formula $SR^6$ wherein $R^6$ is $C_1$-$C_6$ alkyl, $V_n$—$NR^8R^8$, $V_n$—C(O)$NR^8R^9$, $V_n$—$CO_2R^8$, $V_n$-aryl or $V_n$-heteroaryl, V is $C_1$-$C_4$ alkylene, and n is 0 or 1. In certain embodiments, $R^8$ and $R^9$ are independently H or $C_1$-$C_6$ alkyl, or $R^8$ and $R^9$ together with the atom to which they are attached form a 6 membered heteroaryl ring having 1-2 ring nitrogen atoms and optionally substituted with $C_1$-$C_6$ alkyl.

In certain embodiments of Formula I, $R^3$ is —$SCH_3$, —S-cyclohexyl, —$SCH_2$-cyclopentyl, —S-phenyl, —S-(2-chlorophenyl), —S-(2-methoxyphenyl), —S-(3-methoxyphenyl), —S-(4-methoxyphenyl), —$SCH_2$-(2-methoxyphenyl), —$SCH_2$-(3-methoxyphenyl), —$SCH_2$-(4-methoxyphenyl), —$SCH_2$-(phenyl), —$SCH_2CH_2$-(phenyl), —$SCH_2$-(2-chlorophenyl), —$SCH_2$-(3-chlorophenyl), —$SCH_2$-(4-chlorophenyl), —S-(4-pyridyl), —S-(2-pyridyl), —S-(2-thiophenyl), S-(1-methyl-1H-imidazol-2-yl), —S-(thieno[3,2-b]pyridin-7-yl), —S-(1-methyl-1,2-dihydrooxazolo[5,4-b]pyridin-7-yl), —S-(2-chloropyrid-4-yl), —S-(2-chloropyrimid-4-yl), —S-(2-pyrimidyl), —$SCH_2$-(4-pyridyl), —$SCH_2$-(3-pyridyl), —$SCH_2$-(2-pyridyl), —$SCH_2$-(2-thiophenyl), —$SCH_2CH_2$-(1H-imidazol-1-yl), —$S(CH_2)_3$—$N(CH_3)_2$, —$SCH_2$-(4-piperidinyl), —$SCH_2$C(O)-(4-methylpiperazin-1-yl), —$S(CH_2)_2CO_2(CH_3)$, —$S(CH_2)_2CO_2H$, or

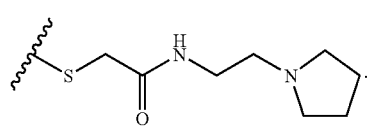 [SMILES: *SCC(=O)NCCN1CCCC1]

In certain embodiments of Formula I, $R^3$ is a group having the formula $SCHR^{6a}R^{6b}$. In certain embodiments, $R^{6a}$ and $R^{6b}$ are independently $C_1$-$C_6$ alkyl, phenyl, pyridyl, C(O)$NR^aR^b$ or piperidinyl [optionally substituted with $C_1$-$C_6$ alkyl 20
or ($C_1$-$C_6$ alkyl)OH]. In certain embodiments, $R^{6a}$ is piperidinyl optionally substituted with methyl or $CH_2CH_2OH$.

In certain embodiments of Formula I, $R^3$ is —S-(1-phenylethyl),

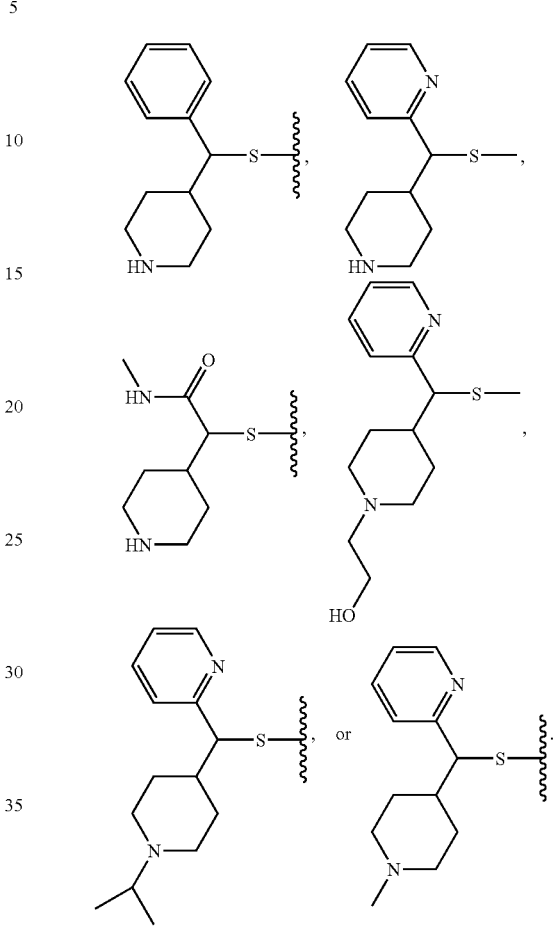

In certain embodiments of Formula I, $R^3$ is a group having the formula $V_n$—$SOR^6$ or $V_n$—$SO_2R^6$. In certain embodiments, $R^6$ is $C_1$-$C_6$ alkyl or phenyl, V is $C_1$-$C_4$ alkylene, and n is 0 or 1.

In certain embodiments of Formula I, $R^3$ is —$S(O)CH_3$, —$S(O)$phenyl, or —$SO_2CH_3$.

In certain embodiments, $R^3$ is $OR^6$ and $R^6$ is H, alkyl, alkenyl or alkynyl, wherein said alkyl, alkenyl and alkynyl are optionally substituted.

In certain embodiments of Formula I, $R^3$ is a group having the formula $V_n$—$OR^6$. In certain embodiments, $R^6$ is $C_1$-$C_6$ alkyl or phenyl (optionally substituted with Cl). In certain embodiments, V is $C_1$-$C_4$ alkylene or $C_2$-$C_4$ alkenylene, and n is 0 or 1.

In certain embodiments of Formula I, $R^3$ is methoxy, hydroxymethyl, 1-hydroxyethyl, benzyloxy, 2-chlorophenoxy, or —CH=$CHOCH_3$.

In certain embodiments of Formula I, $R^3$ is $C_1$-$C_6$ alkyl or $C_2$-$C_6$ alkenyl. In certain embodiments, $R^3$ is methyl, pentyl, or 1-penten-1-yl.

In certain embodiments of Formula I, $R^3$ is a group having the formula $V_n$—Ar wherein Ar is optionally substituted with $OR^8$ or $C_1$-$C_6$ alkyl. In certain embodiments, V is $C_1$-$C_4$ alkylene, and n is 0 or 1.

In certain embodiments of Formula I, $R^3$ is phenyl, benzyl, 1-phenylethyl, 2-phenylethen-1-yl, 1-phenylethen-1-yl, 4-tolyl, or α-hydroxybenzyl.

In certain embodiments of Formula I, $R^3$ is a group having the formula $V_n$-heteroaryl. In certain embodiment, heteroaryl is a 6 membered aromatic ring having one or two ring nitrogen atoms. In certain embodiments, V is $C_1$-$C_4$ alkylene, and n is 0 or 1.

In certain embodiments of Formula I, $R^3$ is 3-pyridyl or 4-pyridyl.

In certain embodiments of Formula I, $R^3$ is phenyl, 2-chlorophenyl, 3-chlorophenyl, 4-chlorophenyl, 4-methylphenyl, 3-methoxyphenyl, 4-methoxyphenyl, 3-pyridyl, or 4-pyridyl.

In certain embodiments of Formula I, $R^3$ is a group having the formula $V_n$—$CO_2R^6$. In certain embodiments, $R^6$ is H or $C_1$-$C_6$ alkyl. In certain embodiments, V is $C_1$-$C_4$ alkylene or $C_2$-$C_4$ alkenylene, and n is 0 or 1.

In certain embodiments of Formula I, $R^3$ is —$(CH_2)_2$—$CO_2CH_3$, —(CH=CH)—$CO_2CH_3$ or $CH_2CH_2CO_2H$.

In certain embodiments of Formula I, $R^3$ is a group having the formula $V_n$—$COR^6$. In certain embodiments, $R^6$ is H or $C_1$-$C_6$ alkyl. In certain embodiments, V is $C_1$-$C_4$ alkylene, and n is 0 or 1.

In certain embodiments of Formula I, $R^3$ is —$C(O)CH_3$, —C(O)H or —$CH_2C(O)H$.

In certain embodiments of Formula I, $R^3$ is a group having the formula $V_n$—$CONR^6R^7$. In certain embodiments, $R^6$ and $R^7$ are independently H, $C_1$-$C_6$ alkyl, or $V_n$-phenyl, or $NR^6R^7$ forms a 6 membered heterocyclyl ring having one or two ring nitrogen atoms and optionally substituted with $C_1$-$C_6$ alkyl. In certain embodiments, V is $C_1$-$C_4$ alkylene, and n is 0 or 1.

In certain embodiments of Formula I, $R^3$ is —$C(O)NH_2$, $C(O)NHCH_2Ph$, —C(O)-(4-methylpiperazin-1-yl) or —$CH_2CH_2C(O)$-(4-methylpiperazin-1-yl).

In certain embodiments of Formula I, $R^3$ is H, Cl, Br or I.

In certain embodiments of Formula I, $R^3$ is chosen from Cl, Br, OMe or SMe.

Exemplary embodiments of compounds of Formula I include, but are not limited to, compounds of the general formulas

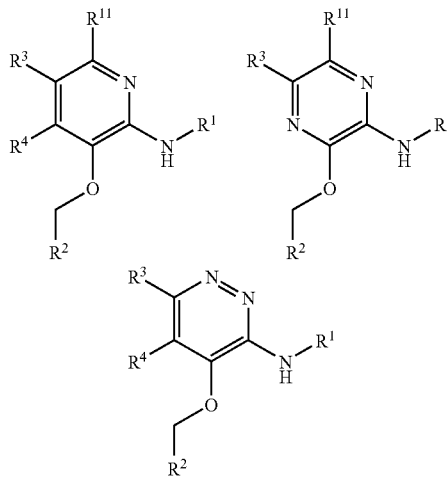

wherein $R^1$, $R^2$, $R^3$, $R^4$ and $R^{11}$ are as defined above.

Additional exemplary embodiments of compounds of Formula I include, but are not limited to, compounds of the general formulas

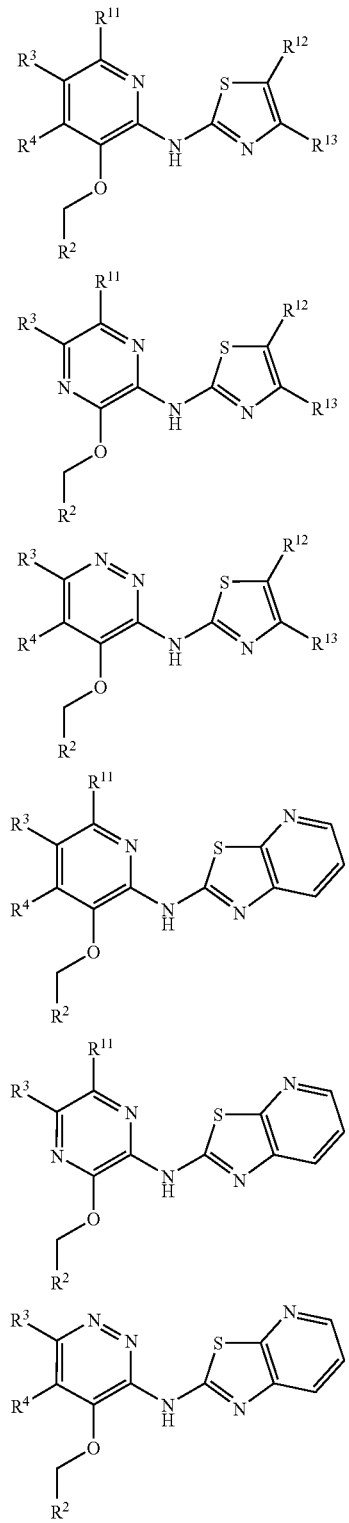

and substituted forms thereof, wherein $R^2$, $R^3$, $R^4$, $R^{11}$, $R^{12}$ and $R^{13}$ are as defined above.

Additional exemplary embodiments of compounds of Formula I include, but are not limited to, compounds of the general formulas

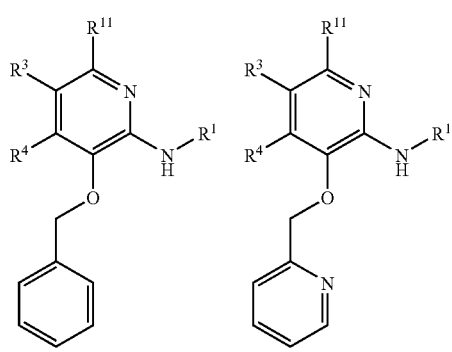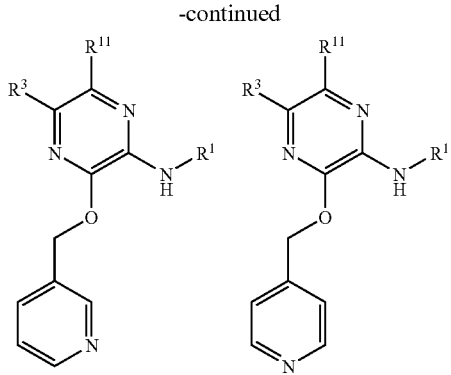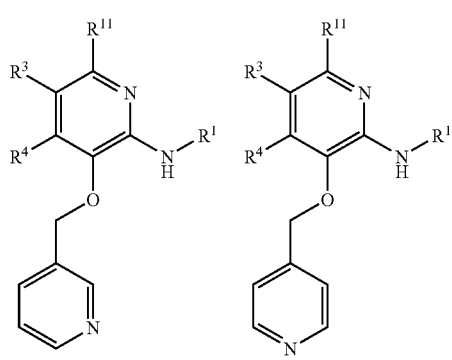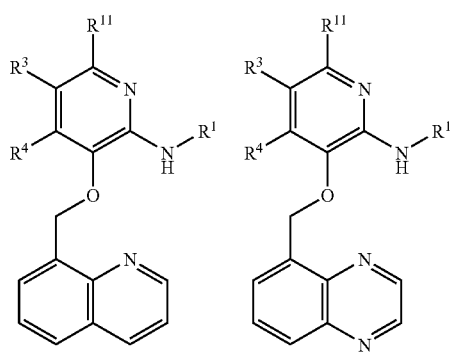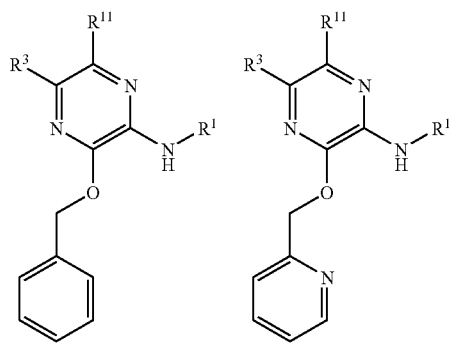

and substituted forms thereof, wherein $R^1$, $R^3$, $R^4$ and $R^{11}$ are as defined above.

Additional exemplary embodiments of compounds of Formula I include, but are not limited to, compounds of the general formulas

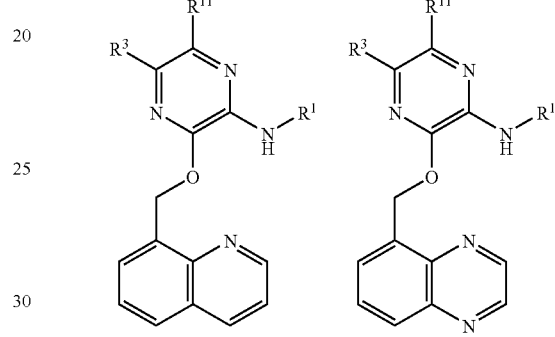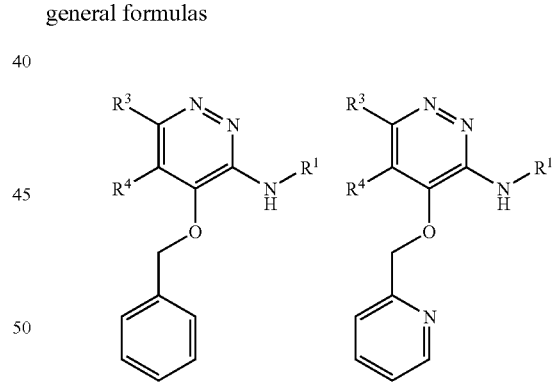

and substituted forms thereof, wherein $R^1$, $R^3$, and $R^{11}$ are as defined above.

Additional exemplary embodiments of compounds of Formula I include, but are not limited to, compounds of the general formulas

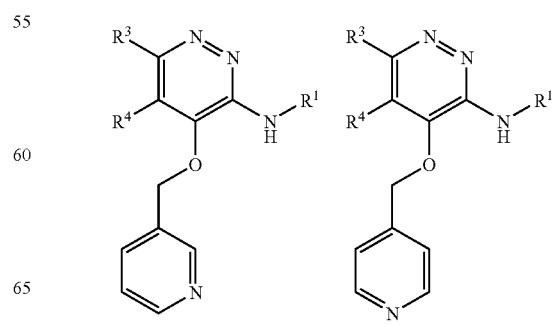

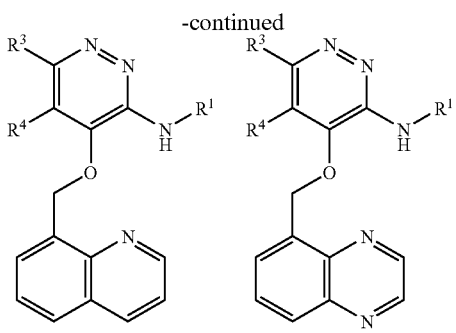

and substituted forms thereof, wherein $R^1$, $R^3$, and $R^4$ are as defined above.

In certain embodiments, the phrase "or $R^6$ and $R^7$ together with the atoms to which they are attached form a saturated or partially unsaturated heterocyclic ring" refers to a ring formed from an $R^6$ and $R^7$ radical attached to the same nitrogen atom, such as in a group having the formula $V_n$—C(=O)NR$^6$R$^7$, $V_n$—NR$^6$R$^7$, or $V_n$—S(O)$_2$NR$^6$R$^7$.

In certain embodiments, the phrase "or $R^6$ and $R^7$ together with the atoms to which they are attached form a saturated or partially unsaturated heterocyclic ring" refers to a ring formed through an $R^6$ and $R^7$ radical attached to different atoms within the same group, such as in a group having the formula $V_n$—NR$^6$C(=O)R$^7$.

In certain embodiments, the phrase "or $R^8$ and $R^9$ together with the atoms to which they are attached form a saturated or partially unsaturated heterocyclic ring" refers to a ring formed through an $R^8$ and $R^9$ radical attached to the same nitrogen atom, such as in a group having the formula $V_n$—C(=O)NR$^8$R$^9$ or $V_n$—NR$^8$R$^9$.

In certain embodiments, the phrase "or $R^8$ and $R^9$ together with the atoms to which they are attached form a saturated or partially unsaturated heterocyclic ring" refers to an $R^8$ and $R^9$ radical attached to different atoms within the same group, such as in a group having the formula $V_n$—NR$^6$C(=O)R$^7$ or $V_n$—NR$^8$C(=O)NR$^9$R$^{10}$.

In certain embodiments, the phrase "or $R^9$ and $R^{10}$ together with the atoms to which they are attached form a saturated or partially unsaturated heterocyclic ring" refers to a ring formed through an $R^9$ and $R^{10}$ radical attached to the same nitrogen atom, such as in a group having the formula $V_n$—NR$^8$C(=O)NR$^9$R$^{10}$.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers, diastereomers mixtures, racemic or otherwise, thereof. Accordingly, this invention also includes all such isomers, including diastereomeric mixtures, pure diastereomers and pure enantiomers of the compounds of this invention. The term "enantiomer" refers to two stereoisomers of a compound which are non-superimposable mirror images of one another. The term "diastereomer" refers to a pair of optical isomers which are not mirror images of one another. Diastereomers have different physical properties, e.g. melting points, boiling points, spectral properties, and reactivities.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

In addition to compounds of Formula I, the invention also includes solvates, pharmaceutically acceptable prodrugs, and pharmaceutically acceptable salts of such compounds.

The phrase "pharmaceutically acceptable" indicates that the substance or composition is compatible chemically and/or toxicologically with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

A "prodrug" is a compound that may be converted under physiological conditions or by solvolysis to the specified compound or to a salt of such compound. Prodrugs include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, cirtulline, homocysteine, homoserine, methyl-alanine, para-benzoylphenylalanine, phenylglycine, propargylglycine, sarcosine, methionine sulfone and tert-butylglycine. Particular examples of prodrugs of this invention include compounds of Formula I covalently joined to a phosphate residue.

Additional types of prodrugs are also encompassed. For instance, a free carboxyl group of a compound of Formula I can be derivatized as an amide or alkyl ester. As another example, compounds of this invention comprising free hydroxy groups may be derivatized as prodrugs by converting the hydroxy group into a group such as, but not limited to, a phosphate ester, hemisuccinate, dimethylaminoacetate, or phosphoryloxymethyloxycarbonyl group, as outlined in *Advanced Drug Delivery Reviews,* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group may be an alkyl ester optionally substituted with groups including, but not limited to, ether, amine and carboxylic acid functionalities, or where the acyl group is an amino acid ester as described above, are also encompassed. Prodrugs of this type are described in *J. Med. Chem.,* 1996, 39, 10. More specific examples include replacement of the hydrogen atom of the alcohol group with a group such as $(C_1-C_6)$alkanoyloxymethyl, 1-$((C_1-C_6)$alkanoyloxy)ethyl, 1-methyl-1-$((C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate).

Free amines of compounds of Formula I can also be derivatized as amides, sulfonamides or phosphonamides. All of these moieties may incorporate groups including, but not limited to, ether, amine and carboxylic acid functionalities. For example, a prodrug can be formed by the replacement of a hydrogen atom in the amine group with a group such as R-carbonyl, RO-carbonyl, NRR'-carbonyl, wherein R and R' are each independently $(C_1-C_{10})$alkyl, $(C_3-C_2)$cycloalkyl, or benzyl, or R-carbonyl is a natural α-aminoacyl or natural α-aminoacyl-natural α-aminoacyl, —C(OH)C(O)OY wherein $Y_1$ is H, $(C_1-C_6)$alkyl or benzyl, —$C(OY_0)Y_1$ wherein $Y_0$ is $(C_1-C_4)$alkyl and $Y_1$ is $(C_1-C_6)$alkyl, carboxy $(C_1-C_6)$alkyl, amino$(C_1-C_4)$alkyl or mono-N— or di-N,N—$(C_1-C_6)$alkylaminoalkyl, or —$C(Y_2)Y_3$ wherein $Y_2$ is H or methyl and $Y_3$ is mono-N— or di-N,N—$(C_1-C_6)$alkylamino, morpholino, piperidin-1-yl or pyrrolidin-1-yl.

For additional examples of prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and Development*, edited by Krogsgaard-Larsen and H. Bundgaard, Chapter 5 "*Design and Application of Prodrugs*," by H. Bundgaard p. 113-191 (1991); c) H. Bundgaard, *Advanced Drug Delivery Reviews*, 8:1-38 (1992); d) H. Bundgaard, et al., *Journal of Pharmaceutical Sciences*, 77:285 (1988); and e) N. Kakeya, et al., *Chem. Pharm. Bull.*, 32:692 (1984), each of which is specifically incorporated herein by reference.

A "pharmaceutically acceptable salt," unless otherwise indicated, includes salts that retain the biological effectiveness of the corresponding free acid or base of the specified compound and are not biologically or otherwise undesirable. A compound of the invention may possess a sufficiently acidic group, a sufficiently basic group, or both functional groups, and accordingly react with any of a number of inorganic or organic bases or acids to form a pharmaceutically acceptable salt. Examples of pharmaceutically acceptable salts include those salts prepared by reaction of the compounds of the present invention with a mineral or organic acid or an inorganic base, such salts including, but not limited to, sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyn-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates. Since a single compound of the present invention may include more than one acidic or basic moiety, the compounds of the present invention may include mono, di or tri-salts in a single compound.

If the inventive compound is a base, the desired pharmaceutically acceptable salt may be prepared by any suitable method available in the art, for example, by treatment of the free base with an acidic compound, for example an inorganic acid such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid such as glucuronic acid or galacturonic acid, an alpha hydroxy acid such as citric acid or tartaric acid, an amino acid such as aspartic acid or glutamic acid, an aromatic acid such as benzoic acid or cinnamic acid, a sulfonic acid such as p-toluenesulfonic acid or ethanesulfonic acid, or the like.

If the inventive compound is an acid, the desired pharmaceutically acceptable salt may be prepared by any suitable method, for example, by treatment of the free acid with an inorganic or organic base. Examples of suitable inorganic salts include those formed with alkali and alkaline earth metals such as lithium, sodium, potassium, barium and calcium. Examples of suitable organic base salts include, for example, ammonium, dibenzylammonium, benzylammonium, 2-hydroxyethylammonium, bis(2-hydroxyethyl)ammonium, phenylethylbenzylamine, dibenzylethylenediamine, and the like salts. Other salts of acidic moieties may include, for example, those salts formed with procaine, quinine and N-methylglucosamine, plus salts formed with basic amino acids such as glycine, ornithine, histidine, phenylglycine, lysine and arginine.

The compounds of Formula I also include other salts of such compounds which are not necessarily pharmaceutically acceptable salts, and which may be useful as intermediates for preparing and/or purifying compounds of Formula I and/or for separating enantiomers of compounds of Formula I.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified is contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2H$, $^3H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Certain isotopically-labeled compounds of the present invention (e.g., those labeled with $^3H$ and $^{14}C$) are useful in compound and/or substrate tissue distribution assays. Tritiated (i.e., $^3H$) and carbon-14 (i.e., $^{14}C$) isotopes are useful for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Positron emitting isotopes such as $^{15}O$, $^{13}N$, $^{11}C$ and $^{18}F$ are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Metabolites of Compounds of Formula I

Also falling within the scope of this invention are the in vivo metabolic products of compounds of Formula I described herein. A "metabolite" is a pharmacologically active product produced through metabolism in the body of a specified compound or salt thereof. Such products may result, for example, from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolites are identified, for example, by preparing a radiolabelled (e.g., $^{14}$C or $^3$H) isotope of a compound of the invention, administering it parenterally in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolites, so long as they are not otherwise found in vivo, are useful in diagnostic assays for therapeutic dosing of the compounds of the invention.

Synthesis of Gluocokinase Activators

Compounds of Formula I may be synthesized by synthetic routes that include processes analogous to those well known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the Beilstein online database).

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

For illustrative purposes, Schemes A-Q show general methods for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

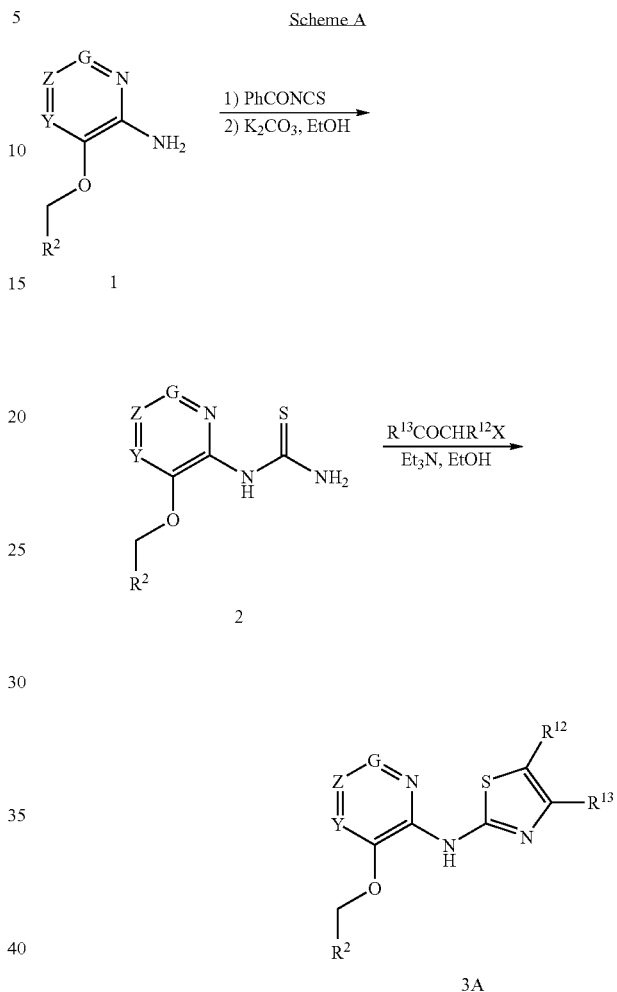

Scheme A shows a method of preparing compounds (3A) of Formula I wherein $R^1$ is thiazolyl. To prepare compound (3A), a 2-aminoheterocycle (1) is reacted with benzoylisothiocyanate to afford a benzoylthiourea intermediate, which is hydrolyzed to the thiourea (2) with a base such as, but not limited to, potassium carbonate in a suitable solvent such as, but not limited to, ethanol. Alternatively, the aminoheterocycle (1) can be treated with an inorganic or ammonium isothiocyanate, e.g., Meckler's procedure, in the presence of an acid to afford the thiourea (2) in one step. Treatment of the thiourea (2) with an α-haloketone $R^{13}COCHR^{12}X$, wherein X=OTs, Cl, Br, I, or $NR_3$ (wherein R=$C_1$-$C_6$ alkyl), in a suitable base such as triethylamine, Hunig's base, DBU, alkali carbonate, sodium hydroxide, etc. and a suitable solvent such as ethanol affords the thiazole (3A). If the desired α-halo ketone $R^{13}COCHR^{12}X$ is not commercially available, it can be prepared by various methods known to those skilled in the art. Examples include, but are not limited to, bromination of commercially or readily synthesized methyl ketones (*Tetrahedron* (1970) 5611-5615; *Organic Synthesis* (1946) 13-15; *Tetrahedron* (1990) 2943-2964), diazomethane treatment of carbonyl chlorides, oxidation of 1-chloro-2-alkanols, bromination of silyl enol ethers, or halogenation of β-keto esters followed by decarboxylation.

Scheme B

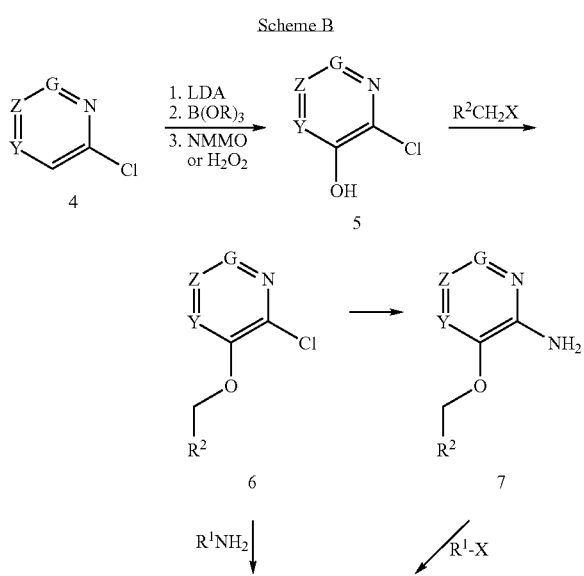

the boronate with a suitable oxidant such as N-methylmorpholine oxide or hydrogen peroxide. The ortho metalated species can also be quenched with $(TMSO)_2$ to obtain the hydroxylated material (5) directly upon acidic workup. The hydroxylated heteroaromatic compound (5) can be alkylated with $R^2CH_2X$ in the presence of a base such as, but not limited to, cesium carbonate and in a suitable solvent such as, but not limited to, DMF to afford compound (6). Alternatively, hydroxylated heteroaromatic compound (5) can be alkylated under Mitsunobu conditions with $R^2CH_2OH$ to afford compound (6). Compound (6) can be converted to compound (7) by the method of Hartwig et al. (for an example of this transformation via analogy see: *Organic Letters* (2001) 2729-2732), or by treatment with a Pd catalyst and benzophenone imine, or by heating in the presence of ammonia (or $NH_2PG$ where PG is a protecting group). Compound (7) can be converted to compound (3) of Formula I upon reaction with an aryl or heteroaryl halide $R^1X$ in the presence of a base catalyst or metal (e.g., copper or palladium) catalyst. Alternatively, compound (6) can be converted directly to a compound (3) of Formula I upon treatment with $R^1NH_2$ via base catalysis or via copper or palladium catalysis; i.e., the Buchwald reaction.

Scheme C

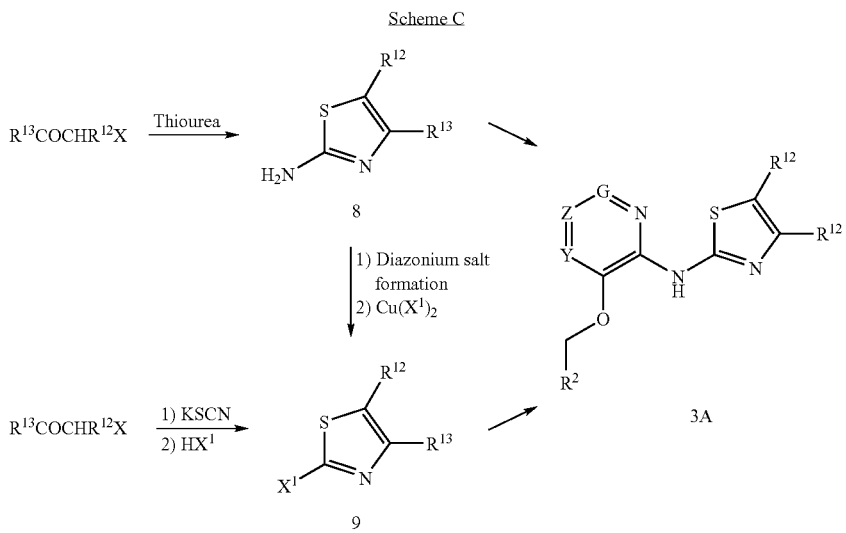

-continued

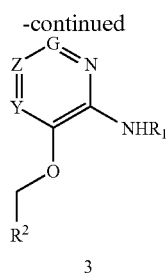

Scheme B shows an alternative method of preparing a compound of Formula I. According to Scheme B, hydroxylated aryl halide (5) (if not commercially available) can be prepared from heteroaryl halide (4) by: 1) ortho metalation with LDA or another suitable base; 2) conversion of the anion to the boronate via reaction with $B(OR)_3$; and 3) oxidation of Scheme C shows a method of preparing 2-aminothiazole and 2-bromothiazole intermediates (8) and (9), respectively, which are suitable for use in preparing compounds of Formula I as shown in Scheme B. According to Scheme C, α-haloketone $R^{13}COCHR^{12}X$ can be treated with thiourea in the presence of a suitable base such as potassium carbonate or triethylamine in an appropriate solvent such as DMF or ethanol to afford aminothiazole (8). The aminothiazole (8) can be converted to a diazonium salt intermediate by numerous methods including, but not limited to, treatment with sodium nitrite in acid or isobutylnitrite. Treatment of the in situ diazonium salt with $Cu(X^1)_2$ ($X^1$=Cl or Br) or HBr affords the corresponding 2-halothiazole (9). Alternatively, using the Hantzsch synthetic method, the α-haloketone $R^{13}COCHR^{12}X$ can be treated first with KSCN, then with HX wherein X is Cl or Br, to provide the 2-halothiazole (9). The 2-halothiazole compounds (8) and (9) can be converted into compound (3A) by the methods shown in Scheme B.

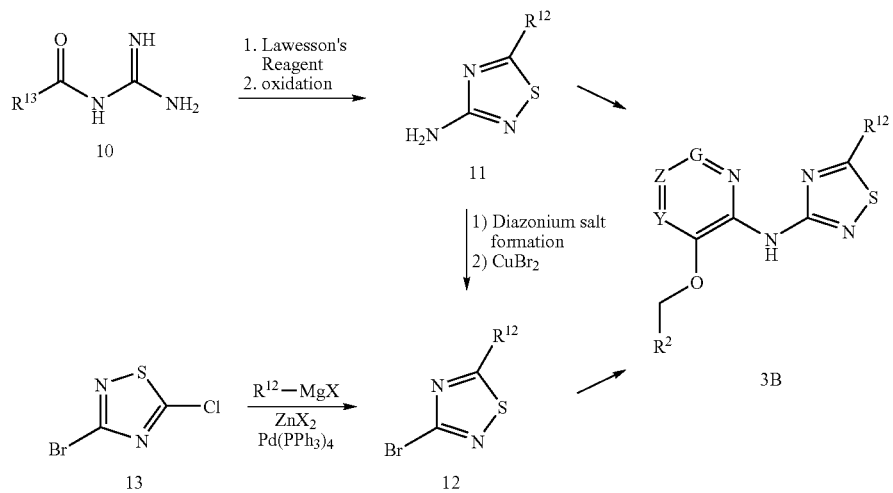

Scheme D shows a method of preparing 3-aminothiadiazole and 3-bromothiadiazole intermediates (11) and (12), respectively, which are suitable for use in preparing compounds of Formula I as shown in Scheme B. According to Scheme D, acylguanidine (10) (*Can. J. Chem.*, (1961) 39, 1017-29) can be treated with Lawesson's reagent or similar reagent in an appropriate solvent such as toluene to afford the corresponding thioamide (EP 0307142). Oxidation of the thioamide to form 3-amino-1,2,4 thiadiazole (11) can be accomplished with bromine, iodine, hydrogen peroxide or nitric acid. Cyclization of compound (10) may also be achieved by treatment with hydroxylamine-O-sulphonic acid in an alcohol solvent such as methanol or ethanol in the presence of pyridine (EP 0307142). Formation of the diazonium salt of compound (11), followed by treatment of the in situ diazonium salt with $CuBr_2$, affords the corresponding 3-bromo-1,2,4-thiadiazole (12) (EP 0307142). The chloro derivative of compound (12) could also be synthesized through the use of $CuCl_2$. Alternatively, palladium-mediated coupling of the commercially available 3-bromo-5-chloro-1,2,4-thiadiazole (13) with a zinc reagent affords 3-bromo-1,2,4-thiadiazole (12) (WO 2003/037894). Intermediate thiadiazoles (11) and (12) can be converted into compound (3B) of Formula I by the methods shown in Scheme B.

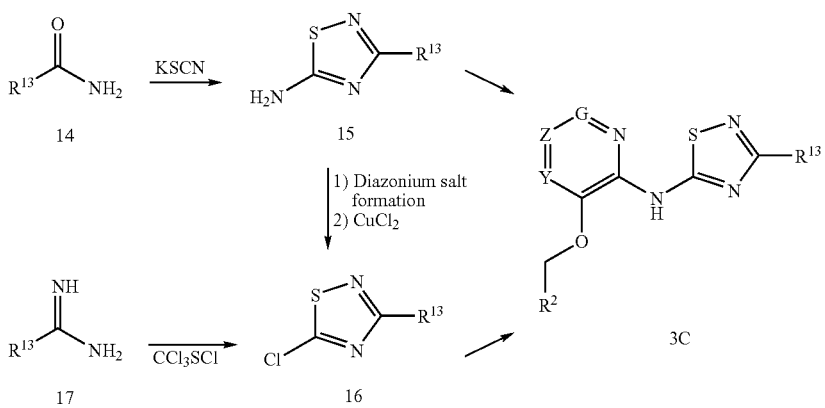

Scheme E shows a method of preparing 5-amino-1,2,4-thiadiazole and 5-chloro-1,2,4-thiadiazole intermediates (15) and (16), respectively, which are suitable for use in preparing compounds of Formula I as shown in Scheme B. According to Scheme E, primary amide (14) can be converted into 5-amino-1,2,4 thiadiazole (15) by heating with KSCN in an appropriate solvent such as methanol or ethanol (*Adv. Heterocycl. Chem.*, (1982) 32, 285). Formation of the diazonium salt of compound (15), followed by treatment of the in situ diazonium salt with $CuCl_2$ affords the corresponding 5-chloro-1,2,4-thiadiazole (16). The corresponding bromo derivative can also be synthesized through the use of $CuBr_2$. Alternatively, reaction of amidine (17) with perchloromethyl mercaptan affords 5-chloro-1,2,4-thiadiazole (16) (*Bioorg. Med. Chem.*, (2003) 11, 5529-5537). Intermediates (15) and (16) can be converted to compound (3C) of Formula I by the methods shown in Scheme B.

Scheme F

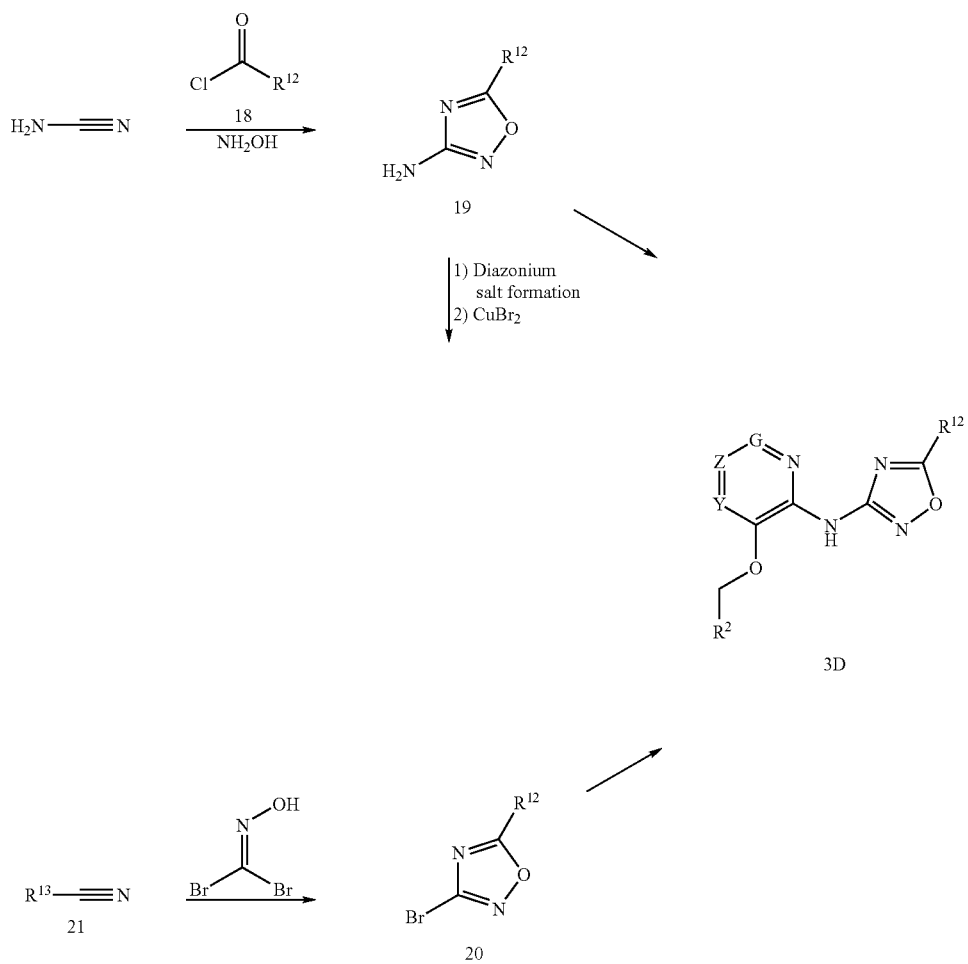

Scheme F shows a method of preparing 3-amino-1,2,4-oxadiazole and 3-bromo-1,2,4-oxadiazole intermediates (19) and (20), respectively, which are suitable for use in preparing compounds of Formula I as shown in Scheme B. According to Scheme F, cyanamide can be reacted with an appropriate acylchloride (18) or the corresponding anhydride, and subsequently reacted with hydroxylamine to afford 3-amino-1,2, 4-oxadiazole (19) (*Heterocycles*, (2002) 57, 811-823). Formation of the diazonium salt of (19), followed by treatment of the in situ diazonium salt with $CuBr_2$ affords the corresponding 3-bromo-1,2,4-oxadiazole (20). The chloro derivative could also be synthesized through the use of $CuCl_2$. Alternatively, alkyl nitrile (21) can be reacted with dibromoformaldoxime (neat) in the presence of an appropriate base such as sodium bicarbonate to afford 3-bromo-1,2,4-oxadiazole (20) (*J. Heterocyclic Chem.*, (1989) 26, 23-24). The oxadiazole intermediates (19) and (20) can be converted into compound (3D) of Formula I by the methods shown in Scheme B.

Scheme G

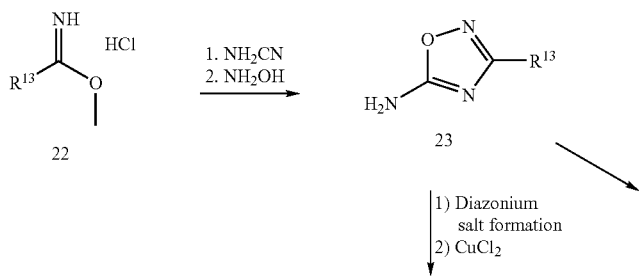

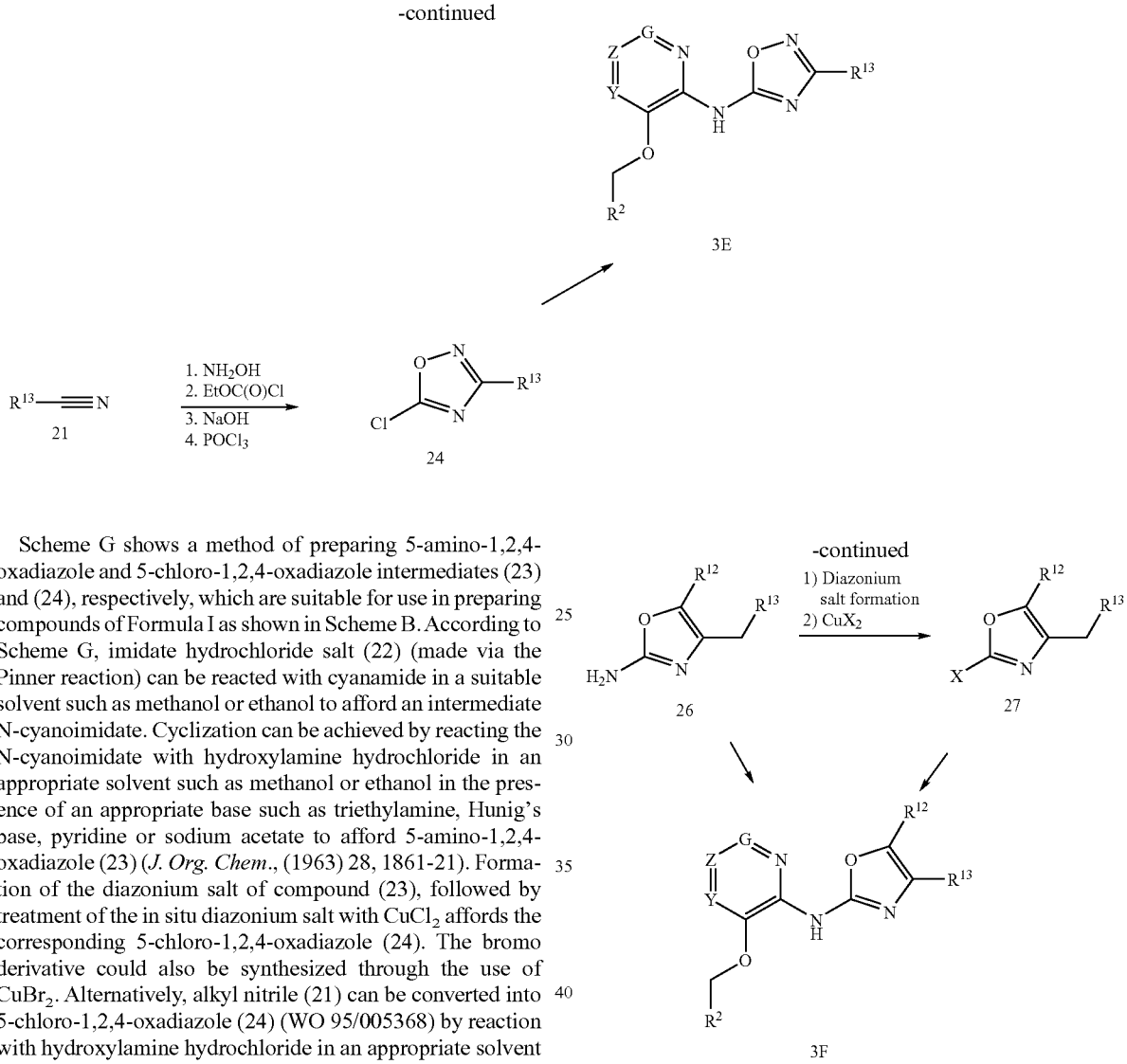

Scheme G shows a method of preparing 5-amino-1,2,4-oxadiazole and 5-chloro-1,2,4-oxadiazole intermediates (23) and (24), respectively, which are suitable for use in preparing compounds of Formula I as shown in Scheme B. According to Scheme G, imidate hydrochloride salt (22) (made via the Pinner reaction) can be reacted with cyanamide in a suitable solvent such as methanol or ethanol to afford an intermediate N-cyanoimidate. Cyclization can be achieved by reacting the N-cyanoimidate with hydroxylamine hydrochloride in an appropriate solvent such as methanol or ethanol in the presence of an appropriate base such as triethylamine, Hunig's base, pyridine or sodium acetate to afford 5-amino-1,2,4-oxadiazole (23) (*J. Org. Chem.*, (1963) 28, 1861-21). Formation of the diazonium salt of compound (23), followed by treatment of the in situ diazonium salt with $CuCl_2$ affords the corresponding 5-chloro-1,2,4-oxadiazole (24). The bromo derivative could also be synthesized through the use of $CuBr_2$. Alternatively, alkyl nitrile (21) can be converted into 5-chloro-1,2,4-oxadiazole (24) (WO 95/005368) by reaction with hydroxylamine hydrochloride in an appropriate solvent such as methanol or ethanol, in the presence of an appropriate base such as triethylamine, Hunig's base, pyridine or sodium acetate, followed by cyclization to a 1,2,4-oxadiazolone with a bisacylating agent such as ethyl chloroformate, carbonyldiimidazole or phosgene. In certain embodiments, the cyclization requires the use of a base such as NaOH, NaH or triethylamine to allow for the formation of the 1,2,4-oxadiazolone. Reaction of the 1,2,4-oxadiazolone with a dehydrating agent such as $POCl_3$, $POBr_3$ or $PCl_5$ affords the 5-halo-1,2,4-oxadiazole (24). The oxadiazole intermediates (23) and (24) can be converted into a compound (3E) of Formula I by the methods shown in Scheme B.

Scheme H shows a method of preparing 2-aminooxazole and 2-halo-oxazole intermediates (26) and (27), respectively, which are suitable for use in preparing compounds of Formula I as shown in Scheme B. According to Scheme H, α-hydroxyketone (25) is reacted with cyanamide to afford 2-aminooxazole (26) (*Aust. J. Chem.* (1985), 38, 447-458). Formation of the diazonium salt of compound (26), followed by treatment of the in situ diazonium salt with $CuX_2$ (where X=Cl or Br) affords the corresponding 5-halo-1,2,4-thiadiazole (27). Intermediates (26) and (27) can be converted into compound (3F) of Formula I by the method of Scheme B.

Scheme H

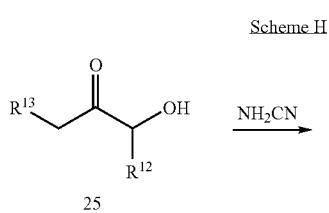

Scheme I

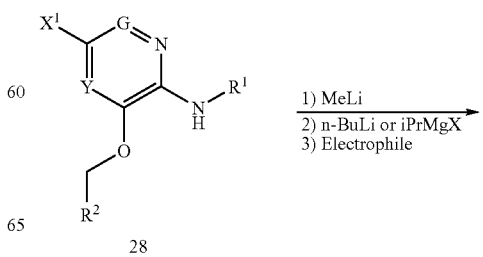

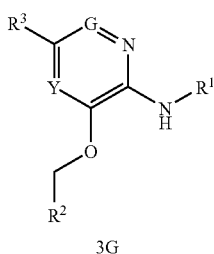

3G

Scheme I shows a method of preparing compound (3G) of Formula I wherein Z is $CR^3$. According to Scheme I, the halo-substituted heterocycle (28) (prepared by the method of Scheme A or B) wherein $X^1$=Cl, Br or I, is first treated with an appropriate amount of methyl lithium solution to remove exchangeable proton(s), and then transmetalated with an alkyl lithium reagent such as n-BuLi, sec-butyl or tert-butyl lithium, or a Grignard reagent such as, i-PrMg-halide. The resulting anion is then quenched with an electrophile to provide compound (3G). Suitable electrophiles include, but are not limited to: 1) aldehydes, 2) nitriles, 3) N-methoxy-N-methylamides (Weinreb amides), 4) dialkylsulphides, 5) hexachloroethane, 6) trialkyl boronates, 7) sulphonyl chlorides, 8) sulfamyl chlorides, 9) isocyanates, 10) carbon dioxide, (11) alkyl halides, (12) trifluoroiodomethane (13) Mander's reagent, and (14) chloroformates. Exemplary compounds of the present invention which can be prepared according to the method of Scheme I include compounds (3G) wherein $R^3$ is alkyl, phenylalkyl, cycloalkyl, hydroxylalkyl (from $R^3Si(CH_2)_nI$), Cl, SH, SR', SOR', $SO_2R'$, OR', I, $SCH_2R'$, $OCH_2R'$, $CO_2H$, CH(OH)—R', and C(=O)R', wherein R' is alkyl, alkenyl, alkynyl, cycloalkyl, or aryl.

Alternatively, the halo-substituted heterocycle (28) can be converted to compound (3G) wherein $R^3$ is alkyl, aryl, heteroaryl, alkenyl or alkynyl, via a metal (e.g., Cu or Pd) mediated coupling reaction such as, but not limited to, the Negishi reaction, the Suzuki reaction, the Sonogashira reaction, or the Stille reaction.

Scheme J shows a method of preparing compounds (3H) of Formula I, wherein Z=C—$SR^3$ or C—$OR^3$, from a halo substituted heterocycle (28). According to Scheme J, the halo-substituted heterocycle (28), prepared by the method of Scheme A or B, can be converted to a thiol or alcohol (29) via one of several procedures. According to one method, the halo-substituted heterocycle (28) is first treated with an appropriate amount of methyl lithium solution to remove exchangeable proton(s), and then transmetalated with an alkyl lithium reagent such as n-BuLi, sec-butyl or tert-butyl lithium, or a Grignard reagent such as, i-PrMg-halide. The resulting anion is then quenched with either elemental sulfur or bis(trimethylsilyl) peroxide to form the corresponding mercapto- or hydroxyl-substituted compound (29). Alternatively, the anion can be quenched with trimethyl borate and oxidized with either hydrogen peroxide (*J. Med. Chem.* (2004) 3089-3104) or N-methyl morpholine oxide (*Syn. Lett.* (1995) 931-932) to afford the phenol (29). As a third synthetic route, the halide (28) can be converted under Pd-mediated conditions to thiol or phenol (29) utilizing potassium triisopropylsilanethiolate (*Tetrahedron Letters* (1994) 3225-3226) or sodium tert-butyldimethylsiloxide (*J. Org. Chem.*, (2002) 5553-5566). The thiol or phenol (29) can be alkylated with a variety of electrophiles using standard reaction conditions to provide the corresponding ether (3H) of Formula I. Suitable electrophiles include, but are not limited to, alkyl halides, benzylic halides, heteroaroyl-$CH_2X$, cycloalkyl halides, Michael acceptors, and activated heteroaryl halides such as, but not limited to, 2-fluorocyanobenzene, 4-fluorocyanobenzene, 2-fluoronitrobenzene, 4-fluoronitrobenzene, 2-chloro-4-nitropyridine, 2-halopyridine, 2-halopyrimidine, 4-halopyrimidine, aryl halides and heteroaryl halides.

An alternative to the above methods is to convert the halide (28) to an alkylsulfide using Pd-mediated conditions with appropriately functionalized sulfides. Examples of such sulfides include, but are not limited to, esters of 3-mercaptopropanoic acid, 3-mercaptopropanenitrile or 2-(trimethylsilyl) ethanethiol. Sulfides of this type can be deprotected to the thiol and alkylated with a variety of electrophiles under standard conditions (*Chemical & Pharmaceutical Bulletin* (1990), 38(10), 2667-75).

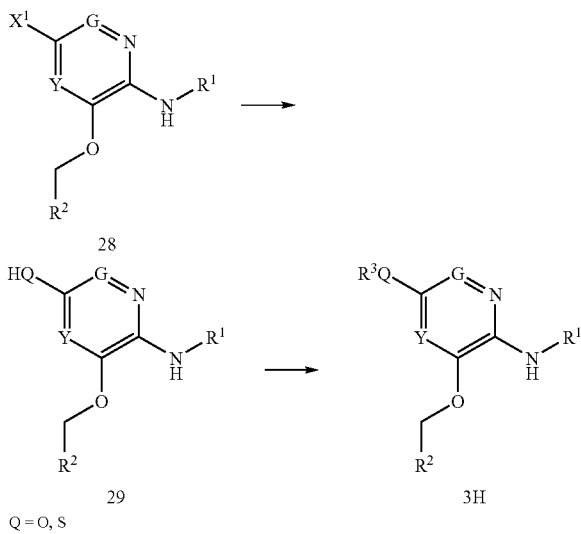

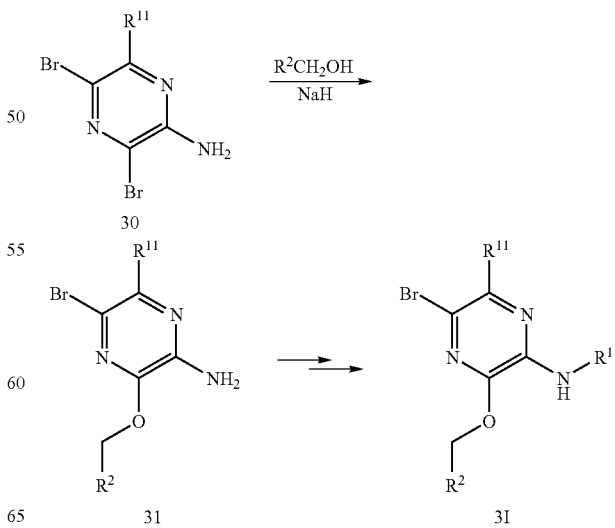

Scheme K shows a method of adding the linker OCH$_2$R$^2$ to a core heterocycle to provide a compound (3I) of Formula I wherein G=CR$^{11}$, X=C—Br, and Y=N. According to Scheme K, 2-amino-3,5-dibromopyrazine (30) is reacted with R$^2$CH$_2$OH in the presence of a suitable base such as K$_2$CO$_3$ or NaH in a suitable solvent such as DMF or ethanol to afford compound (31) regioselectively. Compound (31) can be converted to compound (3I) of Formula I by the method of Scheme A or B. Compound (3I) can be converted into additional 5-substituted compounds of Formula I by the methods shown in Scheme I or J.

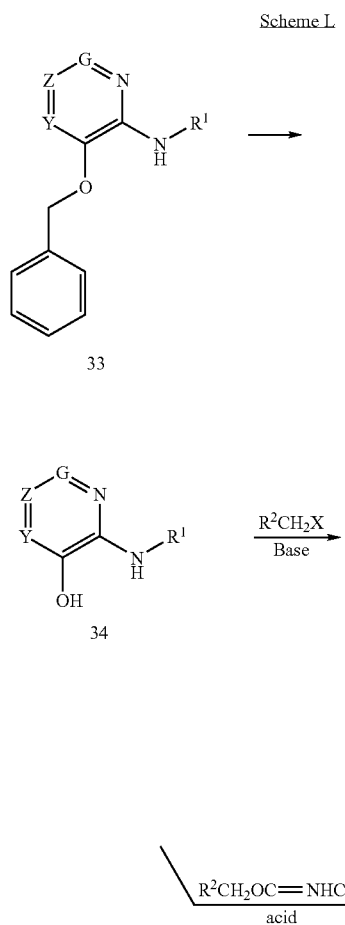

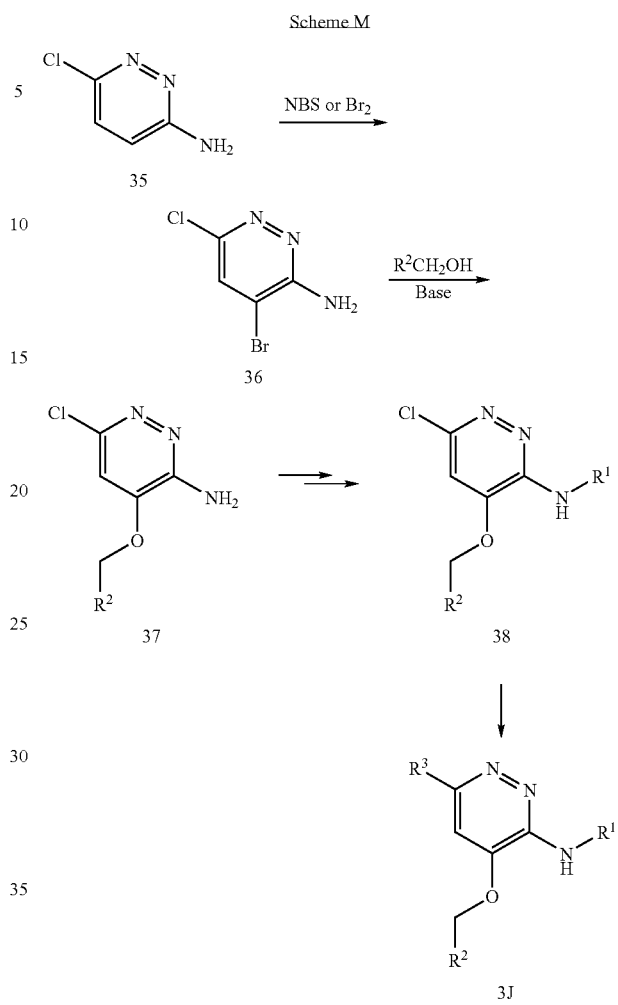

Scheme L shows an alternate method of adding the linker —OCH$_2$R$^2$ to a core heterocycle to provide a compound (3) of Formula I. According to Scheme L, a benzyl ether (33), prepared by the method of Scheme A or B, can be converted to the hydroxyl substituted heterocycle (34), for example by hydrolysis with a strong acid (e.g., 6N HCl) or by hydrogenation (e.g., H$_2$ or ammonium formate in the presence of a metal catalyst). Alkylation of the hydroxylated heterocycle (34) with R$^2$CH$_2$X, wherein X=OTs, OMs, Cl, Br, I, or NR$_3$, in the presence of a base such as, but not limited to, cesium carbonate, in a suitable solvent such as, but not limited to, DMF, affords compound (3) of Formula I. Alternatively, compound (34) can be reacted with a trichloroimidate (R$^2$CH$_2$OC=NHCCl$_3$) in the presence of a strong acid to afford compound (3) of Formula I.

Scheme M shows a method of preparing a compound (3J) of Formula I wherein G=N, Z=CR$^3$, and Y=CH. According to Scheme M, 6-chloropyridazin-3-amine (35) is regioselectively brominated with a suitable brominating agent such as bromine, NBS, etc., to provide compound (36). Reaction of compound (36) with R$^2$CH$_2$OH in the presence of a suitable base such as NaH or cesium carbonate in DMSO or DMF regioselectively affords compound (37). Compound (37) can be converted to the chlorinated compound (38) of Formula I by the method of Scheme A or B. Compound (38) can be converted into a 5-substituted compound (3J) of Formula I by the method of Scheme I or J.

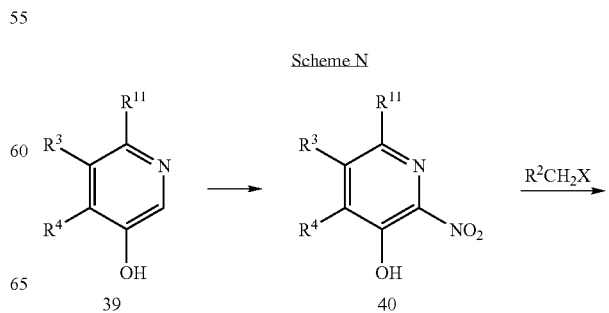

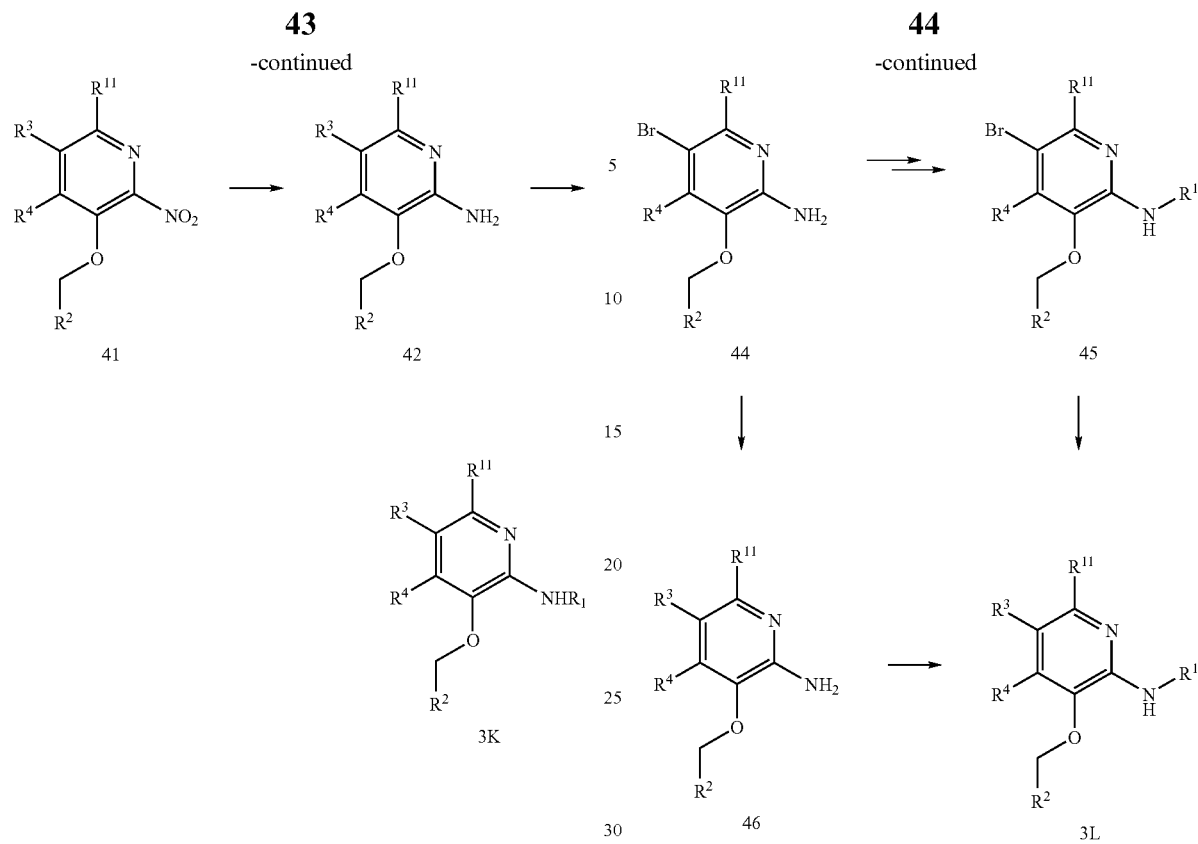

Scheme N shows a method of preparing a compound (3K) of Formula I wherein G=CR¹¹, Z=CR³, and Y=CR⁴. According to Scheme N, the hydroxylated pyridine (40) (if not commercially available) can be prepared from heteroaryl phenol (39) by regioselective nitration via treatment with nitric acid in acetic acid or sulfuric acid. The hydroxylated heteroaromatic compound (40) is alkylated with $R^2CH_2X$ in the presence of a base such as, but not limited to, cesium carbonate in a suitable solvent such as, but not limited to, DMF to afford compound (41). Alternatively, the hydroxylated heteroaromatic compound (40) can be alkylated with $R^2CH_2OH$ under Mitsunobu conditions to afford compound (41). Compound (41) can be converted to a compound (42) by treatment of Zn in acetic acid, or by treatment with Raney Nickel and hydrogen, or by other suitable reduction conditions. Compound (42) can be converted to compound (3K) of Formula I by the method of Scheme A or B.

Scheme O shows a method of preparing a compound (3L) of Formula I wherein G=CR¹¹, Z=CR³, and Y=CR⁴. According to Scheme O, the 2-aminopyridine (43) (which if not commercially available, can be prepared by the method of Scheme L) is regioselectively brominated with a suitable brominating agent such as NBS or bromine to provide compound (44). The brominated product (44) can be converted to compound (45) by the method of Scheme A or B. Compound (45) can be converted to 5-substituted compounds (3L) of Formula I by the method of Scheme I or J. Alternatively, the brominated 2-aminopyridine (44) can be converted to a 5-substituted compound (46) by the method of Scheme I or J, and then the heterocyclyl group $R^1$ can be added to compound (46) by the method of Scheme A or B to provide compound (3L).

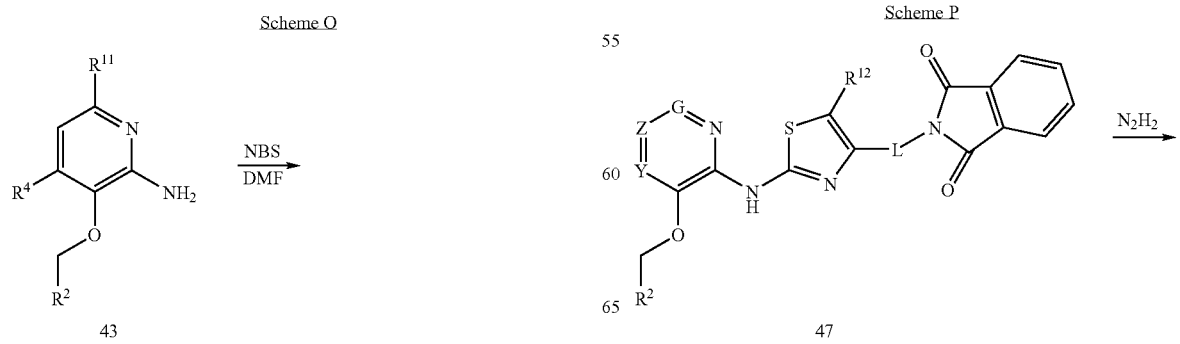

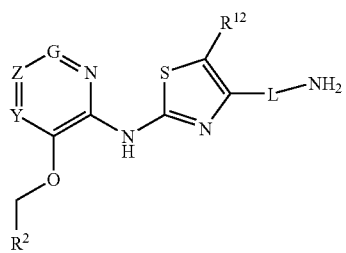

48

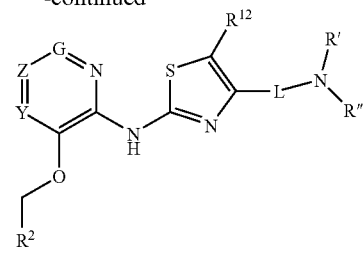

49

Scheme P shows a method of preparing compounds of Formula I wherein $R^1$ is a substituted thiazolyl. According to Scheme P, phthalimide-containing compound (47) wherein L is an alkyl or branched alkyl linker, which can be prepared by the method of Scheme A or B, can be converted to amine (48) via treatment with hydrazine. Amine (48) can be elaborated to the amide, carbamate, urea, thiourea, monoalkylamine, dialkylamine, amidine, or guanidine (49) by routine methods in the literature.

Scheme Q

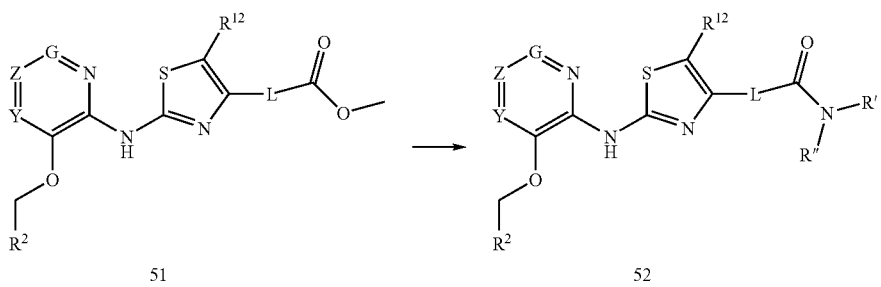

51 → 52

1) R'Li
2) H-

OH-

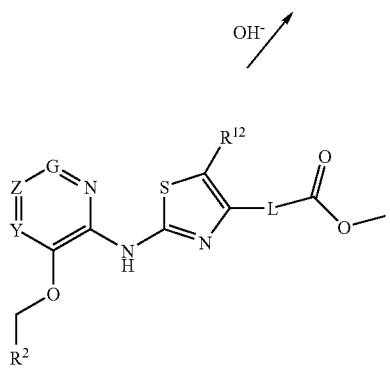

50

H-

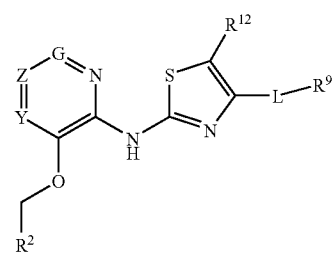

54

-continued

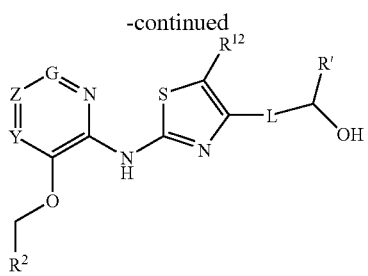

53

Scheme Q shows an alternative method of preparing compounds of Formula I wherein $R^1$ is a substituted thiazolyl. According to Scheme Q, the ester-containing compound (50) wherein L is an alkyl or branched alkyl linker, which can be prepared by the method of Scheme A or B, can be converted to alcohol (53) or carboxylic acid (51) by reduction or hydrolysis with a hydride or hydroxide, respectively. The carboxylic acid (51) can be converted to a primary, secondary or tertiary amide (52) using a variety of amide coupling methods known to those skilled in the art. Compound (51) can also be converted to compound (54), wherein $R^9$ is a heterocyclyl group such as, but not limited to, tetrazolyl, imidazolyl, triazolyl, or thiazoyl, by coupling methods known to those skilled in the art.

In one embodiment, the invention provides a method for preparing a compound of Formula I or a salt thereof comprising:

(a) reacting a compound of the formula

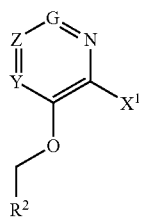

wherein $X^1$ is a leaving group, such as a halogen, such as Cl, with a compound of the formula $R^1NH_2$ in the presence of a base catalyst or metal catalyst; or (b) reacting a compound of the formula

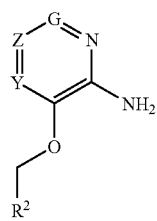

with a compound of the formula $R^1$—$X^2$, wherein $X^2$ is a leaving group, such as a halogen, such as Cl or Br, in the presence of a base catalyst or metal catalyst; or (c) when $R^1$ is

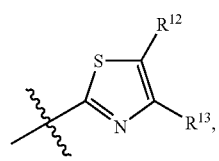

reacting a compound of the formula

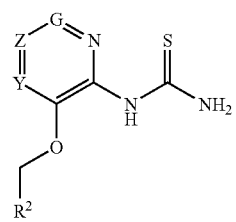

with a compound of the formula $R^{13}COCHR^{12}X^3$, wherein $X^3$ is a leaving group, such as a sulfonate, halogen, or an amino group, such as OTs, Cl, Br, I, or $NR_3$ wherein R is $C_1$-$C_6$ alkyl, in the presence of a base; or (d) for a compound of Formula I wherein Z is C—CH(OH)$R^6$ wherein $R^6$ is $C_1$-$C_6$ alkyl or phenyl, reacting a compound of Formula I wherein Z is CBr with a compound of the formula $R^6$—C(O)H in the presence of a base such as an alkyl lithium (for example methyl lithium and/or butyl lithium); or (e) for a compound having the Formula Ia

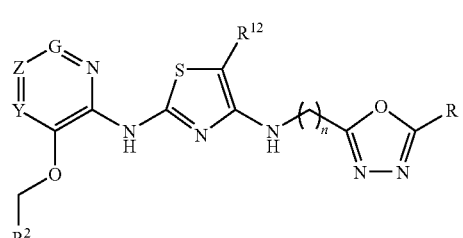

Ia wherein n is 1-6 and R is $C_1$-$C_6$ alkyl (such as methyl), reacting a corresponding compound having the formula Ib

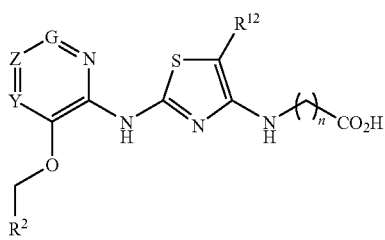

with a compound having the formula $H_2N$—NHC(O)—($C_1$-$C_6$ alkyl), for example $H_2N$—NHC(O)—$CH_3$, followed by treatment with a dehydrating agent such as $POCl_3$; or (f) for a compound having the formula Ic

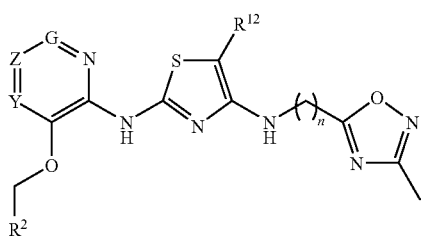

wherein n is 1-6 and R is $C_1$-$C_6$ alkyl (such as methyl), reacting a corresponding compound having the formula Ib

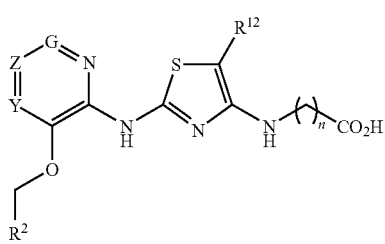

with a compound having the formula HO—NHC(=NH)R, for example HO—NHC(=NH)$CH_3$, in the presence of a coupling reagent such as N-((dimethylamino)fluoromethylene)-N-methylmethanaminium hexafluorophosphate(V) and a base such as an amine base, for example diisopropylethylamine.

In preparing compounds of Formula I, protection of remote functionalities (e.g., primary or secondary amines, etc.) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Methods of Separation

In any of the synthetic methods for preparing compounds of Formula I, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a reaction mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., *J. Chromatogr.*, (1975) 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−)menthyl chloroformate in the presence of base, or Mosher ester, α-methoxy-α-(trifluoromethyl)phenyl acetate (Jacob III. *J. Org. Chem.*, (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, *J. of Chromatogr.*, (1990) 513: 375-378). Enriched or purified enantiomers can be distinguished by methods used to distinguish other chiral molecules with asymmetric carbon atoms, such as optical rotation and circular dichroism.

Methods of Treatment with Compounds of Formula I

The compounds of the present invention can be used as prophylactics or therapeutic agents for treating diseases or disorders mediated by deficient levels of glucokinase activity or which can be treated by activating glucokinase including, but not limited to, diabetes mellitus, impaired glucose tolerance, IFG (impaired fasting glucose) and IFG (impaired fasting glycemia), as well as other diseases and disorders such as those discussed below. Furthermore, the compounds of the present invention can be also used to prevent the progression of the borderline type, impaired glucose tolerance, IFG (impaired fasting glucose) or IFG (impaired fasting glycemia) to diabetes mellitus.

Accordingly, another aspect of the invention provides methods of treating or preventing diseases or conditions described herein by administering to a mammal, such as a human, a therapeutically effective amount of a compound of Formula I, or solvate, metabolite, or pharmaceutically acceptable salt or prodrug thereof, in an amount effective to treat or prevent said disorder. In one embodiment, the method comprises administering to a mammal a compound of Formula I, or a solvate, metabolite, or pharmaceutically acceptable salt or prodrug thereof.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The terms "treat" and "treatment" refer to both therapeutic treatment and prophylactic or preventative measures, wherein the object is to prevent or slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. The terms "treating", "treat", or "treatment" embrace both preventative, i.e., prophylactic, and palliative treatment.

As used herein, the term "mammal" refers to a warm-blooded animal that has or is at risk of developing a disease described herein and includes, but is not limited to, guinea pigs, dogs, cats, rats, mice, hamsters, and primates, including humans.

In certain embodiments, the methods of this invention are useful for treating diabetes mellitus. Diabetes mellitus is a condition where the fasting plasma glucose level (glucose concentration in venous plasma) is greater than or equal to 126 mg/dL (tested on two occasions) and the 2-hour plasma glucose level of a 75 g oral glucose tolerance test (OGTT) is greater than or equal to 200 mg/dL. Additional classic symptoms include polydipsia, polyphagia and polyuria.

In certain embodiments, the methods of this invention are useful for treating the syndrome of impaired glucose tolerance (IGT). IGT is diagnosed by the presentation of a fasting plasma glucose level of less than 126 mg/dL and a 2-hour post-oral glucose challenge lever greater than 140 mg/dL.

The compounds of the present invention can be also used as prophylactics or therapeutic agents of diabetic complications such as, but not limited to, neuropathy, nephropathy, retinopathy, cataract, macroangiopathy, osteopenia, diabetic hyperosmolar coma), infectious diseases (e.g., respiratory infection, urinary tract infection, gastrointestinal tract infection, dermal soft tissue infection, lower limb infection etc.), diabetic gangrene, xerostomia, decreased sense of hearing, cerebrovascular disease, peripheral circulatory disturbance, etc.

The compounds of the present invention can be also used as prophylactics or therapeutic agents in the treatment of diseases and disorders such as, but not limited to, obesity, metabolic syndrome (syndrome X), hyperinsulinemia, hyperinsulinemia-induced sensory disorder, dyslipoproteinemia (abnormal lipoproteins in the blood) including diabetic dyslipidemia, hyperlipidemia, hyperlipoproteinemia (excess of lipoproteins in the blood) including type I, II-a (hypercholesterolemia), II-b, III, IV (hypertriglyceridemia) and V (hypertriglyceridemia), low HDL levels, high LDL levels, atherosclerosis and its sequelae, vascular restenosis, neurodegenerative disease, depression, CNS disorders, liver steatosis, osteoporosis, hypertension, renal diseases (e.g., diabetic nephropathy, glomerular nephritis, glomerulosclerosis, nephrotic syndrome, hypertensive nephrosclerosis, terminal renal disorder etc.), myocardiac infarction, angina pectoris, and cerebrovascular disease (e.g., cerebral infarction, cerebral apoplexy).

The compounds of the present invention can be also used as prophylactics or therapeutic agents in the treatment of diseases and disorders such as, but not limited to, osteoporosis, fatty liver, hypertension, insulin resistant syndrome, inflammatory diseases (e.g., chronic rheumatoid arthritis, spondylitis deformans, osteoarthritis, lumbago, gout, postoperative or traumatic inflammation, remission of swelling, neuralgia, pharyngolaryngitis, cystitis, hepatitis (including non-alcoholic steatohepatitis), pneumonia, inflammatory colitis, ulcerative colitis), pancreatitis, visceral obesity syndrome, cachexia (e.g., carcinomatous cachexia, tuberculous cachexia, diabetic cachexia, hemopathic cachexia, endocrinopathic cachexia, infectious cachexia, cachexia induced by acquired immunodeficiency syndrome), polycystic ovary syndrome, muscular dystrophy, tumor (e.g., leukemia, breast cancer, prostate cancer, skin cancer etc.), irritable bowel syndrome, acute or chronic diarrhea, spondylitis deformans, osteoarthritis, remission of swelling, neuralgia, pharyngolaryngitis, cystitis, SIDS, and the like.

Combination Therapy

The compounds of the present invention can be used in combination with one or more additional drugs such as described below. The dose of the second drug can be appropriately selected based on a clinically employed dose. The proportion of the compound of Formula I and the second drug can be appropriately determined according to the administration subject, the administration route, the target disease, the clinical condition, the combination, and other factors. In cases where the administration subject is a human, for instance, the second drug may be used in an amount of 0.01 to 100 parts by weight per part by weight of the compound of Formula I.

The second compound of the pharmaceutical combination formulation or dosing regimen preferably has complementary activities to the compound of Formula I such that they do not adversely affect each other. Such drugs are suitably present in combination in amounts that are effective for the purpose intended. Accordingly, another aspect of the present invention provides a composition comprising a compound of Formula I, or a solvate, metabolite, or pharmaceutically acceptable salt or prodrug thereof, in combination with a second drug, such as described herein.

The compound of Formula I and the additional pharmaceutically active agent(s) may be administered together in a unitary pharmaceutical composition or separately and, when administered separately this may occur simultaneously or sequentially in any order. Such sequential administration may be close in time or remote in time. The amounts of the compound of Formula I and the second agent(s) and the relative timings of administration will be selected in order to achieve the desired combined therapeutic effect.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

The compounds of the present invention can be used, for example in combination with additional drug(s) such as a therapeutic agent for diabetes mellitus, and/or a therapeutic agent for diabetic complications, as defined above. Examples of known therapeutic agents for diabetes mellitus which can be used in combination with a compound of Formula I include insulin preparations (e.g., animal insulin preparations extracted from the bovine or swine pancreas; human insulin preparations synthesized by a genetic engineering technique using *Escherichia coli* or a yeast), a fragment of insulin or derivatives thereof (e.g., INS-1), agents for improving insulin resistance (e.g., pioglitazone hydrochloride, troglitazone, rosiglitazone or its maleate, GI-262570, JTT-501, MCC-555, YM-440, KRP-297, CS-011, FK-614), alpha-glucosidase inhibitors (e.g., voglibose, acarbose, miglitol, emiglitate), biguanides (e.g., phenformin, metformin, buformin), insulin secretagogues [sulfonylureas (e.g., tolbutamide, glibenclamide, gliclazide, chlorpropamide, tolazamide, acetohexamide, glyclopyramide, glimepiride, glipizide, glybuzole), repaglinide, nateglinide, mitiglinide or its calcium salt hydrate, GLP-1], dipeptidylpeptidase IV inhibitors (e.g., NVP-DPP-278, PT-100), beta-3 agonists (e.g., CL-316243, SR-58611-A, UL-TG-307, SB-226552, AJ-9677, BMS-196085, AZ-40140, etc.), amylin agonists (e.g., pramlintide), phosphotyrosine phosphatase inhibitors (e.g., vanadic acid), gluconeogenesis inhibitors (e.g., glycogen phosphorylase inhibitors, glucose-6-phosphatase inhibitors, glucagon antagonists), SGLT (sodium-glucose cotransporter) inhibitors (e.g., T-1095), and the like.

Examples of known therapeutic agents for diabetic complications include aldose reductase inhibitors (e.g., tolrestat, epalrestat, zenarestat, zopolrestat, minalrestat, fidarestat (SNK-860), CT-112), neurotrophic factors (e.g., NGF, NT-3, BDNF), neurotrophic factor production secretion promoters, PKC inhibitors (e.g., LY-333531), AGE inhibitors (e.g., ALT946, pimagedine, pyratoxathine, N-phenacylthiazolium bromide (ALT766), EXO-226), active oxygen scavengers (e.g., thioctic acid), and cerebral vasodilators (e.g., tiapuride, mexiletine).

The compounds of the present invention can also be used, for example in combination with antihyperlipidemic agents. Epidemiological evidence has firmly established hyperlipidemia as a primary risk factor in causing cardiovascular disease (CVD) due to atherosclerosis. In recent years, emphasis has been placed on lowering plasma cholesterol levels, and low density lipoprotein cholesterol in particular, as an essential step in prevention of CVD. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance. Examples of antihyperlipidemic agents include statin compounds which are cholesterol synthesis inhibitors (e.g., cerivastatin, pravastatin, simvastatin, lovastatin, atorvastatin, fluvastatin, itavastatin or their salts, etc.), squalene synthase inhibitors or fibrate compounds (e.g., bezafibrate, clofibrate, simfibrate, clinofibrate) having a triglyceride lowering action and the like.

The compounds of the present invention can also be used, for example in combination with hypotensive agents. Hypertension has been associated with elevated blood insulin levels, a condition known as hyperinsulinemia. Insulin, a peptide hormone whose primary actions are to promote glucose utilization, protein synthesis and the formation and storage of neutral lipids, also acts to promote vascular cell growth and increase renal sodium retention, among other things. These latter functions can be accomplished without affecting glucose levels and are known causes of hypertension. Peripheral vasculature growth, for example, can cause constriction of peripheral capillaries, while sodium retention increases blood volume. Thus, the lowering of insulin levels in hyperinsulinemics can prevent abnormal vascular growth and renal sodium retention caused by high insulin levels and thereby alleviates hypertension. Examples of hypotensive agents include angiotensin converting enzyme inhibitors (e.g., captopril, enalapril, delapril), angiotensin II antagonists (e.g., candesartan cilexetil, losartan, eprosartan, valsartan, termisartan, irbesartan, tasosartan), calcium antagonists (e.g., manidipine, nifedipine, nicardipine, amlodipine, efonidipine), and clonidine.

The compounds of the present invention can be used in combination with antiobesity agents. The term "obesity" implies an excess of adipose tissue. Obesity is a well-known risk factor for the development of many very common diseases such as diabetes, atherosclerosis, and hypertension. To some extent appetite is controlled by discrete areas in the hypothalamus: a feeding centre in the ventrolateral nucleus of the hypothalamus (VLH) and a satiety centre in the ventromedial hypothalamus (VMH). The cerebral cortex receives positive signals from the feeding center that stimulate eating, and the satiety center modulates this process by sending inhibitory impulses to the feeding center. Several regulatory processes may influence these hypothalamic centers. The satiety center may be activated by the increases in plasma glucose and/or insulin that follow a meal. Examples of antiobesity agents include antiobesity drugs acting on the central nervous system (e.g., dexfenfluramine, fenfluramine, phentermine, sibutramine, anfepramon, dexamphetamine, mazindol, phenylpropanolamine, clobenzorex), pancreatic lipase inhibitors (e.g. orlistat), beta-3 agonists (e.g., CL-316243, SR-58611-A, UL-TG-307, SB-226552, AJ-9677, BMS-196085, AZ-40140), anorectic peptides (e.g., leptin, CNTF (Ciliary Neurotrophic Factor) and cholecystokinin agonists (e.g. lintitript, FPL-15849).

Administration of Compounds of Formula I

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

Pharmaceutical Formulations

In order to use a compound of Formula I or a solvate, metabolite, or pharmaceutically acceptable salt or prodrug thereof, for the therapeutic treatment (including prophylactic treatment) of mammals including humans, it is normally formulated in accordance with standard pharmaceutical practice as a pharmaceutical composition. According to this aspect of the invention there is provided a pharmaceutical composition that comprises a compound of the Formula I, or a solvate, metabolite, or pharmaceutically acceptable salt or prodrug thereof, in association with a pharmaceutically acceptable diluent or carrier.

The pharmaceutical compositions of the invention are formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The therapeutically effective amount of the compound to be administered will be governed by such considerations, and is the minimum amount necessary to prevent, ameliorate, or treat the disorder. The compound of the present invention is typically formulated into pharmaceutical dosage forms to provide an easily controllable dosage of the drug and to enable patient compliance with the prescribed regimen.

The composition for use herein is preferably sterile. In particular, formulations to be used for in vivo administration must be sterile. Such sterilization is readily accomplished, for example, by filtration through sterile filtration membranes. The compound ordinarily can be stored as a solid composition, a lyophilized formulation or as an aqueous solution.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, a milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment. The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more excipients.

The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The formulations may also include one or more stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980). A "liposome" is a small vesicle composed of various types of lipids, phospholipids and/or surfactant which is useful for delivery of a drug (such as the glucokinase inhibitors disclosed herein and, optionally, a chemotherapeutic agent) to a mammal. The components of the liposome are commonly arranged in a bilayer formation, similar to the lipid arrangement of biological membranes.

Sustained-release preparations of compounds of Formula I may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The compositions of the invention may also be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder)

Suitable pharmaceutically-acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), coloring agents, flavoring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavoring and coloring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturally-occurring phosphatides such as soya bean, lecithin, esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavoring and preservative agents.

Syrups and elixirs may be formulated with sweetening agents such as glycerol, propylene glycol, sorbitol, aspartame or sucrose, and may also contain a demulcent, preservative, flavoring and/or coloring agent.

Suppository formulations may be prepared by mixing the active ingredient with a suitable non-irritating excipient that is solid at ordinary temperatures but liquid at the rectal temperature and will therefore melt in the rectum to release the drug. Suitable excipients include, for example, cocoa butter and polyethylene glycols. Formulations suitable for vaginal administration may be presented as pessaries, tampons, creams, gels, pastes, foams or spray formulations containing in addition to the active ingredient such carriers as are known in the art to be appropriate.

Topical formulations, such as creams, ointments, gels and aqueous or oily solutions or suspensions, may generally be obtained by formulating an active ingredient with a conventional, topically acceptable, vehicle or diluent using conventional procedures well known in the art.

Compositions for transdermal administration may be in the form of those transdermal skin patches that are well known to those of ordinary skill in the art.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

The pharmaceutical composition (or formulation) for application may be packaged in a variety of ways depending upon the method used for administering the drug. For example, an article for distribution can include a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings. The formulations may also be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

The amount of a compound of this invention that is combined with one or more excipients to produce a single dosage form will necessarily vary depending upon the subject treated, the severity of the disorder or condition, the rate of administration, the disposition of the compound and the discretion of the prescribing physician. In one embodiment, a suitable amount of a compound of Formula I is administered to a mammal in need thereof. Administration in one embodiment occurs in an amount between about 0.001 mg/kg of body weight to about 60 mg/kg of body weight per day. In another embodiment, administration occurs in an amount between 0.5 mg/kg of body weight to about 40 mg/kg of body weight per day. In some instances, dosage levels below the lower limit of the aforesaid range may be more than adequate, while in other cases still larger doses may be employed without causing any harmful side effect, provided that such larger doses are first divided into several small doses for administration throughout the day. For further information on routes of administration and dosage regimes, see Chapter 25.3 in Volume 5 of *Comprehensive Medicinal Chemistry* (Corwin Hansch; Chairman of Editorial Board), Pergamon Press 1990, which is specifically incorporated herein by reference.

Articles of Manufacture

In another embodiment of the invention, an article of manufacture, or "kit", containing materials useful for the treatment of the disorders described above is provided. In one embodiment, the kit comprises a container comprising a compound of Formula I, or a solvate, metabolite, or pharmaceutically acceptable salt or prodrug thereof. Suitable containers include, for example, bottles, vials, syringes, blister pack, etc. The container may be formed from a variety of materials such as glass or plastic. The container may hold a compound of Formula I or a formulation thereof which is effective for treating the condition and may have a sterile access port (for example, the container may be an intravenous solution bag or a vial having a stopper pierceable by a hypodermic injection needle).

The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. In one embodiment, the label or package inserts indicates that the composition comprising a compound of Formula I can be used to treat a disorder mediated by deficient levels of glucokinase activity, such as diabetes mellitus. The label or package insert may also indicate that the composition can be used to treat other disorders.

In certain embodiments, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to another embodiment, a kit may comprise (a) a first container with a compound of Formula I contained therein; and (b) a second container with a second pharmaceutical formulation contained therein, wherein the second pharmaceutical formulation comprises a second compound useful for treating a disorder mediated by deficient levels of glucokinase activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I and a second pharmaceutical formulation, the kit may further comprise directions for the simultaneous, sequential or separate administration of the first and second pharmaceutical compositions to a patient in need thereof.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. In certain embodiments, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

The compounds of this invention also include the compounds of Examples 1-151 described below. Compounds labeled "Reference Examples" were found to be weakly active in the in vitro assays described below.

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other glucokinase activators of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was done on a Biotage system (Manufacturer: Dyax Corporation) having a silica gel column or on a silica SepPak cartridge (Waters). $^1$H NMR spectra were recorded on a Varian instrument operating at 400 MHz. $^1$H-NMR spectra were obtained as $CDCl_3$ or $d_6$-DMSO solutions (reported in ppm), using (7.25 ppm) or tetramethylsilane (0.00 ppm) as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

3-(Benzyloxy)-5-bromo-N-(4-methylthiazol-2-yl) pyridin-2-amine hydrochloride

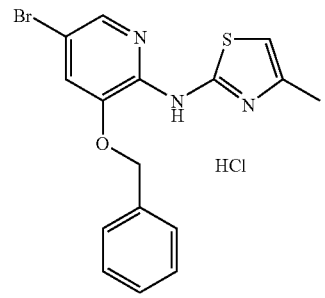 [SMILES: Cc1csc(Nc2ncc(Br)cc2OCc2ccccc2)n1 ; Cl]

Step A: Preparation of 3-(benzyloxy)-5-bromopyridin-2-amine: 3-(Benzyloxy)pyridin-2-amine (25.0 g, 124.9 mmol) was added to acetonitrile (300 mL) and cooled to 0° C. 1-Bromopyrrolidine-2,5-dione (22.22 g, 124.9 mmol) was added portionwise and the reaction mixture was stirred for 15 minutes, then concentrated to dryness. The residue was dissolved in EtOAc and partitioned with water. The organic layer was washed twice with saturated sodium bicarbonate and once with brine. Activated charcoal was added to the organic layer, and the organic layer was warmed to reflux, then cooled, filtered through a plug of celite, and concentrated to give 9.4 g of the title compound. The celite and charcoal were resuspended in EtOAc and filtered through a celite plug to give an additional 3.6 g of the title compound, to provide a total of 12.0 g (34.3% yield). $^1$H NMR ($CDCl_3$) δ 7.74 (d, 1H), 7.41 (m, 5H), 7.08 (d, 1H), 5.04 (s, 2H), 4.74 (bs, 2H). Mass spectrum (apci) m/z=279.1 (M+H).

Step B: Preparation of 1-benzoyl-3-(3-(benzyloxy)-5-bromopyridin-2-yl)thiourea: Using the procedure according to Example 2, Step A, 1,3-(benzyloxy)-5-bromopyridin-2-amine (12.0 g, 42.9 mmol) was reacted with benzoyl isothiocyanate (7.70 g, 47.2 mmol) to provide 1-benzoyl-3-(3-(benzyloxy)-5-bromopyridin-2-yl)thiourea (17.9 g, 94.37% yield) as a yellow solid. $^1$H NMR ($d_6$-DMSO) δ 8.20 (d, 1H), 7.98 (m, 2H), 7.92 (d, 1H), 7.68 (m, 1H), 7.56 (m, 2H), 7.52 (m, 2H), 7.38 (m, 2H), 7.34 (m, 1H) 5.29 (s, 2H). Mass spectrum (apci) m/z=442.0 (M+H).

Step C: Preparation of 1-(3-(benzyloxy)-5-bromopyridin-2-yl)thiourea: A 1 L round-bottom flask was charged with 1-benzoyl-3-(3-(benzyloxy)-5-bromopyridin-2-yl)thiourea (17.9 g, 40.5 mmol) and 3M sodium hydroxide (3.3 mL, 9.9 mmol), and the reaction mixture was refluxed overnight. The reaction mixture was then cooled, poured into water, and filtered to provide 1-(3-(benzyloxy)-5-bromopyridin-2-yl)thiourea (12.6 g, 92.2% yield) as a yellow solid. $^1$H NMR (CDCl$_3$) δ 10.60 (bs, 1H), 8.59 (bs, 1H), 7.87 (d, 1H), 7.40 (m, 5H), 7.30 (d, 1H), 6.90 (m, 1H), 5.15 (s, 2H). Mass spectrum (apci) m/z=340.0 (M+H).

Step D: Preparation of 3-(benzyloxy)-5-bromo-N-(4-methylthiazol-2-yl)pyridin-2-amine hydrochloride: A 1 L round-bottomed flask was charged with 1-chloropropan-2-one (4.833 g, 52.24 mmol), 1-(3-(benzyloxy)-5-bromopyridin-2-yl)thiourea (12.62 g, 37.31 mmol), triethylamine (8.841 mL, 63.43 mmol), and ethanol (30 mL). The reaction mixture was heated to reflux overnight, then poured into water and extracted with methylene chloride. The organic layer was dried over sodium sulfate, filtered, and concentrated to provide 3-(benzyloxy)-5-bromo-N-(4-methylthiazol-2-yl)pyridin-2-amine hydrochloride (11.5 g, 81.9% yield) as a white powder. $^1$H NMR (d$_6$-DMSO) δ 8.05 (d, 1H), 7.77 (m, 1H), 7.59 (m, 2H), 7.43 (m, 2H), 7.37 (m, 1H), 6.79 (s, 1H), 5.33 (s, 2H), 2.29 (s, 3H). Mass spectrum (apci) m/z=378.0 (M+H-HCl). Analysis calculated for C$_{16}$H$_{15}$BrClN$_3$OS: C, 46.56; H, 3.66; N, 10.18. found: C, 46.56; H, 3.77; N, 10.02.

Example 2

3-(Benzyloxy)-N-(4-methylthiazol-2-yl)pyridin-2-amine

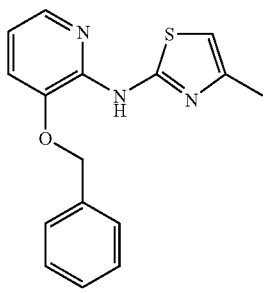 [SMILES: Cc1csc(Nc2ncccc2OCc2ccccc2)n1]

Step A: Preparation of 1-benzoyl-3-(3-(benzyloxy)pyridin-2-yl)thiourea: A 1 L round-bottomed flask was charged with benzoyl isothiocyanate (22.4 g, 137 mmol), 3-(benzyloxy)pyridin-2-amine (25 g, 125 mmol), and THF (200 mL). The reaction mixture was stirred at room temperature for 2 hours and the diluted with hexanes to 1 L, and then filtered to afford 1-benzoyl-3-(3-(benzyloxy)pyridin-2-yl)thiourea (44.4 g, 97.9% yield) as a yellow solid. $^1$H NMR (CDCl$_3$) δ 9.00 (m, 1H), 8.08 (m, 1H), 7.87 (m, 1H), 7.62 (m, 1H), 7.54 (m, 2H), 7.41 (m, 5H), 7.27 (m, 1H), 7.02 (m, 1H), 5.22 (s, 2H). LCMS (25 to 95) R$_t$=2.64 min, (apci) m/z=201, 364 (M+H).

Step B: Preparation of 1-(3-(benzyloxy)pyridin-2-yl)thiourea: A 1 L round-bottomed flask was charged with 1-benzoyl-3-(3-(benzyloxy)pyridin-2-yl)thiourea (44.4 g, 122 mmol), potassium carbonate (20.3 g, 147 mmol), and EtOH (400 mL). The reaction mixture was heated to reflux overnight, then cooled, poured into water (900 mL) and filtered to afford 1-(3-(benzyloxy)pyridin-2-yl)thiourea (34.6 g) as a yellow solid. $^1$H NMR (CDCl$_3$) δ 11.01 (s, 1H), 8.69 (s, 1H), 7.78 (d, 1H), 7.44-7.34 (m, 5H), 7.16 (d, 1H), 7.09 (bs, 1H), 6.91 (dd, 1H), 5.16 (s, 2H). LCMS (25 to 95) R$_t$=2.06 min (apci) m/z=260 (M+H).

Step C: Preparation of 3-(benzyloxy)-N-(4-methylthiazol-2-yl)pyridin-2-amine: A 1 L round-bottomed flask was charged with 1-(3-(benzyloxy)pyridin-2-yl)thiourea (31.7 g, 122 mmol), triethylamine (29.0 mL, 207 mmol), 1-chloropropan-2-one (13.6 mL, 171 mmol), and EtOH (400 mL). The reaction mixture was heated to reflux overnight, then poured into water and extracted with methylene chloride. The organic layer was dried over sodium sulfate, filtered and concentrated to afford 3-(benzyloxy)-N-(4-methylthiazol-2-yl)pyridin-2-amine (32.7 g, 89.9% yield) as a yellow solid. $^1$H NMR (CDCl$_3$) δ 8.58 (s, 1H), 7.93 (m, 1H), 7.39 (m, 5H), 7.08 (d, 1H), 6.80 (dd, 1H), 6.37 (s, 1H), 5.08 (s, 2H), 2.32 (s, 3H). LCMS (25 to 95) R$_t$=2.94 min (apci) m/z=298 (M+H).

Example 3

N-(4-methylthiazol-2-yl)-3-(pyridin-2-ylmethoxy)pyridin-2-amine dihydrochloride

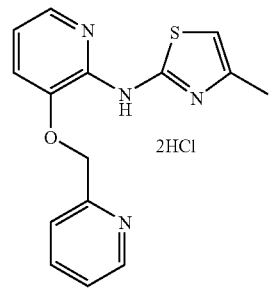 [SMILES: Cc1csc(Nc2ncccc2OCc2ccccn2)n1 ; "2HCl"]

Step A: Preparation of 2-(4-methylthiazol-2-ylamino)pyridin-3-ol: A 250 mL round-bottomed flask was charged 3-(benzyloxy)-N-(4-methylthiazol-2-yl)pyridin-2-amine (11.4 g, 38.3 mmol) in 6M HCl (100 mL), and the reaction mixture was heated to reflux for 10 hours. The reaction mixture was cooled to room temperature, poured onto ice and saturated sodium bicarbonate, filtered, dried under vacuum and triturated with hexanes to afford 2-(4-methylthiazol-2-ylamino)pyridin-3-ol (6.23 g, 78.5% yield) as a pale yellow solid. $^1$H NMR (CD$_3$OD) δ 7.79 (dd, 1H), 7.07 (dd, 1H), 6.79 (dd, 1H), 6.46 (q, 1H), 2.28 (s, 3H). LCMS (5 to 95) R$_t$=2.69 min (apci) m/z=208 (M+H).

Step B: Preparation of N-(4-methylthiazol-2-yl)-3-(pyridin-2-ylmethoxy)pyridin-2-amine dihydrochloride: A vial was charged with 2-(4-methylthiazol-2-ylamino)pyridin-3-ol (75 mg, 0.362 mmol), 2-(bromomethyl)pyridine hydrochloride (75.4 mg, 0.362 mmol), potassium carbonate (175 mg, 1.27 mmol), and DMF (3 mL), and the reaction mixture was stirred overnight at room temperature. The reaction mixture was then poured into water and extracted with ether. The organic layer was washed with brine, dried over sodium sulfate, filtered, concentrated, and purified over silica gel (80% EtOAc in hexanes). The residue was dissolved in 1:1 CH$_2$Cl$_2$:MeOH, and 2M HCl in ether was added. The solution was then concentrated to afford N-(4-methylthiazol-2-yl)-3-(pyridin-2-ylmethoxy)pyridin-2-amine dihydrochloride (96 mg, 71.4% yield) as a tan solid. $^1$H NMR (d$_6$-DMSO) δ 8.77 (d, 1H), 8.19 (t, 1H), 8.07 (d, 1H), 8.04 (d, 1H), 7.67 (m, 2H), 7.16 (dd, 1H), 6.87 (s, 1H), 5.53 (s, 2H), 2.33 (s, 3H). Mass spectrum (apci) m/z=299 (M+H-2HCl).

Example 4

N-(4-methylthiazol-2-yl)-3-(pyridin-3-ylmethoxy) pyridin-2-amine dihydrochloride

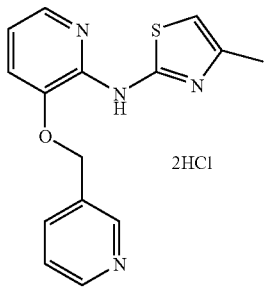 [SMILES: Cc1csc(Nc2ncccc2OCc2cccnc2)n1 ; "2HCl"]

2-(4-Methylthiazol-2-ylamino)pyridin-3-ol (prepared according to Example 3, Step A; 75 mg, 0.362 mmol), 3-(bromomethyl)pyridine hydrochloride (75.4 mg, 0.362 mmol) and potassium carbonate (175 mg, 1.27 mmol) were reacted according to Example 3, Step B, to provide N-(4-methylthiazol-2-yl)-3-(pyridin-3-ylmethoxy)pyridin-2-amine dihydrochloride (67 mg, 49.9% yield) as a tan solid. $^1$H NMR ($d_6$-DMSO) δ 10.15 (bs, 1H), 8.82 (s, 1H), 8.57 (d, 1H), 8.07 (m, 1H), 7.88 (dd, 1H), 7.46 (m, 2H), 6.92 (dd, 1H), 6.58 (s, 1H), 5.29 (s, 2H), 2.24 (s, 3H). Mass spectrum (apci) m/z=299 (M+H-2HCl).

Example 5

N-(4-Methylthiazol-2-yl)-3-(quinolin-8-ylmethoxy) pyridin-2-amine dihydrochloride

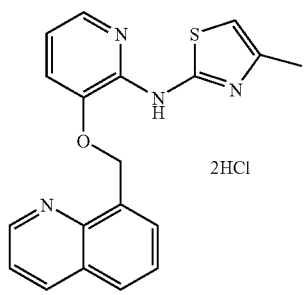 [SMILES: Cc1csc(Nc2ncccc2OCc2cccc3cccnc23)n1 ; "2HCl"]

2-(4-Methylthiazol-2-ylamino)pyridin-3-ol (prepared according to Example 3, Step A; 75 mg, 0.362 mmol), 8-(bromomethyl)quinoline (80.4 mg, 0.362 mmol) and potassium carbonate (125 mg, 0.905 mmol) were reacted according to Example 3, Step B, to provide N-(4-methylthiazol-2-yl)-3-(quinolin-8-ylmethoxy)pyridin-2-amine (148 mg, 97.1% yield). $^1$H NMR ($d_6$-DMSO) δ 9.15 (dd, 1H), 8.62 (d, 1H), 8.23 (m, 1H), 8.12 (d, 1H), 8.05 (d, 1H), 7.75 (m, 3H), 7.19 (m, 1H), 6.90 (s, 1H), 5.91 (s, 2H), 2.33 (s, 3H). Mass spectrum (apci) m/z=349 (M+H-2HCl).

Analysis calculated for $C_{19}H_{18}Cl_2N_4OS \cdot 3.0H_2O$: C, 47.95; H, 5.10; N, 11.77. Found: C, 47.95; H, 5.17; N, 11.22.

Example 6

3-(3-Methoxybenzyloxy)-N-(4-methylthiazol-2-yl) pyridin-2-amine hydrochloride

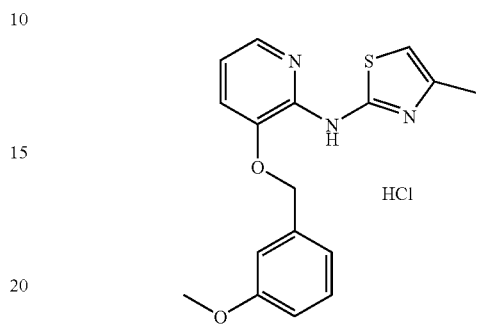

2-(4-Methylthiazol-2-ylamino)pyridin-3-ol (prepared according to Example 3, Step A) (0.150 g, 0.724 mmol), $K_2CO_3$ (0.225 g, 1.63 mmol), and 1-(chloromethyl)-3-methoxybenzene (0.113 g, 0.724 mmol) were reacted according to Example 3, Step B, to provide 3-(3-methoxybenzyloxy)-N-(4-methylthiazol-2-yl)pyridin-2-amine hydrochloride (0.110 g, 46.4% yield). $^1$H NMR (CDCl$_3$) δ 12.34 (bs, 1H), 7.93 (dd, 1H), 7.28 (d, 1H), 7.20 (m, 1H), 7.12 (m, 2H), 6.97 (m, 1H), 6.84 (m, 1H), 6.38 (s, 1H), 5.34 (s, 2H), 3.84 (s, 3H), 2.47 (s, 3H). Mass spectrum (apci) m/z=328.1 (M+H-HCl). Analysis calculated for $C_{17}H_{18}N_3O_2ClS \cdot 0.54DCM$: C, 56.29; H, 5.14; N, 11.23. found: C, 56.29; H, 5.23; N, 11.01.

Example 7

3-(Benzyloxy)-N-(4-methylthiazol-2-yl)-5-(methylthio)pyridin-2-amine hydrochloride

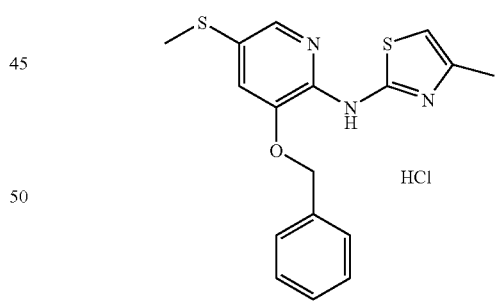

3-(Benzyloxy)-5-bromo-N-(4-methylthiazol-2-yl)pyridin-2-amine (prepared according to Example 1; 0.250 g, 0.664 mmol) was added to THF (30 mL) and cooled to −78° C. MeLi (0.519 mL, 0.831 mmol) was slowly added, and the reaction mixture was stirred for 10 minutes. Butyllithium (0.332 mL, 0.831 mmol) was added, and the reaction mixture was stirred for 15 minutes. 1,2-Dimethyldisulfane (0.438 g, 4.65 mmol) was added, and the reaction mixture was stirred for 15 minutes. Ammonium chloride was added, and the reaction mixture was extracted with $CH_2Cl_2$. The organic layer was purified by silica gel (10-20% EtOAc in hexanes) to give 3-(benzyloxy)-N-(4-methylthiazol-2-yl)-5-(methylthio)

pyridin-2-amine (0.170 g, 74.5% yield). A portion of this compound was dissolved in dichloromethane, 2M HCl in ether was added, and the mixture was concentrated to give the title compound. $^1$H NMR (CDCl$_3$) δ 12.30 (bs, 1H), 7.84 (m, 1H), 7.57 (d, 2H), 7.39 (m, 2H), 7.32 (m, 1H), 7.15 (m, 1H), 6.38 (s, 1H), 5.35 (s, 2H), 2.45 (s, 3H), 2.43 (s, 3H). Mass spectrum (apci) m/z=344.0 (M+H-HCl).

Example 8

3-(Benzyloxy)-5-(methylsulfinyl)-N-(4-methylthiazol-2-yl)pyridin-2-amine hydrochloride

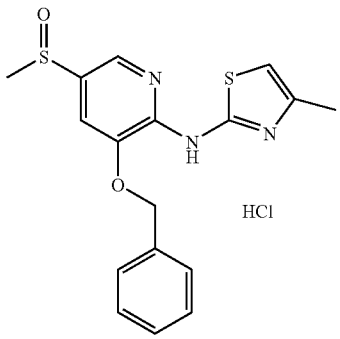

3-(Benzyloxy)-N-(4-methylthiazol-2-yl)-5-(methylthio)pyridin-2-amine (prepared according to Example 7; 0.057 g, 0.166 mmol) was placed in CH$_2$Cl$_2$ (5 mL) and cooled to 0° C. MCPBA (0.0398 g, 0.166 mmol) was added, and the reaction mixture was stirred at room temperature for 2 hours, then quenched with sodium bisulfite and extracted with CH$_2$Cl$_2$. The organic layer was washed with saturated sodium bicarbonate, dried, filtered, and concentrated. The residue was purified by silica gel (40-80% EtOAc in hexanes) to give the free base. The free base was dissolved in CH$_2$Cl$_2$, and 2M HCl in ether was added. The solution was concentrated to give 3-(benzyloxy)-5-(methylsulfinyl)-N-(4-methylthiazol-2-yl)pyridin-2-amine hydrochloride (0.037 g, 56.3% yield). $^1$H NMR (DMSO-d$_6$) δ 8.18 (d, 1H), 7.81 (d, 1H), 7.62 (m, 2H), 7.43 (m, 2H), 7.37 (m, 1H), 6.83 (s, 1H), 5.39 (d, 2H), 2.82 (s, 3H), 2.30 (s, 3H). Mass spectrum (apci) m/z=360.0 (M+H-HCl).

Example 9

3-(Benzyloxy)-5-methyl-N-(4-methylthiazol-2-yl)pyridin-2-amine hydrochloride

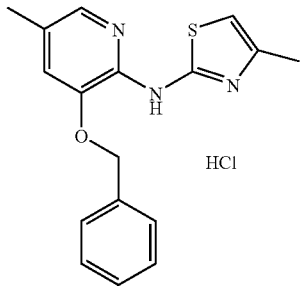

3-(Benzyloxy)-5-bromo-N-(4-methylthiazol-2-yl)pyridin-2-amine (prepared according to Example 1; 0.350 g, 0.930 mmol), MeLi (0.639 mL, 1.02 mmol), butyllithium (0.409 mL, 1.02 mmol), and iodomethane (0.165 g, 1.16 mmol) were reacted according to the method of Example 7 to provide 3-(benzyloxy)-5-methyl-N-(4-methylthiazol-2-yl)pyridin-2-amine hydrochloride (0.037 g, 12.8% yield). $^1$H NMR (DMSO-d$_6$) δ 7.83 (s, 1H), 7.60 (m, 2H), 7.54 (s, 1H), 7.42 (m, 2H), 7.37 (m, 1H), 6.84 (s, 1H), 5.32 (s, 2H), 2.32 (s, 3H), 2.29 (s, 3H). Mass spectrum (apci) m/z=312.1 (M+H-HCl).

Example 10

3-(Benzyloxy)-5-chloro-N-(4-methylthiazol-2-yl)pyridin-2-amine hydrochloride

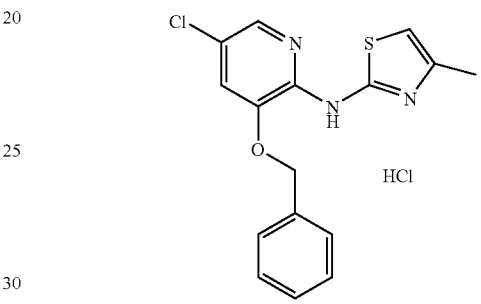

3-(Benzyloxy)-5-bromo-N-(4-methylthiazol-2-yl)pyridin-2-amine (prepared according to Example 1; 0.225 g, 0.598 mmol), MeLi (0.467 mL, 0.747 mmol), butyllithium (0.299 mL, 0.747 mmol), and perchloroethane (0.991 g, 4.19 mmol) were reacted according to the method of Example 7 to provide 3-(benzyloxy)-5-chloro-N-(4-methylthiazol-2-yl)pyridin-2-amine hydrochloride (0.060 g, 30.2% yield). $^1$H NMR (CDCl$_3$) δ 12.43 (bs, 1H), 7.91 (d, 1H), 7.59 (m, 2H), 7.41 (m, 2H), 7.33 (m, 1H), 7.20 (d, 1H), 6.41 (s, 1H), 5.36 (s, 2H), 2.47 (s, 3H). Mass spectrum (apci) m/z=332.1 (M+H-HCl).

Example 11

3-(Benzyloxy)-5-iodo-N-(4-methylthiazol-2-yl)pyridin-2-amine hydrochloride

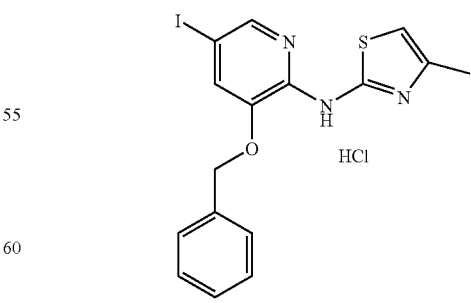

3-(Benzyloxy)-5-bromo-N-(4-methylthiazol-2-yl)pyridin-2-amine (prepared according to Example 1) (0.250 g, 0.664 mmol), MeLi (0.519 mL, 0.831 mmol), butyllithium (0.332 mL, 0.831 mmol) and trifluoromethyliodide (bubbled in excess) were reacted according to the method of Example 7 to provide 3-(benzyloxy)-5-iodo-N-(4-methylthiazol-2-yl)pyridin-2-amine hydrochloride (0.104 g, 37.0% yield). $^1$H NMR (d$_6$-DMSO) δ 8.14 (d, 1H), 7.82 (m, 1H), 7.58 (m, 2H), 7.40 (m, 3H), 6.79 (s, 1H), 5.31 (s, 2H), 2.28 (s, 3H). Mass spectrum (apci) m/z=424.0 (M+H).

Example 12

3-(Benzyloxy)-5-methoxy-N-(4-methylthiazol-2-yl)pyridin-2-amine hydrochloride

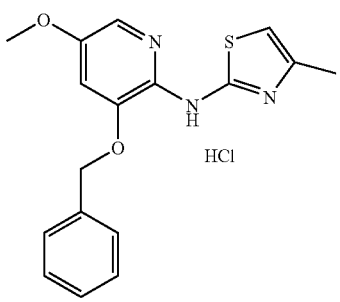

Step A: Preparation of 5-(benzyloxy)-6-(4-methylthiazol-2-ylamino)pyridin-3-ol: 3-(Benzyloxy)-5-bromo-N-(4-methylthiazol-2-yl)pyridin-2-amine (prepared according to Example 1; 1.00 g, 2.66 mmol) was added to THF (30 mL) and cooled to −78° C. MeLi (2.07 mL, 3.32 mmol) was slowly added, and the reaction mixture was stirred for 10 minutes. Butyllithium (1.33 mL, 3.32 mmol) was added, and the reaction mixture was stirred for 15 minutes. Triisopropylborate (0.613 mL, 2.66 mmol) was added, and the reaction mixture was stirred for 30 minutes. The reaction mixture was warmed to 0° C., and methanol (5 mL), 10% aqueous NaOH (5.1 mL, 12.8 mmol), and 30% aqueous H$_2$O$_2$ (1.27 mL, 13.3 mmol) were added. The reaction mixture was stirred at 0° C. for 1 hour, then purified by silica gel (10-20% EtOAc in hexanes) to give 5-(benzyloxy)-6-(4-methylthiazol-2-ylamino)pyridin-3-ol (0.198 g, 23.8% yield). $^1$H NMR (d$_6$-DMSO) δ 7.59 (m, 3H), 7.40 (m, 3H), 7.17 (d, 1H), 6.84 (s, 1H), 5.31 (s, 2H), 2.33 (s, 3H). Mass spectrum (apci) m/z=314.1 (M+H).

Step B: Preparation of 3-(benzyloxy)-5-methoxy-N-(4-methylthiazol-2-yl)pyridin-2-amine hydrochloride: 5-(Benzyloxy)-6-(4-methylthiazol-2-ylamino)pyridin-3-ol (0.080 g, 0.255 mmol) and potassium carbonate (0.0794 g, 0.574 mmol) were added to DMF (3 mL). Iodomethane (0.0362 g, 0.255 mmol) was added, and the reaction mixture was stirred at room temperature overnight. Water was added, and the reaction mixture was extracted with ether. The organic layer was dried, filtered, concentrated and purified by silica gel (15-20% EtOAc in hexanes) to give the title compound as the free base. The free base was dissolved in CH$_2$Cl$_2$, and 2M HCl in ether was added, and then the reaction mixture was concentrated to give 3-(benzyloxy)-5-methoxy-N-(4-methylthiazol-2-yl)pyridin-2-amine hydrochloride (0.016 g, 18.9% yield). $^1$H NMR (d$_6$-DMSO) δ 7.71 (d, 1H), 7.58 (m, 2H), 7.39 (m, 4H), 6.78 (s, 1H), 5.33 (s, 2H), 3.84 (s, 3H), 2.30 (s, 3H). Mass spectrum (apci) m/z=328.1 (M+H-HCl).

Example 13

N-(3-(benzyloxy)pyridin-2-yl)-4-ethylthiazol-2-amine hydrochloride

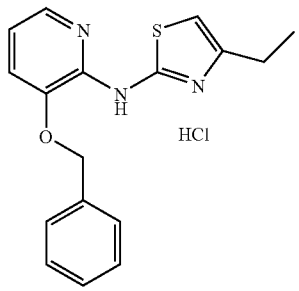 [SMILES: CCc1csc(Nc2ncccc2OCc2ccccc2)n1 ; Cl]

Following the procedure of Example 2, Step C, 1-(3-(benzyloxy)pyridin-2-yl)thiourea (525 mg, 2.02 mmol), 1-bromobutan-2-one (428 mg, 2.83 mmol), and triethylamine (0.480 mL, 3.44 mmol) were reacted in ethanol (20 mL) to provide N-(3-(benzyloxy)pyridin-2-yl)-4-ethylthiazol-2-amine (609 mg) as a yellow oil. The HCl salt was prepared according to Example 3, Step C, to provide N-(3-(benzyloxy)pyridin-2-yl)-4-ethylthiazol-2-amine hydrochloride (585 mg, 83%) as a white powder. $^1$H NMR (d$_6$-DMSO) δ 7.97 (d, 1H), 7.59-7.61 (m, 3H), 7.35-7.42 (m, 3H), 7.12 (m, 1H), 6.86 (s, 1H), 5.34 (s, 2H), 2.67 (q, 2H), 1.23 (t, 3H). Mass spectrum (apci) m/z=312 (100) (M+H-HCl).

Example 14

Methyl 2-(2-(3-(benzyloxy)pyridin-2-ylamino)thiazol-4-yl)acetate

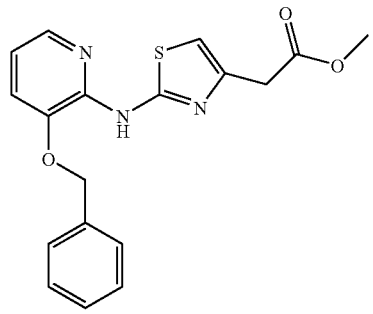 [SMILES: COC(=O)Cc1csc(Nc2ncccc2OCc2ccccc2)n1]

Following the method of Example 2, Step C, 1-(3-(benzyloxy)pyridin-2-yl)thiourea (2.00 g, 7.71 mmol), methyl 4-chloro-3-oxo-butanoate (1.63 g, 10.8 mmol), and triethylamine (1.83 mL, 13.1 mmol) were reacted in methanol (40 mL) to provide methyl 2-(2-(3-(benzyloxy)pyridin-2-ylamino)thiazol-4-yl)acetate (910 mg, 33%) as a yellow oil. $^1$H NMR (d$_6$-DMSO) δ 10.10 (s, 1H), 7.86 (d, 1H), 7.58 (d, 2H), 7.30-7.42 (m, 4H), 6.90 (d, 1H), 6.80 (s, 1H), 5.25 (s, 2H), 3.62 (s, 3H). Mass spectrum (apci) m/z=356 (100) (M+H).

Example 15

N-(3-(benzyloxy)-5-bromopyrazin-2-yl)-4-methylthiazol-2-amine

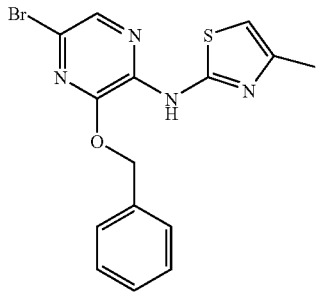 [SMILES: Cc1csc(Nc2ncc(Br)nc2OCc2ccccc2)n1]

Step A: Preparation of 1-benzoyl-3-(3-(benzyloxy)-5-bromopyrazin-2-yl)thiourea: Following the method of Example 1, Step B, benzoyl isothiocyanate (1.47 g, 8.99 mmol) and 3-(benzyloxy)-5-bromopyrazin-2-amine (2.29 g, 8.18 mmol) were reacted in THF (30 mL) to provide 1-benzoyl-3-(3-(benzyloxy)-5-bromopyrazin-2-yl)thiourea (2.38 g, 66%) as a yellow powder. $^1$H NMR (CDCl$_3$) δ 8.15 (bs, 1H), 7.91 (d, 2H), 7.66 (t, 1H), 7.53-7.57 (m, 4H), 7.36-7.44 (m, 3H), 5.55 (s, 2H). Mass spectrum (apci) m/z=202 (100), 443 (45), 445 (43) (M+H).

Step B: Preparation of 1-(3-(benzyloxy)-5-bromopyrazin-2-yl)thiourea: Following the method of Example 1, Step C, 1-benzoyl-3-(3-(benzyloxy)-5-bromopyrazin-2-yl)thiourea (2.38 g, 5.37 mmol), and potassium carbonate (890 mg, 6.44 mmol) were reacted in ethanol (30 mL) to provide 1-(3-(benzyloxy)-5-bromopyrazin-2-yl)thiourea (1.82 g, 53%) as a light gray powder. $^1$H NMR (d$_6$-DMSO) δ 9.62 (bs, 1H), 9.37 (bs, 1H), 8.73 (bs, 1H), 8.03 (s, 1H), 7.55 (d, 2H), 7.38-7.45 (m, 3H), 5.43 (s, 2H).

Step C: Preparation of N-(3-(benzyloxy)-5-bromopyrazin-2-yl)-4-methylthiazol-2-amine: Following the method of Example 1, Step D, 1-(3-(benzyloxy)-5-bromopyrazin-2-yl)thiourea (952 mg, 2.81 mmol), 1-chloropropan-2-one (364 mg, 3.93 mmol) and triethylamine (0.655 mL, 4.77 mmol) were reacted in ethanol (10 mL) to provide N-(3-(benzyloxy)-5-bromopyrazin-2-yl)-4-methylthiazol-2-amine (325 mg, 31%) as a light tan powder. $^1$H NMR (d$_6$-DMSO) δ 8.01 (s, 1H), 7.57 (d, 2H), 7.35-7.43 (m, 3H), 6.62 (s, 1H), 5.42 (s, 2H), 2.32 (s, 3H). Mass spectrum (apci) m/z=377 (100), 379 (97) (M+H).

Example 16

2-(2-(3-(benzyloxy)pyridin-2-ylamino)thiazol-4-yl)ethanol hydrochloride

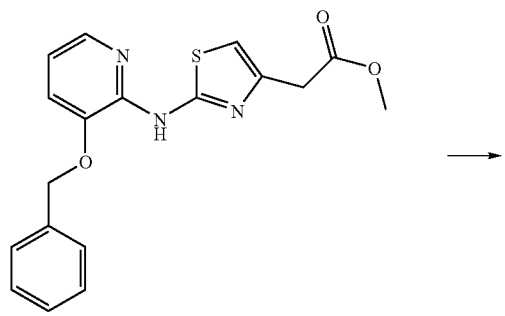

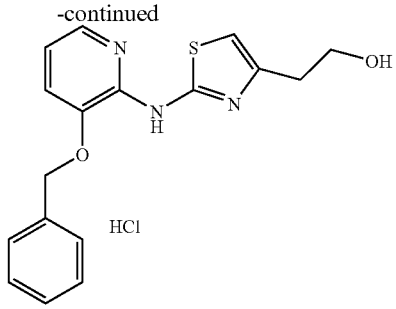

Methyl 2-(2-(3-(benzyloxy)pyridin-2-ylamino)thiazol-4-yl)acetate (prepared according to Example 14; 200 mg, 0.563 mmol) was added to a 1M solution of lithium aluminum hydride (5.63 mL, 5.63 mmol) at 0° C. The reaction mixture was stirred for 40 minutes, then slowly quenched with an excess of sodium sulfate decahydrate by portionwise addition and stirred for one hour. The reaction mixture was filtered, and the solids were washed with THF. The combined filtrates were concentrated, and the residue was purified via MPLC, eluting with ethyl acetate to afford the free base as a white solid. The free base was dissolved in THF (3 mL) and 1M HCl in ether (3 mL) was added. The mixture was diluted with ether (5 mL) and triturated for 20 minutes, then filtered to afford 2-(2-(3-(benzyloxy)pyridin-2-ylamino)thiazol-4-yl)ethanol hydrochloride (91 mg, 44%) as a white powder. $^1$H NMR (d$_6$-DMSO) δ 7.97 (d, 1H), 7.56-7.61 (m, 4H), 7.35-7.44 (m, 3H), 7.12 (m, 1H), 6.91 (s, 1H), 3.70 (t, 2H), 2.81 (t, 2H). Mass spectrum (apci) m/z=328 (100) (M+H).

Example 17

3-(3-Methoxybenzyloxy)-5-bromo-N-(4-methylthiazol-2-yl)pyridin-2-amine hydrochloride

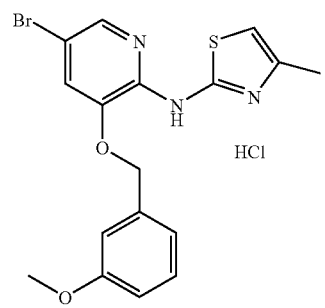 [SMILES: COc1cccc(COc2cc(Br)cnc2Nc2nc(C)cs2)c1 ; Cl]

5-Bromo-2-(4-methylthiazol-2-ylamino)pyridin-3-ol (prepared according to Example 3, Step A; 0.100 g, 0.349 mmol), K$_2$CO$_3$ (0.109 g, 0.786 mmol), and 1-(chloromethyl)-3-methoxybenzene (0.070 g, 0.349 mmol) were reacted according to Example 3, Step B, to provide 3-(3-methoxybenzyloxy)-5-bromo-N-(4-methylthiazol-2-yl)pyridin-2-amine hydrochloride (0.010 g, 7.04% yield). $^1$H NMR (d$_6$-DMSO) δ 7.98 (m, 1H), 7.65 (s, 1H), 7.32 (t, 1H), 7.18 (s, 1H), 7.13 (d, 1H), 6.92 (dd, 1H), 6.66 (s, 1H), 5.27 (s, 2H), 3.77 (s, 3H), 2.25 (s, 3H). Mass spectrum (apci) m/z=406.0 (M+H-HCl).

Example 18

3-(Benzyloxy)-5-(benzylthio)-N-(4-methylthiazol-2-yl)pyridin-2-amine hydrochloride

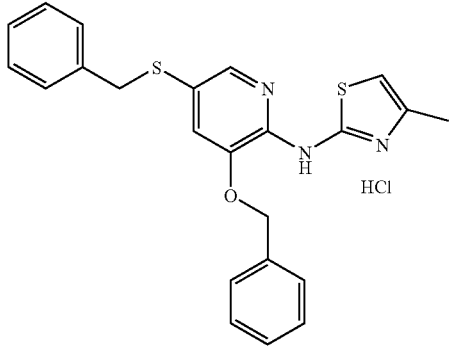 [SMILES: Cc1csc(Nc2ncc(SCc3ccccc3)cc2OCc2ccccc2)n1 ; Cl]

3-(Benzyloxy)-5-bromo-N-(4-methylthiazol-2-yl)pyridin-2-amine (prepared according to Example 1; 0.350 g, 0.930 mmol), MeLi (0.727 mL, 1.16 mmol), butyllithium (0.465 mL 1.16 mmol), and 1,2-dibenzyldisulfane (0.229 g, 0.930 mmol) were reacted according to the method of Example 7 to provide 3-(benzyloxy)-5-(benzylthio)-N-(4-methylthiazol-2-yl)pyridin-2-amine (0.108 g, 27.7% yield). $^1$H NMR (DMSO-$d_6$) δ 7.80 (d, 1H), 7.58 (m, 2H), 7.53 (m, 1H), 7.43 (m, 2H), 7.37 (m, 1H), 7.23 (m, 5H), 6.77 (s, 1H), 5.27 (s, 2H), 4.18 (s, 2H), 2.29 (s, 3H). Mass spectrum (apci) m/z=420.1 (M+H-HCl).

Example 19

1-(5-(Benzyloxy)-6-(4-methylthiazol-2-ylamino)pyridin-3-yl)ethanol

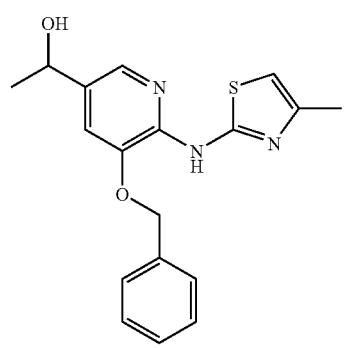 [SMILES: Cc1csc(Nc2ncc(C(C)O)cc2OCc2ccccc2)n1]

3-(Benzyloxy)-5-bromo-N-(4-methylthiazol-2-yl)pyridin-2-amine (prepared according to Example 1) (0.350 g, 0.930 mmol), MeLi (0.727 mL, 1.16 mmol), butyllithium (0.465 mL, 1.16 mmol), and acetaldehyde (0.0410 g, 0.930 mmol) were reacted according to the method of Example 7 to provide 1-(5-(benzyloxy)-6-(4-methylthiazol-2-ylamino)pyridin-3-yl)ethanol (0.187 g, 58.8%). Mass spectrum (apci) m/z=342.1 (M+H).

Example 20

1-(5-(Benzyloxy)-6-(4-methylthiazol-2-ylamino)pyridin-3-yl)ethanone hydrochloride

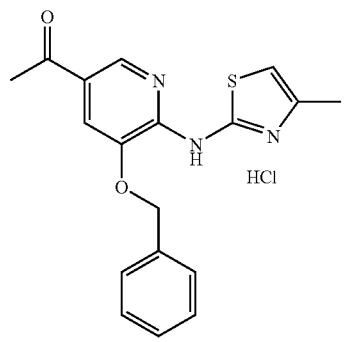 [SMILES: CC(=O)c1cnc(Nc2nc(C)cs2)c(OCc2ccccc2)c1 ; Cl]

1-(5-(Benzyloxy)-6-(4-methylthiazol-2-ylamino)pyridin-3-yl)ethanol (prepared according to Example 19; 0.128 g, 0.375 mmol) was placed in dichloromethane (5 mL). A solution of Dess-Martin periodinane (0.167 g, 0.394 mmol) in dichloromethane (7 mL) was added and the reaction mixture was stirred at room temperature for 20 minutes. 1M NaOH and ether were added, and the layers were separated. The organic layer was washed with 1M NaOH and water, then dried, filtered, and concentrated. The residue was purified by silica gel to provide the free base, which was dissolved in dichloromethane. 2M HCl was added and the solution was concentrated to afford 1-(5-(benzyloxy)-6-(4-methylthiazol-2-ylamino)pyridin-3-yl)ethanone hydrochloride (0.068 g, 48.3% yield). $^1$H NMR (DMSO-$d_6$) δ 8.62 (d, 1H), 7.73 (m, 1H), 7.60 (m, 2H), 7.42 (m, 2H), 7.35 (m, 1H), 6.79 (s, 1H), 5.36 (s, 2H), 2.57 (s, 3H), 2.30 (s, 3H). Mass spectrum (apci) m/z=340.1 (M+H-HCl).

Example 21

2-(2-(3-(Benzyloxy)pyridin-2-ylamino)thiazol-4-yl)acetic acid hydrochloride

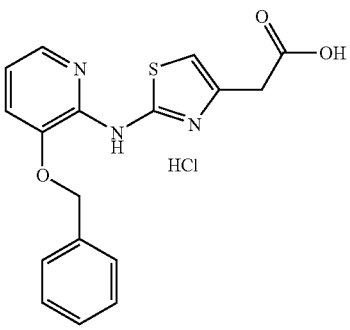 [SMILES: O=C(O)Cc1csc(Nc2ncccc2OCc2ccccc2)n1 ; Cl]

Methyl 2-(2-(3-(benzyloxy)pyridin-2-ylamino)thiazol-4-yl)acetate (prepared according to Example 14; 0.500 g, 1.41 mmol) was dissolved in MeOH (40 mL) and 1M NaOH (5 mL) and the reaction mixture was heated to 60° C. for 2 hours. The reaction mixture was cooled and the solvent was removed. 1N HCl was added to the residue to adjust to about pH 2. The solution was extracted with 10% MeOH in dichloromethane to provide 2-(2-(3-(benzyloxy)pyridin-2-ylamino)thiazol-4-yl)acetic acid hydrochloride (0.319 g, 66.4% yield). $^1$H NMR (DMSO-d$_6$) δ 7.92 (d, 1H), 7.58 (d, 2H), 7.52 (d, 2H), 7.41 (m, 2H), 7.35 (m, 1H), 7.02 (m, 1H), 6.92 (s, 1H), 5.30 (s, 2H), 3.68 (s, 2H). Mass spectrum (apci) m/z=342.1 (N+H-HCl).

Example 22

3-((2-(4-Methylthiazol-2-ylamino)pyridin-3-yloxy)methyl)phenol hydrochloride

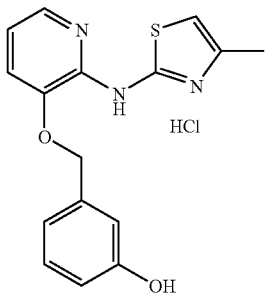 [SMILES: Cc1csc(Nc2ncccc2OCc2cccc(O)c2)n1 ; Cl]

Step A: Preparation of 3-(3-(tert-butyldimethylsilyloxy)benzyloxy)-N-(4-methylthiazol-2-yl)pyridin-2-amine: Following the method according to Example 3, Steps B and C, 5, 2-(4-methylthiazol-2-ylamino)pyridin-3-ol (prepared according to Example 3, Step A; 5.0 g, 24 mmol), (3-(bromomethyl)phenoxy)(tert-butyl)dimethylsilane (7.3 g, 24 mmol) [*J. Med. Chem.* (1992), 35, 3498] and potassium carbonate (8.3 g, 60 mmol) were combined to provide 3-(3-(tert-butyldimethylsilyloxy)benzyloxy)-N-(4-methylthiazol-2-yl)pyridin-2-amine (5.4 g, 48% yield) as a clear and colorless oil. $^1$H NMR (CDCl$_3$) δ 8.61 (bs, 1H), 7.94 (dd, 1H), 7.26 (m, 1H), 7.06 (dd, 1H), 7.00 (m, 1H), 6.84 (m, 2H), 6.79 (dd, 1H), 6.38 (s, 1H), 5.06 (s, 2H), 2.33 (s, 3H), 0.97 (s, 9H), 0.20 (s, 6H). Mass spectrum (apci) m/z=428.2 (M+H).

Step B: Preparation of 3-((2-(4-methylthiazol-2-ylamino)pyridin-3-yloxy)methyl)phenol hydrochloride: A 125 mL round-bottomed flask was charged with 3-(3-(tert-butyldimethylsilyloxy)benzyloxy)-N-(4-methylthiazol-2-yl)pyridin-2-amine (5.4 g, 13 mmol) and THF (50 mL). TBAF (1M in THF, 15 mL, 15 mmol) was added and stirred at room temperature overnight. The reaction was poured into saturated aqueous NH$_4$Cl and extracted with CH$_2$Cl$_2$ (2×100 mL). The organic layer was dried with sodium sulfate, filtered and concentrated in vacuo. The residue was purified over silica gel (30 to 80% EtOAc in hexanes) to afford 3-((2-(4-methylthiazol-2-ylamino)pyridin-3-yloxy)methyl)phenol hydrochloride (3.5 g, 79%) after HCl salt formation. $^1$H NMR (d$_6$-DMSO) δ 9.83 (bs, 1H), 9.50 (bs, 1 h), 7.89 (dd, 1H), 7.38 (d, 1H), 7.22 (t, 1H), 6.98 (m, 2H), 6.91 (dd, 1H), 6.75 (dd, 1H), 6.62 (s, 1H), 5.22 (s, 2H), 2.29 (s, 3H). Mass spectrum (apci) m/z=314.1 (M+H-HCl).

Example 23

2-(2-(2-(3-(Benzyloxy)pyridin-2-ylamino)thiazol-4-yl)ethyl)isoindoline-1,3-dione

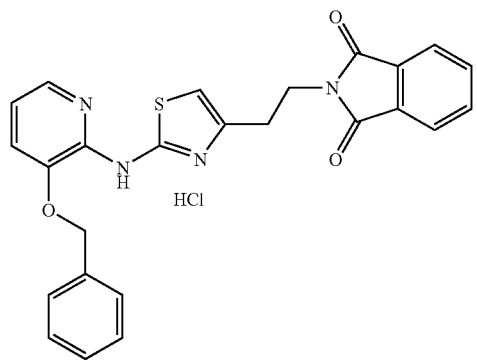 [SMILES: O=C1c2ccccc2C(=O)N1CCc1csc(Nc2ncccc2OCc2ccccc2)n1 ; Cl]

A mixture of 1-(3-(benzyloxy)pyridin-2-yl)thiourea (prepared according to Example 2, Steps A and B) (8.00 g, 30.8 mmol), 2-(4-bromo-3-oxobutyl)isoindoline-1,3-dione (12.8 g, 43.2 mmol; prepared according to *J. Med. Chem.* (1992) 35, 3239-3246), triethylamine (7.31 mL, 52.4 mmol), and ethanol (200 mL) was heated at reflux for 2 hours. The reaction mixture was cooled, diluted with water (200 mL), filtered, washed several times with water and hexanes, and dried. The product was recrystallized the solid from hexanes: methylene chloride (1:1, 250 mL) to afford 2-(2-(2-(3-(benzyloxy)pyridin-2-ylamino)thiazol-4-yl)ethyl)isoindoline-1, 3-dione (13.8 g, 98.0% yield) as a white powder. $^1$H NMR (d$_6$-DMSO) δ 9.93 (bs, 1H), 7.80-7.87 (m, 6H), 7.57 (d, 2H), 7.35-7.43 (m, 4H), 6.89 (m, 1H), 6.70 (s, 1H), 5.25 (s, 2H), 3.88 (t, 2H), 2.91 (t, 2H). Mass spectrum (apci) m/z=457 (M+H).

Example 24

3-(Benzyloxy)-N-(3-methyl-1,2,4-thiadiazol-5-yl)pyridin-2-amine

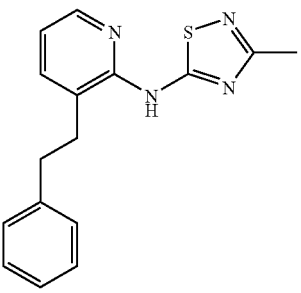 [SMILES: Cc1nsc(Nc2ncccc2CCc2ccccc2)n1]

3-(Benzyloxy)-2-chloropyridine (0.8393 g, 3.821 mmol), 3-methyl-1,2,4-thiadiazol-5-amine (8.684 mL, 3.474 mmol), potassium phosphate (0.8110 g, 3.821 mmol), tris(dibenzylideneacetone)dipalladium (O) (0.07952 g, 0.08684 mmol) and 9,9-dimethyl-4,5-bis(diphenylphosphino)xanthene (0.05527 g, 0.09552 mmol) in toluene (8 mL) and water (3 mL) were reacted according to Example 17, Step B, to afford 3-(benzyloxy)-N-(3-methyl-1,2,4-thiadiazol-5-yl)pyridin-2-amine (0.932 g, 88.13% yield) as light yellow solid. $^1$H NMR (CDCl$_3$) δ 8.9 (s, 1H), 7.97 (dd, J=1.17, 5.07 Hz, 1H), 7.37 (m, 5H), 7.15 (dd, J=1.17, 7.80 Hz, 1H), 6.89 (dd, J=5.07, 7.80 Hz, 1H), 5.09 (s, 2H), 2.47 (s, 3H). Mass spectrum (esi) m/z=299 (100) (M+H).

Example 25 tert-Butyl 2-(3-((2-(4-methylthiazol-2-ylamino)pyridin-3-yloxy)methyl)phenoxy)acetate

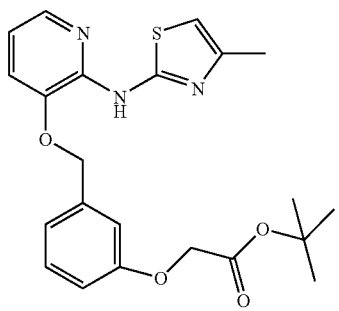 [SMILES: Cc1csc(Nc2ncccc2OCc2cccc(OCC(=O)OC(C)(C)C)c2)n1]

3-((2-(4-Methylthiazol-2-ylamino)pyridin-3-yloxy)methyl)phenol (prepared according to Example 22; 900 mg, 2.87 mmol), potassium carbonate (992 mg, 7.18 mmol), and tert-butyl 2-bromoacetate (0.424 mL, 2.87 mmol) were added to a 100 mL round bottom flask and dissolved in DMF (10 mL). The reaction mixture was stirred for 3 hours, then water (90 mL) was added and the reaction mixture was stirred at room temperature for 1 hour. The resultant solids were filtered and purified over silica gel (20% ethyl acetate in hexanes) to afford tert-butyl 2-(3-((2-(4-methylthiazol-2-ylamino)pyridin-3-yloxy)methyl)phenoxy)acetate (680 mg, 55.4% yield) as a white foam. $^1$H NMR (CDCl$_3$) δ 8.60 (bs, 1H), 7.94 (d, 1H), 7.32 (t, 1H), 7.07 (dd, 1H), 7.03 (m, 1H), 6.95 (m, 1H), 6.89 (dd, 1H), 6.80 (dd, 1H), 6.39 (q, 1H), 5.08 (s, 2H), 4.53 (s, 2H), 2.33 (s, 3H), 1.48 (s, 9H). Mass spectrum (apci) m/z=372 (100), 428 (20).

Example 26

2-(3-((2-(4-Methylthiazol-2-ylamino)pyridin-3-yloxy)methyl)phenoxy)acetic acid trifluoroacetate

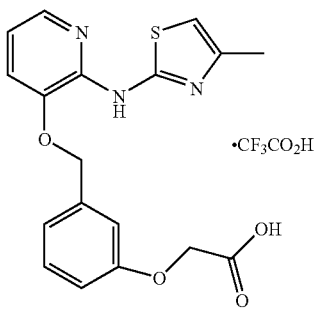 [SMILES: Cc1csc(Nc2ncccc2OCc2cccc(OCC(=O)O)c2)n1 ; "·CF3CO2H"]

tert-Butyl-2-(3-((2-(4-methylthiazol-2-ylamino)pyridin-3-yloxy)methyl)phenoxy)acetate (680 mg, 1.59 mmol) and CH$_2$Cl$_2$ (5 mL) were combined in a 50 mL round-bottomed flask. Trifluoroacetic acid (5 mL) was added and the reaction mixture was stirred at room temperature for 1 hour. The reaction mixture was concentrated and the resultant solid was triturated with 40% methanol in CH$_2$Cl$_2$ to provide 2-(3-((2-(4-methylthiazol-2-ylamino)pyridin-3-yloxy)methyl)phenoxy)acetic acid trifluoroacetate salt (621 mg, 80.4% yield) as a white solid. $^1$H NMR (d$_6$-DMSO) δ 7.92 (dd, 1H), 7.49 (dd, 1 h), 7.32 (t, 1H), 7.16 (m, 2H), 7.00 (dd, 1 h), 6.88 (dd, 1H), 6.72 (q, 1H), 5.26 (s, 2H), 4.69 (s, 2h), 2.29 (d, 3H). Mass spectrum (apci) m/z=372 (M+H-TFA).

Example 27

1-(4-Methylpiperazin-1-yl)-2-(3-((2-(4-methylthiazol-2-ylamino)pyridin-3-yloxy)methyl)phenoxy)ethanone dihydrochloride

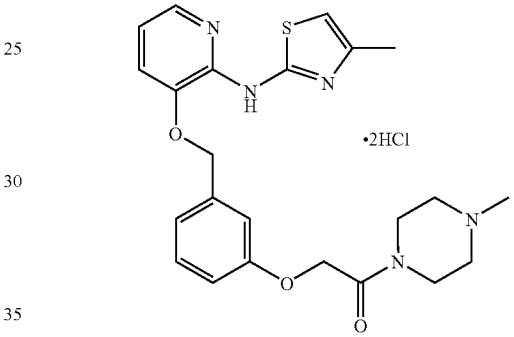

A 1 dram vial was charged with 2-(3-((2-(4-methylthiazol-2-ylamino)pyridin-3-yloxy)methyl)phenoxy)acetic acid trifluoroacetate (prepared according to Example 26; 70 mg, 0.14 mmol), triethylamine (0.10 mL, 0.72 mmol) and THF (2 mL) and cooled to 0° C. Ethyl chloroformate (0.035 mL, 0.36 mmol) was added and the reaction mixture was stirred at 0° C. for 30 minutes. N-methylpiperazine (0.080 mL, 0.72 mmol) was added and the reaction mixture was warmed to room temperature and stirred at room temperature for 1.5 hours. The reaction was poured into water and extracted with EtOAc. The organic layer was dried with sodium sulfate, filtered and concentrated in vacuo. The residue was purified over silica gel (10% methanol in EtOAc to 10% methanol in EtOAc with ammonia) to afford 1-(4-methylpiperazin-1-yl)-2-(3-((2-(4-methylthiazol-2-ylamino)pyridin-3-yloxy)methyl)phenoxy)ethanone dihydrochloride (51.3 mg, 64.2% yield) as a white solid after HCl salt formation. $^1$H NMR (d$_6$-DMSO) δ 11.64 (bs, 2H), 8.00 (dd, 1H), 7.67 (d, 1H), 7.28 (m, 2H), 7.17 (m, 2H), 6.91 (m, 2H), 5.33 (s, 2H), 4.97 (d, 2H), 4.39 (m, 1H), 4.08 (m, 2H), 3.59 (m, 1H), 3.40 (m, 2H), 3.14 (m, 2H), 2.96 (m, 1H), 2.75 (s, 3H), 2.35 (s, 3H). Mass spectrum (apci) m/z=454.2 (M+H-2HCl).

Example 28

N-(2-(Dimethylamino)ethyl)-2-(3-((2-(4-methylthiazol-2-ylamino)pyridin-3-yloxy)methyl)phenoxy)acetamide dihydrochloride

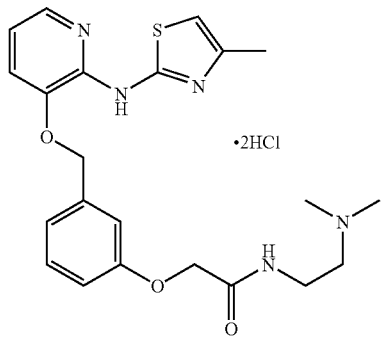 [SMILES: Cc1csc(Nc2ncccc2OCc2cccc(OCC(=O)NCCN(C)C)c2)n1 ; "·2HCl"]

2-(3-((2-(4-Methylthiazol-2-ylamino)pyridin-3-yloxy)methyl)phenoxy)acetic acid trifluoroacetate (prepared according to Example 26; 70 mg, 0.14 mmol), triethylamine (0.10 mL, 0.72 mmol) ethyl chloroformate (0.035 mL, 0.36 mmol) and N1,N1-dimethylethane-1,2-diamine (0.079 mL, 0.72 mmol) were reacted according to the method of Example 30 to provide N-(2-(dimethylamino)ethyl)-2-(3-((2-(4-methylthiazol-2-ylamino)pyridin-3-yloxy)methyl)phenoxy)acetamide dihydrochloride (43.8 mg, 56.1% yield) as a white solid after HCl salt formation. $^1$H NMR ($d_6$-DMSO) δ 11.54 (bs, 1H), 10.76 (bs, 1H), 8.54 (t, 1H), 8.00 (d, 1H), 7.66 (d, 1H), 7.32 (m, 2H), 7.18 (m, 2H), 6.97 (dd, 1H), 6.93 (s, 1H), 5.34 (s, 2H), 4.60 (s, 2H), 3.53 (q, 2H), 3.19 (q, 2H), 2.76 (s, 6H), 2.35 (s, 3H). Mass spectrum (apci) m/z 442.1 (M+H-2HCl).

Example 29

N-(2-(1H-imidazol-5-yl)ethyl)-2-(3-((2-(4-methylthiazol-2-ylamino)pyridin-3-yloxy)methyl)phenoxy)acetamide dihydrochloride

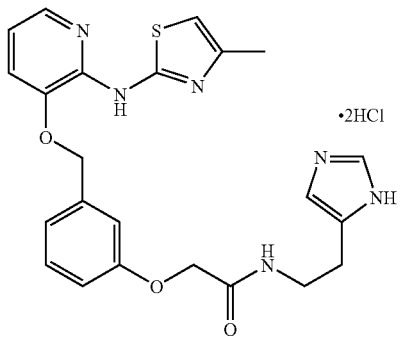 [SMILES: Cc1csc(Nc2ncccc2OCc2cccc(OCC(=O)NCCc3cnc[nH]3)c2)n1 ; "·2HCl"]

2-(3-((2-(4-Methylthiazol-2-ylamino)pyridin-3-yloxy)methyl)phenoxy)acetic acid trifluoroacetate (prepared according to Example 27; 70 mg, 0.14 mmol), triethylamine (0.10 mL, 0.72 mmol) ethyl chloroformate (0.035 mL, 0.36 mmol) and 2-(1H-imidazol-5-yl)ethanamine (80 mg, 0.72 mmol) were reacted according to the method of Example 29 to provide N-(2-(1H-imidazol-5-yl)ethyl)-2-(3-((2-(4-methylthiazol-2-ylamino)pyridin-3-yloxy)methyl)phenoxy)acetamide dihydrochloride (32.7 mg, 40.0% yield) as a white solid after HCl salt formation. $^1$H NMR ($d_6$-DMSO) δ 9.02 (d, 1H), 8.39 (t, 1H), 8.00 (dd, 1H), 7.66 (d, 1H), 7.40 (s, 1H), 7.30 (m, 2H), 7.19 (d, 1H), 7.16 (dd, 1H), 6.93 (s, 1H), 6.88 (dd, 1H), 5.33 (s, 2H), 4.52 (s, 2H), 3.45 (q, 2H), 2.86 (t, 2H), 2.35 (s, 3H). Mass spectrum (apci) m/z=465.2 (M+H-2HCl).

Example 30

2-(2-(3-((2-(4-methylthiazol-2-ylamino)pyridin-3-yloxy)methyl)phenoxy)acetamido)acetic acid hydrochloride

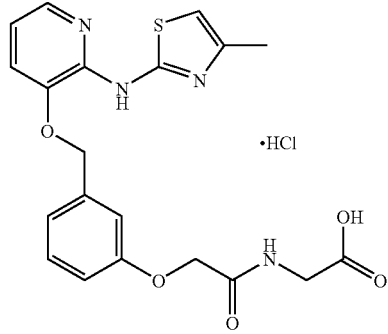 [SMILES: Cc1csc(Nc2ncccc2OCc2cccc(OCC(=O)NCC(=O)O)c2)n1 ; Cl]

2-(3-((2-(4-Methylthiazol-2-ylamino)pyridin-3-yloxy)methyl)phenoxy)acetic acid trifluoroacetate (prepared according to Example 26; 70 mg, 0.14 mmol), triethylamine (0.10 mL, 0.72 mmol), ethyl chloroformate (0.035 mL, 0.36 mmol) and tert-butyl 2-aminoacetate hydrochloride (120 mg, 0.72 mmol) were reacted according to the method of Example 30 to provide 2-(2-(3-((2-(4-methylthiazol-2-ylamino)pyridin-3-yloxy)methyl)phenoxy)acetamido)acetic acid hydrochloride (43.1 mg, 61.1% yield) as a white solid after HCl salt formation. $^1$H NMR ($d_6$-DMSO) δ 10.75 (bs, 1H), 8.54 (t, 1H), 7.95 (d, 1H), 7.55 (d, 1H), 7.35 (d, 1H), 7.22 (m, 1H), 7.17 (d, 1H), 7.06 (dd, 1H), 6.96 (dd, 1H), 6.78 (s, 1H), 5.29 (s, 2H), 4.57 (s, 2H), 3.90 (d, 1H), 3.62 (s, 2H), 2.30 (s, 3H). Mass spectrum (apci) m/z=443.0 (M+H-HCl).

Example 31

3-(Benzyloxy)-N-(4-methylthiazol-2-yl)-5-(phenylthio)pyridin-2-amine hydrochloride

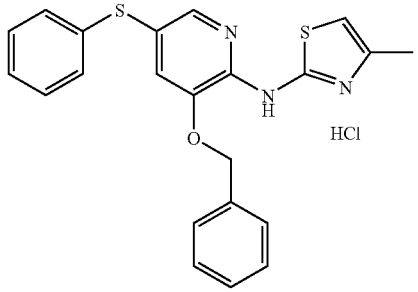 [SMILES: Cc1csc(Nc2ncc(Sc3ccccc3)cc2OCc2ccccc2)n1 ; Cl]

3-(Benzyloxy)-5-bromo-N-(4-methylthiazol-2-yl)pyridin-2-amine (prepared according to Example 1; 0.350 g, 0.930 mmol), MeLi (0.727 mL, 1.16 mmol), butyllithium (0.465 mL 1.16 mmol), and 1,2-diphenyldisulfane (0.203 g, 0.930 mmol) were reacted according to the method of Example 7 to provide 3-(benzyloxy)-N-(4-methylthiazol-2-yl)-5-(phenylthio)pyridin-2-amine hydrochloride (0.182 g, 48.2% yield) after reverse phase purification. $^1$H NMR (DMSO-d$_6$) δ 8.00 (d, 1H), 7.63 (d, 1H), 7.54 (m, 2H), 7.35 (m, 5H), 7.26 (m, 1H), 7.20 (m, 2H), 6.83 (s, 1H), 5.33 (s, 2H), 2.31 (s, 3H). Mass spectrum (apci) m/z=406.1 (M+H-HCl).

Example 32

3-(Benzyloxy)-5-(cyclohexylthio)-N-(4-methylthiazol-2-yl)pyridin-2-amine hydrochloride

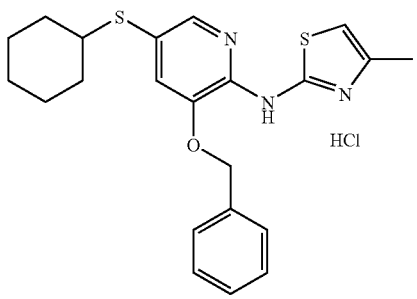 [SMILES: Cc1csc(Nc2ncc(SC3CCCCC3)cc2OCc2ccccc2)n1 ; Cl]

3-(Benzyloxy)-5-bromo-N-(4-methylthiazol-2-yl)pyridin-2-amine (prepared according to Example 1) (0.350 g, 0.930 mmol), MeLi (0.727 mL, 1.16 mmol), butyllithium (0.465 mL 1.16 mmol), and 1,2-dicyclohexyldisulfane (0.214 g, 0.930 mmol) were reacted according to the method of Example 7 to provide 3-(benzyloxy)-5-(cyclohexylthio)-N-(4-methylthiazol-2-yl)pyridin-2-amine hydrochloride (0.028 g, 7.31% yield) after reverse phase purification. $^1$H NMR (DMSO-d$_6$) δ 7.91 (d, 1H), 7.57 (m, 2H), 7.52 (d, 1H), 7.40 (m, 2H), 7.34 (m, 1H), 6.76 (s, 1H), 5.36 (s, 2H), 3.07 (m, 1H), 2.29 (d, 3H), 1.77 (m, 2H), 1.66 (m, 2H), 1.54 (m, 1H), 1.20 (m, 5H). Mass spectrum (apci) m/z=412.1 (M+H-HCl).

Example 33

Methyl 3-(2-(3-(benzyloxy)pyridin-2-ylamino)thiazol-4-yl)propanoate

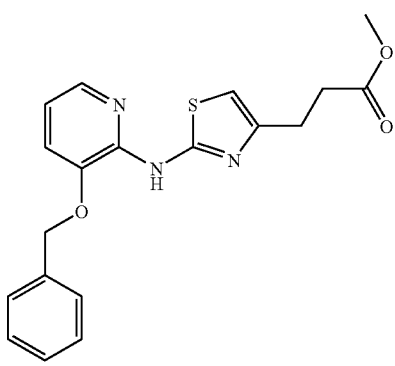 [SMILES: COC(=O)CCc1csc(Nc2ncccc2OCc2ccccc2)n1]

1-(3-(Benzyloxy)pyridin-2-yl)thiourea (3.30 g, 12.7 mmol), methyl 5-bromo-4-oxopentanoate (3.19 g, 15.3 mmol) (prepared according to Synthetic Communications (1994) 2557-2562), and triethylamine (3.10 mL, 22.3 mmol) were heated in methanol (100 mL) at reflux for 3 hours according to the method of Example 2, Step C, to provide methyl 3-(2-(3-(benzyloxy)pyridin-2-ylamino)thiazol-4-yl)propanoate (3.82 g, 81.3% yield) as a light yellow powder: $^1$H NMR (DMSO-d$_6$) δ 9.93 (bs, 1H), 7.86 (d, 1H), 7.57 (d, 2H), 7.34-7.42 (m, 4H), 6.89 (m, 1H), 6.63 (s, 1H), 5.26 (s, 2H), 3.60 (s, 3H), 2.85 (t, 2H), 2.69 (t, 2H). Mass spectrum (esi) m/z=370 (100).

Example 34

3-((3H-Benzo[d]imidazol-4-yl)methoxy)-N-(4-methylthiazol-2-yl)pyridin-2-amine dihydrochloride

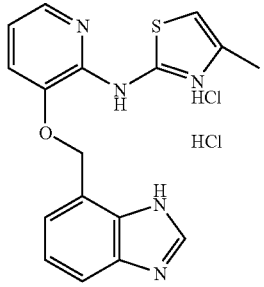

2-(4-Methylthiazol-2-ylamino)pyridin-3-ol (prepared according to Example 3, Step A; 70 mg, 0.338 mmol), potassium carbonate (117 mg, 0.844 mmol) and tert-butyl 4-(bromomethyl)-1H-benzo[d]imidazole-1-carboxylate (105 mg, 0.338 mmol) [Moon, M., J. Med. Chem. (1992), 35(6), 1076] were reacted according to the method of Example 3, Steps B and C, to provide 3-((3H-benzo[d]imidazol-4-yl)methoxy)-N-(4-methylthiazol-2-yl)pyridin-2-amine dihydrochloride (19.6 mg, 14.1% yield) as a white solid after HCl salt formation. $^1$H NMR (d$_6$-DMSO) δ 9.72 (s, 1H), 7.97 (d, 1H), 7.90 (d, 1H), 7.88 (d, 1H), 7.66 (d, 1H), 7.61 (t, 1H), 7.09 (dd, 1H), 6.79 (s, 1H), 5.70 (s, 2H), 2.29 (s, 3H). Mass spectrum (apci) m/z=338.1 (M+H-2HCl).

Example 35

N-(4-Methylthiazol-2-yl)-3-(quinoxalin-5-ylmethoxy)pyridin-2-amine hydrochloride

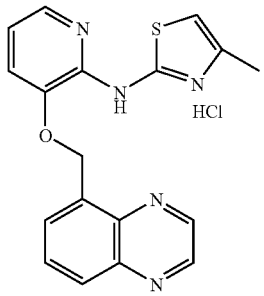 [SMILES: Cc1csc(Nc2ncccc2OCc2cccc3nccnc23)n1 ; Cl]

2-(4-Methylthiazol-2-ylamino)pyridin-3-ol (prepared according to Example 3, Step A; 70 mg, 0.338 mmol), potassium carbonate (117 mg, 0.844 mmol) and 5-(bromomethyl)quinoxaline (75.3 mg, 0.338 mmol) [Hardie, M. J., Org. Biomol. Chem. (2004), 2(20), 2958] were reacted according to Example 3, Steps B and C, to provide N-(4-methylthiazol-2-yl)-3-(quinoxalin-5-ylmethoxy)pyridin-2-amine hydrochloride (41.1 mg, 31.5% yield) as a yellow solid after HCl salt formation. $^1$H NMR (d$_6$-DMSO) δ 9.12 (d, 1H), 9.07 (d, 1H), 8.26 (d, 1H), 8.16 (d, 1H), 8.04 (d, 1H), 7.93 (t, 1H), 7.73 (d, 1H), 7.15 (dd, 1H), 6.85 (s, 1H), 5.88 (s, 2H), 2.33 (s, 3H). Mass spectrum (apci) m/z=350.0 (M+H-HCl).

Example 36

3-(Benzyloxy)-N-(4-methylthiazol-2-yl)-5-(pyridin-3-yl)pyridin-2-amine dihydrochloride

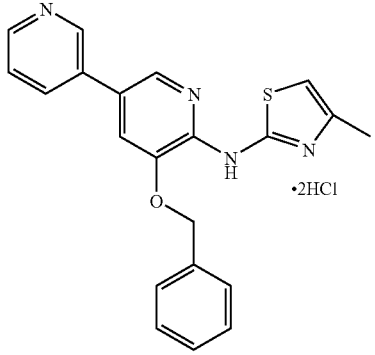 [SMILES: Cc1csc(Nc2ncc(-c3cccnc3)cc2OCc2ccccc2)n1 ; "·2HCl"]

3-(Benzyloxy)-5-bromo-N-(4-methylthiazol-2-yl)pyridin-2-amine (prepared according to Example 1; 0.125 g, 0.332 mmol), pyridin-3-ylboronic acid (0.0490 g, 0.399 mmol), bis(triphenylphosphine)palladium(II) chloride (0.00700 g, 0.00997 mmol), and sodium carbonate (0.106 g, 0.997 mmol) were combined in DME (10 mL), and water (5 mL) and heated overnight at 80° C. The reaction mixture was cooled and partitioned between dichloromethane and water. The layers were separated, and the organic layer was dried, filtered, and concentrated. The residue was purified by silica gel chromatography to afford the title compound as the free base. The free base was dissolved in dichloromethane and 2M HCl in ether was added. The mixture was concentrated to afford 3-(benzyloxy)-N-(4-methylthiazol-2-yl)-5-(pyridin-3-yl)pyridin-2-amine dihydrochloride (0.109 g, 87.6% yield). $^1$H NMR (DMSO-$d_6$) δ 9.27 (m, 1H), 8.81 (d, 1H), 8.75 (d, 1H), 8.48 (d, 1H), 8.08 (m, 1H), 7.97 (m, 1H), 7.66 (d, 2H), 7.43 (m, 2H), 7.37 (m, 1H), 6.82 (s, 1H), 5.45 (s, 2H), 2.31 (s, 3H). Mass spectrum (apci) m/z=375.1 (M+H-2HCl).

Example 37

3-(Benzyloxy)-N-(4-methylthiazol-2-yl)-5-(pyridin-4-Ylpyridin-2-amine dihydrochloride

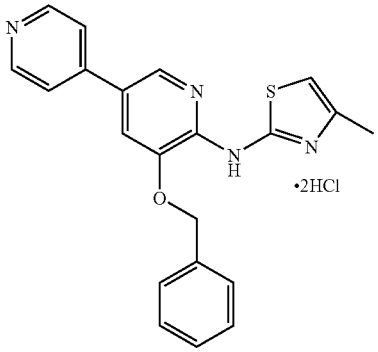 [SMILES: Cc1csc(Nc2ncc(-c3ccncc3)cc2OCc2ccccc2)n1 ; "·2HCl"]

3-(Benzyloxy)-5-bromo-N-(4-methylthiazol-2-yl)pyridin-2-amine (prepared according to Example 1; 0.125 g, 0.332 mmol), pyridin-4-ylboronic acid (0.0490 g, 0.399 mmol), bis(triphenylphosphine)palladium(II) chloride (0.00700 g, 0.00997 mmol), and sodium carbonate (0.106 g, 0.997 mmol) were combined in DME (10 mL) and water (5 mL) and heated overnight at 80° C. The reaction mixture was cooled and partitioned between dichloromethane and water. The layers were separated, and the organic layer was dried, filtered, and concentrated. The residue was purified by silica gel chromatography to afford the title compound as the free base. The free base was dissolve in dichloromethane, and 2M HCl in ether was added. The mixture was concentrated to afford 3-(benzyloxy)-N-(4-methylthiazol-2-yl)-5-(pyridin-3-yl)pyridin-2-amine dihydrochloride (0.109 g, 87.6% yield). $^1$H NMR (DMSO-$d_6$) δ 8.89 (d, 2H), 8.68 (d, 1H), 8.40 (d, 2H), 8.04 (m, 1H), 7.65 (d, 2H), 7.43 (m, 2H), 7.36 (m, 1H), 6.74 (s, 1H), 5.44 (s, 2H), 2.28 (s, 3H). Mass spectrum (apci) m/z=375.1 (M+H-2HCl).

Example 38

3,5-Bis(benzyloxy)-N-(4-methylthiazol-2-yl)pyridin-2-amine hydrochloride

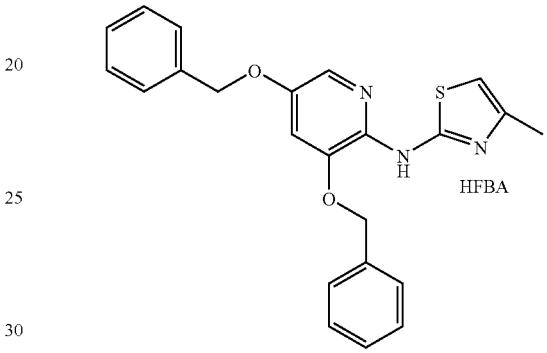

5-(Benzyloxy)-6-(4-methylthiazol-2-ylamino)pyridin-3-ol (prepared according to Example 12, Step A; 0.073 g, 0.233 mmol) and potassium carbonate (0.0724 g, 0.524 mmol) were placed in DMF (3 mL). 1-(Bromomethyl)benzene (0.0398 g, 0.233 mmol) was added and the reaction mixture was stirred at room temperature overnight. Water was added and the reaction mixture was extracted with ether. The organic layer was separated, dried, filtered, and concentrated. The residue was purified by silica gel chromatography (15-20% EtOAc in hexanes) to give 30 mg of crude product. The crude product was purified by reverse phase chromatography to provide 3,5-bis(benzyloxy)-N-(4-methylthiazol-2-yl)pyridin-2-amine HFBA salt (0.01 g, 10.6% yield). $^1$H NMR (DMSO-$d_6$) δ 7.69 (d, 1H), 7.56 (m, 2H), 7.40 (m, 9H), 7.30 (s, 1H), 5.28 (s, 2H), 5.14 (s, 2H), 2.25 (s, 3H). Mass spectrum (apci) m/z 404.1 (M+H-HFBA).

Example 39

2-(2-(3-(Benzyloxy)pyridin-2-ylamino)thiazol-4-yl)-1-(4-methylpiperazin-1-yl)ethanone dihydrochloride

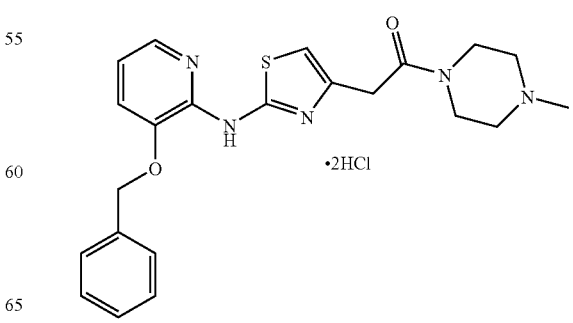

A 100 mL round-bottomed flask was charged with 2-(2-(3-(benzyloxy)pyridin-2-ylamino)thiazol-4-yl)acetic acid (prepared according to Example 24; 0.050 g, 0.1465 mmol) and THF (30 mL) and cooled to −5° C. Triethylamine (0.03112 g, 0.3076 mmol) and ethyl carbonochloridate (0.07002 mL, 0.7323 mmol) were added successively, and the reaction mixture was stirred at −5° C. for 30 minutes. 1-Methylpiperazine (0.07335 g, 0.7323 mmol) was added, and the reaction mixture was stirred at −5° C. for 30 minutes and then at room temperature for 1 hour. The reaction mixture was washed with water, the organic layer was separated, dried and concentrated, and the residue was purified first by silica gel chromatography and then by reverse phase chromatography to give the title compound as the free base. The free base was dissolved in dichloromethane, and 2M HCl in ether was added. The mixture was concentrated to provide 2-(2-(3-(benzyloxy)pyridin-2-ylamino)thiazol-4-yl)-1-(4-methylpiperazin-1-yl)ethanone dihydrochloride (0.024 g, 33.01% yield). $^1$H NMR (DMSO-d6) δ 10.35 (bs, 1H), 10.11 (bs, 1H), 7.89 (dd, 1H), 7.57 (m, 2H), 7.42 (m, 3H), 7.35 (m, 1H), 6.95 (m, 1H), 6.81 (s, 1H), 5.28 (s, 2H), 4.45 (m, 1H), 4.21 (m, 1H), 3.79 (s, 2H), 3.41 (m, 3H), 2.98 (m, 3H), 2.78 (d, 3H). Mass spectrum (apci) m/z=424.2 (M+H-2HCl).

Example 40

2-(2-(3-(Benzyloxy)pyridin-2-ylamino)thiazol-4-yl) acetamide hydrochloride

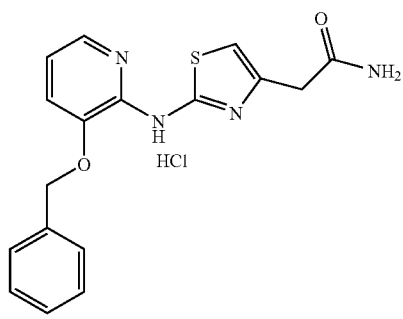 [SMILES: NC(=O)Cc1csc(Nc2ncccc2OCc2ccccc2)n1 ; Cl]

A 100 mL round-bottomed flask was charged with 2-(2-(3-(benzyloxy)pyridin-2-ylamino)thiazol-4-yl)acetic acid (prepared according to Example 24; 0.050 g, 0.1465 mmol) and THF (30 mL) and cooled to −5° C. Triethylamine (0.03112 g, 0.3076 mmol) and ethyl carbonochloridate (0.07002 mL, 0.7323 mmol) were added successively, and the reaction mixture was stirred at −5° C. for 30 minutes. 7M NH$_3$ in methanol (2.186 mL, 15.31 mmol) was added and the reaction mixture was stirred at −5° C. for 30 minutes and then at room temperature for 1 hour. The reaction mixture was washed with water, the organic layer was separated, dried and concentrated, and the residue was purified first by silica gel chromatography and then by reverse phase chromatography to give the title compound as the free base. The free base was dissolved in dichloromethane, and then 2M HCl in ether was added. The mixture was concentrated to provide 2-(2-(3-(benzyloxy)pyridin-2-ylamino)thiazol-4-yl)-1-(4-methylpiperazin-1-yl)ethanone hydrochloride (0.024 g, 33.01% yield). $^1$H NMR (DMSO-d$_6$) δ 11.04 (bs, 1H), 7.97 (d, 1H), 7.59 (m, 4H), 7.42 (m, 2H), 7.36 (m, 1H), 7.17 (bs, 1H), 7.10 (m, 1H), 6.96 (s, 1H), 5.33 (s, 2H), 3.57 (s, 2H). Mass spectrum (apci) m/z=341.0 (M+H-HCl).

Example 41

3-(Benzyloxy)-N-(4-methylthiazol-2-yl)-5-(phenylsulfinyl)pyridin-2-amine hydrochloride

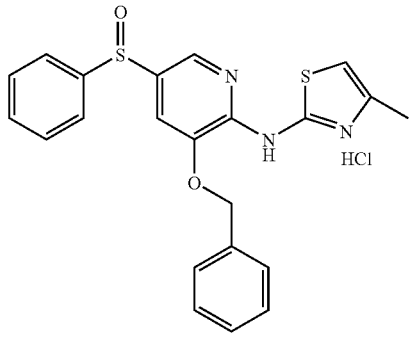 [SMILES: Cc1csc(Nc2ncc(S(=O)c3ccccc3)cc2OCc2ccccc2)n1 ; Cl]

3-(Benzyloxy)-N-(4-methylthiazol-2-yl)-5-(phenylthio) pyridin-2-amine (0.049 g, 0.121 mmol) (prepared according to Example 7; 0.049 g, 0.121 mmol) and MCPBA (0.0398 g, 0.166 mmol) were reacted according to Example 8 to provide 3-(benzyloxy)-N-(4-methylthiazol-2-yl)-5-(phenylsulfinyl) pyridin-2-amine hydrochloride (0.028 g, 50.6% yield). $^1$H NMR (DMSO-d$_6$) δ 8.25 (d, 1H), 7.70 (m, 2H), 7.59 (s, 1H), 7.56 (m, 5H), 7.34 (m, 3H), 6.79 (s, 1H), 5.31 (s, 2H), 2.28 (s, 3H). Mass spectrum (apci) m/z=422.0 (M+H-HCl).

Example 42

Methyl 3-(5-(benzyloxy)-6-(4-methylthiazol-2-ylamino)pyridin-3-ylthio)propanoate

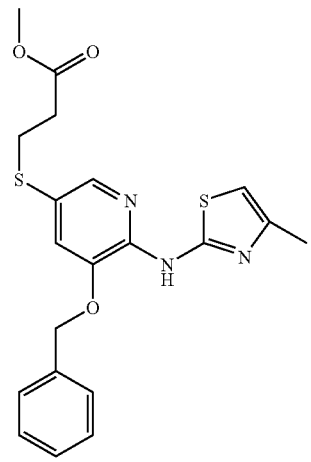 [SMILES: COC(=O)CCSc1cnc(Nc2nc(C)cs2)c(OCc2ccccc2)c1]

A nitrogen purged 50 mL round-bottomed flask was charged with 3-(benzyloxy)-5-bromo-N-(4-methylthiazol-2-yl)pyridin-2-amine (prepared according to Example 1; 1.50 g, 3.99 mmol), Pd$_2$dba$_3$ (0.091 g, 0.099 mmol), 4,5-bis(diphenylphosphino)-9,9-dimethyl-9H-xanthene (0.115 g, 0.199 mmol), and dioxane (20 mL). N-ethyl-N-isopropylpropan-2-amine (1.4 ml, 8.0 mmol) and methyl 3-mercaptopropanoate (0.49 mL, 4.4 mmol) were added and the flask was plunged into a 100° C. oil bath for 2 hours. The reaction mixture was cooled to room temperature and solvent removed. The residue was purified on silica gel (20 to 30% ethyl acetate/hexanes) to afford methyl 3-(5-(benzyloxy)-6-(4-methylthiazol-2-ylamino)pyridin-3-ylthio)propanoate (1.30 g, 78.5% yield) as a white solid. $^1$H NMR (CDCl$_3$) δ 8.57 (bs, 1H), 8.04 (d, 1H), 7.41 (m, 5H), 7.22 (d, 1H), 6.42 (s, 1H), 5.12 (s, 2H), 3.68 (s, 3H), 3.03 (t, 2H), 2.56 (t, 2H), 2.32 (s, 3H); Mass spectrum (apci) m/z=325.0 (100) 416.0 (50).

Example 43

5-(2-Chlorobenzylthio)-3-(benzyloxy)-N-(4-methylthiazol-2-yl)pyridin-2-amine hydrochloride

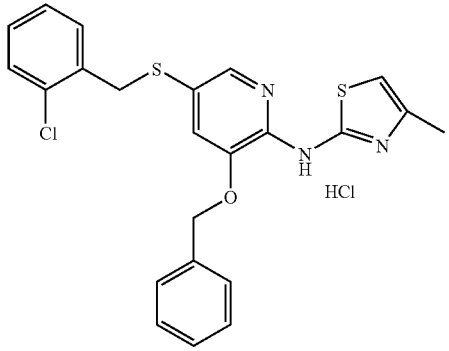 [SMILES: Cc1csc(Nc2ncc(SCc3ccccc3Cl)cc2OCc2ccccc2)n1 ; Cl]

A 1 dram vial was charged with methyl 3-(5-(benzyloxy)-6-(4-methylthiazol-2-ylamino)pyridin-3-ylthio)propanoate (prepared according to Example 42; 70 mg, 0.17 mmol). THF (1 mL) and KOtBu (0.59 mL, 0.59 mmol) were added and the reaction mixture was stirred at room temperature for 5 minutes. 1-(Bromomethyl)-2-chlorobenzene (0.024 mL, 0.19 mmol) was added and the reaction mixture was stirred at room temperature for 30 minutes. Saturated aqueous NH$_4$Cl (1 mL) was added and the reaction mixture was stirred for 10 minutes. The phases were separated and the aqueous phases were washed with EtOAc. The combined organic layers were concentrated and purified on silica gel to afford 5-(2-chlorobenzylthio)-3-(benzyloxy)-N-(4-methylthiazol-2-yl)pyridin-2-amine hydrochloride (48.2 mg, 58.3% yield) as a white solid after HCl salt formation. $^1$H NMR (d$_6$-DMSO) δ 7.80 (d, 1H), 7.60-7.55 (m, 3H), 7.46-7.34 (m, 4H), 7.27 (td, 1H), 7.18 (td, 1H), 7.10 (dd, 1H), 6.81 (q, 1H), 5.31 (s, 2H), 4.22 (s, 2H), 2.30 (d, 3H); Mass spectrum (apci) m/z=238.0 (100), 454.0 (90), 362.9 (80).

Example 44

5-(3-Chlorobenzylthio)-3-(benzyloxy)-N-(4-methylthiazol-2-yl)pyridin-2-amine hydrochloride

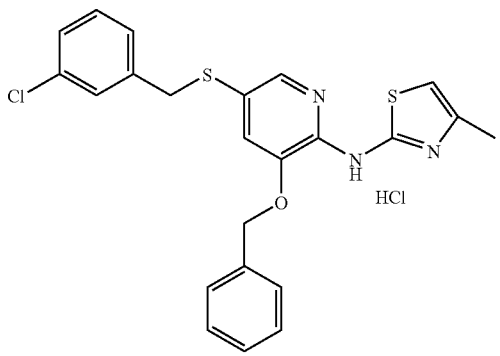 [SMILES: Cc1csc(Nc2ncc(SCc3cccc(Cl)c3)cc2OCc2ccccc2)n1 ; Cl]

Methyl 3-(5-(benzyloxy)-6-(4-methylthiazol-2-ylamino)pyridin-3-ylthio)propanoate (prepared according to Example 42; 70 mg, 0.17 mmol), KOtBu (0.59 mL, 0.59 mmol) and 1-(bromomethyl)-3-chlorobenzene (0.022 mL, 0.17 mmol) were reacted according to the method of Example 43 to afford 5-(3-chlorobenzylthio)-3-(benzyloxy)-N-(4-methylthiazol-2-yl)pyridin-2-amine hydrochloride (64.2 mg, 77.70% yield) as a white solid after HCl salt formation. $^1$H NMR (d$_6$-DMSO) δ 10.85 (bs, 1H), 7.80 (d, 1H), 7.60-7.53 (m, 3H), 7.45-7.33 (m, 3H), 7.31-7.25 (m, 3H), 7.12 (m, 1H), 6.78 (s, 1H), 5.29 (s, 2H), 4.19 (s, 2H), 2.29 (d, 3H); Mass spectrum (apci) m/z=238.0 (100), 454.0 (95), 362.9 (80).

Example 45

5-(4-Chlorobenzylthio)-3-(benzyloxy)-N-(4-methylthiazol-2-yl)pyridin-2-amine hydrochloride

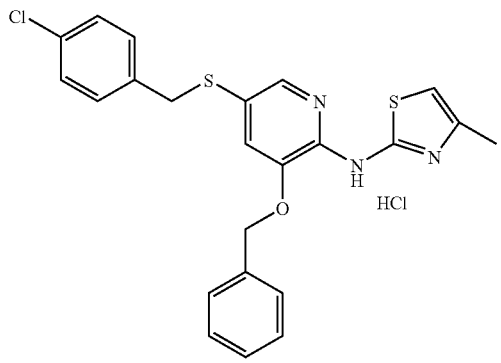 [SMILES: Cc1csc(Nc2ncc(SCc3ccc(Cl)cc3)cc2OCc2ccccc2)n1 ; Cl]

Methyl 3-(5-(benzyloxy)-6-(4-methylthiazol-2-ylamino)pyridin-3-ylthio)propanoate (prepared according to Example 42; 70 mg, 0.17 mmol), KOtBu (0.59 mL, 0.59 mmol) and 1-chloro-4-(chloromethyl)benzene (27 mg, 0.17 mmol) were reacted according to the method of Example 43 to afford 5-(4-chlorobenzylthio)-3-(benzyloxy)-N-(4-methylthiazol-2-yl)pyridin-2-amine hydrochloride (57.2 mg, 69.2% yield) as a white solid after HCl salt formation. $^1$H NMR (d$_6$-DMSO) δ 10.85 (bs, 1H), 7.79 (d, 1H), 7.57 (m, 2H), 7.53 (d, 1H), 7.45-7.34 (m, 3H), 7.30 (m, 2H), 7.18 (m, 2H), 6.78 (s, 1H), 5.29 (s, 2H), 4.17 (s, 2H), 2.29 (d, 3H); Mass spectrum (apci) m/z=238.0 (100), 454.0 (75), 362.9 (60).

Example 46

3-(Benzyloxy)-N-(4-methylthiazol-2-yl)-5-(pyridin-2-ylmethylthio)pyridin-2-amine dihydrochloride

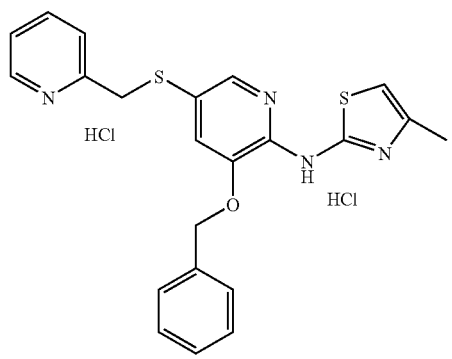 [SMILES: Cc1csc(Nc2ncc(SCc3ccccn3)cc2OCc2ccccc2)n1 ; Cl ; Cl]

Methyl 3-(5-(benzyloxy)-6-(4-methylthiazol-2-ylamino) pyridin-3-ylthio)propanoate prepared according to Example 42; 70 mg, 0.17 mmol), KOtBu (0.59 mL, 0.59 mmol) and 2-(bromomethyl)pyridine hydrobromide (42.6 mg, 0.17 mmol) were reacted according to the method of Example 43 to afford 3-(benzyloxy)-N-(4-methylthiazol-2-yl)-5-(pyridin-2-ylmethylthio)pyridin-2-amine dihydrochloride (51.6 mg, 62.1% yield) as a white solid after HCl salt formation. $^1$H NMR (d$_6$-DMSO) δ 10.80 (bs, 1H), 8.63 (d, 1H), 8.04 (t, 1H), 7.81 (d, 1H), 7.60-7.53 (m, 4H), 7.49-7.34 (m, 4H), 6.76 (s, 1H), 5.30 (s, 2H), 4.42 (s, 2H), 2.28 (d, 3H); Mass spectrum (apci) m/z=330.0 (100), 421.0 (95), 238.0 (50).

Example 47

3-(Benzyloxy)-N-(4-methylthiazol-2-yl)-5-(pyridin-3-ylmethylthio)pyridin-2-amine dihydrochloride

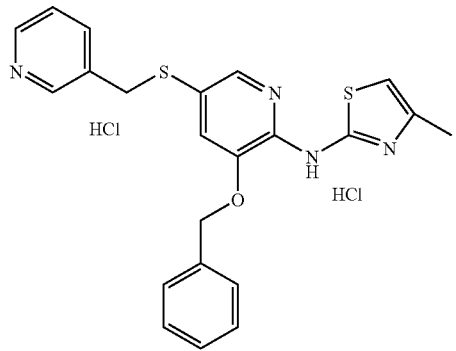 [SMILES: Cc1csc(Nc2ncc(SCc3cccnc3)cc2OCc2ccccc2)n1 ; Cl ; Cl]

Methyl 3-(5-(benzyloxy)-6-(4-methylthiazol-2-ylamino) pyridin-3-ylthio)propanoate (prepared according to Example 42; 70 mg, 0.17 mmol), KOtBu (0.59 mL, 0.59 mmol) and 3-(chloromethyl)pyridine hydrochloride (27.6 mg, 0.17 mmol were reacted according to the method of Example 43 to afford 3-(benzyloxy)-N-(4-methylthiazol-2-yl)-5-(pyridin-3-ylmethylthio)pyridin-2-amine dihydrochloride (44.2 mg, 53.2% yield) as a white solid after HCl salt formation. $^1$H NMR (d$_6$-DMSO) δ 8.68 (dd, 1H), 8.65 (d, 1H), 8.11 (m, 1H), 7.80-7.75 (m, 2H), 7.60-7.55 (m, 3H), 7.45-7.34 (m, 3H), 6.75 (s, 1H), 5.30 (s, 2H), 4.34 (s, 2H), 2.28 (d, 3H); Mass spectrum (apci) m/z=238.0 (100), 330.0 (70), 421.0 (60).

Example 48

3-(Benzyloxy)-N-(4-methylthiazol-2-yl)-5-(pyridin-4-ylmethylthio)pyridin-2-amine dihydrochloride

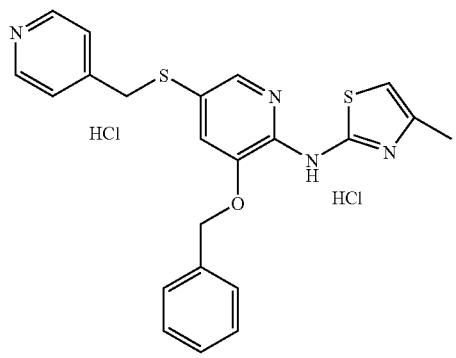 [SMILES: Cc1csc(Nc2ncc(SCc3ccncc3)cc2OCc2ccccc2)n1 ; Cl ; Cl]

Methyl 3-(5-(benzyloxy)-6-(4-methylthiazol-2-ylamino) pyridin-3-ylthio)propanoate (prepared according to Example 42; 70 mg, 0.17 mmol), KOtBu (0.59 mL, 0.59 mmol) and 4-(chloromethyl)pyridine hydrochloride (27.6 mg, 0.17 mmol) were reacted according to the method of Example 43 to afford 3-(benzyloxy)-N-(4-methylthiazol-2-yl)-5-(pyridin-4-ylmethylthio)pyridin-2-amine dihydrochloride (47.9 mg, 57.6% yield) as a white solid after HCl salt formation. $^1$H NMR (d$_6$-DMSO) δ 8.72 (m, 2H), 7.77 (d, 1H), 7.71 (m, 2H), 7.58 (m, 3H), 7.45-7.34 (m, 3H), 6.73 (s, 1H), 5.30 (s, 2H), 4.42 (s, 2H), 2.27 (d, 3H); Mass spectrum (apci) m/z=421.0 (100), 330.0 (45), 238.0 (40).

Example 49

5-(2-Methoxybenzylthio)-3-(benzyloxy)-N-(4-methylthiazol-2-yl)pyridin-2-amine hydrochloride

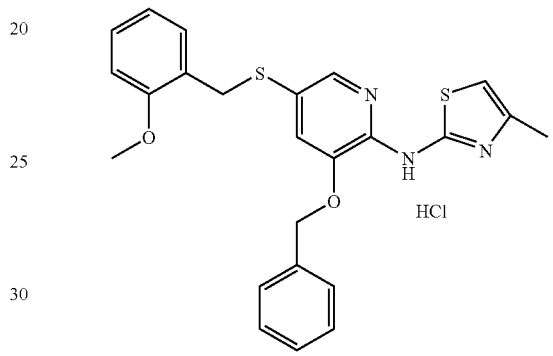

Methyl 3-(5-(benzyloxy)-6-(4-methylthiazol-2-ylamino) pyridin-3-ylthio)propanoate (prepared according to Example 42; 70 mg, 0.17 mmol), KOtBu (0.59 mL, 0.59 mmol) and 1-(chloromethyl)-2-methoxybenzene (0.023 mL, 0.17 mmol) were reacted according to the method of Example 43 to afford 5-(2-methoxybenzylthio)-3-(benzyloxy)-N-(4-methylthiazol-2-yl)pyridin-2-amine hydrochloride (63.3 mg, 77.3% yield) as a white solid after HCl salt formation. $^1$H NMR (d$_6$-DMSO) δ 7.79 (d, 1H), 7.57 (m, 2H), 7.49 (d, 1H), 7.45-7.33 (m, 3H), 7.23 (m, 1H), 6.98 (m, 2H), 6.79 (m, 2H), 5.28 (s, 2H), 4.09 (s, 2H), 3.74 (s, 3H), 2.29 (s, 3H); Mass spectrum (apci) m/z=450.0 (100), 359.0 (45), 238.0 (40).

Example 50

5-(3-Methoxybenzylthio)-3-(benzyloxy)-N-(4-methylthiazol-2-yl)pyridin-2-amine hydrochloride

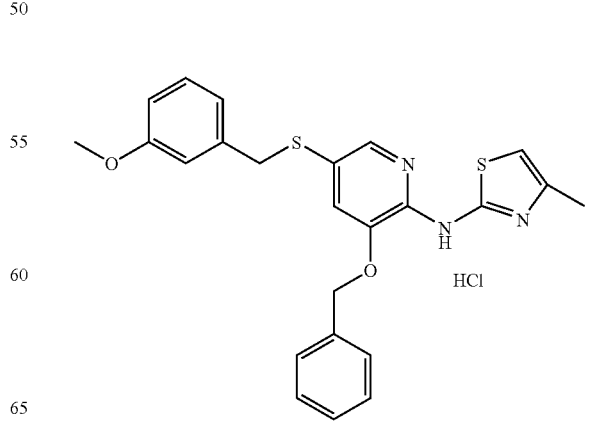

Methyl 3-(5-(benzyloxy)-6-(4-methylthiazol-2-ylamino)pyridin-3-ylthio)propanoate (prepared according to Example 42; 70 mg, 0.17 mmol), KOtBu (0.59 mL, 0.59 mmol) and 1-(chloromethyl)-3-methoxybenzene (0.024 mL, 0.17 mmol) were reacted according to the method of Example 43 to afford 5-(3-methoxybenzylthio)-3-(benzyloxy)-N-(4-methylthiazol-2-yl)pyridin-2-amine hydrochloride (61.7 mg, 75.4% yield) as a white solid after HCl salt formation. $^1$H NMR (d$_6$-DMSO) δ 7.84 (d, 1H), 7.57 (m, 3H), 7.44-7.33 (m, 3H), 7.17 (t, 3H), 6.80 (m, 4H), 5.29 (s, 2H), 4.17 (s, 2H), 3.68 (s, 3H), 2.30 (s, 3H); Mass spectrum (apci) m/z=450.0 (100), 359.0 (80), 238.0 (75).

Example 51

5-(4-Methoxybenzylthio)-3-(benzyloxy)-N-(4-methylthiazol-2-yl)pyridin-2-amine hydrochloride

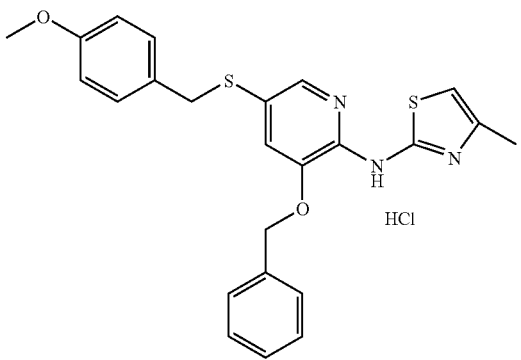

Methyl 3-(5-(benzyloxy)-6-(4-methylthiazol-2-ylamino)pyridin-3-ylthio)propanoate (prepared according to Example 42; 70 mg, 0.17 mmol), KOtBu (0.59 mL, 0.59 mmol) and 1-(chloromethyl)-4-methoxybenzene (0.023 mL, 0.17 mmol) were reacted according to the method of Example 43 to afford 5-(4-methoxybenzylthio)-3-(benzyloxy)-N-(4-methylthiazol-2-yl)pyridin-2-amine hydrochloride (64.1 mg, 78.3% yield) as a white solid after HCl salt formation. $^1$H NMR (d$_6$-DMSO) δ 7.82 (d, 1H), 7.60-7.54 (m, 3H), 7.45-7.34 (m, 3H), 7.13 (m, 2H), 6.82 (m, 3H), 5.30 (s, 2H), 4.14 (s, 2H), 3.70 (s, 3H), 2.30 (d, 3H); Mass spectrum (apci) m/z=450.0 (M+H-HCl).

Example 52

3-(Benzyloxy)-N-(4-methylthiazol-2-yl)-5-(piperidin-4-ylmethylthio)pyridin-2-amine dihydrochloride

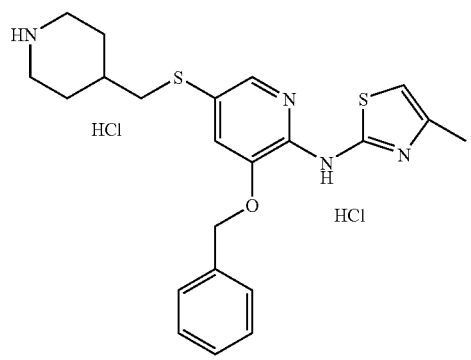 [SMILES: Cc1csc(Nc2ncc(SCC3CCNCC3)cc2OCc2ccccc2)n1 ; Cl ; Cl]

Methyl 3-(5-(benzyloxy)-6-(4-methylthiazol-2-ylamino)pyridin-3-ylthio)propanoate (prepared according to Example 42; 70 mg, 0.17 mmol), KOtBu (0.59 mL, 0.59 mmol) and tert-butyl 4-(bromomethyl)piperidine-1-carboxylate (46.9 mg, 0.17 mmol) were reacted according to the method of Example 43 to afford 3-(benzyloxy)-N-(4-methylthiazol-2-yl)-5-(piperidin-4-ylmethylthio)pyridin-2-amine dihydrochloride (54.4 mg, 64.6% yield) as a white solid after HCl salt formation. $^1$H NMR (d$_6$-DMSO) δ 9.20 (bs, 1H), 9.00 (bs, 1H), 7.97 (m, 1H), 7.65 (m, 3H), 7.45-7.30 (m, 3H), 6.90 (s, 1H), 5.41 (s, 2H), 3.75-3.45 (m, 3H), 3.20 (m, 2H), 2.95 (m, 2H), 2.76 (m, 2H), 2.34 (s, 3H), 1.88 (m, 2H), 1.64 (m, 1H), 1.42 (m, 2H); Mass spectrum (apci) m/z=427.1 (M+H-2HCl).

Example 53

5-(2-(1H-Imidazol-1-yl)ethylthio)-3-(benzyloxy)-N-(4-methylthiazol-2-yl)pyridin-2-amine dihydrochloride

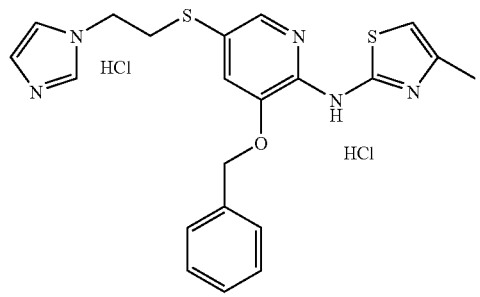 [SMILES: Cc1csc(Nc2ncc(SCCn3ccnc3)cc2OCc2ccccc2)n1 ; Cl ; Cl]

Methyl 3-(5-(benzyloxy)-6-(4-methylthiazol-2-ylamino)pyridin-3-ylthio)propanoate (prepared according to Example 42; 70 mg, 0.17 mmol), KOtBu (0.59 mL, 0.59 mmol) and 1-(2-chloroethyl)-1H-imidazole hydrochloride (28.1 mg, 0.17 mmol) were reacted according to the method of Example 43 to afford 5-(2-(1H-imidazol-1-yl)ethylthio)-3-(benzyloxy)-N-(4-methylthiazol-2-yl)pyridin-2-amine dihydrochloride (28.1 mg, 33.6% yield) as a tan solid after HCl salt formation. $^1$H NMR (d$_6$-DMSO) δ 9.16 (t, 1H), 7.96 (d, 1H), 7.75 (t, 1H), 7.66 (t, 1H), 7.64-7.59 (m, 3H), 7.45-7.33 (m, 3H), 6.77 (s, 1H), 5.34 (s, 2H), 4.35 (t, 2H), 3.47 (t, 2H), 2.29 (d, 3H); Mass spectrum (apci) m/z=424.0 (100) 328.0 (75) 238.0 (35).

Example 54

3-(Benzyloxy)-N-(4-methylthiazol-2-yl)-5-(pyridin-2-ylthio)pyridin-2-amine dihydrochloride

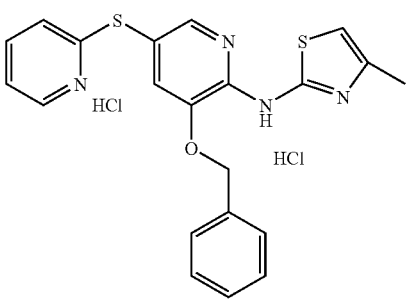 [SMILES: Cc1csc(Nc2ncc(Sc3ccccn3)cc2OCc2ccccc2)n1 ; Cl ; Cl]

3-(Benzyloxy)-5-bromo-N-(4-methylthiazol-2-yl)pyridin-2-amine (prepared according to Example 1) (0.125 g, 0.332 mmol), MeLi (0.260 mL, 0.415 mmol), butyllithium (0.166 mL, 0.415 mmol), and 1,2-di(pyridin-2-yl)disulfane (0.0732 g, 0.332 mmol) were reacted according to the method of Example 7 to provide (benzyloxy)-N-(4-methylthiazol-2-yl)-5-(pyridin-2-ylthio)pyridin-2-amine dihydrochloride (0.058 g, 36.4% yield). $^1$H NMR (DMSO-$d_6$) δ 8.37 (m, 1H), 8.12 (d, 1H), 7.74 (d, 1H), 7.63 (m, 1H), 7.57 (m, 2H), 7.39 (m, 3H), 7.17 (m, 1H), 6.94 (d, 1H), 6.85 (s, 1H), 5.34 (s, 2H), 2.32 (s, 3H). Mass spectrum (apci) m/z=407.0 (M+H-2HCl).

Example 55

3-(Benzyloxy)-N-(4-methylthiazol-2-yl)-5-(pyridin-4-ylthio)pyridin-2-amine dihydrochloride

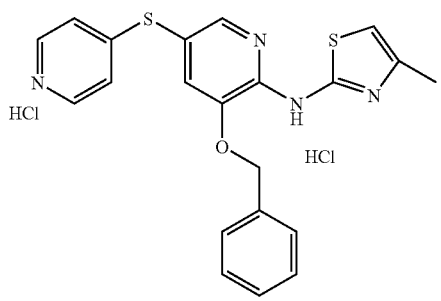 [SMILES: Cl ; Cc1csc(Nc2ncc(Sc3ccncc3)cc2OCc2ccccc2)n1 ; Cl]

3-(Benzyloxy)-5-bromo-N-(4-methylthiazol-2-yl)pyridin-2-amine (prepared according to Example 1) (0.125 g, 0.332 mmol), MeLi (0.260 mL, 0.415 mmol), butyllithium (0.166 mL, 0.415 mmol), and 1,2-di(pyridin-4-yl)disulfane (0.0732 g, 0.332 mmol) were reacted according to the method of Example 7 to provide (benzyloxy)-N-(4-methylthiazol-2-yl)-5-(pyridin-4-ylthio)pyridin-2-amine dihydrochloride (0.057 g, 35.8% yield). $^1$H NMR (DMSO-$d_6$) δ 8.53 (m, 2H), 8.14 (m, 1H), 7.67 (s, 1H), 7.57 (d, 2H), 7.49 (d, 2H), 7.39 (m, 3H), 6.72 (s, 1H), 5.30 (s, 2H), 2.28 (s, 3H). Mass spectrum (apci) m/z=407.0 (M+H-2HCl).

Example 56

3-(Benzyloxy)-N-(4-methylthiazol-2-yl)-5-(thiophen-2-ylthio)pyridin-2-amine hydrochloride

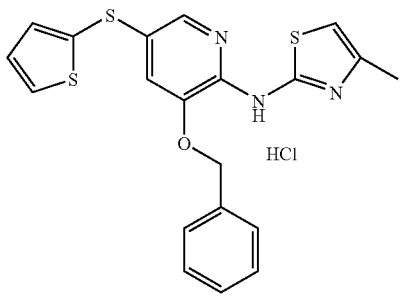 [SMILES: Cc1csc(Nc2ncc(Sc3cccs3)cc2OCc2ccccc2)n1 ; Cl]

3-(Benzyloxy)-5-bromo-N-(4-methylthiazol-2-yl)pyridin-2-amine (prepared according to Example 1) (0.125 g, 0.332 mmol), MeLi (0.260 mL, 0.415 mmol), butyllithium (0.166 mL, 0.415 mmol), and 2-(2-(thiophen-2-yl)disulfanyl)thiophene (0.0765 g, 0.332 mmol) were reacted according to the method of Example 7 to provide 3-(benzyloxy)-N-(4-methylthiazol-2-yl)-5-(thiophen-2-ylthio)pyridin-2-amine hydrochloride (0.063 g, 42.3% yield). $^1$H NMR (DMSO-$d_6$) δ 7.86 (d, 1H), 7.77 (m, 1H), 7.51 (m, 3H), 7.36 (m, 4H), 7.15 (m, 1H), 6.83 (s, 1H), 5.30 (s, 2H), 2.30 (s, 3H). Mass spectrum (apci) m/z=412.0 (M+H-HCl).

Example 57

5-benzyl-3-(benzyloxy)-N-(4-methylthiazol-2-yl)pyridin-2-amine hydrochloride

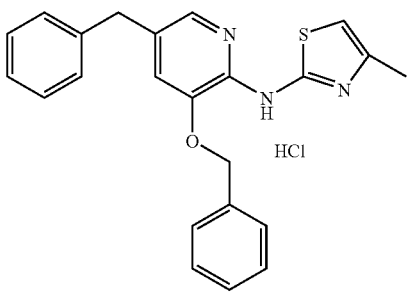 [SMILES: Cc1csc(Nc2ncc(Cc3ccccc3)cc2OCc2ccccc2)n1 ; Cl]

3-(Benzyloxy)-5-bromo-N-(4-methylthiazol-2-yl)pyridin-2-amine (prepared according to Example 1) (0.125 g, 0.332 mmol), 9-benzyl-9-bora-bicyclo[3.3.1]nonane (1.99 mL, 0.997 mmol), PdCl$_2$(dppf) dichloromethane adduct (0.0273 g, 0.0332 mmol), were placed in DMF (6 mL), and water (0.6 mL) and heated to 60° C. for 18 hours. The reaction mixture was cooled and partitioned between water and DCM. The layers were separated and the organic layer was dried, filtered, and concentrated. Crude material was purified by silica gel to give the free base of the title compound (92%). The free base was purified by reverse phase chromatography. The purified free base was dissolved in DCM and 2M HCl was added. The mixture was concentrated to give 5-benzyl-3-(benzyloxy)-N-(4-methylthiazol-2-yl)pyridin-2-amine (0.038 g, 29.5% yield). $^1$H NMR (DMSO-$d_6$) δ 7.88 (s, 1H), 7.57 (m, 3H), 7.38 (m, 3H), 7.27 (m, 4H), 7.21 (m, 1H), 6.83 (s, 1H), 5.29 (s, 2H), 3.94 (s, 2H), 2.31 (s, 3H). Mass spectrum (apci) m/z=388.1 (M+H-HCl).

Example 58

Methyl 3-(2-(3-(benzyloxy)-5-bromopyridin-2-ylamino)thiazol-4-yl)propanoate

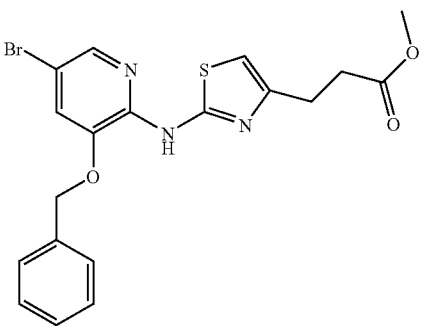 [SMILES: COC(=O)CCc1csc(Nc2ncc(Br)cc2OCc2ccccc2)n1]

1-(3-(Benzyloxy)-5-bromopyridin-2-yl)thiourea (2.00 g, 5.91 mmol), methyl 5-bromo-4-oxopentanoate (1.48 g, 7.10 mmol) (prepared according to *Synthetic Communications* (1994) 2557-2562), and triethylamine (1.44 mL, 10.3 mmol) were heated in methanol (50 mL) at reflux for 3 hours according to the method of Example 2, Step C, to provide methyl 3-(2-(3-(benzyloxy)-5-bromopyridin-2-ylamino)thiazol-4-yl)propanoate as a light yellow powder. $^1$H NMR (DMSO-d$_6$) δ 10.26 (bs, 1H), 7.97 (s, 1H), 7.35-7.63 (m, 6H), 6.66 (bs, 1H), 5.29 (s, 2H), 3.59 (s, 3H), 2.85 (t, 2H), 2.69 (t, 2H). Mass spectrum (esi) m/z=448 (96), 450 (100).

Example 59

Methyl 3-(2-(3-(benzyloxy)-5-bromopyrazin-2-ylamino)thiazol-4-yl)propanoate

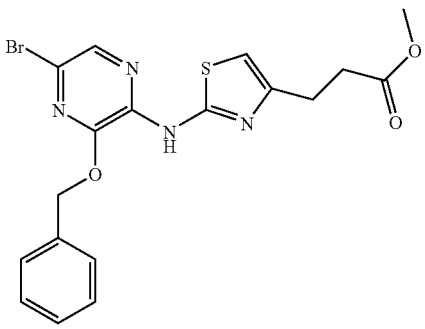 [SMILES: COC(=O)CCc1csc(Nc2ncc(Br)nc2OCc2ccccc2)n1]

1-(3-(Benzyloxy)-5-bromopyrazin-2-yl)thiourea (2.00 g, 5.91 mmol), methyl 5-bromo-4-oxopentanoate (1.48 g, 7.10 mmol) (prepared according to *Synthetic Communications* (1994) 2557-2562), and triethylamine (1.44 mL, 10.3 mmol) were heated in methanol (50 mL) at reflux for 3 hours according to the method of Example 2, Step C, to provide methyl 3-(2-(3-(benzyloxy)-5-bromopyridin-2-ylamino)thiazol-4-yl)propanoate (1.51 g, 57%) as a white powder: $^1$H NMR (DMSO-d$_6$) δ 11.16 (bs, 1H), 8.02 (s, 1H), 7.59 (d, 2H), 7.36-7.44 (m, 3H), 6.71 (bs, 1H), 5.43 (s, 2H), 3.59 (s, 3H), 2.85 (t, 2H), 2.69 (t, 2H). Mass spectrum (esi) m/z=449 (96), 451 (100).

Example 60

3-(Benzyloxy)-5-(4-methoxyphenylthio)-N-(4-methylthiazol-2-yl)pyridin-2-amine hydrochloride

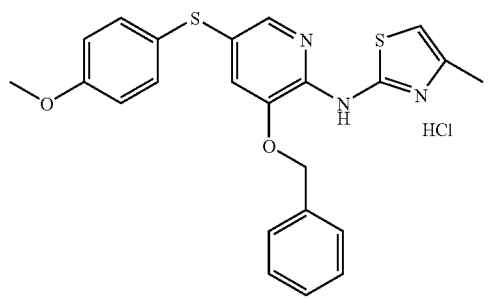

3-(Benzyloxy)-5-bromo-N-(4-methylthiazol-2-yl)pyridin-2-amine (0.125 g, 0.332 mmol), 4,5-bis(diphenylphosphino)-9,9-dimethyl-9H-xanthene (0.0192 g, 0.0332 mmol), Pd$_2$dba$_3$ (0.0152 g, 0.0166 mmol), N-ethyl-N-isopropylpropan-2-amine (0.116 mL, 0.664 mmol), 4-methoxybenzenethiol (0.0466 g, 0.332 mmol) were reacted according to Example 42 to provide 3-(benzyloxy)-5-(4-methoxyphenylthio)-N-(4-methylthiazol-2-yl)pyridin-2-amine hydrochloride (0.028 g, 19.4% yield) after salt formation. $^1$H NMR (DMSO-d$_6$) δ 7.83 (d, 1H), 7.49 (m, 3H), 7.35 (m, 5H), 6.94 (d, 2H), 6.78 (s, 1H), 5.28 (s, 2H), 3.77 (s, 3H), 2.29 (s, 3H). Mass spectrum (apci) m/z=436.1 (M+H-HCl).

Example 61

3-(Benzyloxy)-5-(3-methoxyphenylthio)-N-(4-methylthiazol-2-yl)pyridin-2-amine hydrochloride

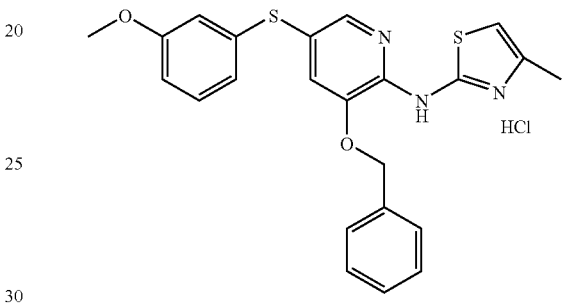

3-(Benzyloxy)-5-bromo-N-(4-methylthiazol-2-yl)pyridin-2-amine (0.125 g, 0.332 mmol), 4,5-bis(diphenylphosphino)-9,9-dimethyl-9H-xanthene (0.0192 g, 0.0332 mmol), Pd$_2$dba$_3$ (0.0152 g, 0.0166 mmol), N-ethyl-N-isopropylpropan-2-amine (0.116 ml, 0.664 mmol), 3-methoxybenzenethiol (0.0466 g, 0.332 mmol) were reacted according to Example 42 to provide 3-(benzyloxy)-5-(3-methoxyphenylthio)-N-(4-methylthiazol-2-yl)pyridin-2-amine hydrochloride (0.035 g, 24.2% yield). $^1$H NMR (DMSO-d$_6$) δ 8.00 (d, 1H), 7.57 (d, 1H), 7.53 (d, 2H), 7.37 (m, 3H), 7.22 (t, 1H), 6.81 (dd, 1H), 6.75 (m, 2H), 6.69 (s, 1H), 5.30 (s, 2H), 3.70 (s, 3H), 2.29 (s, 3H). Mass spectrum (apci) m/z=436.1 (M+H-HCl).

Example 62

3-(benzyloxy)-5-(2-methoxyphenylthio)-N-(4-methylthiazol-2-yl)pyridin-2-amine hydrochloride

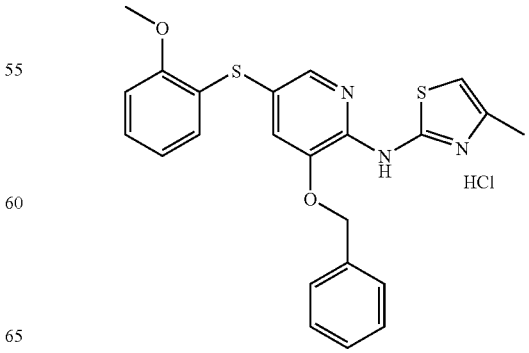

3-(Benzyloxy)-5-bromo-N-(4-methylthiazol-2-yl)pyridin-2-amine (0.125 g, 0.332 mmol), 4,5-bis(diphenylphosphino)-9,9-dimethyl-9H-xanthene (0.0192 g, 0.0332 mmol), Pd₂dba₃ (0.0152 g, 0.0166 mmol), N-ethyl-N-isopropylpropan-2-amine (0.116 mL, 0.664 mmol), 2-methoxybenzenethiol (0.0466 g, 0.332 mmol) were reacted according to Example 42 to provide 3-(benzyloxy)-5-(2-methoxyphenylthio)-N-(4-methylthiazol-2-yl)pyridin-2-amine hydrochloride (0.103 g, 65.7% yield) after salt formation. ¹H NMR (DMSO-d₆) δ 7.93 (d, 1H), 7.59 (d, 1H), 7.53 (d, 2H), 7.38 (m, 3H), 7.25 (m, 1H), 7.05 (d, 1H), 6.86 (m, 2H), 6.79 (dd, 1H), 5.32 (s, 2H), 3.82 (s, 3H), 2.32 (s, 3H). Mass spectrum (apci) m/z=436.1 (M+H-HCl).

Example 63

3-(Benzyloxy)-5-(2-chlorophenylthio)-N-(4-methylthiazol-2-yl)pyridin-2-amine hydrochloride

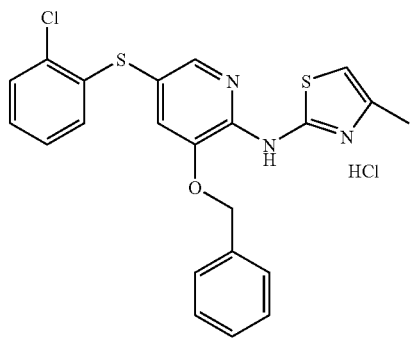 [SMILES: Cc1csc(Nc2ncc(Sc3ccccc3Cl)cc2OCc2ccccc2)n1 ; Cl]

3-(Benzyloxy)-5-bromo-N-(4-methylthiazol-2-yl)pyridin-2-amine (0.125 g, 0.332 mmol), 4,5-bis(diphenylphosphino)-9,9-dimethyl-9H-xanthene (0.0192 g, 0.0332 mmol), Pd₂dba₃ (0.0152 g, 0.0166 mmol), N-ethyl-N-isopropylpropan-2-amine (0.116 mL, 0.664 mmol), 2-chlorobenzenethiol (0.048 g, 0.3322 mmol) were reacted according to Example 42 to provide 3-(benzyloxy)-5-(2-chlorophenylthio)-N-(4-methylthiazol-2-yl)pyridin-2-amine hydrochloride (0.025 g, 17.10% yield) after salt formation. ¹H NMR (DMSO-d₆) δ 8.04 (d, 1H), 7.62 (d, 1H), 7.54 (m, 2H), 7.50 (m, 1H), 7.37 (m, 3H), 7.20 (m, 2H), 6.77 (s, 1H), 6.73 (m, 1H), 5.32 (s, 2H), 2.30 (s, 3H). Mass spectrum (apci) m/z=440.0 (M+H-HCl).

Example 64

3-(Benzyloxy)-N-(4-methylthiazol-2-yl)-5-(phenethylthio)pyridin-2-amine hydrochloride

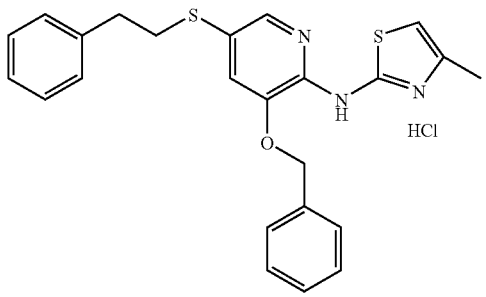 [SMILES: Cc1csc(Nc2ncc(SCCc3ccccc3)cc2OCc2ccccc2)n1 ; Cl]

3-(Benzyloxy)-5-bromo-N-(4-methylthiazol-2-yl)pyridin-2-amine (0.125 g, 0.332 mmol), 4,5-bis(diphenylphosphino)-9,9-dimethyl-9H-xanthene (0.0192 g, 0.0332 mmol), Pd₂dba₃ (0.0152 g, 0.0166 mmol), N-ethyl-N-isopropylpropan-2-amine (0.116 mL, 0.664 mmol), 2-phenylethanethiol (0.0459 g, 0.332 mmol) were reacted according to Example 42 to provide 3-(benzyloxy)-N-(4-methylthiazol-2-yl)-5-(phenethylthio)pyridin-2-amine hydrochloride (0.106 g, 73.6% yield) after salt formation. ¹H NMR (DMSO-d₆) δ 7.93 (d, 1H), 7.57 (m, 3H), 7.40 (m, 2H), 7.35 (m, 1H), 7.28 (m, 2H), 7.19 (m, 3H), 6.75 (s, 1H), 5.34 (s, 2H), 3.18 (t, 2H), 2.78 (t, 2H), 2.28 (s, 3H). Mass spectrum (apci) m/z 434.1.0 (M+H-HCl).

Example 65

Methyl 3-(2-(5-benzyl-3-(benzyloxy)pyrazin-2-ylamino)thiazol-4-yl)propanoate hydrochloride

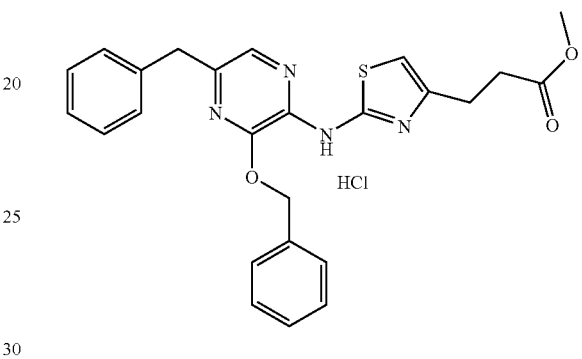

Methyl 3-(2-(3-(benzyloxy)-5-bromopyrazin-2-ylamino)thiazol-4-yl)propanoate (0.826 g, 1.84 mmol), 9-benzyl-9-bora-bicyclo[3.3.1]nonane (11.0 mL, 5.51 mmol), PdCl₂(dppf) dichloromethane adduct (0.151 g, 0.184 mmol), were placed in DMF (25 mL), and water (2.5 mL) and heated to 60° C. for 90 minutes. Cooled reaction mixture to room temperature and partitioned between water and DCM. Layers were separated, dried, filtered, and concentrated. Purified by silica gel to give methyl 3-(2-(5-benzyl-3-(benzyloxy)pyrazin-2-ylamino)thiazol-4-yl)propanoate (0.667 g, 78.8% yield). 28 mg of this was dissolved in DCM and 2M HCl was added and concentrated to give methyl 3-(2-(5-benzyl-3-(benzyloxy)pyrazin-2-ylamino)thiazol-4-yl)propanoate hydrochloride (0.027 g, 93%) ¹H NMR (DMSO-d₆) δ 7.79 (s, 1H), 7.52 (m, 2H), 7.32 (m, 4H), 7.27 (d, 4H), 7.20 (m, 1H), 5.44 (s, 2H), 3.93 (s, 2H), 3.60 (s, 3H), 2.86 (m, 2H), 2.68 (m, 2H). Mass spectrum (apci) m/z=461.1.0 (M+H-HCl).

Example 66

3-(2-(5-benzyl-3-(benzyloxy)pyrazin-2-ylamino)thiazol-4-yl)propanoic acid hydrochloride

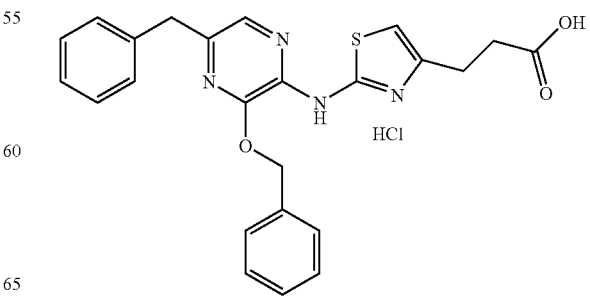

Methyl 3-(2-(5-benzyl-3-(benzyloxy)pyrazin-2-ylamino)thiazol-4-yl)propanoate (0.640 g, 1.39 mmol) was dissolved in MeOH (25 mL) and 1M NaOH (5 mL) and the reaction mixture was heated at 60° C. for 2 hours. The reaction mixture was cooled and the methanol was removed. 1N HCl was added to adjust the pH to 2. The solution was filtered and the filtrate was dried to provide 3-(2-(5-benzyl-3-(benzyloxy)pyrazin-2-ylamino)thiazol-4-yl)propanoic acid hydrochloride (0.508 g, 75.7% yield). $^1$H NMR (DMSO-$d_6$) δ 7.81 (s, 1H), 7.52 (m, 2H), 7.33 (m, 3H), 7.28 (d, 4H), 7.21 (m, 1H), 6.70 (s, 1H), 5.45 (m, 2H), 3.95 (s, 2H), 2.83 (t, 2H), 2.60 (t, 2H). Mass spectrum (apci) m/z=447.1.0 (M+H-HCl).

Example 67

3-(2-(3-(Benzyloxy)pyridin-2-ylamino)thiazol-4-yl)propanoic acid

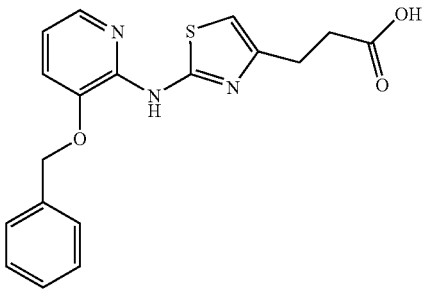 [SMILES: O=C(O)CCc1csc(Nc2ncccc2OCc2ccccc2)n1]

Methyl 3-(2-(3-(benzyloxy)pyridin-2-ylamino)thiazol-4-yl)propanoate (2.00 g, 5.41 mmol) was dissolved in THF (5 mL), and a solution of lithium hydroxide monohydrate (469 mg, 11.18 mmol) in water (1 mL) was added at room temperature. The resulting mixture was stirred at room temperature for 18 hours. The mixture was concentrated in vacuo to remove most of the THF, and the resulting aqueous phase was acidified to pH 3 with 2 M aqueous HCl. The resulting cloudy mixture was extracted with $CH_2Cl_2$ (3×10 mL), and the combined organic phases were washed with brine (10 mL), dried ($Na_2SO_4$), filtered and concentrated in vacuo to a white solid. The solid was further dried under high vacuum overnight to provide the title compound as an off-white powder (1.79 g, 5.04 mmol, 93% yield). $^1$H NMR (DMSO-$d_6$) δ 2.60 (t, J=7.0 Hz, 2H), 2.82 (t, J=7.2 Hz, 2H), 5.26 (s, 2H), 6.62 (s, 1H), 6.89 (dd, J=7.8, 5.1 Hz, 1H), 7.35 (m, 4H), 7.57 (s, 1H), 7.58 (m, 1H), 7.86 (dd, J=1.5, 5 Hz, 1H), 9.96 (br s, 1H), 12.14 (br s, 1H); Mass spectrum (apci) m/z 354.0 (M−H).

Example 68

3-(2-(3-(Benzyloxy)pyridin-2-ylamino)thiazol-4-yl)-N-(2-(pyrrolidin-1-yl)ethyl)propanamide

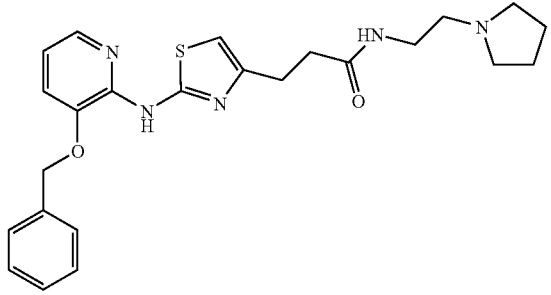 [SMILES: O=C(CCc1csc(Nc2ncccc2OCc2ccccc2)n1)NCCN1CCCC1]

3-(2-(3-(Benzyloxy)pyridin-2-ylamino)thiazol-4-yl)propanoic acid (40 mg, 0.113 mmol), 2-(pyrrolidin-1-yl)ethanamine (0.0171 mL, 0.135 mmol), 1H-benzo[d][1,2,3]triazol-1-ol hydrate (22.4 mg, 0.146 mmol) and 4-methylmorpholine (0.0173 ml, 0.158 mmol) were placed in an 8.5 mL screw-cap vial. The reaction mixture was cooled to 0° C. in an ice bath, and N1-((ethylimino)methylene)-N3,N3-dimethylpropane-1,3-diamine hydrochloride (33.0 mg, 0.172 mmol) was added as a solid. The mixture was stirred at 0° C. and then allowed to warm to room temp overnight. The reaction mixture was concentrated under high vacuum to remove DMF, and the residue was partitioned between dichloromethane and saturated aqueous $NaHCO_3$ diluted with an equal part of water. The organic phase was washed with once with water, then with brine, and dried by passing through a plug of anhydrous sodium sulfate. The solution was concentrated in vacuo and dried under high vacuum to provide the title compound as a colorless oil. $^1$H NMR ($CDCl_3$) δ 1.76 (s, 4H), 2.56 (m, 4H), 2.59 (dd, J=5.6, 12.9 Hz, 4H), 3.01-2.94 (m, 4H), 3.37 (dd, J=11.3, 5.5 Hz, 2H), 5.13 (s, 2H), 6.75 (bs, 1H), 6.47 (s, 1H), 6.82 (dd, J=8.2, 5.1 Hz, 2H), 7.10 (dd, J=1.2, 7.9, Hz, 1H), 7.42 (br s, 4H), 7.94 (dd, J=1.2, 5 Hz, 1H), 8.59 (bs, 1H); Mass spectrum (apci) m/z=452.2 (M+H).

The following compounds were also prepared according to the procedure of Example 1, Step D.

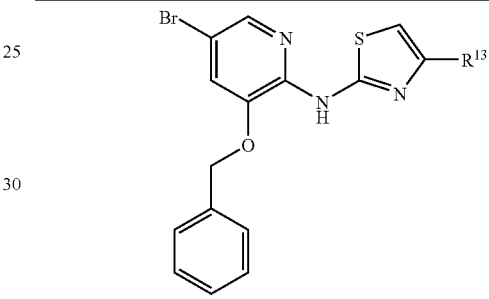

| Ex. | $R^{13}$ | Name | $^1$H NMR (DMSO-$d_6$) |
|---|---|---|---|
| 69 | Et | N-(3-(Benzyloxy)-5-bromopyridin-2-yl)-4-ethylthiazol-2-amine | δ 1.20 (t, 3H), 2.60 (q, 2H), 5.29 (s, 2H), 6.61 (s, 1H), 7.31-7.45 (m, 3H), 7.58-7.62 (m, 3H), 7.97 (s, 1H), 10.21 (bs, 1H). |
| 70 | i-Bu | N-(3-(Benzyloxy)-5-bromopyridin-2-yl)-4-isobutylthiazol-2-amine | δ 0.88 (d, 6H), 1.99 (m, 1H), 2.43 (d, 2H), 5.28 (s, 2H), 6.61 (s, 1H), 7.32-7.44 (m, 3H), 7.58-7.62 (m, 3H), 7.96 (s, 1H), 10.18 (bs, 1H). |
| 71 | n-Bu | N-(3-(Benzyloxy)-5-bromopyridin-2-yl)-4-butylthiazol-2-amine | δ 0.89 (t, 3H), 1.31 (m, 2H), 1.61 (m, 2H), 2.57 (t, 2H), 5.28 (s, 2H), 6.61 (s, 1H), 7.32-7.44 (m, 3H), 7.58-7.62 (m, 3H), 7.96 (s, 1H), 10.20 (bs, 1H). |
| 72 | i-Pr | N-(3-(Benzyloxy)-5-bromopyridin-2-yl)-4-isopropylthiazol-2-amine | δ 1.22 (d, 6H), 2.66 (septet, 1H), 5.29 (s, 2H), 6.60 (s, 1H), 7.33-7.44 (m, 3H), 7.58-7.62 (m, 3H), 7.96 (s, 1H), 10.17 (bs, 1H). |
| 73 | c-hex | N-(3-(Benzyloxy)-5-bromopyridin-2-yl)-4-cyclohexylthiazol-2-amine | δ 1.20 (m, 1H), 1.25-1.43 (m, 4H), 1.67 (m, 1H), 1.74 (m, 2H), 1.96 (m, 2H), 2.53 (m, 1H), 5.28 (s, 2H), 6.58 (s, 1H), 7.33-7.44 (m, 3H), 7.57-7.62 (m, 3H), 7.96 (s, 1H), 10.13 (bs, 1H). |
| 74 | c-Pr | N-(3-(Benzyloxy)-5-bromopyridin-2-yl)-4-cyclopropylthiazol-2-amine | δ 0.75-0.85 (m, 4H), 1.94 (m, 1H), 5.28 (s, 2H), 6.62 (s, 1H), 7.33-7.44 (m, 3H), 7.56-7.62 (m, 3H), 7.96 (s, 1H), 10.10 (bs, 1H). |

The following compounds were also prepared according to the procedure of Example 42.

| Ex. | Structure | Name | Data |
|---|---|---|---|
| 75 | 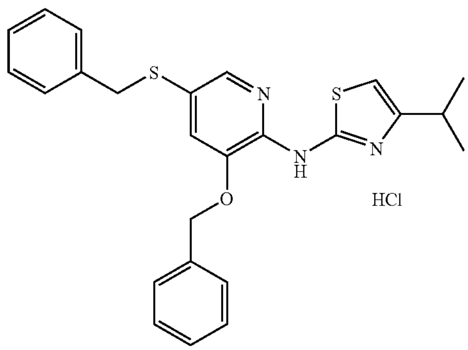 [SMILES: CC(C)c1csc(Nc2ncc(SCc3ccccc3)cc2OCc2ccccc2)n1 ; Cl] | N-(3-(benzyloxy)-5-(benzylthio)pyridin-2-yl)-4-isopropylthiazol-2-amine hydrochloride | $^1$H NMR (DMSO-$d_6$) δ 10.95 (bs, 1H), 7.81 (d, 1H), 7.59 (t, 3H), 7.45-7.33 (m, 3H), 7.29-7.18 (m, 5H), 6.80 (s, 1H), 5.30 (s, 2H), 4.19 (s, 2H), 2.98 (m, 1H), 1.25 (d, 6H). Mass spectrum (apci) m/z = 448.1 (M + H − HCl). |
| 76 | 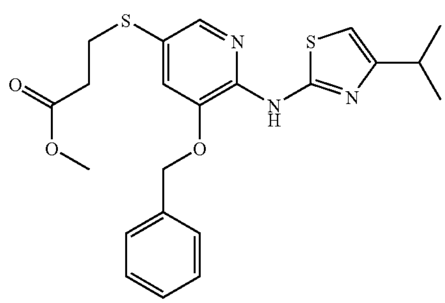 [SMILES: COC(=O)CCSc1cnc(Nc2nc(C(C)C)cs2)c(OCc2ccccc2)c1] | methyl 3-(5-(benzyloxy)-6-(4-isopropylthiazol-2-ylamino)pyridin-3-ylthio)propanoate | $^1$H NMR (CDCl$_3$) δ 8.57 (s, 1H), 8.03 (d, 1H), 7.42 (m, 5H), 7.21 (d, 1H), 6.42 (m, 1H), 5.12 (s, 2H), 3.68 (s, 3H), 3.02 (t, 2H), 2.94 (m, 1H), 2.55 (t, 2H), 1.27 (d, 6H). Mass spectrum (esi) m/z = 444.2 (M + H). |
| 77 | 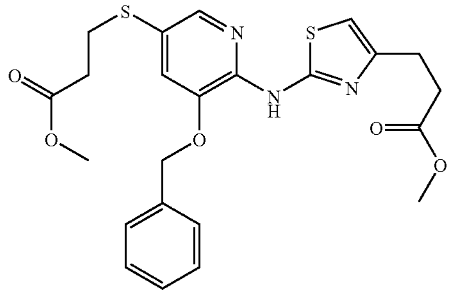 [SMILES: COC(=O)CCSc1cnc(Nc2nc(CCC(=O)OC)cs2)c(OCc2ccccc2)c1] | methyl 3-(2-(3-(benzyloxy)-5-(3-methoxy-3-oxopropylthio)pyridin-2-ylamino)thiazol-4-yl)propanoate | $^1$H NMR (CDCl$_3$) δ 8.56 (bs, 1H), 8.03 (d, 1H), 7.42 (m, 5H), 7.22 (d, 1H), 6.47 (m, 1H), 5.12 (s, 2H), 3.68 (s, 3H), 3.67 (s, 3H), 3.03 (t, 2H), 2.97 (m, 2H), 2.71 (t, 2H), 2.56 (t, 2H). Mass spectrum (esi) m/z = 488.1 (M + H). |

The following compounds were also prepared according to the procedure of Example 43.

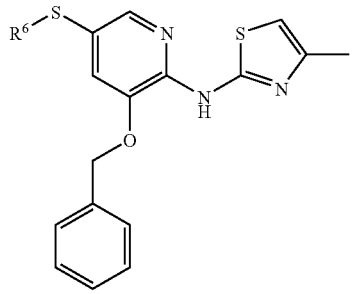

| Ex. | R⁶ | Name | Data |
|---|---|---|---|
| 78 | (piperidin-4-yl with phenyl substituent) | N-(3-(benzyloxy)-5-(phenyl(piperidin-4-yl)methylthio)pyridin-2-yl)-4-methylthiazol-2-amine dihydrochloride | $^1$H NMR (DMSO-d$_6$) - 10.65 (bs, 1H), 8.85 (d, 1H), 8.53 (m, 1H), 7.69 (d, 1H), 7.54 (d, 2H), 7.43 (d, 2H), 7.37 (m, 1H), 7.30-7.12 (m, 6H), 6.72 (s, 1H), 5.18 (s, 2H), 4.20 (d, 1H), 3.31 (m, 1H), 3.17 (m, 1H), 2.88 (m, 1H), 2.76 (m, 1H), 2.26 (s, 3H), 2.24 (m, 1H), 2.10 (m, 1H), 1.50 (m, 2H), 1.30 (m, 1H). Mass spectrum (apci) m/z = 503.1 (M + H − 2HCl). |
| 79 | (1-phenylethyl) | N-(3-(benzyloxy)-5-(1-phenylethylthio)pyridin-2-yl)-4-methylthiazol-2-amine hydrochloride | $^1$H NMR (DMSO-d$_6$) - 10.70 (bs, 1H), 7.77 (d, 1H), 7.56 (d, 2H), 7.45-7.33 (m, 4H), 7.30-7.18 (m, 5H), 6.75 (s, 1H), 5.23 (s, 2H), 4.48 (q, 1H), 2.28 (s, 3H), 1.50 (d, 3H). Mass spectrum (apci) m/z = 434.0 (M + H − HCl). |
| 80 | (cyclopentylmethyl) | N-(3-(benzyloxy)-5-(cyclopentylmethylthio)pyridin-2-yl)-4-methylthiazol-2-amine hydrochloride | $^1$H NMR (DMSO-d$_6$) - 10.95 (bs, 1H), 7.92 (m, 1H), 7.61-7.55 (m, 3H), 7.44-7.32 (m, 3H), 6.82 (s, 1H), 5.37 (s, 2H), 2.92 (d, 2H), 2.31 (s, 3H), 1.89 (m, 1H), 1.70 (m, 2H), 1.57 (m, 2H), 1.46 (m, 2H), 1.20 (m, 2H). Mass spectrum (apci) m/z = 412.1 (M + H − HCl). |
| 81 | (thiophen-2-ylmethyl) | N-(3-(benzyloxy)-5-(thiophen-2-ylmethylthio)pyridin-2-yl)-4-methylthiazol-2-amine hydrochloride | $^1$H NMR (DMSO-d$_6$) - 10.70 (bs, 1H), 7.85 (d, 1H), 7.60-7.54 (m, 3H), 7.45-7.33 (m, 4H), 6.86 (dd, 1H), 6.80 (dd, 1H), 6.75 (s, 1H), 5.28 (s, 2H), 4.43 (s, 2H), 2.28 (s, 3H). Mass spectrum (apci) m/z = 426.0 (M + H − HCl). |
| 82 | (3-(dimethylamino)propyl) | N-(3-(benzyloxy)-5-(3-(dimethylamino)propylthio)pyridin-2-yl)-4-methylthiazol-2-amine dihydrochloride | $^1$H NMR (DMSO-d$_6$) - 10.55 (bs, 1H), 10.24 (bs, 1H), 7.96 (d, 1H), 7.60 (m, 3H), 7.45-7.32 (m, 3H), 6.72 (s, 1H), 5.34 (s, 2H), 3.12 (m, 2H), 2.99 (t, 2H), 2.71 (d, 6H), 2.27 (s, 3H), 1.85 (m, 2H). Mass spectrum (apci) m/z = 415.1 (M + H − 2HCl). |

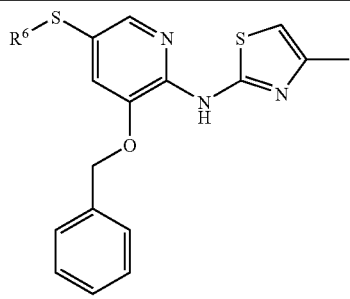

| Ex. | R⁶ | Name | Data |
|---|---|---|---|
| 83 | (CH₂C(CH₃)- C(O)NH-CH₂CH₂-pyrrolidine) | 2-(5-(benzyloxy)-6-(4-methylthiazol-2-ylamino)pyridin-3-ylthio)-N-(2-(pyrrolidin-1-yl)ethyl)acetamide dihydrochloride | $^1$H NMR (DMSO-d$_6$) - 10.70 (bs, 1H), 10.38 (bs, 1H), 8.49 (t, 1H), 7.95 (m, 1H), 7.66 (s, 1H), 7.60 (d, 2H), 7.45-7.33 (m, 3H), 6.75 (s, 1H), 5.32 (s, 2H), 3.69 (s, 2H), 3.51 (m, 2H), 3.40 (m, 2H), 3.15 (m, 2H), 2.91 (m, 2H), 2.28 (s, 3H), 1.94 (m, 2H), 1.83 (m, 2H). Mass spectrum (apci) m/z = 484.2 (M + H − 2HCl). |
| 84 | (CH₂C(CH₃)- C(O)-4-methylpiperazine) | 2-(5-(benzyloxy)-6-(4-methylthiazol-2-ylamino)pyridin-3-ylthio)-1-(4-methylpiperazin-1-yl)ethanone dihydrochloride | $^1$H NMR (DMSO-d$_6$) - 10.57 (bs, 1H), 10.47 (bs, 1H), 7.96 (m, 1H), 7.59 (m, 3H), 7.45-7.34 (m, 3H), 6.70 (s, 1H), 5.29 (s, 2H), 4.38 (d, 2H), 4.10 (d, 2H), 4.01 (d, 2H), 3.43 (m, 2H), 3.02 (m, 2H), 2.79 (d, 3H), 2.26 (s, 3H). Mass spectrum (apci) m/z = 470.1 (M + H − 2HCl). |

The following compounds were also prepared according to the procedure of Example 43.

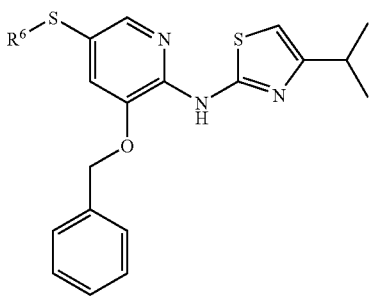

| Ex. | R⁶ | Name | Data |
|---|---|---|---|
| 85 | (CH₂CH₂-imidazole) | N-(5-(2-(1H-imidazol-1-yl)ethylthio)-3-(benzyloxy)pyridin-2-yl)-4-isopropylthiazol-2-amine dihydrochloride | $^1$H NMR (DMSO-d$_6$) δ 10.80 (bs, 1H), 9.16 (s, 1H), 7.97 (d, 1H), 7.75 (m, 1H), 7.66-7.60 (m, 4H), 7.42 (t, 2H), 7.35 (m, 1H), 6.78 (s, 1H), 5.35 (s, 2H), 4.35 (t, 2H), 3.49 (t, 2H), 2.96 (m, 1H), 1.25 (d, 6H). Mass spectrum (esi) m/z = 452.2 (M + H − 2HCl). |

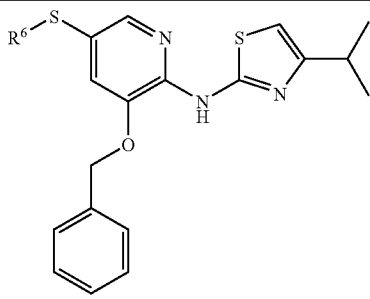

| Ex. | R⁶ | Name | Data |
|---|---|---|---|
| 86 | 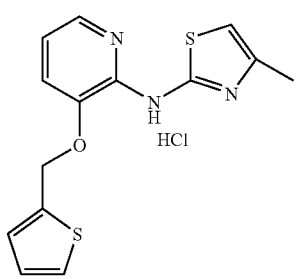 | N-(3-(benzyloxy)-5-(piperidin-4-ylmethylthio)pyridin-2-yl)-4-isopropylthiazol-2-amine dihydrochloride | $^1$H NMR (DMSO-d$_6$) δ 10.70 (bs, 1H), 8.81 (bs, 1H), 8.55 (bs, 1H), 7.93 (m, 1H), 7.61 (d, 2H), 7.56 (s, 1H), 7.44-7.32 (m, 3H), 6.75 (s, 1H), 5.35 (s, 2H), 3.22 (m, 2H), 2.95 (m, 1H), 2.90 (d, 2H), 2.77 (m, 2H), 1.88 (m, 2H), 1.62 (m, 1H), 1.36 (m, 2H), 1.24 (d, 6H). |

Example 87

4-Methyl-N-(3-(thiophen-2-ylmethoxy)pyridin-2-yl)thiazol-2-amine hydrochloride

Example 88

5-(Benzyloxy)-6-(4-methylthiazol-2-ylamino)nicotinaldehyde

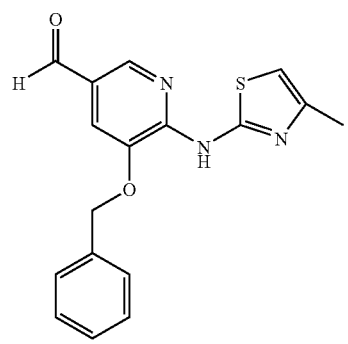 [SMILES: Cc1csc(Nc2ncc(C=O)cc2OCc2ccccc2)n1]

2-(4-Methylthiazol-2-ylamino)pyridin-3-ol (prepared according to Example 3, Step A; 200 mg, 0.96 mmol), 2-(chloromethyl)thiophene (160 mg, 0.96 mmol) and potassium carbonate (333 mg, 2.4 mmol) were reacted according to Example 3, Step B, to provide the title compound (47 mg, 14% yield) as a tan solid. $^1$H NMR (d$_6$-DMSO) δ 10.90 (bs, 1H), 7.98 (m, 1H), 7.69 (m, 1H), 7.59 (m, 1H), 7.35 (m, 1H), 7.12 (m, 1H), 7.06 (m, 1H), 6.83 (s, 1H), 5.52 (s, 2H), 2.31 (s, 3H). Mass spectrum (apci) m/z=304 (M+H-HCl).

3-(Benzyloxy)-5-bromo-N-(4-methylthiazol-2-yl)pyridin-2-amine (prepared according to Example 1; 1.0 g, 2.66 mmol), MeLi (1.83 ml, 2.92 mmol), butyl lithium (1.17 ml, 2.92 mmol), and N,N-dimethylformamide (0.823 ml, 10.6 mmol) were reacted according to the method of Example 7 to provide the title compound (650 mg, 75.2% yield) as a pale yellow solid. $^1$H NMR (CDCl$_3$) δ 9.91 (s, 1H), 8.88 (bs, 1H), 8.40 (d, 1H), 7.56 (d, 1H), 7.42 (m, 5H), 6.51 (m, 1H), 5.17 (s, 2H), 2.35 (s, 3H). Mass spectrum (apci) m/z=326.0 (M+H).

Example 89

N-(3-(benzyloxy)-5-(morpholinomethyl)pyridin-2-yl)-4-methylthiazol-2-amine dihydrochloride

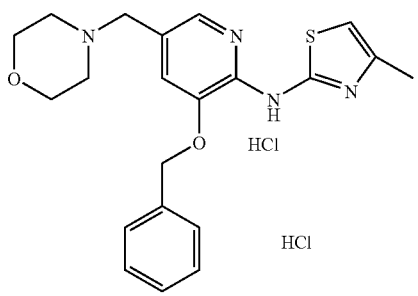 [SMILES: Cc1csc(Nc2ncc(CN3CCOCC3)cc2OCc2ccccc2)n1 ; Cl ; Cl]

A 20 mL vial was charged with 5-(benzyloxy)-6-(4-methylthiazol-2-ylamino)nicotinaldehyde (100 mg, 0.31 mmol) and THF (3 mL). morpholine (0.032 ml, 0.37 mmol) was added and the reaction was stirred for 10 minutes. NaBH(OAc)$_3$ (326 mg, 1.54 mmol) was added and the reaction was stirred for 30 minutes. The reaction was poured into saturated sodium bicarbonate and extracted with EtOAc. The organic layer was washed with water and brine and then dried with sodium sulfate, filtered and concentrated in vacuo. The residue was purified on silica gel (0 to 10% methanol in EtOAc containing ammonia) to afford the title compound (101.7 mg, 70.49% yield) as a white solid after HCl salt formation. $^1$H NMR (DMSO-d$_6$) δ 11.77 (bs, 1H), 11.05 (bs, 1H), 8.08 (m, 2H), 7.64 (d, 2H), 7.45-7.32 (m, 3H), 6.83 (s, 1H), 5.35 (s, 2H), 4.32 (d, 2H), 3.87 (m, 4H), 3.20 (d, 2H), 3.03 (m, 2H), 2.31 (s, 3H). Mass spectrum (apci) m/z=397.1 (M+H-2HCl).

Example 90

N-(3-(benzyloxy)-5-((pyridin-2-ylamino)methyl)pyridin-2-yl)-4-methylthiazol-2-amine dihydrochloride

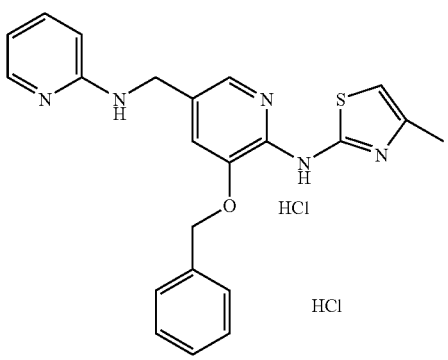 [SMILES: Cc1csc(Nc2ncc(CNc3ccccn3)cc2OCc2ccccc2)n1 ; Cl ; Cl]

5-(benzyloxy)-6-(4-methylthiazol-2-ylamino)nicotinaldehyde (prepared according to preparation 88, 70 mg, 0.215 mmol), pyridin-2-amine (22.3 mg, 0.237 mmol) and NaBH(OAc)$_3$ (73.0 mg, 0.344 mmol) were reacted overnight according to the method of Example 89 to provide the title compound (24.2 mg, 23.6% yield) after reverse phase purification and HCl salt formation. $^1$H NMR (DMSO-d$_6$) δ 11.00 (bs, 1H), 9.34 (bs, 1H), 8.06 (s, 1H), 7.95 (m, 2H), 7.80 (s, 1H), 7.60 (d, 2H), 7.41-7.30 (m, 3H), 7.14 (d, 1H), 6.91 (t, 1H), 6.81 (s, 1H), 5.31 (s, 2H), 4.66 (d, 2H), 2.30 (s, 3H). Mass spectrum (apci) m/z=404.0 (M+H-2HCl).

Example 91

(5-(benzyloxy)-6-(4-methylthiazol-2-ylamino)pyridin-3-yl)methanol

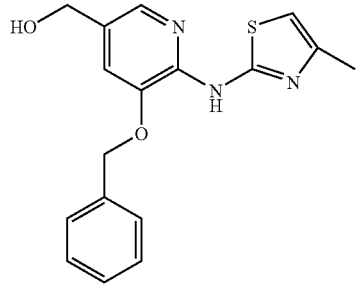 [SMILES: Cc1csc(Nc2ncc(CO)cc2OCc2ccccc2)n1]

The title compound was isolated as a side-product from the reaction of example 90 (20 mg, 28% yield). $^1$H NMR (CDCl$_3$) δ 8.62 (bs, 1H), 7.90 (s, 1H), 7.42 (m, 5H), 7.20 (s, 1H), 6.39 (s, 1H), 5.11 (s, 2H), 4.63 (s, 2H), 2.33 (s, 3H), 1.84 (bs, 1H). Mass spectrum (apci), m/z 328.0 (M+H).

Example 92

(E)-methyl 3-(5-(benzyloxy)-6-(4-methylthiazol-2-ylamino)pyridin-3-yl)acrylate

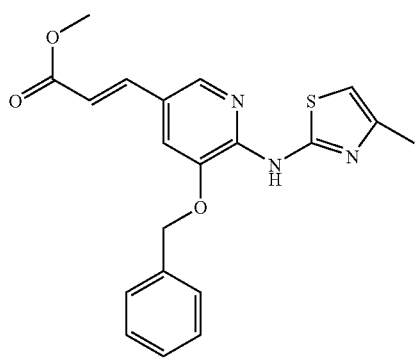 [SMILES: COC(=O)/C=C/c1cnc(Nc2nc(C)cs2)c(OCc2ccccc2)c1]

A 25 mL round-bottomed flask was charged with 5-(benzyloxy)-6-(4-methylthiazol-2-ylamino)nicotinaldehyde (500 mg, 1.54 mmol) and THF (10 mL). Methyl(triphenylphosphoranylidene)acetate (668 mg, 2.00 mmol) was added and the reaction was stirred at room temperature for 1 hour. An additional 668 mg of methyl(triphenylphosphoranylidene)acetate was added and the reaction was stirred overnight. The solids were filtered off and the filtrate was purified on a silica gel column (1:1 EtOAc:Hexanes) to afford (E)-methyl 3-(5-(benzyloxy)-6-(4-methylthiazol-2-ylamino)pyridin-3-yl)acrylate (450 mg, 76.8% yield) as a yellow foam. $^1$H NMR (CDCl$_3$) 8.69 (s, 1H), 8.07 (d, 1H), 7.65 (d, 1H), 7.42 (m, 5H), 7.25 (m, 1H), 6.45 (m, 1H), 6.30 (d, 1H), 5.15 (s, 2H), 3.81 (s, 3H), 2.33 (s, 3H). Mass spectrum (apci) m/z=382.0 (M+H).

Example 93

Methyl 3-(5-(benzyloxy)-6-(4-methylthiazol-2-ylamino)pyridin-3-yl)propanoate

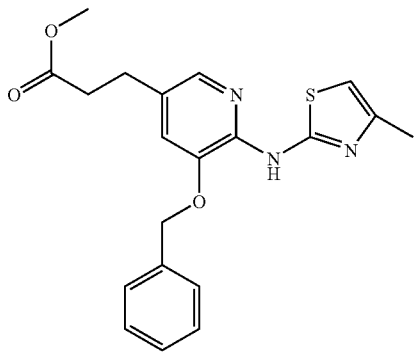 [SMILES: COC(=O)CCc1cnc(Nc2nc(C)cs2)c(OCc2ccccc2)c1]

A 25 mL round-bottomed flask was charged with (E)-methyl 3-(5-(benzyloxy)-6-(4-methylthiazol-2-ylamino)pyridin-3-yl)acrylate (430 mg, 1.13 mmol), 4-methylbenzenesulfonohydrazide (1050 mg, 5.64 mmol) and toluene (10 mL). The reaction was heated to reflux for 12 hours. The reaction was partitioned between saturated aqueous sodium bicarbonate and ethyl acetate. The organic phase was dried over sodium sulfate, filtered and concentrated. The residue was purified on silica gel (20% EtOAc in hexanes) to afford the title compound (140 mg, 32.4% yield) as a white solid. $^1$H NMR (CDCl$_3$) δ 8.49 (s, 1H), 7.80 (d, 1H), 7.41 (m, 5H), 7.00 (d, 1H), 6.37 (q, 1H), 5.08 (s, 2H), 3.67 (s, 3H), 2.89 (t, 2H), 2.61 (t, 2H), 2.31 (d, 3H). Mass spectrum (apci) m/z=384.1 (M+H).

Example 94

3-(5-(Benzyloxy)-6-(4-methylthiazol-2-ylamino)pyridin-3-yl)propanoic acid hydrochloride

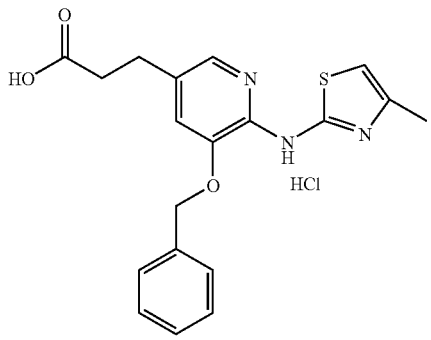 [SMILES: Cc1csc(Nc2ncc(CCC(=O)O)cc2OCc2ccccc2)n1 ; Cl]

A 25 mL round-bottomed flask was charged with methyl 3-(5-(benzyloxy)-6-(4-methylthiazol-2-ylamino)pyridin-3-yl)propanoate (125 mg, 0.326 mmol) and EtOH (3 mL). Potassium hydroxide (183 mg, 3.26 mmol) was added and stirred at ambient temperature for 2.5 hours. The reaction was poured into water and extracted with methylene chloride. The aqueous layer was acidified to pH 1 with HCl and the resultant precipitate was filtered to afford the title compound (108 mg, 81.6% yield) as a white solid. $^1$H NMR (DMSO-d$_6$) δ 12.12 (bs, 1H), 9.73 (bs, 1H), 7.72 (s, 1H), 7.58 (m, 2H), 7.45-7.30 (m, 4H), 6.54 (s, 1H), 5.22 (s, 2H), 2.76 (t, 2H), 2.54 (t, 2H), 2.22 (s, 3H). Mass spectrum (apci) m/z=370.1 (M+H-HCl).

Example 95

3-(5-(Benzyloxy)-6-(4-methylthiazol-2-ylamino)pyridin-3-yl)-1-(4-methylpiperazin-1-yl)propan-1-one dihydrochloride

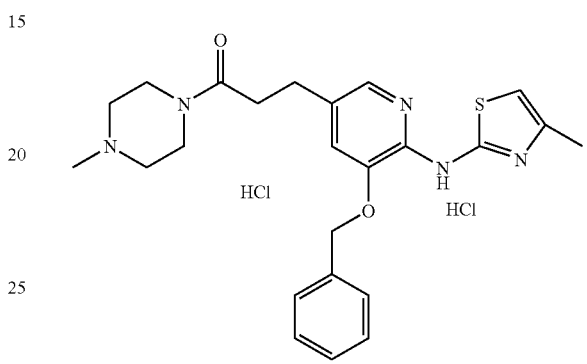

A 10 mL round-bottomed flask was charged with 3-(5-(benzyloxy)-6-(4-methylthiazol-2-ylamino)pyridin-3-yl)propanoic acid (60 mg, 0.16 mmol), triethylamine (0.091 ml, 0.65 mmol), and THF (3 mL). The reaction was cooled to 0° C., ethyl carbonochloridate (0.017 ml, 0.17 mmol) was added, and the reaction was stirred at 0° C. for 20 minutes. 1-Methylpiperazine (0.036 ml, 0.32 mmol) was added and stirred at 0° C. for 1.5 hours. The reaction was partitioned between EtOAc and water. The organic layer was dried with sodium sulfate, filtered and concentrated in vacuo. The residue was purified on a silica gel column (15% methanol in EtOAc with NH$_4$OH) to afford the title compound (59.8 mg, 70.2% yield) as a white solid after HCl salt formation. $^1$H NMR (DMSO-d$_6$) δ 11.25 (bs, 1H), 11.05 (bs, 1H), 7.89 (s, 1H), 7.62 (m, 3H), 7.45-7.33 (m, 3H), 6.83 (s, 1H), 5.32 (s, 2H), 4.43 (d, 1H), 4.06 (d, 1H), 3.47 (t, 1H), 3.38 (d, 2H), 3.01 (m, 2H), 2.84 (m, 3H), 2.74 (m, 5H), 2.32 (s, 3H). Mass spectrum (apci) m/z=452.2 (M+H-2HCl).

Example 96

(E)-N-(3-(benzyloxy)-5-(3-(dimethylamino)prop-1-enyl)pyridin-2-yl)-4-methylthiazol-2-amine dihydrochloride

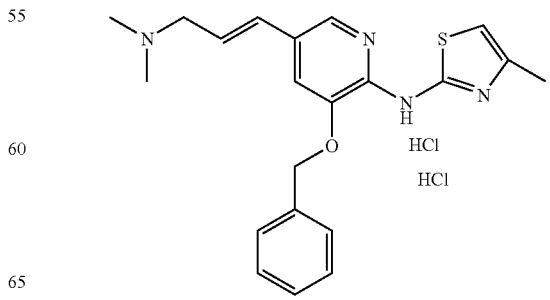

A 25 mL round-bottomed flask was charged with [2-(dimethylamino)ethyl]triphenylphosphonium bromide (1114 mg, 2.69 mmol) and THF (5 mL). The reaction was cooled to 0° C. under nitrogen. Butyllithium (1.08 ml, 2.69 mmol) was added slowly and the reaction was stirred for 50 minutes. A solution of 5-(benzyloxy)-6-(4-methylthiazol-2-ylamino)nicotinaldehyde (350 mg, 1.08 mmol) in THF (5 mL) was added and the reaction was stirred at ambient temperature for 1.5 hours. The reaction was partitioned between EtOAc and water. The organic layer was dried with sodium sulfate, filtered and concentrated in vacuo. The residue was purified on a silica gel column (10 to 20% methanol in EtOAc with NH$_4$OH) to afford the title compound (250 mg, 51.3% yield) after HCl salt formation. $^1$H NMR (DMSO-d$_6$) δ 10.85 (bs, 1H), 10.49 (bs, 1H), 8.03 (d, 1H), 7.78 (s, 1H), 7.63 (d, 2H), 7.45-7.33 (m, 3H), 6.82 (m, 3H), 6.45 (m, 1H), 5.37 (s, 2H), 3.85 (m, 2H), 2.77 (d, 6H), 2.30 (s, 3H). Mass spectrum (apci) m/z=381.1 (M+H-2HCl).

Example 97

3-(Benzyloxy)-5-(3-(dimethylamino)propyl)-N-(4-methylthiazol-2-yl)pyridin-2-amine dihydrochloride

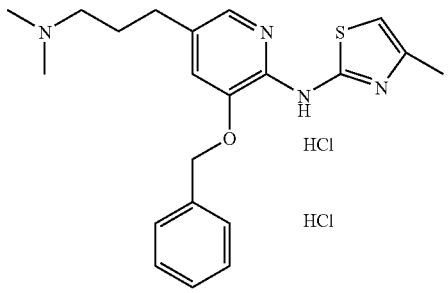

(E)-3-(benzyloxy)-5-(3-(dimethylamino)prop-1-enyl)-N-(4-methylthiazol-2-yl)pyridin-2-amine (140 mg, 0.368 mmol) and 4-methylbenzenesulfonohydrazide (343 mg, 1.84 mmol) were reacted according to the method of Example 93 to afford the title compound (52 mg, 31.0% yield) as a white solid after HCl salt formation. $^1$H NMR (DMSO-d$_6$) δ 11.05 (bs, 1H), 10.66 (bs, 1H), 7.87 (s, 1H), 7.62 (m, 3H), 7.45-7.32 (m, 3H), 6.83 (s, 1H), 5.34 (s, 2H), 2.98 (m, 2H), 2.71 (d, 6H), 2.66 (t, 2H), 2.31 (s, 3H), 2.01 (m, 2H). Mass spectrum (apci) m/z=383.2 (M+H-2HCl).

Example 98

N-(3-(Benzyloxy)-5-(2-methoxyvinyl)pyridin-2-yl)-4-methylthiazol-2-amine

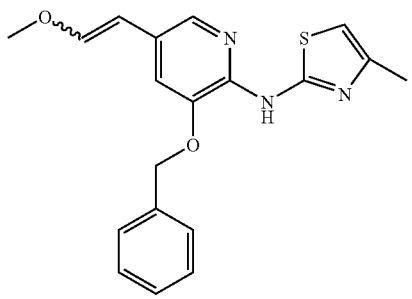

A 250 mL round-bottomed flask was charged with (methoxymethyl)triphenylphosphonium chloride (6.8 g, 20 mmol), THF (40 mL) and cooled to −78° C. under nitrogen. Butyllithium (8.0 ml, 20 mmol) was slowly added and stirred for 30 min at 0° C. The reaction was cooled to −78° C. and 5-(benzyloxy)-6-(4-methylthiazol-2-ylamino)nicotinaldehyde (2.6 g, 8.0 mmol) dissolved in THF (10 mL) was added slowly and stirred at −78° C. and slowly warmed to ambient temperature. After stirring for 2 hours the reaction was partitioned between EtOAc and water. The organic layer was dried with sodium sulfate, filtered and concentrated in vacuo. The residue was purified on a silica gel column (15 to 25% EtOAc/hexanes) to afford the title compound (2.0 g, 71% yield) as a pale yellow foam (about a 1:1 mixture of E and Z isomers). Mass spectrum (apci) m/z=354.1 (M+H).

Example 99

2-(5-(Benzyloxy)-6-(4-methylthiazol-2-ylamino)pyridin-3-yl)acetaldehyde

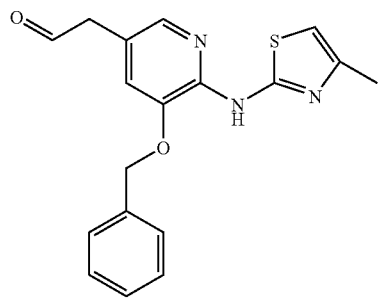 [SMILES: Cc1csc(Nc2ncc(CC=O)cc2OCc2ccccc2)n1]

A 250 mL round-bottomed flask was charged with N-(3-(benzyloxy)-5-(2-methoxyvinyl)pyridin-2-yl)-4-methylthiazol-2-amine (1.93 g, 5.46 mmol) and THF (25 mL). 1M HCl (27.3 ml, 27.3 mmol) was added and the reaction was stirred at 50° C. overnight. The reaction was partitioned between EtOAc and water. The organic phase was dried with sodium sulfate, filtered and concentrated in vacuo. The residue was purified on silica gel (30 to 50% EtOAc/hexanes) to afford the title compound (1.0 g, 54.0% yield) as a clear and colorless oil. $^1$H NMR (CDCl$_3$) δ 9.75 (t, 1H), 8.55 (s, 1H), 7.82 (m, 1H), 7.40 (m, 5H), 6.96 (d, 1H), 6.40 (m, 1H), 5.09 (s, 2H), 3.66 (d, 2H), 2.32 (s, 3H). Mass spectrum (apci) m/z=340.1 (M+H).

Example 100

2-(5-(Benzyloxy)-6-(4-methylthiazol-2-ylamino)pyridin-3-yl)ethanol hydrochloride

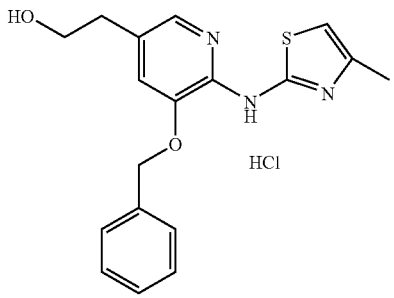 [SMILES: Cc1csc(Nc2ncc(CCO)cc2OCc2ccccc2)n1 ; Cl]

A 20 mL vial was charged with 2-(5-(benzyloxy)-6-(4-methylthiazol-2-ylamino)pyridin-3-yl)acetaldehyde (50 mg, 0.15 mmol), NaBH$_4$ (11 mg, 0.29 mmol), and EtOH (2 mL). The reaction was stirred at room temperature for 10 minutes and aqueous NH$_4$Cl was added. The mixture was extracted with EtOAc. The organic layer was dried with sodium sulfate, filtered and concentrated in vacuo. The residue was purified on silica gel (1:1 EtOAc:Hexanes) to afford the title compound (37 mg, 66% yield) as a white solid after HCl salt formation. $^1$H NMR (DMSO-d$_6$) δ 11.03 (bs, 1H), 7.85 (d, 1H), 7.59 (t, 3H), 7.45-7.33 (m, 3H), 6.83 (s, 1H), 5.31 (s, 2H), 3.61 (t, 2H), 2.72 (t, 2H), 2.32 (s, 3H). Mass spectrum (apci) m/z=342.1 (M+H-HCl).

Example 101

N-(3-(Benzyloxy)-5-(pent-1-enyl)pyridin-2-yl)-4-methylthiazol-2-amine

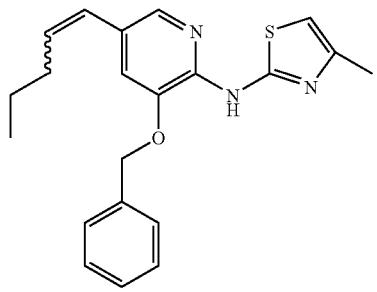 [SMILES: CCCC=Cc1cnc(Nc2nc(C)cs2)c(OCc2ccccc2)c1]

The title compound was isolated as a side product from the reaction of Example 98 (360 mg, 12% yield) as a mixture of E and Z isomers. Mass spectrum (apci) m/z=366.1 (M+H).

Example 102

N-(3-(Benzyloxy)-5-pentylpyridin-2-yl)-4-methylthiazol-2-amine hydrochloride

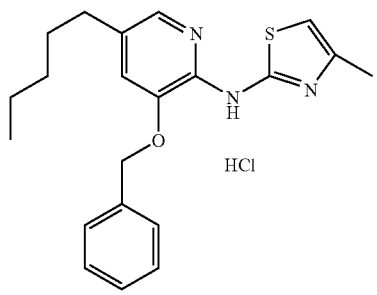 [SMILES: CCCCCc1cnc(Nc2nc(C)cs2)c(OCc2ccccc2)c1 ; Cl]

N-(3-(benzyloxy)-5-(pent-1-enyl)pyridin-2-yl)-4-methylthiazol-2-amine (360 mg, 0.98 mmol) and 4-methylbenzenesulfonohydrazide (733 mg, 3.94 mmol) were reacted according to Example 93 to afford the title compound (150.2 mg, 37.7% yield) as a white solid after HCl salt formation. $^1$H NMR (DMSO-$d_6$) 11.24 (bs, 1H), 7.83 (d, 1H), 7.61 (d, 2H), 7.56 (d, 2H), 7.44-7.32 (m, 3H), 6.87 (s, 1H), 5.34 (s, 2H), 2.57 (t, 2H), 2.33 (s, 3H), 1.57 (m, 2H), 1.35-1.18 (m, 4H), 0.85 (t, 3H). Mass spectrum (apci) m/z=368.1 (M+H-HCl).

Example 103

2-(4-Methylthiazol-2-ylamino)-5-(pyridin-2-ylmethylthio)pyridin-3-ol dihydrochloride

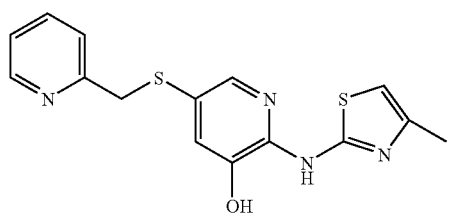

A 250 mL round-bottomed flask was charged with 3-(benzyloxy)-N-(4-methylthiazol-2-yl)-5-(pyridin-2-ylmethylthio)pyridin-2-amine (prepared in Example 46, 6.6 g, 16 mmol), 2-aminoethanethiol hydrochloride (2.7 g, 24 mmol), and 6M HCl (125 mL). The reaction was heated to reflux for 3 hours. The reaction was concentrated on rotary evaporator to about 40 mL and the resultant solids were removed by filtration. The filtrate was further concentrated and the resultant solids were removed by filtration. This procedure was repeated. The solids were combined to afford the title compound (4.6 g, 73% yield) as a white solid. $^1$H NMR (DMSO-$d_6$) δ 11.63 (bs, 1H), 8.75 (m, 1H), 8.32 (td, 1H), 7.82 (d, 1H), 7.77 (m, 2H), 7.35 (d, 1H), 6.92 (d, 1H), 4.50 (s, 2H), 2.34 (s, 3H). Mass spectrum (apci) m/z=331.1 (M+H-2HCl).

The following compounds were prepared according to the procedure of Example 3, Step B using 2-(4-methylthiazol-2-ylamino)-5-(pyridin-2-ylmethylthio)pyridin-3-ol dihydrochloride (prepared according to Example 103).

| Ex. | R² | Name | Data |
|---|---|---|---|
| 104 | pyridin-2-ylmethyl | 4-methyl-N-(3-(pyridin-2-ylmethoxy)-5-(pyridin-2-ylmethylthio)pyridin-2-yl)thiazol-2-amine trihydrochloride | $^1$H NMR (DMSO-$d_6$) δ 8.84 (d, 1H), 8.71 (d, 1H), 8.28 (m, 2H), 8.11 (d, 1H), 7.87 (d, 1H), 7.80-7.67 (m, 4H), 6.83 (s, 1H), 5.60 (s, 2H), 4.57 (s, 2H), 2.30 (s, 3H). Mass spectrum (apci) m/z = 422.1 (M + H − 3HCl). |
| 105 | pyridin-3-ylmethyl | 4-methyl-N-(5-(pyridin-2-ylmethylthio)-3-(pyridin-3-ylmethoxy)pyridin-2-yl)thiazol-2-amine trihydrochloride. | $^1$H NMR (DMSO-$d_6$) δ 9.24 (s, 1H), 8.90 (d, 1H), 8.69 (d, 1H), 8.65 (d, 1H), 8.13 (t, 1H), 8.03 (dd, 1H), 7.85 (d, 1H), 7.70 (s, 1H), 7.61 (m, 2H), 6.75 (s, 1H), 5.49 (s, 2H), 4.49 (s, 2H), 2.28 (s, 3H). Mass spectrum (apci) m/z = 422.1 (M + H − 3HCl). |

-continued

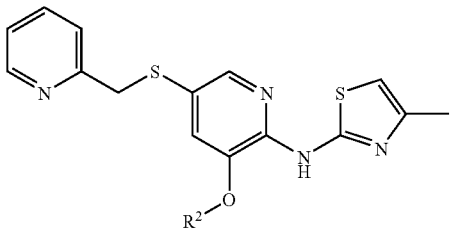

| Ex. | R² | Name | Data |
|---|---|---|---|
| 106 | (quinolin-8-ylmethyl) | 4-methyl-N-(5-(pyridin-2-ylmethylthio)-3-(quinolin-8-ylmethoxy)pyridin-2-yl)thiazol-2-amine | ¹H NMR (DMSO-d₆) δ 9.26 (dd, 1H), 8.67 (d, 1H), 8.59 (d, 1H), 8.20-8.09 (m, 3H), 7.91 (d, 1H), 7.77-7.70 (m, 3H), 7.64 (d, 1H), 7.60 (d, 1H), 6.79 (s, 1H), 5.80 (s, 2H), 4.46 (s, 2H), 2.31 (s, 3H). Mass spectrum (apci) m/z = 472.1 (M + H). |
| 107 | (3-methoxybenzyl) | N-(3-(3-methoxybenzyloxy)-5-(pyridin-2-ylmethylthio)pyridin-2-yl)-4-methylthiazol-2-amine dihydrochloride | ¹H NMR (CDCl₃) δ 8.66 (d, 1H), 8.22 (t, 1H), 7.86 (d, 1H), 7.76 (t, 1H), 7.51 (m, 2H), 7.30 (t, 1H), 7.17 (d, 1H), 7.13 (s, 1H), 6.86 (dd, 1H), 6.54 (s, 1H), 5.44 (s, 2H), 4.58 (s, 2H), 3.85 (s, 3H), 2.47 (s, 3H). Mass spectrum (apci) m/z = 451.1 (M + H − 2HCl). |

Example 108

3-(Benzyloxy)-5-(2-chloropyridin-4-ylthio)-N-(4-methylthiazol-2-yl)pyridin-2-amine dihydrochloride

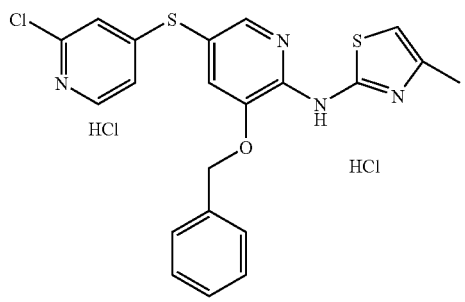 [SMILES: Cc1csc(Nc2ncc(Sc3ccnc(Cl)c3)cc2OCc2ccccc2)n1 ; Cl ; Cl]

A 1 dram vial was charged with methyl 3-(5-(benzyloxy)-6-(4-methylthiazol-2-ylamino)pyridin-3-ylthio)propanoate (70 mg, 0.168 mmol) and DMSO (2 mL). Potassium 2-methylpropan-2-olate (56.7 mg, 0.505 mmol) was added and the reaction was stirred for 5 minutes. 2-Chloro-4-nitropyridine (53.4 mg, 0.337 mmol) was added and the reaction was stirred for 10 minutes. The reaction was poured into saturated aqueous NH₄Cl and extracted with EtOAc. The organic phase was washed with water. The organic layer was dried with sodium sulfate, filtered and concentrated in vacuo. The residue was purified on a silica gel column (20% EtOAc/hexanes) to afford the title compound (45.7 mg, 52.8% yield) as a white solid after HCl salt formation. ¹H NMR (DMSO-d₆) δ 10.92, (bs, 1H), 8.15 (m, 2H), 7.69 (d, 1H), 7.56 (m, 2H), 7.43-7.32 (m, 3H), 7.10 (d, 1H), 6.97 (dd, 1H), 6.80 (s, 1H), 5.34 (s, 2H), 2.30 (s, 3H). Mass spectrum (apci) m/z=441.0 (M+H-2HCl).

The following compounds were prepared according to the procedure of Example 108.

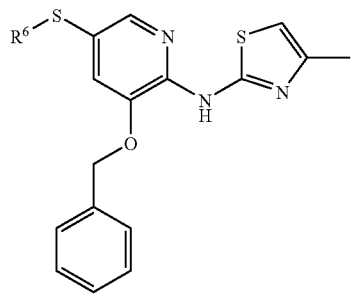

| Ex. | R⁶ | Name | Data |
|---|---|---|---|
| 109 | (2-chloropyrimidin-4-yl) | 3-(benzyloxy)-5-(2-chloropyrimidin-4-ylthio)-N-(4-methylthiazol-2-yl)pyridin-2-amine dihydrochloride | ¹H NMR (DMSO-d₆) δ 10.86 (bs, 1H), 8.40 (d, 1H), 8.14 (d, 1H), 7.73 (s, 1H), 7.57 (m, 2H), 7.44-7.33 (m, 3H), 6.98 (d, 1H), 6.78 (s, 1H), 5.32 (s, 2H), 2.30 (s, 3H). Mass spectrum (apci) m/z = 442.1 (M + H − 2HCl). |

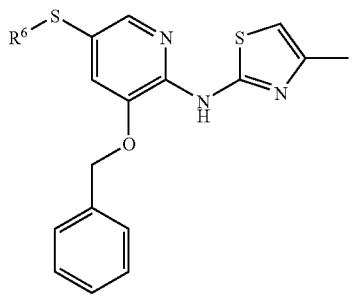

| Ex. | R$^6$ | Name | Data |
|---|---|---|---|
| 110 | pyrimidin-2-yl | 3-(benzyloxy)-N-(4-methylthiazol-2-yl)-5-(pyrimidin-2-ylthio)pyridin-2-amine dihydrochloride | $^1$H NMR (DMSO-d$_6$) δ 11.00 (bs, 1H), 8.58 (d, 2H), 8.12 (s, 1H), 7.8 (s, 1H), 7.58 (m, 2H), 7.43-7.33 (m, 3H), 7.27 (t, 1H), 6.84 (s, 1H), 5.32 (s, 2H), 2.32 (s, 3H). Mass spectrum (apci) m/z = 408.1 (M + H − 2HCl). |
| 111 | thieno[3,2-b]pyridin-7-yl | 3-(benzyloxy)-N-(4-methylthiazol-2-yl)-5-(thieno[3,2-b]pyridin-7-ylthio)pyridin-2-amine dihydrochloride | $^1$H NMR (DMSO-d$_6$) δ 8.54 (d, 1H), 8.35 (d, 1H), 8.22 (d, 1H), 7.75 (d, 1H), 7.70 (d, 1H), 7.55 (m, 2H), 7.41-7.32 (m, 3H), 6.89 (d, 1H), 6.79 (s, 1H), 5.32 (s, 2H), 2.30 (s, 3H). Mass spectrum (apci) m/z = 463.1 (M + H − 2HCl). |
| 112 | 3-methylisoxazolo[5,4-b]pyridin-4-yl | 3-(benzyloxy)-5-(3-methylisoxazolo[5,4-b]pyridin-4-ylthio)-N-(4-methylthiazol-2-yl)pyridin-2-amine dihydrochloride | $^1$H NMR (DMSO-d$_6$) δ 10.84 (bs, 1H), 8.25 (d, 1H), 8.17 (d, 1H), 7.70 (s, 1H), 7.55 (m, 2H), 7.42-7.33 (m, 3H), 6.76 (s, 1H), 6.51 (d, 1H), 5.32 (s, 2H), 2.73 (s, 3H), 2.30 (s, 3H). Mass spectrum (apci) m/z = 462.1 (M + H − 2HCl). |

Example 113

3-(Benzyloxy)-5-bromo-N-(4-(piperidin-4-yl)thiazol-2-yl)pyridin-2-amine dihydrochloride

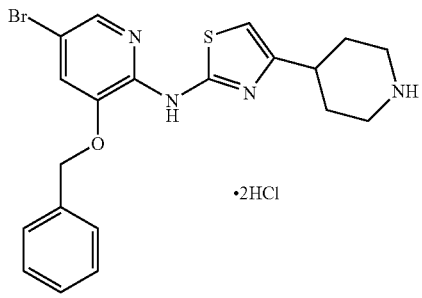 [SMILES: Brc1cnc(Nc2nc(C3CCNCC3)cs2)c(OCc2ccccc2)c1 ; "·2HCl"]

1-(3-(Benzyloxy)-5-bromopyridin-2-yl)thiourea (200 mg, 0.59 mmol), triethylamine (0.144 ml, 1.03 mmol) and tert-butyl 4-(2-bromoacetyl)piperidine-1-carboxylate (253 mg, 0.82 mmol) were reacted according to the procedure in Example 1, Step D to afford the title compound (157.6 mg, 51.4% yield) as a white solid after HCl salt formation. $^1$H NMR (DMSO-d$_6$) δ 10.30 (bs, 1H), 8.83 (bs, 1H), 8.60 (bs, 1H), 7.99 (dd, 1H), 7.67 (d, 1H), 7.59 (m, 2H), 7.45-7.33 (m, 3H), 6.75 (s, 1H), 5.30 (s, 2H), 3.32 (d, 2H), 3.05-2.85 (m, 3H), 2.11 (d, 2H), 1.79 (m, 2H). Mass spectrum (apci) m/z=445.2 (M+H-2HCl).

Example 114

N-(3-(Benzyloxy)-5-bromopyridin-2-yl)thiazolo[5,4-b]pyridin-2-amine

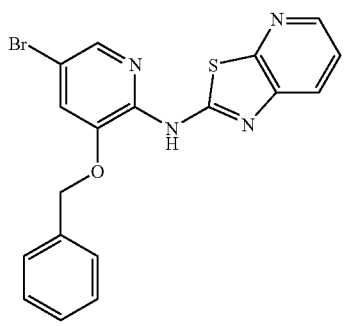 [SMILES: Brc1cnc(Nc2nc3cccnc3s2)c(OCc2ccccc2)c1]

3-(Benzyloxy)-5-bromopyridin-2-amine (10.0 g, 35.83 mmol) was added to a mixture of 2-chloro-3-isothiocyanato-pyridine (6.112 g, 35.83 mmol) in DMF. The reaction was stirred at 80° C. for an hour, then at 110° C. for two hours. The reaction was cooled, diluted in water (200 mL) and 2N NaOH (35 mL), stirred for 30 minutes, and then filtered. The wet solids were washed with water, then dissolved in dichloromethane (300 mL) dried over $MgSO_4$, and filtered. Hexane (300 mL) was added to the combined filtrates, the mixture was concentrated to 500 mL, and then mixture stirred for 30 minutes. The mixture was filtered to afford the first crop of the title compound. The mother liquor was concentrated to 500 mL (until most of the dichloromethane was removed), filtered, washed with hexanes to afford a second crop of the title compound. The two crops combined afforded the title compound (10.2 g, 68.7%) as light yellow crystals: $^1$H NMR ($CDCl_3$) δ 5.14 (s, 2H), 7.30-7.33 (m, 2H), 7.42-7.48 (m, 5H), 7.87 (d, 1H), 8.10 (s, 1H), 8.40 (d, 1H), 8.67 (bs, 1H).

Example 115

N-(3-(Benzyloxy)-5-(phenylthio)pyridin-2-yl)thiazolo[5,4-b]pyridin-2-amine hydrochloride

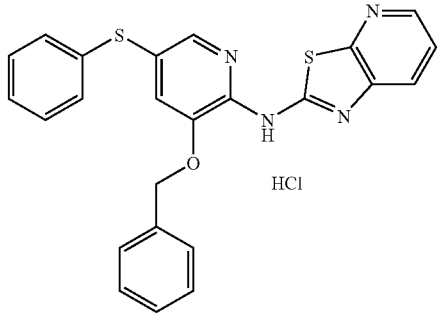 [SMILES: c1ccc(COc2cc(Sc3ccccc3)cnc2Nc2nc3cccnc3s2)cc1 ; Cl]

N-(3-(benzyloxy)-5-bromopyridin-2-yl)thiazolo[5,4-b]pyridin-2-amine (100 mg, 0.242 mmol), methyllithium (0.181 ml, 0.290 mmol), butyllithium (0.116 ml, 0.290 mmol) and 1,2-diphenyldisulfane (79.2 mg, 0.363 mmol) were reacted according to the procedure of Example 7 to afford the title compound (48.2 mg, 41.6% yield) as a pale yellow solid after HCl salt formation. $^1$H NMR (DMSO-$d_6$) δ 11.06 (bs, 1H), 8.38 (dd, 1H), 8.05 (d, 1H), 7.97 (d, 1H), 7.58 (d, 1H), 7.54 (m, 2H), 7.44 (dd, 1H), 7.41-7.17 (m, 8H), 5.31 (s, 2H). Mass spectrum (apci) m/z=443.1 (M+H-HCl).

Example 116

N-(3-(benzyloxy)-5-(pyridin-2-ylthio)pyridin-2-yl)thiazolo[5,4-b]pyridin-2-amine dihydrochloride

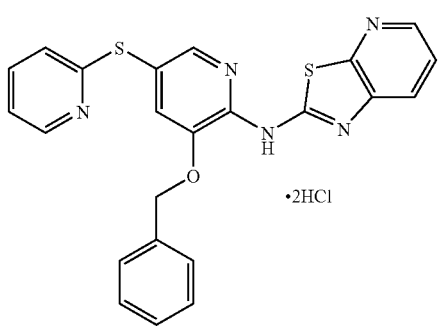 [SMILES: c1ccc(COc2cc(Sc3ccccn3)cnc2Nc2nc3cccnc3s2)cc1 ; "·2HCl"]

N-(3-(benzyloxy)-5-bromopyridin-2-yl)thiazolo[5,4-b]pyridin-2-amine (100 mg, 0.242 mmol), methyllithium (0.181 ml, 0.290 mmol), butyllithium (0.116 ml, 0.290 mmol) and 2-(2-(pyridin-2-yl)disulfanyl)pyridine (80.0 mg, 0.363 mmol) were reacted according to the procedure in Example 7 to afford the title compound (57.6 mg, 49.6% yield) as a pale yellow solid after HCl salt formation. $^1$H NMR (DMSO-$d_6$) δ 11.13 (bs, 1H), 8.33 (m, 2H), 8.15 (d, 1H), 7.99 (d, 1H), 7.70 (d, 1H), 7.62 (td, 1H), 7.57 (m, 2H), 7.45 (dd, 1H), 7.42-7.32 (m, 3H), 7.15 (ddd, 1H), 6.92 (d, 1H), 5.33 (s, 2H). Mass spectrum (apci) m/z=444.1 (M+H-2HCl).

Example 117

2-(3-(Benzyloxy)-5-bromopyridin-2-ylamino)thiazolo[5,4-b]pyridine-6-carboxylic acid

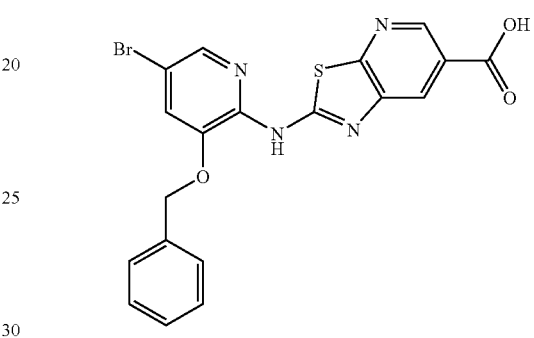

A 10 mL round-bottomed flask was charged with methyl 2-(3-(benzyloxy)-5-bromopyridin-2-ylamino)thiazolo[5,4-b]pyridine-6-carboxylate (80 mg, 0.17 mmol) and EtOH (3 mL). Sodium hydroxide (0.51 ml, 0.51 mmol) was added and stirred overnight. The methanol was removed and the residue was partitioned between methylene chloride and 0.5 N HCl. Solid $K_2CO_3$ was added to adjust to pH 5 and additional methanol was added. The organic layer was dried with sodium sulfate, filtered and concentrated in vacuo to afford the title compound (80 mg, 103% yield) as an off-white solid. $^1$H NMR (DMSO-$d_6$) δ 11.0 (bs, 1H), 8.85 (d, 1H), 8.26 (d, 1H), 8.10 (d, 1H), 7.75 (d, 1H), 7.61 (d, 2H), 7.42 (t, 2H), 7.36 (m, 1H), 5.33 (s, 2H). Mass spectrum (apci) m/z=457.1 (M+H).

Example 118

(E)-3-(benzyloxy)-N-(4-methylthiazol-2-yl)-5-styrylpyridin-2-amine

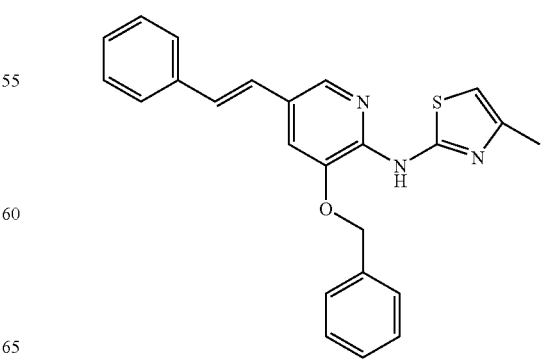

3-(Benzyloxy)-5-bromo-N-(4-methylthiazol-2-yl)pyridin-2-amine (0.300 g, 0.797 mmol), (E)-styrylboronic acid (0.142 g, 0.957 mmol), Pd(PPh$_3$)$_4$ (0.0461 g, 0.0399 mmol), and sodium carbonate (0.254 g, 2.39 mmol) were added to DME (10 mL) and water (5 mL) and heated at 80° C. for 18 hours. An additional 0.5 eq of (E)-styrylboronic acid, Pd(PPh$_3$)$_4$, and 2M sodium carbonate were added and the reaction was heated at 80° C. for an additional 6 hrs. The reaction mixture was cooled and partitioned between water and dichloromethane. The layers were separated, dried, filtered, and concentrated to provide the title compound (0.314 g, 98.6% yield). $^1$H NMR (CDCl$_3$) δ 8.03 (d, 1H), 7.63 (d, 2H), 7.49 (m, 2H), 7.39 (m, 5H), 7.32 (m, 2H), 6.98 (s, 2H), 6.39 (s, 1H), 5.42 (s, 2H), 2.46 (s, 3H). Mass spectrum (apci) m/z=400.0 (M+H).

Example 119

3-(Benzyloxy)-N-(4-methylthiazol-2-yl)-5-phenethylpyridin-2-amine trifluoromethyl acetate salt

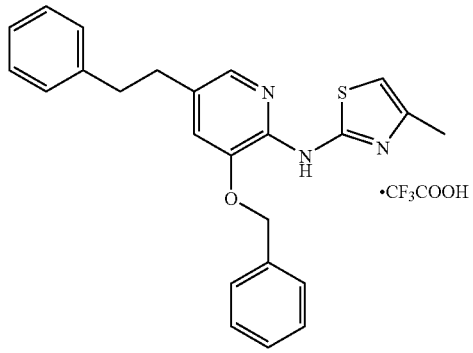 [SMILES: Cc1csc(Nc2ncc(CCc3ccccc3)cc2OCc2ccccc2)n1 ; "·CF3COOH"]

(E)-3-(benzyloxy)-N-(4-methylthiazol-2-yl)-5-styrylpyridin-2-amine (0.314 g, 0.786 mmol) and 4-methylbenzenesulfonohydrazide (1.46 g, 7.86 mmol) were added to dimethoxyethane (15 mL). NaOAc (0.645 g, 7.86 mmol) was dissolved in water (3 mL) and added to the above solution, and the reaction was refluxed for 18 hours. The reaction was cooled to room temperature and partitioned between water and dichloromethane. The layers were separated, dried, filtered, and concentrated. The residue was purified by silica gel chromatography to give 90% pure product. The product was purified by reverse phase chromatography to provide the title compound (0.1062 g, 33.65% yield) as the TFA salt. $^1$H NMR (DMSO-d$_6$) δ 7.72 (s, 1H), 7.58 (d, 2H), 7.44 (m, 3H), 7.38 (m, 1H), 7.26 (m, 2H), 7.18 (m, 3H), 6.68 (s, 1H), 5.25 (s, 2H), 2.87 (m, 4H), 2.27 (s, 3H). Mass spectrum (apci) m/z=402.1 (M+H—CO$_2$CF$_3$).

Example 120

3-(Benzyloxy)-N-(4-methylthiazol-2-yl)-5-(1-phenylvinyl)pyridin-2-amine hydrochloride

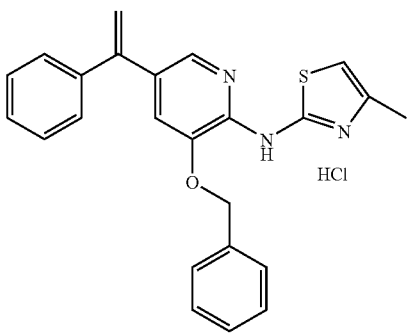 [SMILES: C=C(c1ccccc1)c1cnc(Nc2nc(C)cs2)c(OCc2ccccc2)c1 ; Cl]

3-(Benzyloxy)-5-bromo-N-(4-methylthiazol-2-yl)pyridin-2-amine (0.250 g, 0.664 mmol), MeLi (0.519 ml, 0.831 mmol), butyllithium (0.332 ml, 0.831 mmol), and acetophenone (0.0798 g, 0.664 mmol) were reacted according to the method of Example 7. 1M HCl was added and the reaction mixture was stirred at ambient temperature for 2 hours. The reaction mixture was poured onto ice and saturated sodium bicarbonate and extracted twice with dichloromethane. The organic layer was dried, filtered, and concentrated. The residue was purified by silica gel chromatography (5-10% EtOAc in hexane) to provide the title compound (0.125 g, 47.1% yield) after HCl salt formation. $^1$H NMR (DMSO-d$_6$) δ 7.81 (d, 1H), 7.54 (m, 2H), 7.48 (m, 1H), 7.37 (m, 6H), 7.30 (m, 2H), 6.81 (s, 1H), 5.60 (s, 1H), 5.54 (s, 1H), 5.33 (s, 2H), 2.31 (s, 3H). Mass spectrum (apci) m/z=400.1 (M+H-HCl)

Example 121

3-(Benzyloxy)-N-(4-methylthiazol-2-yl)-5-(1-phenylethyl)pyridin-2-amine hydrochloride

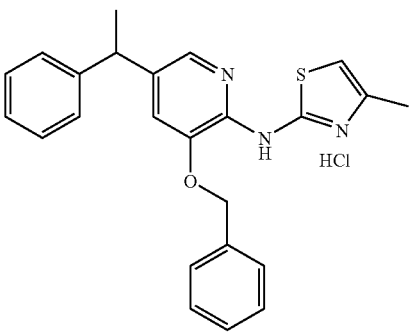 [SMILES: Cc1csc(Nc2ncc(C(C)c3ccccc3)cc2OCc2ccccc2)n1 ; Cl]

3-(Benzyloxy)-N-(4-methylthiazol-2-yl)-5-(1-phenylvinyl)pyridin-2-amine (0.90 g, 2.3 mmol), 4-methylbenzenesulfonohydrazide (4.2 g, 23 mmol) and NaOAc (1.8 g, 23 mmol) were reacted according to Example 119 to provide the title compound (0.0313 g, 34.6% yield). $^1$H NMR (DMSO-d$_6$) δ 7.88 (s, 1H), 7.55 (m, 3H), 7.37 (m, 3H), 7.29 (m, 4H), 7.20 (m, 1H), 6.81 (s, 1H), 5.31 (s, 2H), 4.19 (m, 1H), 2.30 (s, 3H), 1.61 (d, 3H). Mass spectrum (apci) m/z=402.1 (M+H-HCl).

Example 122

Methyl 3-(2-(5-benzyl-3-(benzyloxy)pyridin-2-ylamino)thiazol-4-yl)propanoate hydrochloride

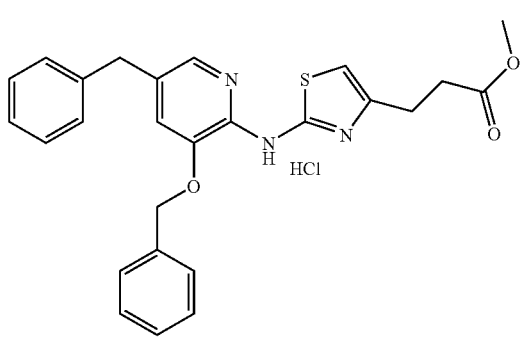 [SMILES: COC(=O)CCc1csc(Nc2ncc(Cc3ccccc3)cc2OCc2ccccc2)n1 ; Cl]

Methyl 3-(2-(3-(benzyloxy)-5-bromopyridin-2-ylamino)thiazol-4-yl)propanoate (0.200 g, 0.446 mmol), 9-benzyl-9-bora-bicyclo[3.3.1]nonane (2.68 ml, 1.34 mmol), PdCl$_2$ (dppf) dichloromethane adduct (0.0367 g, 0.0446 mmol), and Cs$_2$CO$_3$ (4.36 g, 1.34 mmol) were reacted according to Example 65 to provide the title compound (0.108 g, 52.7% yield). $^1$H NMR (DMSO-d$_6$) δ 7.82 (s, 1H), 7.55 (d, 2H), 7.47 (s, 1H), 7.30 (m, 8H), 6.74 (s, 1H), 5.26 (s, 2H), 3.91 (s, 2H), 3.60 (s, 3H), 2.88 (t, 2H), 2.71 (t, 2H). Mass spectrum (apci) m/z=460.2 (M+H-HCl).

Example 123

3-(2-(5-Benzyl-3-(benzyloxy)pyridin-2-ylamino)thiazol-4-yl)propanoic acid hydrochloride

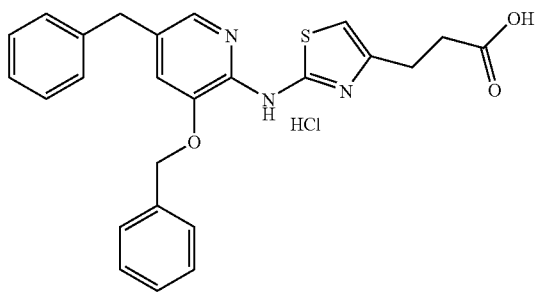 [SMILES: O=C(O)CCc1csc(Nc2ncc(Cc3ccccc3)cc2OCc2ccccc2)n1 ; Cl]

Methyl 3-(2-(5-benzyl-3-(benzyloxy)pyridin-2-ylamino)thiazol-4-yl)propanoate (0.090 g, 0.20 mmol), MeOH (8 mL), and 1M NaOH (3 mL) were reacted according to Example 66 to provide the title compound (0.029 g, 31% yield). $^1$H NMR (DMSO-d$_6$) δ 7.79 (s, 1H), 7.74 (d, 2H), 7.37 (m, 4H), 7.28 (m, 2H), 7.24 (m, 3H), 6.67 (s, 1H), 5.24 (s, 2H), 3.89 (s, 2H), 2.82 (t, 2H), 2.59 (t, 2H). Mass spectrum (apci) m/z=446.2 (M+H-HCl).

Example 124 tert-Butyl 4-(hydroxy(pyridin-2-yl methyl)piperidine-1-carboxylate

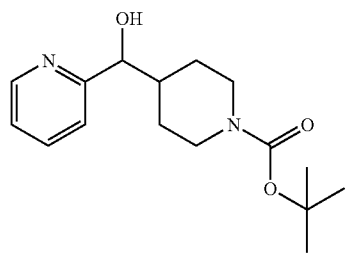 [SMILES: CC(C)(C)OC(=O)N1CCC(C(O)c2ccccn2)CC1]

2-Bromopyridine (13.89 g, 87.92 mmol) was added to THF (100 mL) and cooled to −78° C. Butyl lithium (35.17 ml, 87.92 mmol) was added slowly and the reaction was stirred for 5 minutes. tert-Butyl 4-formylpiperidine-1-carboxylate (15.0 g, 70.33 mmol) in THF (50 mL) was added slowly to the above solution and the reaction mixture was stirred at −78° C. for 90 minutes. Ammonium chloride was added and the reaction mixture was extracted with dichloromethane. The reaction was concentrated and purified by silica gel chromatography (80-90% EtOAc in hexanes) to give the title compound (13.45 g, 65.41% yield). $^1$H NMR (DMSO-d$_6$) δ 8.48 (d, 1H), 7.77 (dt, 1H), 7.43 (d, 1H), 7.24 (dd, 1H), 5.33 (d, 1H), 4.39 (t, 1H), 3.92 (m, 2H), 2.60 (m, 2H), 1.87 (m, 1H), 1.37 (m, 11H), 1.18 (m, 2H).

Example 125

N-(3-(Benzyloxy)-5-(piperidin-4-yl(pyridin-2-yl)methylthio)pyridin-2-yl)thiazolo[5,4-b]pyridin-2-amine di-trifluoroacetic acid salt

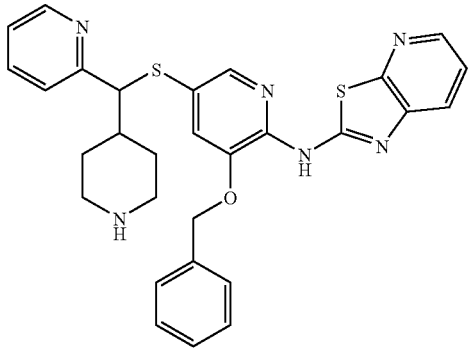 [SMILES: c1ccc(COc2cc(SC(c3ccccn3)C3CCNCC3)cnc2Nc2nc3cccnc3s2)cc1]

Step A: tert-Butyl 4-(hydroxy(pyridin-2-yl)methyl)piperidine-1-carboxylate (Prepared in Example 124; 8.00 g, 27.4 mmol) and TEA (11.4 ml, 82.1 mmol) were combined and cooled to 0° C. Methanesulfonyl chloride (2.65 ml, 34.2 mmol) was added and the reaction mixture was stirred at ambient temperature for 18 hours. Water was added and the reaction mixture was extracted with dichloromethane. The organic layer was dried, filtered, and concentrated to give tert-butyl 4-((methylsulfonyloxy)(pyridin-2-yl)methyl)piperidine-1-carboxylate (9.9 g, 97.7% yield). $^1$H NMR (DMSO-$d_6$) δ 10.88 (bs, 1H), 8.49 (d, 1H), 8.35 (d, 1H), 7.95 (m, 1H), 7.75 (s, 1H), 7.65 (t, 1H), 7.57 (d, 2H), 7.42 (m, 3H), 7.36 (m, 1H), 7.31 (s, 1H), 7.21 (m, 1H), 7.14 (d, 1H), 5.23 (s, 2H), 4.19 (d, 1H), 3.98 (m, 1H), 3.84 (m, 1H), 2.14 (m, 2H), 1.37 (m, 10H), 1.20 (m, 3H), 1.01 (m, 1H).

Step B: tert-Butyl 4-((methylsulfonyloxy)(pyridin-2-yl)methyl)piperidine-1-carboxylate was reacted according to the method of Example 42 to provide the title compound. $^1$H NMR (DMSO-$d_6$) δ 8.52 (m, 2H), 8.36 (m, 1H), 8.16 (bs, 1H), 7.94 (m, 1H), 7.83 (d, 1H), 7.72 (dt, 1H), 7.57 (d, 2H), 7.43 (m, 3H), 7.38 (m, 1H), 7.26 (m, 3H), 5.21 (s, 2H), 4.29 (d, 1H), 3.33 (d, 1H), 3.20 (d, 1H), 2.85 (m, 2H), 2.29 (m, 2H), 1.50 (m, 2H), 1.34 (m, 1H). Mass spectrum (apci) m/z=541.2 (M+H-2TFA).

Example 126

Ethyl 3-(5-(benzyloxy)-6-(thiazolo[5,4-b]pyridin-2-ylamino)pyridin-3-ylthio)propanoate

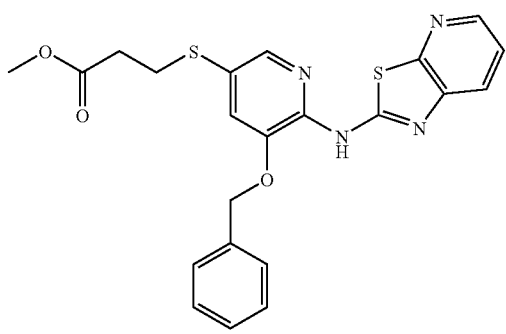 [SMILES: COC(=O)CCSc1cnc(Nc2nc3cccnc3s2)c(OCc2ccccc2)c1]

A 500 mL round-bottomed flask was charged with N-(3-(benzyloxy)-5-bromopyridin-2-yl)thiazolo[5,4-b]pyridin-2-amine (2.00 g, 4.839 mmol), 4,5-bis(diphenylphosphino)-9,9-dimethyl-9H-xanthene (0.1400 g, 0.2420 mmol), Pd$_2$dba$_3$ (0.1108 g, 0.1210 mmol), methyl 3-mercaptopropanoate (0.5628 ml, 5.081 mmol), N-ethyl-N-isopropylpropan-2-amine (1.686 ml, 9.678 mmol), and dioxane (125 mL). The reaction mixture was heated at 95° C. under nitrogen for three hours. Saturated ammonium chloride and dichloromethane were added. The reaction mixture was filtered and the solids were washed with water to the title compound (2.425 g, 110.7% yield) containing a small amount of diisopropylethylamine impurity. $^1$H NMR (DMSO-$d_6$) δ 10.89 (s, 1H), 8.36 (d, 1H), 7.96 (d, 1H), 7.95 (s, 1H), 7.60 (m, 3H), 7.42 (m, 3H), 7.35 (m, 1H), 5.34 (s, 2H), 3.59 (s, 3H), 3.12 (t, 2H), 2.54 (t, 2H). Mass spectrum (apci) m/z=453.1 (M+H).

Example 127

N-(3-(Benzyloxy)-5-(piperidin-4-ylmethylthio)pyridin-2-yl)thiazolo[5,4-b]pyridin-2-amine di-trifluoroacetic acid

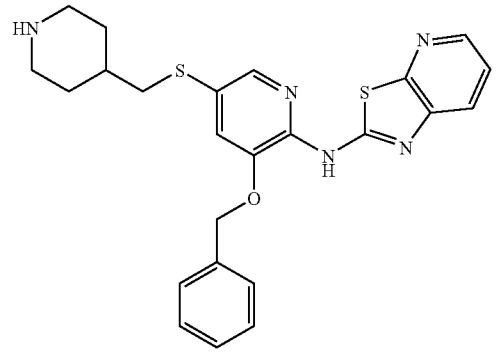 [SMILES: c1ccc(COc2cc(SCC3CCNCC3)cnc2Nc2nc3cccnc3s2)cc1]

Prepared according to the method of Example 43. $^1$H NMR (DMSO-$d_6$) δ 8.54 (bs, 1H), 8.36 (dd, 1H), 8.20 (bs, 1H), 7.98 (d, 1H), 7.89 (d, 1H), 7.61 (d, 2H), 7.55 (d, 1H), 7.42 (m, 3H), 7.36 (m, 1H), 5.35 (s, 2H), 3.25 (d, 2H), 2.92 (d, 2H), 2.81 (m, 2H), 1.90 (m, 2H), 1.64 (m, 1H), 1.32 (m, 2H). Mass spectrum (apci) m/z=464.2 (M+H-2TFA).

Example 128

N-(3-(benzyloxy)-5-(thieno[3,2-b]pyridin-7-ylthio)pyridin-2-yl)thiazolo[5,4-b]pyridin-2-amine

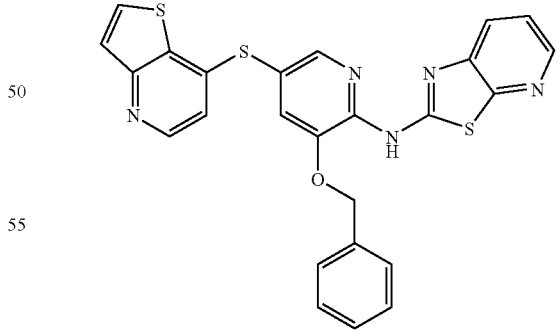

Prepared according to the method of Example 108. $^1$H NMR (DMSO-$d_6$) δ 11.26 (s, 1H), 8.44 (d, 1H), 8.40 (m, 1H), 8.25 (d, 1H), 8.18 (d, 1H), 8.02 (m, 1H), 7.76 (s, 1H), 7.61 (d, 1H), 7.56 (d, 2H), 7.46 (m, 1H), 7.37 (m, 3H), 6.73 (d, 1H), 5.35 (s, 2H). Mass spectrum (apci) m/z=500.1 (M+H).

Example 129

Methyl 2-(3-(benzyloxy)-5-bromopyridin-2-ylamino)thiazolo[5,4-b]pyridine-6-carboxylate

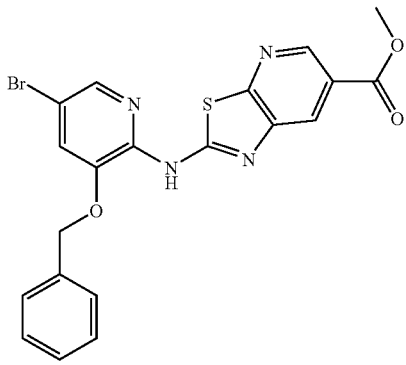 [SMILES: COC(=O)c1cnc2sc(Nc3ncc(Br)cc3OCc3ccccc3)nc2c1]

Step A: Preparation of methyl 6-chloro-5-isothiocyanatonicotinate: Thiophosgene (6.367 g, 55.37 mmol) in dichloromethane (10 mL) was added to a mixture of methyl 5-amino-6-chloronicotinate (8.61 g, 46.14 mmol) and sodium carbonate (9.781 g, 92.29 mmol) in dichloromethane (200 mL). The reaction mixture was stirred for four days at ambient temperature. The reaction mixture was washed with water and brine, dried, and concentrated. The residue was purified via MPLC (Biotage) eluting with 12:1 hexane:ethyl acetate to afford methyl 6-chloro-5-isothiocyanatonicotinate (8.03 g, 76.1% yield) as a white solid: $^1$H NMR (CDCl$_3$) δ 3.97 (s, 3H), 8.09 (s, 1H), 8.84 (s, 1H).

Step B: Preparation of 2-(3-(benzyloxy)-5-bromopyridin-2-ylamino)thiazolo[5,4-b]pyridine-6-carboxylate: 3-(Benzyloxy)-5-bromopyridin-2-amine (1.50 g, 5.37 mmol) was added to a mixture of methyl 6-chloro-5-isothiocyanatonicotinate (1.23 g, 5.37 mmol) in DMF (4 mL). The reaction mixture was stirred at 80° C. for an hour, then at 110° C. for 2 hours. The reaction mixture was cooled, partitioned between dichloromethane (200 mL) and water (200 mL) and 2N NaOH (15 mL). The organic layer was washed with water and brine, dried, and concentrated. The residue was dissolved in warm dichloromethane (70 mL), and to this was added warm hexanes (40° C.) (250 mL). The solution was cooled to ambient temperature and the resulting solids were collected by filtration to afford methyl 2-(3-(benzyloxy)-5-bromopyridin-2-ylamino)thiazolo[5,4-b]pyridine-6-carboxylate (1.77 g, 69.9% yield) as a white powder. $^1$H NMR (CDCl$_3$) δ 3.98 (s, 3H), 5.15 (s, 2H), 7.35 (s, 1H), 7.46 (m, 5H), 8.10 (s, 1H), 8.42 (s, 1H), 8.76 (bs, 1H), 9.02 (s, 1H).

Example 130

N-(3-(Benzyloxy)-5-(2-chlorophenoxy)pyridin-2-yl)-4-methylthiazol-2-amine hydrochloride

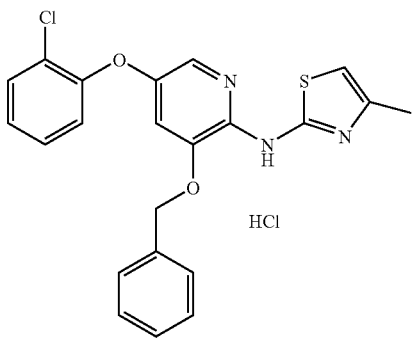 [SMILES: Cc1csc(Nc2ncc(Oc3ccccc3Cl)cc2OCc2ccccc2)n1 ; Cl]

Step A: Preparation of 3-(benzyloxy)-5-chloro-2-nitropyridine: 1-(Bromomethyl)benzene (7.905 ml, 66.46 mmol) was added to a mixture of cesium carbonate (21.65 g, 66.46 mmol) and 5-chloro-2-nitropyridin-3-ol (11.6 g, 66.46 mmol) in DMF (50 mL). The reaction mixture was stirred overnight at ambient temperature, then partitioned between ethyl acetate and water, washed with water and brine, dried, and concentrated to afford 3-(benzyloxy)-5-chloro-2-nitropyridine (16.0 g, 91.0% yield) as a light yellow powder. $^1$H NMR (CDCl$_3$) δ 5.25 (s, 2H), 7.41 (m, 5H), 7.53 (s, 1H), 8.04 (s, 1H).

Step B: Preparation of 3-(benzyloxy)-5-(2-chlorophenoxy)-2-nitropyridine: A mixture of 3-(benzyloxy)-5-chloro-2-nitropyridine (1.00 g, 3.78 mmol), potassium carbonate (2.09 g, 15.1 mmol), 2-chlorophenol (1.46 g, 11.3 mmol) and DMF (16 mL) was heated at 100° C. for 2 hours. The reaction mixture was cooled, partitioned between a 1:1 mixture of ethyl acetate (60 mL) and ether and water (60 mL). The organic layer was washed with 2N NaOH (30 mL), water, and brine, dried, and concentrated. The residue was purified by MPLC (Biotage) eluting with 5:1 hexane:ethyl acetate to afford 3-(benzyloxy)-5-(2-chlorophenoxy)-2-nitropyridine (0.73 g, 54.2% yield) as a light yellow solid. $^1$H NMR (CDCl$_3$) δ 5.16 (s, 2H), 6.90 (s, 1H), 7.09 (d, 1H), 7.28-7.37 (m, 7H), 7.52 (d, 1H), 7.72 (s, 1H).

Step C: Preparation of 3-(benzyloxy)-5-(2-chlorophenoxy)pyridin-2-amine: Zinc (1.34 g, 20.5 mmol) was added slowly to a solution of 3-(benzyloxy)-5-(2-chlorophenoxy)-2-nitropyridine (0.730 g, 2.05 mmol) in acetic acid (20 mL) in a water bath. The reaction mixture was stirred 2 hours, then diluted with dichloromethane (100 mL) and filtered through Celite. The pad was washed several times with dichloromethane, and the combined filtrates were concentrated. The residue was partitioned between ethyl acetate and 2N NaOH, and the organic layer was washed with brine, dried, and concentrated to afford 3-(benzyloxy)-5-(2-chlorophenoxy)pyridin-2-amine (0.66 g, 98.7% yield) as a light yellow oil. $^1$H NMR (CDCl$_3$) δ 4.85 (bs, 2H), 5.03 (s, 2H), 6.79-6.83 (m, 2H), 7.02 (t, 1H), 7.14 (t, 1H), 7.37-7.47 (m, 7H).

Step D: Preparation of N-(3-(benzyloxy)-5-(2-chlorophenoxy)pyridin-2-ylcarbamothioyl)benzamide: Benzoyl isothiocyanate (0.330 g, 2.02 mmol) was added to a solution of 3-(benzyloxy)-5-(2-chlorophenoxy)pyridin-2-amine (0.660 g, 2.02 mmol) in THF (4 mL). The reaction mixture was stirred for 2 hours at room temperature, diluted with hexanes, filtered, and washed with hexanes to afford 1-benzoyl-3-(3-(benzyloxy)-5-(2-chlorophenoxy)pyridin-2-yl)thiourea (0.92 g, 93.0% yield) as a light yellow powder. $^1$H NMR (CDCl$_3$) δ 5.16 (s, 2H), 6.95 (s, 1H), 7.00-8.04 (m, 17H).

Step E: Preparation of 1-(3-(benzyloxy)-5-(2-chlorophenoxy)pyridin-2-yl)thiourea: A mixture of 1-benzoyl-3-(3-(benzyloxy)-5-(2-chlorophenoxy)pyridin-2-yl)thiourea (0.92 g, 1.88 mmol), potassium carbonate (0.519 g, 3.76 mmol), and ethanol was refluxed (15 mL) for 2 hours. The reaction mixture was cooled, diluted with water (100 mL), and filtered, and the solids were washed with water. The solids were dissolved in dichloromethane, dried over MgSO$_4$, filtered, and concentrated to afford a 4:1 mixture of 1-(3-(benzyloxy)-5-(2-chlorophenoxy)pyridin-2-yl)thiourea (0.758 g). $^1$H NMR (CDCl$_3$) δ 5.11 (s, 2H), 6.77 (bs, 1H), 6.90 (s, 1H), 6.93 (d, 1H), 7.15 (t, 1H), 7.23 (t, 1H), 7.32-7.48 (m, 7H), 8.60 (bs, 1H), 10.71 (bs, 1H).

Step F: Preparation of N-(3-(benzyloxy)-5-(2-chlorophenoxy)pyridin-2-yl)-4-methylthiazol-2-amine hydrochloride: A mixture of 1-(3-(benzyloxy)-5-(2-chlorophenoxy)pyridin-2-yl)thiourea (0.280 g, 0.660 mmol), 1-chloropropan-2-one (0.0733 g, 0.792 mmol), triethylamine (0.161 ml, 1.16 mmol), and ethanol (10 mL) was heated at reflux overnight. The reaction mixture was cooled and partitioned between ethyl acetate:ether (1:1) and water. The organic layer was washed with water, brine, dried, and concentrated. The residue was purified via MPLC (Biotage) eluting with 3:1 hexane:ethyl acetate to afford a free base of the title compound as a light yellow oil. The oil was dissolved in ether (6 mL), and 1M HCl in ether (2 mL) was added. The mixture was sonicated to break up the white solid. Hexanes (5 mL) were added, and the mixture was sonicated and filtered. The solids were washed with hexanes and dried to provide 3-(benzyloxy)-5-(2-chlorophenoxy)-N-(4-methylthiazol-2-yl)pyridin-2-amine hydrochloride (0.215 g, 70.7% yield) as a white powder. $^1$H NMR (DMSO-d$_6$) δ 2.31 (s, 3H), 5.33 (s, 2H), 6.82 (s, 1H), 7.01 (d, 1H), 7.22 (t, 1H), 7.32-7.43 (m, 5H), 7.51-7.62 (m, 5H), 7.67 (d, 1H).

Example 131

Methyl 3-(2-(3-(benzyloxy)-5-(2-chlorophenoxy)pyridin-2-ylamino)thiazol-4-yl)propanoate hydrochloride

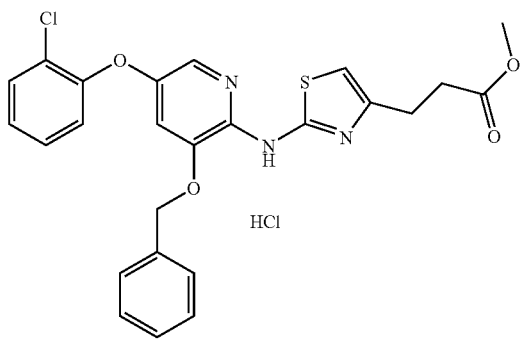 [SMILES: COC(=O)CCc1csc(Nc2ncc(Oc3ccccc3Cl)cc2OCc2ccccc2)n1 ; Cl]

A mixture of 1-(3-(benzyloxy)-5-(2-chlorophenoxy)pyridin-2-yl)thiourea (0.471 g, 1.11 mmol), methyl 5-bromo-4-oxopentanoate (0.279 g, 1.33 mmol), triethylamine (0.271 ml, 1.94 mmol), and ethanol (10 mL) was heated at reflux for 2 hours, cooled, partitioned between ethyl acetate and 2N NaOH, washed with water and brine, dried, and concentrated. The residue was purified by MPLC (Biotage) eluting with 3:1 hexane:ethyl acetate to afford methyl 3-(2-(3-(benzyloxy)-5-(2-chlorophenoxy)pyridin-2-ylamino)thiazol-4-yl)propanoate (0.392 g, 71.2% yield) as a white viscous oil/wax. The compound (70 mg) was dissolved in ether (2 mL) and 1N HCl in ether (0.5 mL) was added. The mixture was stirred 5 minutes, and hexanes (5 mL) were added. The mixture was decanted, and a mixture of hexanes:ether (2:1, 3 mL) was added three times with three decantations. The solid material was dried to afford methyl 3-(2-(3-(benzyloxy)-5-(2-chlorophenoxy)pyridin-2-ylamino)thiazol-4-yl)propanoate hydrochloride (0.058 g, 9.81% yield) as a white solid. $^1$H NMR (DMSO-d$_6$) δ 2.73 (t, 2H), 3.61 (s, 3H), 2.91 (t, 2H), 5.32 (s, 2H), 6.82 (s, 1H), 6.99 (d, 1H), 7.21 (t, 1H), 7.31-7.43 (m, 4H), 7.47 (d, 1H), 7.55-7.66 (m, 5H).

Example 132

N-(3-(Benzyloxy)-5-bromopyridin-2-yl)-5-chloro-4-ethylthiazol-2-amine

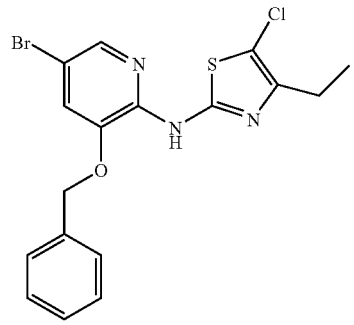 [SMILES: CCc1nc(Nc2ncc(Br)cc2OCc2ccccc2)sc1Cl]

1-Chloropyrrolidine-2,5-dione (0.103 g, 0.769 mmol) was added to a solution of 3-(benzyloxy)-5-bromo-N-(4-ethylthiazol-2-yl)pyridin-2-amine (0.25 g, 0.641 mmol) in acetonitrile (6 mL). The reaction mixture was stirred for 1 hour and then partitioned between ether and water. The organic layer was washed with brine, dried, and concentrated. The residue was purified by MPLC (Biotage) eluting with 6:1 hexane:ethyl acetate to afford 3-(benzyloxy)-5-bromo-N-(5-chloro-4-ethylthiazol-2-yl)pyridin-2-amine (0.154 g, 56.6% yield) as a light yellow powder. $^1$H NMR (DMSO-d$_6$) δ 1.17 (t, 3H), 2.58 (q, 2H), 5.28 (s, 2H), 7.30-7.43 (m, 3H), 7.59 (d, 2H), 7.66 (s, 1H), 7.98 (s, 1H), 10.79 (bs, 1H).

Example 133

N-(3-(Benzyloxy)-5-bromopyridin-2-yl)-4,5-dimethylthiazol-2-amine hydrochloride

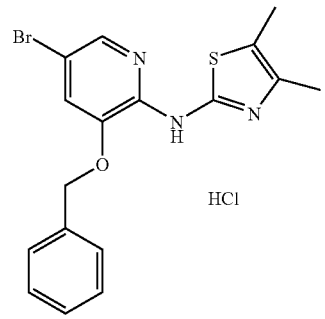 [SMILES: Cc1nc(Nc2ncc(Br)cc2OCc2ccccc2)sc1C ; Cl]

A mixture of 1-(3-(benzyloxy)-5-bromopyridin-2-yl)thiourea (0.50 g, 1.48 mmol), 3-chlorobutan-2-one (0.236 g, 2.22 mmol), triethylamine (0.412 ml, 2.96 mmol), and ethanol (15 mL) was heated overnight. The reaction mixture was cooled, partitioned between ethyl acetate and water, washed with water and brine, dried, and concentrated. The residue was purified by MPLC eluting with 5:1 hexane:ethyl acetate to afford the free base of the title compound (104 mg) as a tacky oil. The free base was dissolved in ether (4 mL) and a 1M solution of HCl in ether was added (1.5 mL). The mixture was stirred 10 minutes and filtered. The solids were washed with ether, hexanes, and dried to afford 3-(benzyloxy)-5-bromo-N-(4,5-dimethylthiazol-2-ylpyridin-2-amine hydrochloride (0.093 g, 14.7% yield). $^1$H NMR (DMSO-d$_6$) δ 2.21 (s, 3H), 2.26 (s, 3H), 5.34 (s, 2H), 7.35-7.44 (m, 3H), 7.58 (d, 2H), 7.81 (s, 1H), 8.05 (s, 1H).

Example 134

N-(2-(2-(3-(Benzyloxy)pyridin-2-ylamino)thiazol-4-yl)ethyl)acetamide hydrochloride

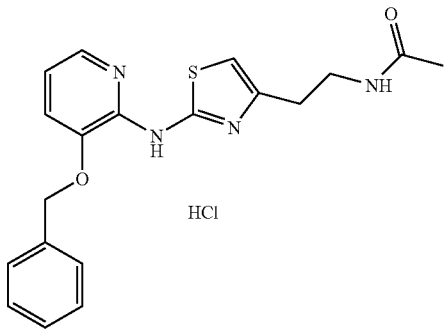 [SMILES: CC(=O)NCCc1csc(Nc2ncccc2OCc2ccccc2)n1 ; Cl]

Step A: Preparation of 4-(2-aminoethyl)-N-(3-(benzyloxy)pyridin-2-yl)thiazol-2-amine: A mixture of 2-(2-(2-(3-(benzyloxy)pyridin-2-ylamino)thiazol-4-yl)ethyl)isoindoline-1,3-dione (13.8 g, 30.2 mmol) and hydrazine hydrate (3.03 g, 60.5 mmol) in methanol (150 mL) was heated at reflux for 3 hours, then cooled and concentrated. The crude residue was used in the next step without purification.

Step B: Preparation of N-(2-(2-(3-(benzyloxy)pyridin-2-ylamino)thiazol-4-yl)ethyl)acetamide hydrochloride: Crude 4-(2-aminoethyl)-N-(3-(benzyloxy)pyridin-2-yl)thiazol-2-amine (0.50 g, 1.53 mmol) was dissolved in DMF (20 mL), and triethylamine (0.854 ml, 6.13 mmol) was added, followed by the addition of acetyl chloride (0.240 g, 3.06 mmol). The reaction mixture was stirred for 2 hours, then partitioned between ethyl acetate and water. The organic layer was washed with water and brine, dried, and concentrated. The residue was dissolved in THF (10 mL) and 1N HCl in ether (2 mL) was added. The mixture was diluted in ether (15 mL) and triturated for 15 minutes, and the solids were filtered, washed with ether and hexanes, and dried to afford the title compound (0.290 g, 46.8% yield) as a light yellow powder. $^1$H NMR (DMSO-$d_6$) δ 1.80 (s, 3H), 2.80 (m, 2H), 3.37 (m, 2H), 5.34 (s, 2H), 6.96 (s, 1H), 7.15 (m, 1H), 7.32-7.43 (m, 3H), 7.57-7.66 (m, 3H), 8.00 (d, 1H), 8.05 (t, 1H), 8.20 (bs, 1H), 11.35 (bs, 1H).

Example 135

1-(2-(2-(3-(Benzyloxy)pyridin-2-ylamino)thiazol-4-yl)ethyl)-3-phenylurea

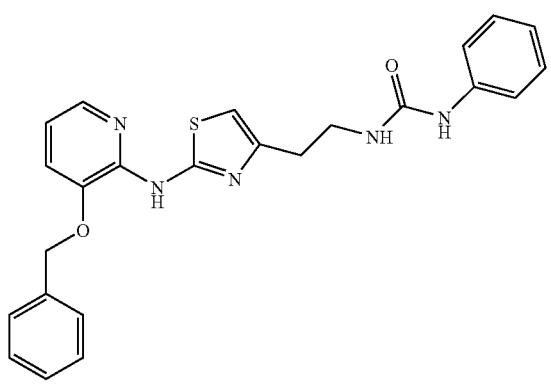 [SMILES: O=C(NCCc1csc(Nc2ncccc2OCc2ccccc2)n1)Nc1ccccc1]

Crude 4-(2-aminoethyl)-N-(3-(benzyloxy)pyridin-2-yl)thiazol-2-amine (Example 134, Step A; 0.25 g, 0.766 mmol) was dissolved in DMF (10 mL), and 1-isocyanatobenzene (0.182 g, 1.53 mmol) was added. The reaction mixture was stirred for 2 hours, then partitioned between ethyl acetate and water. The organic layer was washed with water and brine, dried, and concentrated. The residue was purified via MPLC (Biotage) eluting with 2:3 hexane:ethyl acetate to afford the title compound (0.122 g, 35.8% yield) as a light yellow powder. $^1$H NMR (DMSO-$d_6$) δ 2.75 (t, 2H), 3.42 (q, 2H), 5.27 (s, 2H), 6.19 (t, 1H), 6.70 (s, 1H), 6.86-6.91 (m, 2H), 7.20 (t, 2H), 7.34-7.43 (m, 6H), 7.58 (d, 2H), 7.87 (d, 1H), 8.48 (s, 1H), 9.94 (s, 1H).

Example 136

1-(2-(2-(3-(Benzyloxy)pyridin-2-ylamino)thiazol-4-yl)ethyl)-3-ethylurea

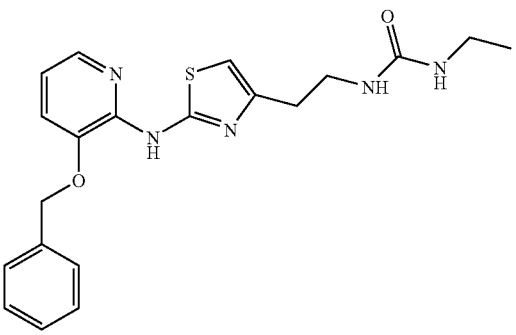 [SMILES: CCNC(=O)NCCc1csc(Nc2ncccc2OCc2ccccc2)n1]

Crude 4-(2-aminoethyl)-N-(3-(benzyloxy)pyridin-2-yl)thiazol-2-amine (Example 134, Step A; 0.25 g, 0.766 mmol) was dissolved in DMF (20 mL), and isocyanatoethane (0.109 g, 1.53 mmol) was added. The reaction mixture was stirred for 2 hours, then partitioned between ethyl acetate and water. The organic layer was washed with water and brine, dried, and concentrated. The residue was purified via MPLC (Biotage) eluting with ethyl acetate to afford the title compound (0.092 g, 30.2% yield) as a light yellow powder. $^1$H NMR (DMSO-$d_6$) δ 0.97 (t, 3H), 2.67 (t, 2H), 2.98 (m, 2H), 3.29 (m, 2H), 5.26 (s, 2H), 5.82 (bt, 2H), 6.64 (s, 1H), 6.88 (m, 1H), 7.32-7.43 (m, 4H), 7.58 (d, 2H), 7.85 (d, 1H), 7.95 (s, 1H), 9.91 (s, 1H).

Example 137

N-(2-(2-(3-(Benzyloxy)pyridin-2-ylamino)thiazol-4-yl)ethyl)benzamide

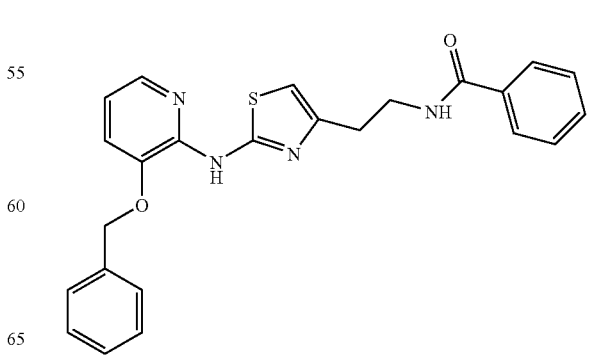

Crude 4-(2-aminoethyl)-N-(3-(benzyloxy)pyridin-2-yl)thiazol-2-amine (Example 134, Step A; 0.25 g, 0.766 mmol) was dissolved in DMF (10 mL), and triethylamine (0.427 ml, 3.06 mmol) was added, followed by benzoyl chloride (0.215 g, 1.53 mmol). The reaction mixture was stirred 2 hours, then partitioned between ethyl acetate and water. The organic layer was washed with water and brine, dried, and concentrated. The residue was purified via MPLC (Biotage) eluting with 2:3 hexane:ethyl acetate to provide the title compound (0.072 g, 21.8% yield) as a white powder. $^1$H NMR (DMSO-$d_6$) δ 2.85 (t, 2H), 3.58 (m, 2H), 5.26 (s, 2H), 6.69 (s, 1H), 6.89 (m, 1H), 7.32-7.59 (m, 9H), 7.82-7.87 (m, 3H), 8.55 (t, 1H), 9.95 (s, 1H).

Example 138

N'-(2-(2-(3-benzyloxy)pyridin-2-ylamino)thiazol-4-yl)ethyl)-N,N-dimethyl sulfonamide

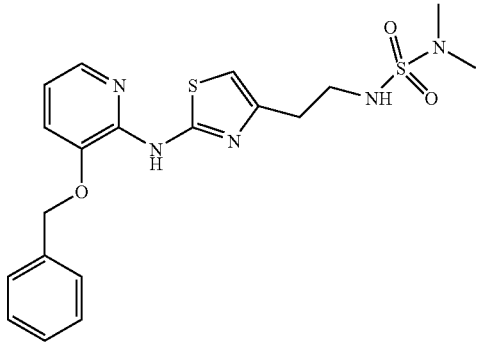 [SMILES: CN(C)S(=O)(=O)NCCc1csc(Nc2ncccc2OCc2ccccc2)n1]

Crude 4-(2-aminoethyl)-N-(3-(benzyloxy)pyridin-2-yl)thiazol-2-amine (Example 134, Step A; 0.25 g, 0.766 mmol) was dissolved in DMF (10 mL), and triethylamine (0.427 ml, 3.06 mmol) was added, followed by dimethylsulfamoyl chloride (0.220 g, 1.53 mmol). The reaction mixture was stirred 2 hours, then partitioned between ethyl acetate and water. The organic layer was washed with water and brine, dried, and concentrated. The crude residue was dissolved in a minimal amount of dichloromethane, and hexanes were added until the solution was cloudy, and the solution was triturated for 30 minutes. The resulting solids were collected by filtration, and recrystallized from hot EtOH (8 mL) and water (1 mL). After cooling, the solids were collected by filtration, washed with water, and dried to afford the title compound (0.142 g, 42.8% yield) as white crystals. $^1$H NMR (DMSO-$d_6$) δ 2.64 (s, 6H), 2.76 (t, 2H), 3.21 (q, 2H), 5.26 (s, 2H), 6.69 (s, 1H), 6.89 (m, 1H), 7.26 (t, 1H), 7.33-7.44 (m, 4H), 7.57 (d, 2H), 7.85 (d, 1H), 9.99 (s, 1H).

Example 139

N-(3-(Benzyloxy)pyridin-2-yl)thiazolo[5,4-b]pyridin-2-amine

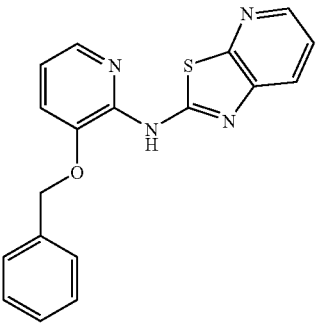 [SMILES: c1ccc(COc2cccnc2Nc2nc3cccnc3s2)cc1]

A mixture of 2-chloro-3-isothiocyanatopyridine (0.342 g, 2.00 mmol) and 3-(benzyloxy)pyridin-2-amine (0.401 g, 2.00 mmol) in ethylene glycol (2 mL) was heated at 120° C. for 3 hours. The reaction mixture was cooled and partitioned between ethyl acetate and water. The organic layer was washed with brine, dried and concentrated. The residue was purified by MPLC eluting with 4:1 hexane:ethyl acetate to afford the title compound as a wax. The wax was triturated with 10:1 hexanes:dichloromethane (11 mL), filtered, and dried to afford N-(3-(benzyloxy)pyridin-2-yl)thiazolo[5,4-b]pyridin-2-amine (0.095 g, 14.2% yield) as a light yellow powder. $^1$H NMR (DMSO-$d_6$) δ 5.30 (s, 2H), 7.03 (m, 1H), 7.32-7.43 (m, 4H), 7.50 (d, 1H), 7.60 (d, 2H), 7.93-7.97 (m, 2H), 8.35 (d, 1H), 10.71 (s, 1H).

Additional compounds, shown in Tables 1, 2, and 3, were prepared by the methods disclosed herein.

TABLE 1

| Ex. # | $R^2$ | $R^{12}$ | $R^{13}$ | Compound Name/$^1$H NMR |
|---|---|---|---|---|
| A1 | 2-chlorophenyl | H | Me | 3-(2-chlorobenzyloxy)-N-(4-methylthiazol-2-yl)pyridin-2-amine; $^1$H NMR (CDCl$_3$) δ 2.46 (s, 3H), 5.43 (s, 2H), 6.40 (s, m), 7.04 (dd, 1H), 7.28 (m, 2H), 7.38 (m, 2H), 7.98 (d, 1H), 8.07 (d, 1H). |

TABLE 1-continued

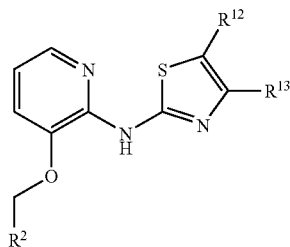

| Ex. # | R² | R¹² | R¹³ | Compound Name/¹H NMR |
|---|---|---|---|---|
| B1 | 2,6-dichorophenyl | H | Me | 3-(2,6-dichlorobenzyloxy)-N-(4-methylthiazol-2-yl)pyridin-2-amine; ¹H NMR (CDCl₃) δ 2.42 (s, 3H), 5.53 (s, 2H), 6.35 (s, 1H), 7.06 (dd, 1H), 7.28 (d, 2H), 7.37 (m, 2H), 7.98 (d, 1H). |
| C1 | phenyl | H | COOH | 2-(3-(benzyloxy)pyridin-2-ylamino)thiazole-4-carboxylic acid; ¹H NMR (CD₃OD) δ 7.91 (dd, 1H), 7.84 (s, 1H), 7.53 (m, 1H), 7.51 (m, 1H), 7.32-7.45 (m, 4H), 6.98 (m, 1H), 5.30 (s, 2H) |
| D1 | 2-methoxyphenyl | H | Me | 3-(2-methoxybenzyloxy)-N-(4-methylthiazol-2-yl)pyridin-2-amine: ¹H NMR (DMSO-d₆) δ 2.23 (s, 3H), 3.88 (s, 3H), 5.18 (s, 2H), 6.58 (s, 1H), 6.92 (m, 1H), 6.98 (t, 1H), 7.08 (d, 1H), 7.33-7.41 (m, 2H), 7.53 (d, 1H), 7.88 (d, 1H), 9.64 (s, 1H). |
| E1 | phenyl | H | H | 3-(benzyloxy)-N-(thiazol-2-yl)pyridin-2-amine; ¹H NMR (DMSO-d₆) δ 7.99 (dt, 1H), 7.60 (m, 4H), 7.45-7.34 (m, 3H), 7.25 (d, 1H), 7.11 (dd, 1H), 5.35 (s, 2H). |
| F1 | phenyl | H | Et | 3-(benzyloxy)-N-(4-ethylthiazol-2-yl)pyridin-2-amine; ¹H NMR (CDCl₃) δ 1.26 (t, 3H), 2.67 (q, 2H), 5.11 (s, 2H), 6.39 (s, 1H), 6.81 (dd, 1H), 7.09 (d, 1H), 7.40 (m, 5H), 7.94 (d, 1H), 8.60 (bs, 1H). |
| G1 | ![2-acetamidophenyl] | H | Me | N-(2-((2-(4-methylthiazol-2-ylamino)pyridin-3-yloxy)methyl)phenyl)acetamide; H NMR (DMSO-d₆) δ 10.45 (bs, 1H), 9.59 (s, 1H), 7.92 (dd, 1H), 7.59 (d, 1H), 7.45 (d, 1H), 7.39 (d, 1H), 7.35 (t, 1H), 7.23 (t, 1H), 7.00 (dd, 1H), 6.72 (s, 1H), 5.22 (s, 2H), 2.28 (s, 3H), 2.06 (s, 3H). |
| H1 | ![3-(4-methylpiperazine-1-carbonyl)phenyl] | H | Me | (4-methylpiperazin-1-yl)(3-((2-(4-methylthiazol-2-ylamino)pyridin-3-yloxy)methyl)phenyl)methanone ¹H NMR (DMSO-d₆) δ 2.13 (s, 3H), 2.12-2.23 (bm, 2H), 2.25 (s, 3H), 2.26-2.38 (bm, 2H), 3.21 (bm, 2H), 3.59 (bm, 2H), 5.30 (s, 2H), 6.57 (s, 1H), 6.86 (dd, 1H), 7.32 (d, 1H), 7.37 (d, 1H), 7.46 (t, 1H), 7.59 (s, 1H), 7.65 (d, 1H), 7.85 (d, 1H), 10.06 (s, 1H). |

TABLE 2

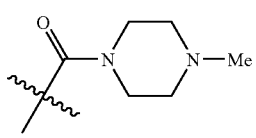 [SMILES: *C(=O)N1CCN(C)CC1]

| Ex. # | R² | R³ | Compound Name/¹H NMR |
|---|---|---|---|
| A2 | phenyl | Me | 3-(benzyloxy)-6-methyl-N-(4 methylthiazol-2-yl)pyridin-2-amine; ¹H NMR (DMSO-d₆) δ, 2.29 (s, 3H), 2.32 (s, 3H), 5.32 (s, 2H), 6.84 (s, 1H), 7.37 (m, 1H), 7.42 (m, 2H), 7.54 (s, 1H), 7.60 (m, 2H), 7.83 (s, 1H). |
| B2 | phenyl | 3-pyridyl | 3-(benzyloxy)-N-(4-methylthiazol-2-yl)-5-(pyridin-3-yl)pyridin-2-amine; ¹H NMR (DMSO-d₆) δ 2.31 (s, 3H), 5.45 (s, 2H), 6.82 (s, 1H), 7.37 (m, 1H), 7.43 (m, 2H), 7.66 (d, 2H), 7.97 (m, 1H), 8.08 (m, 1H), 8.48 (d, 1H), 8.75 (d, 1H), 8.81 (d, 1H), 9.27 (m, 1H). |
| C2 | phenyl | 4-pyridyl | 3-(benzyloxy)-N-(4-methylthiazol-2-yl)-5-(pyridin-4-yl)pyridin-2-amine; ¹H NMR (DMSO-d₆) δ 2.28 (s, 3H), 5.44 (s, 2H), 6.74 (s, 1H), 7.36 (m, 1H), 7.43 (m, 2H), 7.65 (d, 2H), 8.04 (m, 1H), 8.40 (d, 2H), 8.68 (d, 1H), 8.89 (d, 2H). |
| D2 | phenyl | SO₂Me | 3-(benzyloxy)-5-(methylsulfonyl)-N-(4-methylthiazol-2-yl)pyridin-2-amine; ¹H NMR (DMSO-d₆) δ, 2.28 (s, 3H), 3.25 (s, 3H), 5.37 (s, 2H), 6.77 (s, 1H), 7.37 (m, 1H), 7.43 (m, 2H), 7.61 (d, 2H), 7.78 (d, 1H), 8.36 (d, 1H). |
| E2 | phenyl | p-tolyl | 3-(benzyloxy)-N-(4-methylthiazol-2-yl)-5-p-tolylpyridin-2-amine; ¹H NMR (DMSO-d₆) δ 2.29 (s, 3H), 2.35 (s, 3H), 5.42 (s, 2H), 6.74 (s, 1H), 7.29 (d, 2H), 7.36 (t, 1H), 7.43 (t, 2H), 7.62 (m, 4H), 7.78 (s, 1H), 8.23 (d, 1H). |
| F2 | phenyl | C(=O)NH₂ | 5-(benzyloxy)-6-(4-methylthiazol-2-ylamino)nicotinamide; ¹H NMR (DMSO-d₆) δ 2.31 (s, 3H), 5.35 (s, 2H), 6.83 (s, 1H), 7.36 (m, 1H), 7.42 (t, 2H), 7.48 (bs, 1H), 7.61 (d, 2H), 7.91 (d, 1H), 8.06 (bs, 1H), 8.49 (d, 1H). |
| G2 | phenyl | 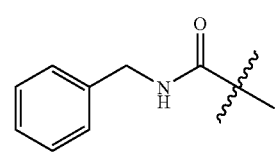 [SMILES: *C(=O)NCc1ccccc1] | (5-(benzyloxy)-6-(4-methylthiazol-2-ylamino)pyridin-3-yl)(4-methylpiperazin-1-yl)methanone; ¹H NMR (DMSO-d₆) δ 2.28 (s, 3H), 2.70 (d, 3H), 3.10 (m, 4H), 3.39 (m, 4H), 5.31 (s, 2H), 6.71 (s, 1H), 7.35 (m, 1H), 7.42 (t, 2H), 7.48 (s, 1H), 7.59 (d, 2H), 8.02 (d, 1H). |
| H2 | phenyl | (benzylamide group) | N-benzyl-5-(benzyloxy)-6-(4-methylthiazol-2-ylamino)nicotinamide: ¹H NMR (DMSO-d₆) δ 2.29 (s, 3H), 4.50 (d, 2H), 5.34 (s, 2H), 6.77 (s, 1H), 7.25 (m, 1H), 7.35 (m, 5H), 7.42 (t, 2H), 7.60 (d, 2H), 7.90 (s, 1H), 8.50 (d, 1H), 9.10 (m, 1H). |

TABLE 2-continued

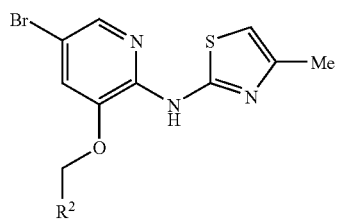

| Ex. # | R² | R³ | Compound Name/¹H NMR |
|---|---|---|---|
| I2 | ![quinoline] | H | N-(4-methylthiazol-2-yl)-3-(quinolin-8-ylmethoxy)pyridin-2-amine; ¹H NMR (DMSO-d₆) δ 9.15 (dd, 1H), 8.62 (d, 1H), 8.23 (m, 1H), 8.12 (d, 1H), 8.05 (d, 1H), 7.75 (m, 3H), 7.19 (m, 1H), 6.90 (s, 1H), 5.91 (s, 2H), 2.33 (s, 3H) |
| J2 | ![quinoline] | Br | 5-bromo-N-(4-methylthiazol-2-yl)-3-(quinolin-8-ylmethoxy)pyridin-2-amine |
| K2 | Ph | —SCH₂(c-pentyl) | N-(3-(benzyloxy)-5-(cyclopentylmethylthio)pyridin-2-yl)-4-methylthiazol-2-amine; ¹H NMR (DMSO-d₆) - 10.95 (bs, 1H), 7.92 (m, 1H), 7.61-7.55 (m, 3H), 7.44-7.32 (m, 3H), 6.82 (s, 1H), 5.37 (s, 2H), 2.92 (d, 2H), 2.31 (s, 3H), 1.89 (m, 1H), 1.70 (m, 2H), 1.57 (m, 2H), 1.46 (m, 2H), 1.20 (m, 2H). |
| L2 | Ph | —SCH(Me)Ph | N-(3-(benzyloxy)-5-(1-phenylethylthio)pyridin-2-yl)-4-methylthiazol-2-amine; ¹H NMR (DMSO-d₆) - 10.70 (bs, 1H), 7.77 (d, 1H), 7.56 (d, 2H), 7.45-7.33 (m, 4H), 7.30-7.18 (m, 5H), 6.75 (s, 1H), 5.23 (s, 2H), 4.48 (q, 1H), 2.28 (s, 3H), 1.50 (d, 3H). |
| M2 | Ph | ![phenyl-piperidinyl-methylthio] | N-(3-(benzyloxy)-5-(phenyl(piperidin-4-yl)methylthio)pyridin-2-yl)-4-methylthiazol-2-amine; ¹H NMR (DMSO-d₆) δ 10.65 (bs, 1H, 8.85 (d, 1H), 8.53 (m 1H), 7.69 (d, 1H), 7.54 (d, 2H), 7.43 (d, 2H), 7.37 (m, 1H), 7.30-7.12 (m, 6H), 6.72 (s, 1H), 5.18 (s, 2H), 4.20 (d, 1H), 3.31 (m, 1H), 3.17 (m, 1H), 2.88 (m, 1H), 2.76 (m, 1H), 2.26 (s, 3H), 2.24 (m, 1H), 2.10 (m, 1H), 1.50 (m, 2H), 1.30 (m, 1H). |

TABLE 3

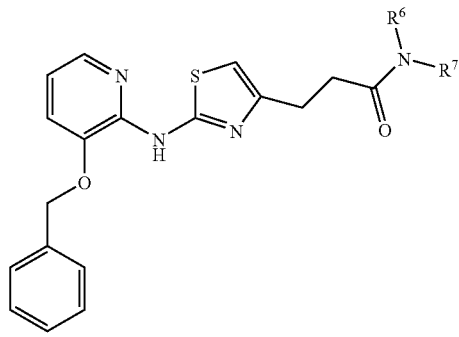

| Ex. # | NR⁶R⁷ | Compound Name/¹H NMR/MS |
|---|---|---|
| A3 | HN-CH₂CH₂-morpholine | 3-(2-(3-(Benzyloxy)pyridin-2-ylamino)thiazol-4-yl)-N-(2-morpholinoethyl)propanamide; $^1$H NMR (CDCl$_3$) δ 2.19 (m, 5H), 2.60 (m, 2H), 2.98 (m, 3H), 3.30 (m, 2H), 3.60 (m, 4H), 5.14 (s, 2H), 6.06 (br s, 1H), 6.50 (s, 1H), 6.83 (m, 1H), 7.14 (m, 1H), 7.41 (m, 5H), 7.98 (m, 1H), 8.58 (br s, 1H); LCMS m/z 468.1 (M + H)⁺. |
| B3 | HN-(CH₂)₃-morpholine | 3-(2-(3-(Benzyloxy)pyridin-2-ylamino)thiazol-4-yl)-N-(3-morpholinopropyl)propanamide; $^1$H NMR (CDCl$_3$) δ 1.60 (m, 2H), 2.37 (m, 5H), 2.54 (m, 2H), 2.98 (m, 3H), 3.30 (m, 2H), 3.62 (m, 4H), 5.15 (s, 2H), 6.48 (s, 1H), 6.63 (br s, 1H), 6.82 (m, 1H), 7.15 (m, 1H), 7.41 (m, 5H), 7.97 (m, 1H), 8.58 (br s, 1H); LCMS m/z 482.2 (M + H)⁺. |
| C3 | MeN(CH₂)₂NMe₂ with N-Me | 3-(2-(3-(Benzyloxy)pyridin-2-ylamino)thiazol-4-yl)-N-(2-(dimethylamino)ethyl)-N-methylpropanamide; $^1$H NMR (CDCl$_3$) δ 2.20 (s, 3H) and 2.23 (s, 6H total), 2.40 (m, 2H), 2.70 (m, 2H), 3.00 (m, 5H), 3.18 (m, 1H), 3.50 (m, 1H), 5.12 (s, 2H), 6.48 (s, 1H), 6.80 (m, 1H), 7.10 (m, 1H), 7.40 (m, 5H), 7.97 (m, 1H), 8.58 (br s, 1H); LCMS m/z 440.1 (M + H)⁺. |
| D3 | HN-CH₂CH₂-NH-iPr | 3-(2-(3-(Benzyloxy)pyridin-2-ylamino)thiazol-4-yl)-N-(2-(isopropylamino)ethyl)propanamide; $^1$H NMR (CDCl$_3$) δ 1.00 (d, 6H), 2.59 (m, 2H), 2.70 (m, 2H), 2.79 (m, 1H), 2.99 (m, 3H), 3.33 (m, 2H), 5.14 (s, 2H), 6.45 (s, 1H), 6.83 (m, 1H), 7.12 (m, 1H), 7.41 (m, 5H), 7.96 (m, 1H); LCMS m/z 440.1 (M + H)⁺. |
| E3 | 4-ethylpiperazine | 3-(2-(3-(Benzyloxy)pyridin-2-ylamino)thiazol-4-yl)-1-(4-ethylpiperazin-1-yl)propan-1-one; $^1$H NMR (CDCl$_3$) δ 1.08 (t, 3H), 2.41 (m, 6H), 2.72 (q, 2H), 2.99 (m, 4H), 3.50 (m, 2H), 3.68 (br s, 2H), 5.15 (s, 2H), 6.48 (s, 1H), 6.83 (m, 1H), 7.12 (m, 1H), 7.40 (m, 5H), 7.97 (m, 1H), 8.57 (br s, 1H); LCMS m/z 452.1 (M + H)⁺. |

Example 140

3-(benzyloxy)-5-(1-methyl-1H-imidazol-2-ylthio)-N-(4-methylthiazol-2-yl)pyridin-2-amine dihydrochloride

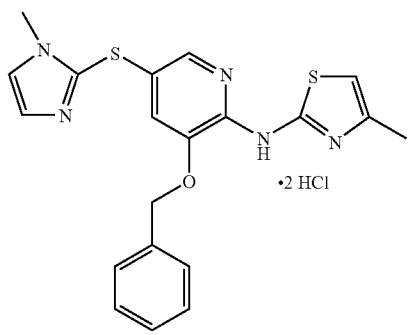 [SMILES: Cc1csc(Nc2ncc(Sc3nccn3C)cc2OCc2ccccc2)n1 ; "·2 HCl"]

3-(Benzyloxy)-5-bromo-N-(4-methylthiazol-2-yl)pyridin-2-amine (0.125 g, 0.332 mmol), 4,5-bis(diphenylphosphino)-9,9-dimethyl-9H-xanthene (0.0192 g, 0.0332 mmol), Pd$_2$dba$_3$ (0.0152 g, 0.0166 mmol), N-ethyl-N-isopropylpropan-2-amine (0.116 ml, 0.664 mmol), 1-methyl-1H-imidazole-2-thiol (0.0379 g, 0.332 mmol) were reacted according to Example 42 to provide 3-(benzyloxy)-5-(1-methyl-1H-imidazol-2-ylthio)-N-(4-methylthiazol-2-yl)pyridin-2-amine dihydrochloride (0.0786 g, 49.0% yield) after HCl salt formation. $^1$H NMR (DMSO-d$_6$) δ 8.16 (d, 1H), 7.81 (d, 1H), 7.78 (s, 1H), 7.73 (d, 1H), 7.53 (d, 2H), 7.41-7.34 (m, 3H), 6.74 (s, 1H), 5.31 (s, 2H), 3.85 (s, 3H), 2.46 (s, 3H). Mass spectrum (apci) m/z=410.0 (M+H-2HCl).

Example 141

(5-(Benzyloxy)-6-(4-methylthiazol-2-ylamino)pyridin-3-yl)(phenyl)methanol hydrochloride

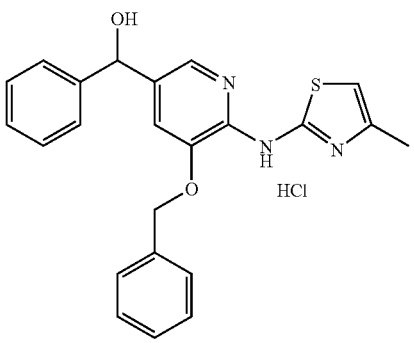 [SMILES: Cc1csc(Nc2ncc(C(O)c3ccccc3)cc2OCc2ccccc2)n1 ; "HCl"]

3-(Benzyloxy)-5-bromo-N-(4-methylthiazol-2-yl)pyridin-2-amine (Example 1; 0.350 g, 0.930 mmol), MeLi (0.727 ml, 1.16 mmol), butyllithium (0.465 ml, 1.16 mmol), and benzaldehyde (0.0987 g, 0.930 mmol) were reacted according to Example 7 to provide (5-(benzyloxy)-6-(4-methylthiazol-2-ylamino)pyridin-3-yl)(phenyl)methanol (0.182 g, 48.5% yield) after HCl salt formation. $^1$H NMR (DMSO-d$_6$) δ 7.94 (s, 1H), 7.58 (s, 1H), 7.55 (d, 2H), 7.40-7.28 (m, 7H), 7.22 (m, 1H), 6.81 (s, 1H), 5.75 (s, 1H), 5.29 (s, 2H), 2.30 (s, 3H). Mass spectrum (apci) m/z=404.1 (M+H-HCl).

Example 142

Ethyl 2-(2-(3-(benzyloxy)-5-bromopyridin-2-ylamino)thiazol-4-yl)acetate

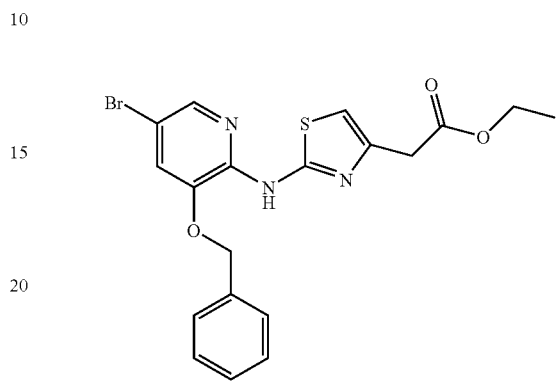

Prepared by the method of Example 58. $^1$H NMR (DMSO-d$_6$) δ 1.19 (t, J=7.1 Hz, 3H), 3.66 (s, 2H), 4.06-4.11 (m, 2H), 5.29 (s, 2H), 6.84 (s, 1H), 7.34 (t, J=7.2 Hz, 1H), 7.41 (t, J=7.2 Hz, 2H), 7.59 (d, J=7.0 Hz, 2H), 7.63 (d, J=1.8 Hz, 1H), 7.97 (d, J=1.8 Hz, 1H), 10.43 (s, 1H). Mass spectrum (apci) m/z=448 (M+H).

Example 143

3-(2-(3-(Benzyloxy)-5-bromopyridin-2-ylamino)thiazol-4-yl)propanoic acid

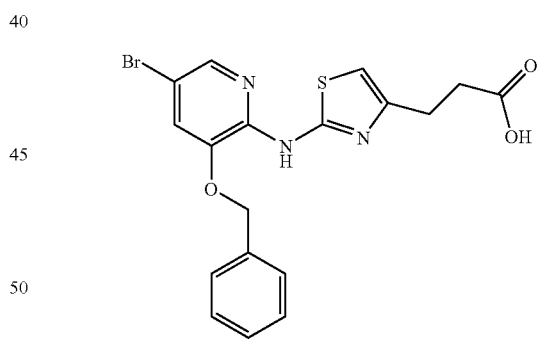

Methyl 3-(2-(3-(benzyloxy)-5-bromopyridin-2-ylamino)thiazol-4-yl)propanoate (Example 58; 1.500 g, 3.346 mmol) was dissolved in THF (50 mL) and water (25 mL), followed by the addition of sodium hydroxide (0.2676 g, 6.691 mmol), and the mixture was at ambient temperature for 16 hours. The mixture was concentrated, and partitioned between DCM and saturated aqueous NH$_4$Cl. The layers were separated and the aqueous was extracted with DCM/THF and then 100% THF. The combined organics were dried over Na$_2$SO$_4$, filtered and concentrated to give 3-(2-(3-(benzyloxy)-5-bromopyridin-2-ylamino)thiazol-4-yl)propanoic acid (1.42 g, 98% yield) as white solids. $^1$H NMR (DMSO-d$_6$) δ 2.58 (t, J=7.6 Hz, 2H), 2.82 (t, J=7.6 Hz, 2H), 5.29 (s, 2H), 6.65 (s, 1H), 7.35 (t, J=7.2

Hz, 1H), 7.41 (t, J=7.2 Hz, 2H), 7.58 (s, 1H), 7.60 (s, 1H), 7.62 (d, J=2.0 Hz, 1H), 7.96 (d, J=1.8 Hz, 1H); Mass Spectrum (apci) 434 (M+H).

Example 144

2-(2-(3-(Benzyloxy)-5-bromopyridin-2-ylamino)thiazol-4-yl)acetic acid

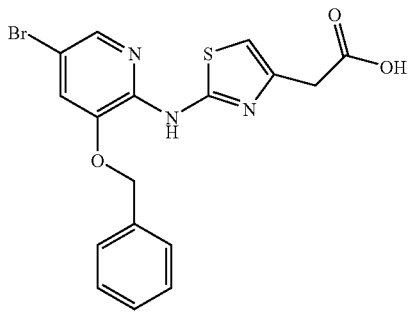 [SMILES: O=C(O)Cc1csc(Nc2ncc(Br)cc2OCc2ccccc2)n1]

Prepared by the method of Example 143. $^1$H NMR (DMSO-$d_6$) δ 3.52 (s, 2H), 5.29 (s, 2H), 6.77 (s, 1H), 7.34 (t, J=7.2 Hz, 1H), 7.41 (t, J=7.3 Hz, 2H), 7.57 (s, 1H), 7.59 (s, 1H), 7.62 (d, J=2.0 Hz, 1H), 7.97 (d, J=2.0 Hz, 1H). Mass Spectrum (apci) 420 (M+H).

Example 145

N-(3-(Benzyloxy)-5-bromopyridin-2-yl)-4-(2-(5-methyl-1,3,4-oxadiazol-2-yl)ethyl)thiazol-2-amine

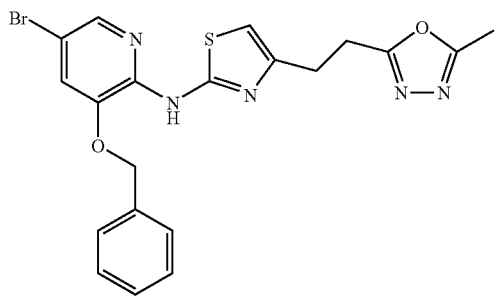 [SMILES: Cc1nnc(CCc2csc(Nc3ncc(Br)cc3OCc3ccccc3)n2)o1]

Step A: To a mixture of 3-(2-(3-(benzyloxy)-5-bromopyridin-2-ylamino)thiazol-4-yl)propanoic acid (Example 143; 0.300 g, 0.691 mmol), HOBT-H$_2$O (0.159 g, 1.04 mmol), DIEA (0.253 ml, 1.45 mmol), EDCI (0.199 g, 1.04 mmol), and acetohydrazide (0.102 g, 1.38 mmol) was added THF (20 mL) and the mixture was stirred at 50° C. overnight. The mixture was concentrated to dryness, diluted with DCM, washed with water, dried over Na$_2$SO$_4$ and concentrated to a crude residue of N'-acetyl-3-(2-(3-(benzyloxy)-5-bromopyridin-2-ylamino)thiazol-4-yl)propanehydrazide.

Step B: The crude N'-acetyl-3-(2-(3-(benzyloxy)-5-bromopyridin-2-ylamino)thiazol-4-yl)propanehydrazide (0.339 g, 0.691 mmol) was added acetonitrile (25 mL), POCl$_3$ (0.380 ml, 4.15 mmol) and the mixture heated at 50° C. overnight. Additional POCl$_3$ (0.5 mL) was added and the reaction was stirred for 3 days 50° C. Additional 0.5 ml POCl$_3$ (0.5 mL) was added and the reaction was stirred at 50° C. for an additional 18 hours. The reaction was then concentrated to dryness, diluted with water, extracted with DCM, dried over Na$_2$SO$_4$, filtered, concentrated to a residue and purified by prep HPLC and then on a silica gel column, eluting with 75% EtOAc/Hexanes, to give 3-(benzyloxy)-5-bromo-N-(4-(2-(5-methyl-1,3,4-oxadiazol-2-yl)ethyl)thiazol-2-yl)pyridin-2-amine (0.092 g, 28% yield) as a white solid. $^1$H NMR (DMSO-$d_6$) δ 2.44 (s, 3H), 3.01 (t, J=7.6 Hz, 2H), 3.17 (t, J=7.6 Hz, 2H), 5.29 (s, 2H), 6.73 (s, 1H), 7.35 (t, J=7.2 Hz, 1H), 7.42 (t, J=7.2 Hz, 2H), 7.59 (d, J=7.2 Hz, 2H), 7.63 (d, J=1.6 Hz, 1H), 7.97 (d, J=1.8 Hz, 1H), 10.31 (s, 1H); Mass Spectrum (apci) 472 (M+H).

Example 146

N-(3-(Benzyloxy)-5-bromopyridin-2-yl)-4-((5-methyl-1,3,4-oxadiazol-2-yl)methyl)thiazol-2-amine

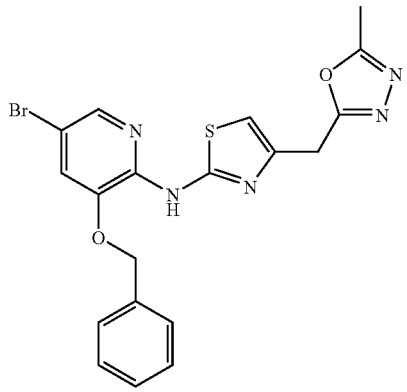 [SMILES: Cc1nnc(Cc2csc(Nc3ncc(Br)cc3OCc3ccccc3)n2)o1]

Prepared by the method of Example 145. $^1$H NMR (DMSO-$d_6$) δ 2.45 (s, 3H), 4.21 (s, 2H), 5.28 (s, 2H), 6.94 (s, 1H), 7.34 (t, J=7.2 Hz, 1H), 7.40 (t, J=7.3 Hz, 2H), 7.58 (d, J=7.0 Hz, 2H), 7.63 (d, J=1.8 Hz, 1H), 7.97 (d, J=2.0 Hz, 1H), 10.52 (s, 1H). Mass Spectrum (apci) 458 (M+H).

Example 147

N-(3-(Benzyloxy)-5-bromopyridin-2-yl)-4-(2-(3-methyl-1,2,4-oxadiazol-5-yl)ethyl)thiazol-2-amine

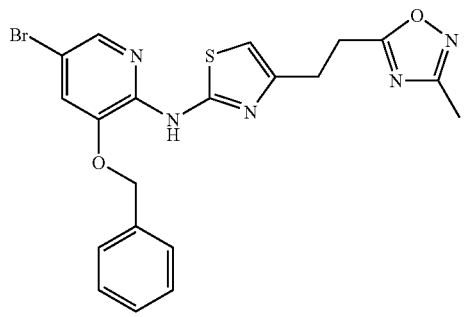 [SMILES: Cc1noc(CCc2csc(Nc3ncc(Br)cc3OCc3ccccc3)n2)n1]

To a mixture of 3-(2-(3-(benzyloxy)-5-bromopyridin-2-ylamino)thiazol-4-yl)propanoic acid (0.200 g, 0.461 mmol), N,N-diisopropylethylamine (0.0882 ml, 0.507 mmol) in DMF (5 mL) at ambient temperature was added N-((dimethylamino)fluoromethylene)-N-methylmethanaminium hexafluorophosphate(V) (0.122 g, 0.461 mmol). The mixture was stirred for 30 minutes at ambient temperature, and then N-hydroxyacetamidine (0.0375 g, 0.507 mmol) was added in one portion. The reaction mixture was heated at 110° C. overnight and then cooled to ambient temperature. Ethyl acetate was added and the organic layer was washed with water. The combined organic layers were dried over Na$_2$SO$_4$, filtered, and concentrated to a residue that was purified on a silica gel column, eluting with 40% EtOAc/Hexanes. The isolated material was recrystallized from EtOAc/Hexanes and dried under high vacuum to afford 3-(benzyloxy)-5-bromo-N-(4-(2-(3-methyl-1,2,4-oxadiazol-5-yl)ethyl)thiazol-2-yl)pyridin-2-amine (0.110 g, 50% yield) as a tan solid. $^1$H NMR (DMSO-d$_6$) δ 2.30 (s, 3H), 3.05 (t, J=7.6 Hz, 2H), 3.26 (t, J=7.6 Hz, 2H), 5.29 (s, 2H), 6.73 (s, 1H), 7.35 (t, J=7.2 Hz, 1H), 7.42 (t, J=7.2 Hz, 2H), 7.58 (s, 1H), 7.60 (s, 1H), 7.63 (d, J=1.6 Hz, 1H), 7.97 (d, J=2.0 Hz, 1H), 10.32 (s, 1H); Mass Spectrum (apci) 472 (M+H).

Example 148

N-(3-(Benzyloxy)-5-bromopyridin-2-yl)-4-((3-methyl-1,2,4-oxadiazol-5-yl)methyl)thiazol-2-amine

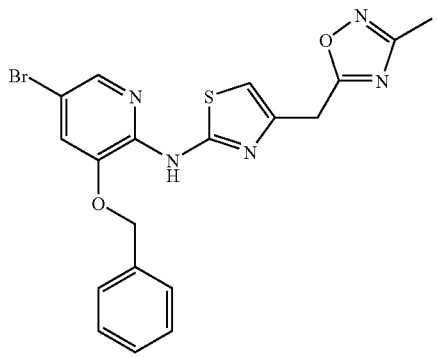 [SMILES: Cc1noc(Cc2csc(Nc3ncc(Br)cc3OCc3ccccc3)n2)n1]

Prepared by the method of Example 147. $^1$H NMR (DMSO-d$_6$) δ 2.31 (s, 3H), 4.30 (s, 2H), 5.28 (s, 2H), 6.94 (s, 1H), 7.34 (t, J=7.3 Hz, 1H), 7.40 (t, J=7.2 Hz, 2H), 7.58 (d, J=7.2 Hz, 2H), 7.63 (d, J=1.8 Hz, 1H), 7.98 (d, J=2.0 Hz, 1H), 10.51 (s, 1H). Mass Spectrum (apci) 458 (M+H).

Example 149

N-(3-(Benzyloxy)-5-bromopyridin-2-yl)-4-(2-(5-methyloxazol-2-yl)ethyl)thiazol-2-amine

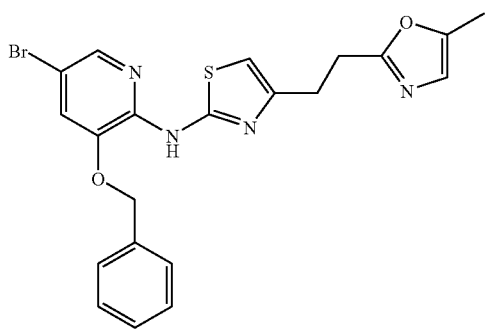 [SMILES: Cc1cnc(CCc2csc(Nc3ncc(Br)cc3OCc3ccccc3)n2)o1]

Step A: A mixture of 3-(2-(3-(benzyloxy)-5-bromopyridin-2-ylamino)thiazol-4-yl)propanoic acid (0.300 g, 0.691 mmol), HOBT.H$_2$O (0.159 g, 1.04 mmol), EDCI (0.199 g, 1.04 mmol), DIEA (0.253 ml, 1.45 mmol), and 1-aminopropan-2-one hydrochloride (0.303 g, 2.76 mmol) in THF (20 mL) was stirred at 60° C. overnight and then at ambient temperature for 4 days. The mixture was concentrated, diluted with DCM, washed with water, dried over Na$_2$SO$_4$, filtered and concentrated to a crude residue of 3-(2-(3-(benzyloxy)-5-bromopyridin-2-ylamino)thiazol-4-yl)-N-(2-oxopropyl)propanamide.

Step B: To the crude product of Step A (0.338 g, 0.691 mmol) was added acetonitrile (25 mL) POCl$_3$ (0.379 ml, 4.14 mmol) and the reaction heated at 50° C. overnight. The mixture was concentrated to dryness, diluted with water, extracted with DCM, dried over Na$_2$SO$_4$, filtered, concentrated and purified on a silica gel column, eluting with 3% MeOH/DCM, to give 3-(benzyloxy)-5-bromo-N-(4-(2-(5-methyloxazol-2-yl)ethyl)thiazol-2-yl)pyridin-2-amine (0.015 g, 5% yield) as a white solid. $^1$H NMR (DMSO-d$_6$) δ 2.24 (s, 3H), 2.97-3.05 (m, 4H), 5.29 (s, 2H), 6.68 (s, 2H), 7.35 (t, J=7.3 Hz, 1H), 7.42 (t, J=7.3 Hz, 2H), 7.58 (s, 1H), 7.60 (s, 1H), 7.63 (s, 1H), 7.96 (d, J=1.8 Hz, 1H), 10.30 (s, 1H); Mass Spectrum (apci) 471 (M+H).

Example 150

N-(3-(Benzyloxy)-5-bromopyridin-2-yl)-4-((5-methyloxazol-2-yl)methyl)thiazol-2-amine

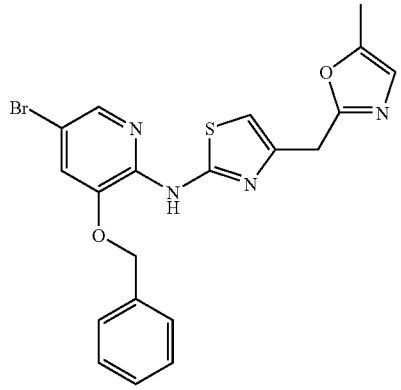 [SMILES: Cc1cnc(Cc2csc(Nc3ncc(Br)cc3OCc3ccccc3)n2)o1]

Prepared by the method of Example 149. $^1$H NMR (DMSO-d$_6$) δ 2.23 (s, 3H), 4.05 (s, 2H), 5.28 (s, 2H), 6.72 (d, J=1.2 Hz, 1H), 6.83 (s, 1H), 7.34 (t, J=7.3 Hz, 1H), 7.40 (t, J=7.3 Hz, 2H), 7.58 (d, J=7.0 Hz, 2H), 7.62 (d, J=2.0 Hz, 1H), 7.97 (d, J=2.0 Hz, 1H), 10.45 (s, 1H). Mass Spectrum (apci) 457 (M+H).

Example 151

3-(2-(3-(benzyloxy)-5-(2-chlorophenoxy)pyridin-2-ylamino)thiazol-4-yl)propanoic acid hydrochloride

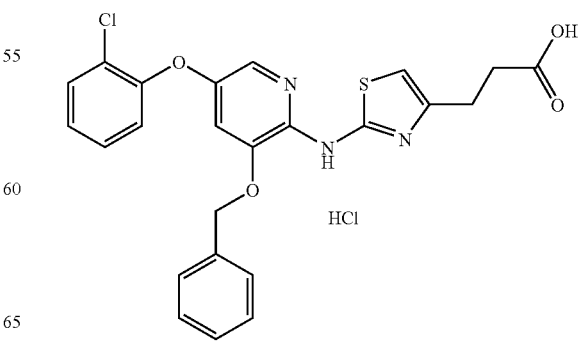

A mixture of methyl 3-(2-(3-(benzyloxy)-5-(2-chlorophenoxy)pyridin-2-ylamino)thiazol-4-yl)propanoate (Example 131; 0.315 g, 0.635 mmol), 1M aqueous sodium hydroxide (0.953 ml, 0.953 mmol), and methanol (6 mL) was heated at 65° C. for one hour. The reaction mixture was then cooled and partitioned between chloroform and saturated ammonium chloride, and the aqueous layer was extracted twice with chloroform. The combined organic layers were washed with brine, dried, and concentrated. The residue was dissolved in THF (2 mL) and ether (2 mL, and 1N HCl in ether (1.5 mL) was added. The mixture was stirred 5 minutes, and then hexanes (3 mL) were added. The solids were isolated by filtration to afford 3-(2-(3-(benzyloxy)-5-(2-chlorophenoxy)pyridin-2-ylamino)thiazol-4-yl)propanoic acid hydrochloride (0.245 g, 74.4% yield) as a white powder. $^1$H NMR (DMSO-$d_6$) δ 2.64 (t, 2H), 2.87 (t, 3H), 5.32 (s, 2H), 6.81 (s, 1H), 6.99 (d, 1H), 7.21 (t, 1H), 7.31-7.43 (m, 4H), 7.47 (d, 1H), 7.55-7.66 (m, 4H).

Example A

In Vitro Glucokinase Assays

The in vitro efficacy of glucokinase activators of the present invention was assessed in two separate assays: an $EC_{50}$ assay to evaluate the potency of each compound at a fixed, physiologically relevant concentration of glucose, and a glucose $S_{0.5}$ assay at a fixed, near saturating (if possible) concentration of compound to evaluate its effect on the $V_m$ and $S_{0.5}$ for glucose. For each of these assays, glucokinase activity was estimated by monitoring the increase in absorbance at 340 nm in a coupled assay system containing $NAD^+$ and glucose 6-phosphate dehydrogenase. Assays were conducted at 30° C. using a thermostatically controlled absorbance plate reader (Spectramax 340PC, Molecular Devices Corp.) and clear, 96-well, flat bottom, polystyrene plates (Costar 3695, Corning). Each 50-μL assay mixture contained 10 mM $K^+$MOPS, pH 7.2, 2 mM $MgCl_2$, 50 mM KCl, 0.01% Triton X-100, 2% DMSO, 1 mM DTT, 1 mM ATP, 1 mM $NAD^+$, 5 U/mL glucose 6-phosphate dehydrogenase, approximately 5 nM human glucokinase and (depending on the assay) varying concentrations of glucose and test compound. The absorbance at 340 nm was monitored kinetically over a period of 5 minutes (10 s/cycle), and rates were estimated from the slopes of linear fits to the raw data.

Glucokinase $EC_{50}$ Assay:

For this assay, the glucose concentration was fixed at 5 mM, while the control or test compound was varied over a 10-point, 3-fold dilution series and typically ranged from a high dose of 50 μM to a low dose of approximately 2.5 nM. A standard, four-parameter logistic model (Equation 1) was fit to the raw data (rate versus concentration of compound):

$$y = A + \frac{B - A}{1 + \left[\frac{C}{x}\right]^D} \quad (1)$$

where x is the concentration of compound, y is the estimated rate, A and B are the lower and upper asymptotes, respectively, C is the $EC_{50}$ and D is the Hill slope. The $EC_{50}$ is defined as the midpoint or inflection point between the upper and lower asymptotes. A compound was identified as a glucokinase activator if it stimulated the activity of glucokinase 25 percent or more above that observed in the absence of the compound.

Glucose $S_{0.5}$ Assay:

For this assay, the concentration of control or test compound was fixed at or near a saturating concentration, if possible, typically 50 μM, while the glucose concentration was varied over a 10-point, 2-fold dilution series ranging from 80 to approximately 0.16 mM. The same four-parameter logistic model used for the $EC_{50}$ assay (Equation 1) was employed to estimate the relevant kinetic parameters. In this assay, the definitions for the variables and parameters are similar except that x represents the concentration of glucose, B is the rate at saturating glucose ($V_m$), C is the $S_{0.5}$ for glucose (the concentration of glucose at $V_m/2$) and D is the Hill Coefficient. The $S_{0.5}$ for compounds of Examples 1-141, A1-H1, A2-M2, and A3-E3 is in the range of 1.5 and 7.5 mM. For certain compounds of the invention, the $S_{0.5}$ is in the range of 1.5 and 4.0 mM.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be resorted to falling within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:
1. A compound selected from the Formula

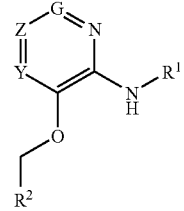

and pharmaceutically acceptable salts thereof, wherein:
G is N or $CR^{11}$;
Z is N or $CR^3$;
Y is N or $CR^4$, wherein at least one of G or Z is not N;
$R^1$ is

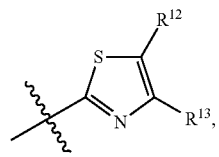

$R^2$ is a monocyclic or bicyclic aryl or heteroaryl, wherein said monocyclic and bicyclic aryl and heteroaryl are optionally substituted with one or more groups independently selected from alkyl, alkenyl, alkynyl, heteroalkyl, saturated and partially unsaturated $V_n$-cycloalkyl, saturated and partially unsaturated $V_n$-heterocycloalkyl, $V_n$-aryl, $V_n$-heteroaryl, F, Cl, Br, I, $CF_3$, cyano, $V_n$—$OR^6$, $V_n$—C(=O)$R^6$, $V_n$—C(=O)$OR^6$, $V_n$—OC(=O)$R^6$, $V_n$—O($CH_2$)$_n$C(=O)$OR^6$, $V_n$—O($CH_2$)C(=O)

NR⁶R⁷, V$_n$—C(=O)NR⁶R⁷, V$_n$—NR⁶R⁷, V$_n$—NR⁶C(=O)R⁷, V$_n$—SR⁶, V$_n$—S(O)R⁶, and V$_n$—S(O)₂R⁶, wherein said alkyl, alkenyl, alkynyl, heteroalkyl, V$_n$-cycloalkyl, V$_n$-heterocycloalkyl, V$_n$-aryl, and V$_n$-heteroaryl are optionally substituted with one or more groups independently selected from oxo, alkyl, alkenyl, alkynyl, heteroalkyl, saturated and partially unsaturated V$_n$-cycloalkyl, saturated and partially unsaturated V$_n$-heterocycloalkyl, V$_n$-aryl, V$_n$-heteroaryl, F, Cl, Br, I, CF₃, cyano, V$_n$—OR⁸, V$_n$—C(=O)R⁸, V$_n$—C(=O)OR⁸, V$_n$—OC(=O)R⁸, V$_n$—C(=O)NR⁸R⁹, V$_n$—NR⁸R⁹, V$_n$—NR⁸C(=O)R⁹, V$_n$—SR⁸, V$_n$—S(O)R⁸, and V$_n$—S(O)₂R⁸;

R³ is H, alkyl, alkenyl, alkynyl, heteroalkyl, saturated or partially unsaturated V$_n$-cycloalkyl, saturated or partially unsaturated V$_n$-heterocycloalkyl, V$_n$-aryl, V$_n$-heteroaryl, F, Cl, Br, I, CN, V$_n$—OR⁶, V$_n$—C(=O)R⁶, V$_n$—C(=O)OR⁶, V$_n$—OC(=O)R⁶, V$_n$—C(=O)NR⁶R⁷, V$_n$—NR⁶R⁷, V$_n$—NR⁶C(=O)R⁷, V$_n$—SR⁶, V$_n$—S(O)R⁶, V$_n$—S(O)₂R⁶, or V$_n$—S(O)₂NR⁶R⁷, wherein said alkyl, alkenyl, alkynyl, heteroalkyl, V$_n$-cycloalkyl, V$_n$-heterocycloalkyl, V$_n$-aryl, and V$_n$-heteroaryl are optionally substituted with one or more groups independently selected from oxo, alkyl, alkenyl, alkynyl, heteroalkyl, saturated and partially unsaturated V$_n$-cycloalkyl, saturated and partially unsaturated V$_n$-heterocycloalkyl, V$_n$-aryl, V$_n$-heteroaryl, F, Cl, Br, I, CF₃, cyano, V$_n$—OR⁸, V$_n$—C(=O)R⁸, V$_n$—C(=O)OR⁸, V$_n$—OC(=O)R⁸, V$_n$—C(=O)NR⁸R⁹, V$_n$—NR⁸R⁹, V$_n$—NR⁸C(=O)R⁹, V$_n$—SR⁸, V$_n$—S(O)R⁸, V$_n$—S(O)₂R⁸, and V$_n$—S(O)₂NR⁸R⁹;

R⁴ is H, methyl, ethyl, F, Cl, Br, I, CF₃, CHF₂, or CH₂F;

R⁶ and R⁷ are independently H, alkyl, alkenyl, alkynyl, saturated or partially unsaturated V$_n$-cycloalkyl, saturated or partially unsaturated V$_n$-heterocycloalkyl, V$_n$-aryl, V$_n$-heteroaryl, V$_n$—OR⁸, V$_n$—NR⁸R⁹, V$_n$—C(=O)NR⁸R⁹, or V$_n$—C(=O)R⁸, wherein said alkyl, alkenyl, alkynyl, V$_n$-cycloalkyl, V$_n$-heterocycloalkyl, V$_n$-aryl, and V$_n$-heteroaryl are optionally substituted with one or more groups independently selected from oxo, alkyl, alkenyl, alkynyl, heteroalkyl, saturated and partially unsaturated V$_n$-cycloalkyl, saturated and partially unsaturated V$_n$-heterocycloalkyl, V$_n$-aryl, V$_n$-heteroaryl, F, Cl, Br, I, CF₃, cyano, V$_n$—OR⁸, V$_n$—C(=O)R⁸, V$_n$—C(=O)OR⁸, V$_n$—OC(=O)R⁸, V$_n$—C(=O)NR⁸R⁹, V$_n$—NR⁸R⁹, V$_n$—NR⁸C(=O)R⁹, V$_n$—SR⁸, V$_n$—S(O)R⁸, V$_n$—S(O)₂R⁸, and V$_n$—S(O)₂NR⁸R⁹;

or R⁶ and R⁷ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, F, Cl, Br, I, V$_n$—OR⁸, V$_n$—C(=O)OR⁸, V$_n$—C(=O)NR⁸R⁹, V$_n$—NR⁸R⁹, V$_n$—NR⁸C(=O)R⁹, V$_{ii}$—NR⁸C(=O)NR⁹R¹⁰, alkyl, alkenyl, and alkynyl;

R⁸, R⁹ and R¹⁰ are independently H, alkyl, alkenyl, alkynyl, saturated or partially unsaturated V$_n$-cycloalkyl, saturated or partially unsaturated V$_n$-heterocycloalkyl, V$_n$-aryl or V$_n$-heteroaryl, wherein said alkyl, alkenyl, alkynyl, V$_n$-cycloalkyl, V$_n$-heterocycloalkyl, V$_n$-aryl and V$_n$-heteroaryl are optionally substituted with one or more groups independently selected from oxo, alkyl, alkenyl, alkynyl, saturated and partially unsaturated V$_n$-cycloalkyl, saturated and partially unsaturated V$_n$-heterocycloalkyl, V$_n$-aryl, V$_n$-heteroaryl, F, Cl, Br, I, V$_n$—OR$^a$, V$_n$—NR$^a$R$^b$, V$_n$—C(=O)OR$^a$, V$_n$—C(=O)NR$^a$R$^b$, and V$_n$—NR$^a$C(=O)R$^b$, or R⁸ and R⁹ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, alkyl, alkenyl, alkynyl, F, Cl, Br, I, V$_n$—OR$^a$, and CN;

or R⁹ and R¹⁰ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, alkyl, alkenyl, alkynyl, F, Cl, Br, I, V$_n$—OR$^a$, and CN;

R¹¹ is H, methyl, ethyl, F, Cl, Br, I, CF₃, CHF₂, CH₂F, OH, O—(C₁-C₄ alkyl), or NH₂;

R¹² is hydrogen;

R¹³ is selected from H, Cl, methyl, ethyl, isopropyl, butyl, isobutyl, cyclopropyl, cyclohexyl, —CH₂CH₂OH, —CO₂H, —(CH₂)₂CO₂H, —CH₂CO₂CH₃, —(CH₂)₂CO₂CH₃, —CH₂C(O)NH₂, —(CH₂)₂NHC(O)CH₃, CH₂CH₂NHSO₂—N(CH₃)₂, 4-piperidyl, —(CH₂-isoincloline-1,3-dion-2-yl,

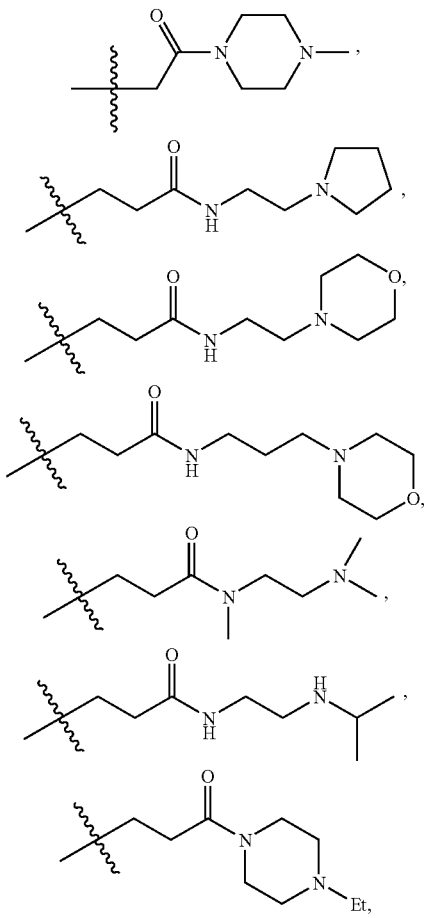

-continued

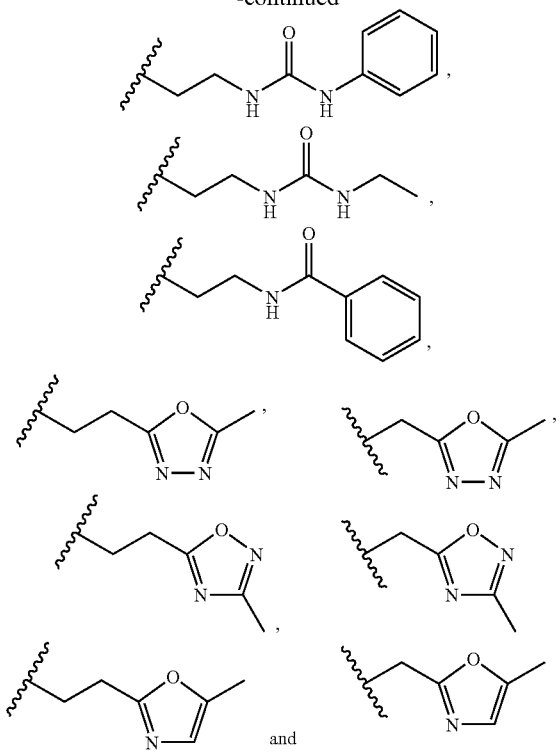

Rᵃ and Rᵇ are independently H, alkyl, alkenyl, alkynyl, saturated or partially unsaturated $V_n$-cycloalkyl, saturated or partially unsaturated $V_n$-heterocycloalkyl, $V_n$-aryl, or $V_n$-heteroaryl, wherein said alkyl, alkenyl, alkynyl, saturated or partially unsaturated $V_n$-cycloalkyl, saturated or partially unsaturated $V_n$-heterocycloalkyl, $V_n$-aryl, or $V_n$-heteroaryl are optionally substituted by OH;

V is alkylene having from 1 to 4 carbons, or alkenylene or alkynylene each having from 2 to 4 carbons, wherein said alkylene, alkenylene, or alkynylene are optionally substituted with one or more groups independently selected from alkyl, alkenyl, alkynyl, heteroalkyl, saturated and partially unsaturated $V_n$-cycloalkyl, saturated and partially unsaturated $V_n$-heterocycloalkyl, $V_n$-aryl, $V_n$-heteroaryl, F, Cl, Br, I, CF₃, cyano, $V_n$—OR⁸, $V_n$—C(=O)OR⁸, $V_n$—OC(=O)R⁸, $V_n$—C(=O)NR⁸R⁹, $V_n$—NR⁸R⁹, and $V_n$—NR⁸C(=O)R⁹; and n is 0, 1, 2, 3 or 4.

2. The compound of claim 1 and pharmaceutically acceptable salts thereof, wherein:
G is CR¹¹;
Z is CR³;
Y is N or CR⁴; and
R⁴ and R¹¹ are H.

3. The compound of claim 1 and pharmaceutically acceptable salts thereof, wherein R² is
(i) heteroaryl selected from pyridyl, quinolinyl, quinoxalinyl, benzo[d]thiazolyl, 1H-benzo[d]imidazolyl, thiophenyl, tetrahydroquinolinyl, tetrahydroisoquinolinyl, thiazolyl and substituted forms thereof; or
(ii) phenyl optionally substituted with one or two groups independently selected from Cl, C₁-C₆ alkyl, $V_n$—OR⁶, $V_n$—C(=O)NR⁶R⁷, $V_n$—NR⁶C(=O)R⁷, $V_n$—OCH₂C(=O)OR⁶ and $V_n$—O(CH₂)ₙ—C(=O)NR⁶R⁷, wherein each V is independently C₁-C₄ alkylene and each n is independently 0 or 1.

4. The compound of claim 3 and pharmaceutically acceptable salts thereof, wherein R² is
(i) 2-pyridyl, 3-pyridyl, 8-quinolinyl, 8-quinoxalinyl, 1H-benzo[d]imidazole-7-yl, 2-thienyl; or
(ii) phenyl optionally substituted with one or two groups independently selected from Cl, —OCH₃, OH, —OC(=O)H, —NHC(=O)Me, —OCH₂C(=O)OH, —OCH₂C(=O)NH(CH₂)₂NMe₂, —OCH₂C(=O)NHCH₂COOH,

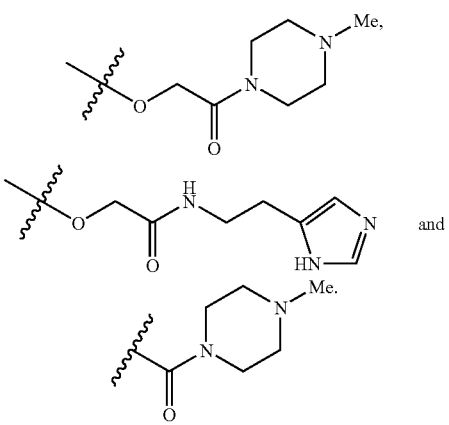

5. The compound of claim 4 and pharmaceutically acceptable salts thereof, wherein R² is phenyl, 2-methoxyphenyl, 3-methoxyphenyl, 3-hydroxyphenyl, 3-(OCH₂CO₂t-Bu)phenyl, 3-(OCH₂CO₂H)phenyl, 3-(OCH₂C(O)NHCH₂CO₂H)phenyl, 2-chlorophenyl, 2,6-dichlorophenyl, 2-acetamidephenyl,

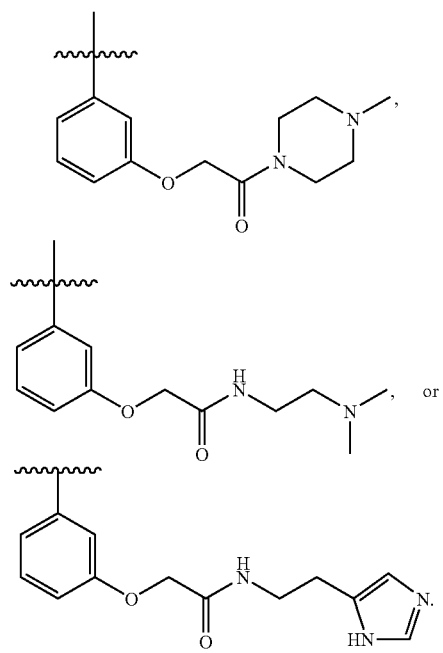

6. The compound of claim 1 and pharmaceutically acceptable salts thereof, wherein R³ is H, Cl, Br, I, $V_n$—OR⁶, $V_n$—SR⁶, $V_n$—S(O)R⁶, $V_n$—S(O)₂R⁶, $V_n$—C(=O)NR⁶R⁷, $V_n$—C(=O)OR⁶, $V_n$—C(=O)R⁶, V—NR⁶R⁶, $V_n$-aryl, $V_n$-heteroaryl, C₁-C₆ alkyl or C₂-C₆ alkenyl, wherein V is C₁-C₄ alkylene n is 0 or 1.

7. The compound of claim 6 and pharmaceutically acceptable salts thereof, wherein $R^3$ is:

(i) —SCH$_3$, —S-cyclohexyl, —SCH$_2$-cyclopentyl, —S-phenyl, —S-(2-chlorophenyl), —S-(2-methoxyphenyl), —S-(3-methoxyphenyl), —S-(4-methoxyphenyl), —SCH$_2$-(2-methoxyphenyl), —SCH$_2$-(3-methoxyphenyl), —SCH$_2$-(4-methoxyphenyl), —SCH$_2$-(phenyl), —SCH$_2$CH$_2$-(phenyl), —SCH$_2$-(2-chlorophenyl), —SCH$_2$-(3-chlorophenyl), —SCH$_2$-(4-chlorophenyl), —S-(4-pyridyl), —S-(2-pyridyl), —S-(2-thiophenyl), S-(1-methyl-1H-imidazol-2-yl), —S-(thieno[3,2-b]pyridin-7-yl), —S-(1-methyl-1,2-dihydrooxazolo[5,4-b]pyridin-7-yl), —S-(2-chloropyrid-4-yl), —S-(2-chloropyrimid-4-yl), —S-(2-pyrimidyl), —SCH$_2$-(4-pyridyl), —SCH$_2$-(3-pyridyl), —SCH$_2$-(2-pyridyl), —SCH$_2$-(2-thiophenyl), —SCH$_2$CH$_2$-(1H-imidazol-1-yl), —S(CH$_2$)$_3$—N(CH$_3$)$_2$, —SCH$_2$-(4-piperidinyl), —SCH$_2$C(O)-(4-methylpiperazin-1-yl), —S(CH$_2$)$_2$CO$_2$(CH$_3$), —S(CH$_2$)$_2$CO$_2$H, or

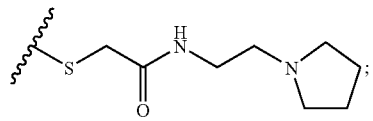 [SMILES: *SCC(=O)NCCN1CCCC1]

(ii) —S-(1-phenylethyl),

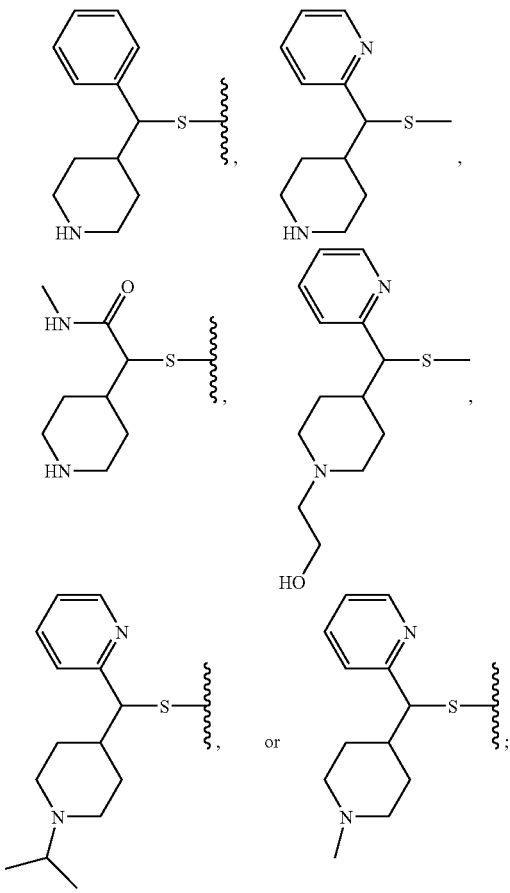

(iii) —S(O)CH$_3$, —S(O)phenyl, or —SO$_2$CH$_3$;
(iv) methoxy, hydroxymethyl, 1-hydroxyethyl, benzyloxy, 2-chlorophenoxy, or —CH═CHOCH$_3$;
(v) methyl, pentyl, or 1-penten-1-yl;
(vi) phenyl, benzyl, 1-phenylethyl, 2-phenylethen-1-yl, 1-phenylethen-1-y, 4-tolyl, or α-hydroxybenzyl;
(vii) —(CH$_2$)$_2$—CO$_2$CH$_3$, —(CH$_2$CH)—CO$_2$CH$_3$, or CH$_2$CH$_2$CO$_2$H;
(viii) 3-pyridyl or 4-pyridyl;
(ix) —C(O)CH$_3$, —C(O)H or —CH$_2$C(O)H;
(x) —C(O)NH$_2$, C(O)NHCH$_2$Ph, —C(O)-(4-methylpiperazin-1-yl) or —CH$_2$CH$_2$C(O)-(4-methylpiperazin-1-yl);
(xi) —CH$_2$NH-(2-pyridyl), —CH$_2$-(4-morpholinyl), —(CH$_2$)$_3$—N(CH$_3$)$_2$ or —CH═CH—CH$_2$N(CH$_3$)$_2$; or
(xii) H, Cl, Br or I.

8. A composition comprising a compound or a pharmaceutically acceptable salt thereof of claim 1 and a pharmaceutically acceptable diluent or carrier.

9. A compound selected from the Formula

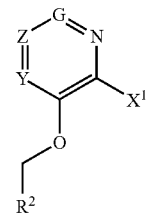

and pharmaceutically acceptable salts thereof, wherein:
G is N or CR$^{11}$;
Z is N or CR$^3$;
Y is N or CR$^4$, wherein at least one of G or Z is not N;
$R^1$ is

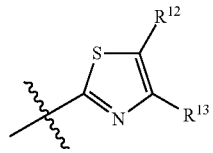

$R^2$ is a monocyclic or bicyclic aryl or heteroaryl, wherein said monocyclic and bicyclic aryl and heteroaryl are optionally substituted with one or more groups independently selected from alkyl, alkenyl, alkynyl, heteroalkyl, saturated and partially unsaturated V$_n$-cycloalkyl, saturated and partially unsaturated V$_n$-heterocycloalkyl, V$_n$-aryl, V$_n$-heteroaryl, F, Cl, Br, I, CF$_3$, cyano, V$_n$—OR$^6$, V$_n$—C(═O)R$^6$, V$_n$—C(═O)OR$^6$, V$_n$—OC(═O)R$^6$, V$_n$—O(CH$_2$)$_n$—C(═O)OR$^6$, V$_n$—O(CH$_2$)C(═O)NR$^6$R$^7$, V$_n$—C(═O)NR$^6$R$^7$, V$_n$—NR$^6$R$^7$, V$_n$—NR$^6$C(═O)R$^7$, V$_n$—SR$^6$, V$_n$—S(O)R$^6$, and V$_n$—S(O)$_2$R$^6$, wherein said alkyl, alkenyl, alkynyl, heteroalkyl, V$_n$-cycloalkyl, V$_n$-heterocycloalkyl, V$_n$-aryl, and V$_n$-heteroaryl are optionally substituted with one or more groups independently selected from oxo, alkyl, alkenyl, alkynyl, heteroalkyl, saturated and partially unsaturated V$_n$-cycloalkyl, saturated and partially unsaturated V$_n$-heterocycloalkyl, V$_n$-aryl, V$_n$-heteroaryl, F, Cl, Br, I, CF$_3$, cyano, V$_n$—OR$^8$, V$_n$—C(═O)R$^8$, V$_n$—C(═O)OR$^8$, V$_n$—OC(═O)R$^8$, V$_n$—C(═O)NR$^8$R$^9$, V$_n$—NR$^8$R$^9$, V$_n$—NR$^8$C(═O)R$^9$, V$_n$—SR$^8$, V$_n$—S(O)R$^8$, and V$_n$—S(O)$_2$R$^8$;

R³ is (i) —SCH₃, —S-cyclohexyl, —SCH₂-cyclopentyl, —S-phenyl, —S-(2-chlorophenyl), —S-(2-methoxyphenyl), —S-(3-methoxyphenyl), —S-(4-methoxyphenyl), —SCH₂-(2-methoxyphenyl), —SCH₂-(3-methoxyphenyl), —SCH₂-(4-methoxyphenyl), —SCH₂-(phenyl), —SCH₂CH₂-(phenyl), —SCH₂-(2-chlorophenyl), —SCH₂-(3-chlorophenyl), —SCH₂-(4-chlorophenyl), —S-(4-pyridyl), —S-(2-pyridyl), —S-(2-thiophenyl), S-(1-methyl-1H-imidazol-2-yl), —S-(thieno[3,2-b]pyridin-7-yl), —S-(1-methyl-1,2-dihydrooxazolo[5,4-b]pyridin-7-yl), —S-(2-chloropyrid-4-yl), —S-(2-chloropyrimid-4-yl), —S-(2-pyrimidyl), —SCH₂-(4-pyridyl), —SCH₂-(3-pyridyl), —SCH₂-(2-pyridyl), —SCH₂-(2-thiophenyl), —SCH₂CH₂-(1H-imidazol-1-yl), —S(CH₂)₃—N(CH₃)₂, —SCH₂-(4-piperidinyl), —SCH₂C(O)-(4-methylpiperazin-1-yl), —S(CH₂)₂CO₂(CH₃), —S(CH₂)₂CO₂H, or

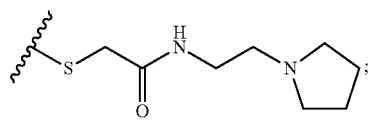 [SMILES: *SCC(=O)NCCN1CCCC1]

(ii) —S-(1-phenylethyl),

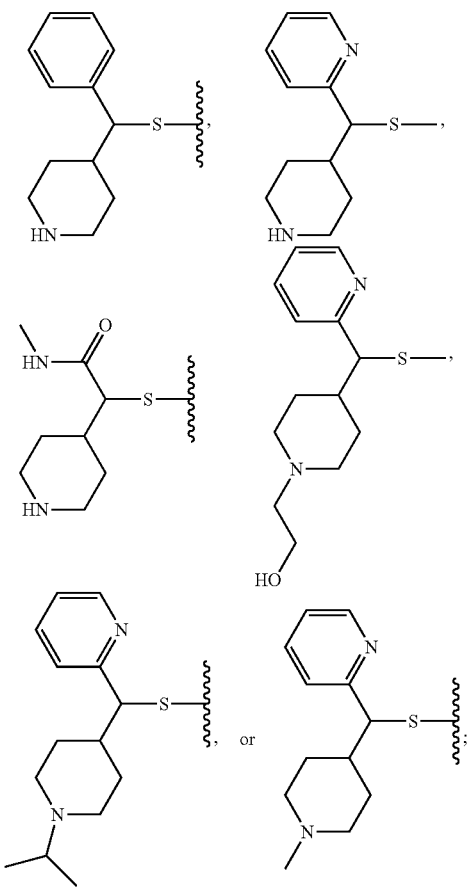

(iii) —S(O)CH₃, —S(O)phenyl, or —SO₂CH₃;
(iv) methoxy, hydroxymethyl, 1-hydroxyethyl, benzyloxy, 2-chlorophenoxy, or —CH=CHOCH₃;
(v) methyl, pentyl, or 1-penten-1-yl;
(vi) phenyl, benzyl, 1-phenylethyl, 2-phenylethen-1-yl, 1-phenylethen-1-y, 4-tolyl, or α-hydroxybenzyl;
(vii) —(CH₂)₂—CO₂CH₃, —(CH=CH)—CO₂CH₃, or CH₂CH₂CO₂H;
(viii) 3-pyridyl or 4-pyridyl;
(ix) —C(O)CH₃, —C(O)H or —CH₂C(O)H;
(x) —C(O)NH₂, C(O)NHCH₂Ph, —C(O)-(4-methylpiperazin-1-yl) or —CH₂CH₂C(O)-(4-methylpiperazin-1-yl);
(xi) —CH₂NH-(2-pyridyl), —CH₂-(4-morpholinyl), —(CH₂)₃—N(CH₃)₂ or —CH=CH—CH₂N(CH₃)₂; or
(xii) H, Cl, Br or I;

R⁴ is H, methyl, ethyl, F, Cl, Br, I, CF₃, CHF₂, or CH₂F;

R⁶ and R⁷ are independently H, alkyl, alkenyl, alkynyl, saturated or partially unsaturated $V_n$-cycloalkyl, saturated or partially unsaturated $V_n$-heterocycloalkyl, $V_n$-aryl, $V_n$-heteroaryl, $V_n$—OR⁸, $V_n$—NR⁸R⁹, $V_n$—C(=O)NR⁸R⁹, or $V_n$—C(=O)R⁸, wherein said alkyl, alkenyl, alkynyl, $V_n$-cycloalkyl, $V_n$-heterocycloalkyl, $V_n$-aryl, and $V_n$-heteroaryl are optionally substituted with one or more groups independently selected from oxo, alkyl, alkenyl, alkynyl, heteroalkyl, saturated and partially unsaturated $V_n$-cycloalkyl, saturated and partially unsaturated $V_n$-heterocycloalkyl, $V_n$-aryl, $V_n$-heteroaryl, F, Cl, Br, I, CF₃, cyano, $V_n$—OR⁸, $V_n$—C(=O)R⁸, $V_n$—C(=O)OR⁸, $V_n$—OC(=O)R⁸, $V_n$—C(=O)NR⁸R⁹, $V_n$—NR⁸R⁹, $V_n$—NR⁸C(=O)R⁹, $V_n$—SR⁸, $V_n$—S(O)R⁸, $V_n$—S(O)₂R⁸, and $V_n$—S(O)₂NR⁸R⁹;

or R⁶ and R⁷ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, F, Cl, Br, I, $V_n$—OR⁸, $V_n$—C(=O)OR⁸, $V_n$—C(=O)NR⁸R⁹, $V_n$—NR⁸R⁹, $V_n$—NR⁸C(=O)R⁹, $V_n$—NR⁸C(=O)NR⁹R¹⁰, alkyl, alkenyl, and alkynyl;

R⁸, R⁹ and R¹⁰ are independently H, alkyl, alkenyl, alkynyl, saturated or partially unsaturated $V_n$-cycloalkyl, saturated or partially unsaturated $V_n$-heterocycloalkyl, $V_n$-aryl or $V_n$-heteroaryl, wherein said alkyl, alkenyl, alkynyl, $V_n$-cycloalkyl, $V_n$-heterocycloalkyl, $V_n$-aryl and $V_n$-heteroaryl are optionally substituted with one or more groups independently selected from oxo, alkyl, alkenyl, alkynyl, saturated and partially unsaturated $V_n$-cycloalkyl, saturated and partially unsaturated $V_n$-heterocycloalkyl, $V_n$-aryl, $V_n$-heteroaryl, F, Cl, Br, I, $V_n$—OR$^a$, $V_n$—NR$^a$R$^b$, $V_n$—C(=O)OR$^a$, $V_n$—C(=O)NR$^a$R$^b$, and $V_n$—NR$^a$C(=O)R$^b$, or R⁸ and R⁹ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, alkyl, alkenyl, alkynyl, F, Cl, Br, I, $V_n$—OR$^a$, and CN;

or R⁹ and R¹⁰ together with the atoms to which they are attached form a saturated or partially unsaturated heterocyclic ring, wherein said heterocyclic ring optionally comprises one or more additional ring heteroatoms independently selected from N, O or S, wherein said heterocyclic ring is optionally substituted with one or more groups independently selected from oxo, alkyl, alkenyl, alkynyl, F, Cl, Br, I, $V_n$— OR$^a$, and CN;

$R^{11}$ is H, methyl, ethyl, F, Cl, Br, I, $CF_3$, $CHF_2$, $CH_2F$, OH, O—($C_1$-$C_4$ alkyl), or $NH_2$;

$R^{12}$ is hydrogen;

$R^{13}$ is H, alkyl, alkenyl, alkynyl, heteroalkyl, saturated or partially unsaturated $V_n$-cycloalkyl, saturated or partially unsaturated $V_n$-heterocycloalkyl, $V_n$-aryl, $V_n$-heteroaryl, F, Cl, Br, I, $CF_3$, cyano, $V_n$—$OR^6$, $V_n$—C(=O)$R^6$, $V_n$—C(=O)$OR^6$, $(CH_2)_nOC$(=O)$R^6$, $V_n$—C(=O)$NR^6R^7$, $V_n$—$NR^6R^7$, $V_n$—$NR^6C$(=O)$R^7$, $V_n$—$SR^6$, $V_n$—S(O)$R^6$, $V_n$—S(O)$_2R^6$, $V_n$—NHC(O)$NHR^a$ or $V_n$—$NHSO_2NR^aR^b$, wherein said alkyl, alkenyl, alkynyl, $V_n$-cycloalkyl, $V_n$-heterocycloalkyl, $V_n$-aryl, and $V_n$-heteroaryl are optionally substituted with one or more groups independently selected from oxo, F, Cl, Br, I, $CF_3$, cyano, $V_n$—$OR^8$, $V_n$—C(=O)$OR^8$, $V_n$—OC(=O)$R^8$, $V_n$—C(=O)$NR^8R^9$, $V_n$—$NR^8R^9$, $V_n$—$NR^8C$(=O)$R^9$, $C_1$-$C_6$ alkyl, $C_2$-$C_6$ alkenyl, $C_2$-$C_6$ alkynyl, saturated and partially unsaturated $V_n$-cycloalkyl, saturated and partially unsaturated $V_n$-heterocycloalkyl, $V_n$-aryl, and $V_n$-heteroaryl, wherein said heterocycloalkyl is optionally substituted with one or more oxo;

$R^a$ and $R^b$ are independently H, alkyl, alkenyl, alkynyl, saturated or partially unsaturated $V_n$-cycloalkyl, saturated or partially unsaturated $V_n$-heterocycloalkyl, $V_n$-aryl, or $V_n$-heteroaryl, wherein said alkyl, alkenyl, alkynyl, saturated or partially unsaturated $V_n$-cycloalkyl, saturated or partially unsaturated $V_n$-heterocycloalkyl, $V_n$-aryl, or $V_n$-heteroaryl are optionally substituted by OH;

V is alkylene having from 1 to 4 carbons, or alkenylene or alkynylene each having from 2 to 4 carbons, wherein said alkylene, alkenylene, or alkynylene are optionally substituted with one or more groups independently selected from alkyl, alkenyl, alkynyl, heteroalkyl, saturated and partially unsaturated $V_n$-cycloalkyl, saturated and partially unsaturated $V_n$-heterocycloalkyl, $V_n$-aryl, $V_n$-heteroaryl, F, Cl, Br, I, $CF_3$, cyano, $V_n$—$OR^8$, $V_n$—C(=O)$OR^8$, $V_n$—OC(=O)$R^8$, $V_n$—C(=O)$NR^8R^9$, $V_n$—$NR^8R^9$, and $V_n$—$NR^8C$(=O)$R^9$; and n is 0, 1, 2, 3 or 4, with the proviso that $R^{13}$ cannot be phenyl.

10. The compound of claim 9 and pharmaceutically acceptable salts thereof wherein:

$R^{13}$ is H, alkyl, alkenyl, alkynyl, heteroalkyl, saturated or partially unsaturated $V_n$-cycloalkyl, saturated or partially unsaturated $V_n$-heterocycloalkyl, $V_n$-aryl, $V_n$-heteroaryl, F, Cl, Br, I, $CF_3$, cyano, $V_n$—$OR^6$, $V_n$—C(=O)$R^6$, $V_n$—C(=O)$OR^6$, $(CH_2)_nOC$(=O)$R^6$, $V_n$—C(=O)$NR^6R^7$, $V_n$—$NR^6R^7$, $V_n$—$NR^6C$(=O)$R^7$, $V_n$—$SR^6$, $V_n$—S(O)$R^6$, or $V_n$—S(O)$_2R^6$, wherein said alkyl, alkenyl, alkynyl, $V_n$-cycloalkyl, $V_n$-heterocycloalkyl, $V_n$-aryl, and $V_n$-heteroaryl are optionally substituted with one or more groups independently selected from oxo, F, Cl, Br, I, $CF_3$, cyano, $V_n$—$OR^8$, $V_n$—C(=O)$OR^8$, $V_n$—OC(=O)$R^8$, $V_n$—C(=O)$NR^8R^9$, $V_n$—$NR^8R^9$, $V_n$—$NR^8C$(=O)$R^9$, alkyl, alkenyl, alkynyl, saturated and partially unsaturated $V_n$-cycloalkyl, saturated and partially unsaturated $V_n$-heterocycloalkyl, $V_n$-aryl, and $V_n$-heteroaryl, wherein said heterocycloalkyl is optionally substituted with one or more oxo.

11. The compound of claim 9 and pharmaceutically acceptable salts thereof, wherein:

G is CR'';

Z is $CR^3$;

Y is N or $CR^4$; and $R^4$ and $R^{11}$ are H.

12. The compound of claim 9 and pharmaceutically acceptable salts thereof, wherein $R^{13}$ is selected from H, Cl, $C_1$-$C_6$ alkyl, $C_2$-$C_6$ alkenyl, $V_n$-heterocyclyl (optionally substituted with $C_1$-$C_6$ alkyl), $V_n$—$OR^6$, $V_n$—C(=O)$OR^6$, $V_n$—C(=O)$NR^6R^7$, $V_n$—$NR^6R^7$, $V_n$—$NR^6C$(=O)$R^7$, $V_n$—$NR^aC$(O)$NHR^b$, $V_n$—$NHSO_2$—$NR^aR^b$, and $V_n$-heteroaryl (optionally substituted with $C_1$-$C_6$ alkyl), wherein each V is independently $C_1$-$C_4$ alkylene or $C_2$-$C_4$ alkenylene and each n is independently 0 or 1.

13. The compound of claim 9 and pharmaceutically acceptable salts thereof, wherein $R^2$ is
  (i) heteroaryl selected from pyridyl, quinolinyl, quinoxalinyl, benzo[d]thiazolyl, 1H-benzo[d]imidazolyl, thiophenyl, tetrahydroquinolinyl, tetrahydroisoquinolinyl, thiazolyl and substituted forms thereof; or
  (ii) phenyl optionally substituted with one or two groups independently selected from Cl, $C_1$-$C_6$ alkyl, $V_n$—$OR^6$, $V_n$—C(=O)$NR^6R^7$, $V_n$—$NR^6C$(=O)$R^7$, $V_n$—$OCH_2C$(=O)$OR^6$ and $V_n$—O$(CH_2)_nC$(=O)$NR^6R^7$, wherein each V is independently $C_1$-$C_4$ alkylene and each n is independently 0 or 1.

14. The compound of claim 9 and pharmaceutically acceptable salts thereof, wherein $R^2$ is
  (i) 2-pyridyl, 3-pyridyl, 8-quinolinyl, 8-quinoxalinyl, 1H-benzo[d]imidazole-7-yl, 2-thienyl; or
  (ii) phenyl optionally substituted with one or two groups independently selected from Cl, —$OCH_3$, OH, —OC(=O)H, —NHC(=O)Me, —$OCH_2C$(=O)OH, —$OCH_2C$(=O)NH$(CH_2)_2NMe_2$, —$OCH_2C$(=O)NHCH$_2$COOH,

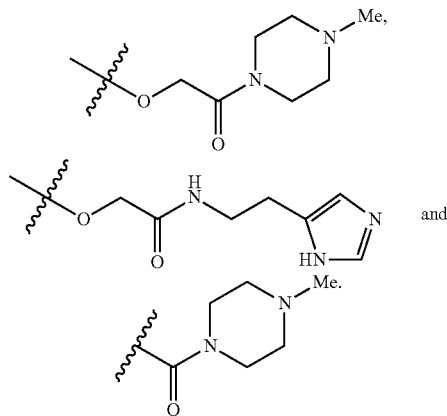

15. The compound of claim 9 and pharmaceutically acceptable salts thereof, wherein $R^2$ is phenyl, 2-methoxyphenyl, 3-methoxyphenyl, 3-hydroxyphenyl, 3-(OCH$_2$CO$_2$t-Bu)phenyl, 3-(OCH$_2$CO$_2$H)phenyl, 3-(OCH$_2$C(O)NHCH$_2$CO$_2$H)phenyl, 2-chlorophenyl, 2,6-dichlorophenyl, 2-acetamidephenyl,

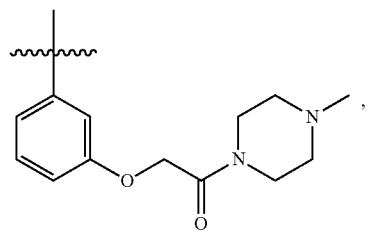

-continued
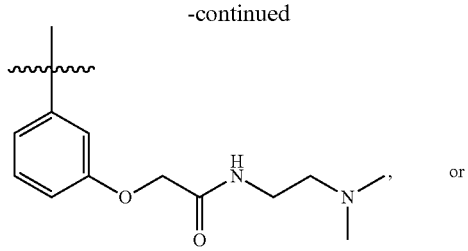
or
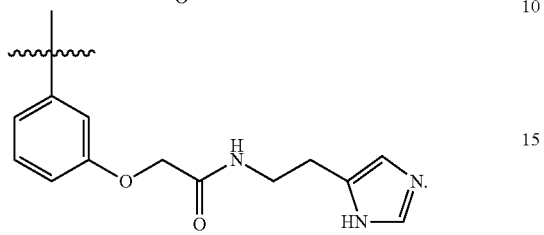
16. A composition comprising a compound or a pharmaceutically acceptable salt thereof of claim 9 and a pharmaceutically acceptable diluent or carrier.
* * * * *